US011105747B2

(12) United States Patent
Verma et al.

(10) Patent No.: US 11,105,747 B2
(45) Date of Patent: Aug. 31, 2021

(54) SPECTROSCOPIC METHODS TO DETECT AND CHARACTERIZE MICROORGANISMS

(71) Applicant: Spectral Platforms, Inc., Monrovia, CA (US)

(72) Inventors: Ravi Verma, Monrovia, CA (US); Changjun Yu, Pasadena, CA (US)

(73) Assignee: Spectral Platforms, Inc., Monrovia, CA (US)

( * ) Notice: Subject to any disclaimer, the term of this patent is extended or adjusted under 35 U.S.C. 154(b) by 16 days.

(21) Appl. No.: 15/925,601

(22) Filed: Mar. 19, 2018

(65) Prior Publication Data
US 2018/0292324 A1 Oct. 11, 2018

Related U.S. Application Data

(60) Provisional application No. 62/614,216, filed on Jan. 5, 2018, provisional application No. 62/473,876, filed on Mar. 20, 2017.

(51) Int. Cl.
| G01N 21/65 | (2006.01) |
| C12Q 1/04 | (2006.01) |
| C12Q 1/18 | (2006.01) |
| G01N 21/64 | (2006.01) |
| C12Q 1/14 | (2006.01) |

(52) U.S. Cl.
CPC .............. *G01N 21/65* (2013.01); *C12Q 1/04* (2013.01); *C12Q 1/14* (2013.01); *C12Q 1/18* (2013.01); *G01N 21/6428* (2013.01); *G01N 21/6486* (2013.01); *G01N 21/6408* (2013.01); *G01N 2201/06113* (2013.01)

(58) Field of Classification Search
None
See application file for complete search history.

(56) References Cited

U.S. PATENT DOCUMENTS

| 4,187,285 A | 2/1980 | Meeks et al. |
| 4,226,846 A | 10/1980 | Saklad |
| 5,134,126 A | 7/1992 | Hector et al. |
| 5,916,596 A | 6/1999 | Desai et al. |
| 6,040,906 A | 3/2000 | Harhay |
| 2004/0014655 A1 | 1/2004 | Hegedus et al. |
| 2005/0004011 A1 | 1/2005 | Cavaleri et al. |
| 2005/0009788 A1 | 1/2005 | Lockwood et al. |
| 2005/0064028 A1 | 3/2005 | Hegedus et al. |
| 2005/0075337 A1 | 4/2005 | Lockwood et al. |
| 2005/0089901 A1 | 4/2005 | Porter et al. |
| 2007/0232536 A1 | 10/2007 | Hegedus et al. |
| 2008/0220989 A1* | 9/2008 | Tseng .................. B01J 19/0046 506/38 |
| 2010/0143883 A1 | 6/2010 | Wilson et al. |
| 2013/0052636 A1 | 2/2013 | Verma et al. |
| 2014/0081133 A1 | 3/2014 | Nie et al. |
| 2015/0309040 A1 | 10/2015 | Chang et al. |
| 2016/0299135 A1 | 10/2016 | Cameron et al. |
| 2016/0324933 A1 | 11/2016 | Verma et al. |

FOREIGN PATENT DOCUMENTS

| EP | 0326618 | 8/1989 |
| EP | 2359859 | 8/2011 |
| JP | S63297664 | 12/1988 |
| WO | WO 1998014174 | 4/1998 |

(Continued)

OTHER PUBLICATIONS

Partali et al. Comparative Biochemistry and Physiology, Part B: Biochemistry & Molecular Biol. (1985) 82B(4): 767-72 (Year: 1985).*
Henmi, et al (1989) "Astaxanthin and/or Canthaxanthin-actomyosin Complex in Salmon Muscle"; *Nippon Suisan Gakkaishi* 55(9); pp. 1583-1589.
Jehlička, et al (2014) "Potential and Limits of Raman Spectroscopy for Carotenoid Detection in Microorganisms: Implications for Astrobiology"; *Philos Trans of Royal Soc. A Math Phys Eng Sci*, 372 (2030); pp. 1-17.
Li, et al (2015) "β-Carotene and Astaxanthin With Human and Bovine Serum Albumins"; *Food Chem* 179; pp. 213-221.
BioNavis Ltd.; "Interactions of small molecular weight drugs with human serum albumin"; Application Note # 121. 2 pages.
Fasano Mauro, et al; (2005) The Extraordinary Ligand Binding Properties of Human Serum *Albumin; IUBMB Life.* 57(12): pp. 787-796.

(Continued)

*Primary Examiner* — Susan M Hanley
(74) *Attorney, Agent, or Firm* — Khin K. Chin; Bozicevic, Field & Francis LLP

(57) ABSTRACT

Methods and systems for Resonant Raman spectroscopy are provided. Methods according to certain embodiments include irradiating a sample with a monochromatic light source at a first irradiation intensity and a second irradiation intensity, determining the intensity of one or more of the Resonant Raman scattering and fluorescence scattering at the first irradiation intensity and second irradiation intensity, calculating a rate of change of one or more of the intensity of Resonant Raman scattering and fluorescence in response to the change in irradiation intensity from the first irradiation intensity to the second irradiation intensity and comparing one or more of the rate of change in the intensity of Resonant Raman scattering and the rate of change in the intensity of fluorescence scattering with the rate of change in the irradiation intensity by the monochromatic light source to determine the Resonant Raman response of the sample. Methods also include determining the presence or absence of a microorganism in a sample and correcting for variations associated with measurement instrumentation (e.g., monochromatic light source) and variations associated with the sample (e.g., fluorescence from non-target compounds). Also provided are methods for determining the antimicrobial susceptibility of a microorganism to an antimicrobial agent as well as methods for characterizing a phenotype of an unknown microorganism in a sample. Systems for practicing the subject methods are also provided.

21 Claims, 47 Drawing Sheets

(56) References Cited

FOREIGN PATENT DOCUMENTS

| WO | 1999013914 | 3/1999 |
|---|---|---|
| WO | WO 2003106699 | 12/2003 |
| WO | WO 2004011423 | 2/2004 |
| WO | 2005066612 | 7/2005 |
| WO | 2007078635 | 7/2007 |
| WO | 2009018544 | 2/2009 |
| WO | WO 2015021300 | 2/2015 |
| WO | WO 2017020000 | 2/2017 |

OTHER PUBLICATIONS

Gülseren Ibrahim, et al; (2007) "Structural and functional changes in ultrasonicated bovine serum albumin solutions"; *Ultrasonics Sonochemistry* 14; pp. 173-183.

Hoskins (1984) "Resonance Raman Spectroscopy of β-Carotene and lycopene"; *Journal of Chemical Education* 61, No. 5; pp. 460-462.

Khan Salman, et al (2015) "Improved efficiency and stability of secnidazole—An ideal delivery system"; *Saudi J Biol Sci.*22(1); pp. 42-49.

López-Ramírez, et al (2010) "Trans-cis isomerisation of the carotenoid lycopene upon complexation with cholesteric polyester carriers investigated by Raman spectroscopy and density functional theory"; *Journal of Raman Spectroscopy*; pp. 1170-1177.

Merlin, Jean Claude (1985) "Resonance Raman spectroscopy of carotenoids and carotenoid-containing systems"; *Pure and Applied Chemistry* 57(5); pp. 785-792.

Militello, Valeria, et al (2004) "Aggregation kinetics of bovine serum albumin studied by FTIR spectroscopy and light scattering"; *Biophysical Chemistry* 107; pp. 175-187.

Paál, Krisztina, et al; (2001) "High affinity binding of paclitaxel to human serum albumin"; *Eur. J. Biochem.* 268; pp. 2187-2191.

Rehman and Khan (2015) "Understanding the interaction between human serum albumin and anti bacterial/ anti-cancer compounds"; *Curr Pharm Des.* 21(14); pp. 1785-1799.

Rodríguez, Galdón B, et al; (2013) "Spectroscopic study of the interaction between lycopene and bovine serum albumin"; *Luminescence.* 28(5); pp. 765-770.

Sivertsen, Annfrid, et al; (2014) "Synthetic cationic antimicrobial peptides bind with their hydrophobic parts to drug site II of human serum albumin"; *BMC Struct Biol.* 14/4; doi: 10.1186/1472-6807-14/4; pp. 1-14.

Tang K, et al; (2005) "Interaction of daunomycin antibiotic with human serum albumin: investigation by resonant mirror biosensor technique, fluorescence spectroscopy and molecular modeling methods"; *J Pharm Biomed Anal.* 39(3-4); pp. 404-410.

Varshney A, et al; (2010) "Ligand binding strategies of human serum albumin: how can the cargo be utilized?"; *Chirality.* 22(1); pp. 77-87.

Wang, Rongsheng E, et al; (2012) "A Homogeneous Fluorescent Sensor for Human Serum Albumin"; *J Pharm Biomed Anal.* 63; pp. 165-169.

Yang F, et al; (2014) "Interactive association of drugs binding to human serum albumin"; *Int J Mol Sci.* 15(3); pp. 3580-3595.

Zhong Dongping, et al; (2000) "Femtosecond studies of protein-ligand hydrophobic binding and dynamics: human serum albumin"; *Proc Natl Acad Sci U S A.* 97(26); pp. 14056-14061.

Davis, Charles Patrick; *Chapter 6: Normal Flora*;; Baron (Medical Microbiology 4th edition, Galveston TX, University of Texas Medical Branch at Galveston, Chapter 6; pp. 1-10 (Year: 1996).

Yang Wenjing, et al (2016) "Low-fouling electrospun PLLA films modified with zwitterionic poly(sulfobetaine methacrylate)-catechol conjugates"; Acta Biomater. 40; pp. 92-99.

\* cited by examiner

SPECTROSCOPIC METHODS TO DETECT AND CHARACTERIZE MICROORGANISMS

CROSS-REFERENCE

This application claims the benefit of U.S. Provisional Patent Application No. 62/614,216, filed Jan. 5, 2018, and U.S. Provisional Patent Application No. 62/473,876, filed Mar. 20, 2017, which applications are incorporated herein by reference in their entireties.

GOVERNMENT RIGHTS

This Invention was made with government support under (W911NF13C0047) awarded by the US Department of Defense. The government has certain rights in the invention.

INTRODUCTION

Raman spectroscopy is used to characterize the vibrational, rotational and other low frequency molecular motions of compounds and is commonly employed to provide data for identifying the presence of particular molecules in a sample. Raman scattering is the inelastic scattering of monochromatic light (e.g., ultraviolet, visible or near infrared) where the light interacts with molecular vibrations resulting in a shift in energy by the scattered photons. The application of this method to the study of the conformations of biological molecules has developed only slowly because of numerous difficulties such as the great complexity of the spectra, poor quality spectra obtained from dilute solution and the large volumes needed.

The strong enhancement (10 to $10^6$ fold) observed when the radiation used to excite the Raman spectra lies in an electronic absorption band of a chromophore allows the analysis of specific vibrational modes of the chromophore, even if it is included in a complex biological medium at very low concentration. Since many natural chromophores play important roles in many biological activities, Raman spectroscopy is often used to probe different biological processes. Detection and structural analysis of very small concentrations of biological pigments is possible in the presence of large amounts of non-absorbing species.

SUMMARY

Aspects of the present disclosure include methods and systems for Resonant Raman spectroscopy. Methods according to certain embodiments include irradiating a sample with a monochromatic light source at a first irradiation intensity and a second irradiation intensity, determining the intensity of one or more of the Resonant Raman scattering and fluorescence scattering at the first irradiation intensity and second irradiation intensity, calculating a rate of change of one or more of the intensity of Resonant Raman scattering and fluorescence scattering in response to the change in irradiation intensity from the first irradiation intensity to the second irradiation intensity and comparing one or more of the rate of change in the intensity of Resonant Raman scattering and the rate of change in the intensity of fluorescence scattering with the rate of change in the irradiation intensity by the monochromatic light source to determine the spectroscopic response of the sample. In some embodiments, the spectroscopic response (e.g., Resonant Raman scattering and/or fluorescence scattering) of the sample is indicative of a physical change over time in the sample. In other embodiments, the spectroscopic response of the sample is indicative of a chemical change over time in the sample. In still other embodiments, the spectroscopic response of the sample is indicative of the presence of an actively metabolizing microorganism in the sample. In some embodiments, the monochromatic light source is a laser. In some embodiments, the sample includes a hydrophobic compound and an albumin protein. For example, the hydrophobic compound may be incorporated into the albumin protein. The hydrophobic compound is, in certain instances, a carotenoid, such as lycopene. In certain embodiments, the sample includes a hydrophobic compound, an albumin protein and a reducing agent. The reducing agent is, in certain instances, glutathione or a derivative thereof. In other embodiments, the sample includes a hydrophobic compound, an albumin protein and a free radical scavenger. The free radical scavenger is, in certain instances, bilirubin or a derivative thereof.

In some instances, methods include irradiating the sample over a plurality of irradiation intensities by the monochromatic light source over a period of time and determining one or more of a rate of change in the intensity of Resonant Raman scattering and a rate of change in the intensity of fluorescence scattering. In other instances, methods include irradiating a first sample over a plurality of intensities by the monochromatic light source for a period of time and determining one or more of a rate of change in the intensity of Resonant Raman scattering and a rate of change in the intensity of fluorescence scattering for the first sample; calculating a net signal for the first sample by comparing one or more of a normalized rate of change in the intensity of Resonant Raman scattering and a normalized rate of change in the intensity of fluorescence scattering for the first sample with a normalized rate of change in the irradiation intensity of the first sample by the monochromatic light source; irradiating a second sample over a plurality of intensities by the monochromatic light source for the period of time and determining one or more of a rate of change in the intensity of Resonant Raman scattering and a rate of change in the intensity of fluorescence scattering for the second sample; and calculating a net signal for the second sample by comparing one or more of a normalized rate of change in the intensity of Resonant Raman scattering and a normalized rate of change in the intensity for the second sample with a normalized rate of change in the irradiation intensity of the second sample by the monochromatic light source. In some embodiments, methods further include comparing the net signal for of the first sample with the net signal for the second sample. Based on the compared calculated net signal, methods may include one or more of: 1) determining that the first sample and second sample are different; 2) determining that the first sample comprises a different gaseous composition from the second sample; and 3) determining that the first sample or the second sample comprises actively metabolizing microorganisms.

Aspects of the present disclosure also include methods for determining the presence of a microorganism in a sample. Methods according to certain embodiments, include combining in a sample holder the sample with a reagent that contains albumin with an incorporated ligand; irradiating the sample with a monochromatic light source that is absorbed by the ligand, with either an invariant light intensity or one that varies over time focused at an interface between the sample and a surface of the sample holder; collecting scattered light from the irradiated sample and measuring a Raman signal and a fluorescence signal from the scattered light at a plurality of different times; calculating a rate of change in intensity of the Raman signal and fluorescence signal for the sample over time; correcting the calculated rates of change in the intensities of the Raman signal and the fluorescence signal to obtain a net signal; and determining the presence of a microorganism in the sample based on a comparison of the net signal versus one or more preset thresholds.

In some embodiments, the one or more present thresholds are set by implementing the method on one or more control samples that contains an inoculum in an amount at a lower limit of concentration in a clinically infected sample.

In some instances, correcting the rate of change in the intensities of the Raman signal and the fluorescence signal includes characterizing a spectral output from a standard sample. In other instances, correcting the rate of change in the intensities of the fluorescence signal includes characterizing a fluorescence output from the reagent.

In certain embodiments, correcting the rate of change in the intensities of the Raman signal and the fluorescence signal includes determining a rate of change in total output from a standard reference sample and calculating a net signal as the rate of change in the intensity of the Resonant Raman scattering minus the rate of change in the intensity of Resonant Raman scattering from the standard sample.

In other embodiments, correcting the rate of change in the intensities of the Raman signal and the fluorescence signal includes determining a rate of change in the intensity of fluorescent scattering from a standard reference sample and calculating a net signal as the rate of change in the intensity of the Resonant Raman scattering minus the rate of change in the intensity of fluorescent scattering from the standard sample.

In some embodiments, methods further include pretreating the albumin prior to incorporating the ligand, such as for example by contacting the albumin with a reducing agent (e.g., glutathione). The reducing agent is, in certain instances, sufficient to reduce the disulfide bonds in the albumin. In other embodiments, the albumin is pretreated with a disulfide crosslinking agent. In some instances, the disulfide crosslinking agent includes a core that is cleaved by enzymes or a metabolite produced by the microorganism in the sample. In certain instances, the disulfide crosslinking agent is a compound of Formula (I):

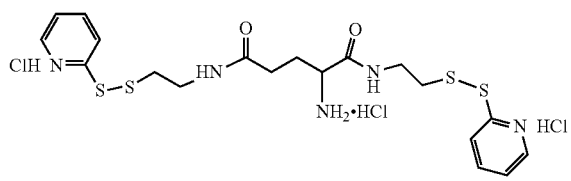

Aspects of the present disclosure also include determining the presence of a microorganism (e.g., an actively metabolizing microorganism) in a sample with Resonant Raman scattering. Methods according to certain embodiments include irradiating a sample over a plurality of intensities by a monochromatic light source for a period of time and calculating a rate of change in the intensity of Resonant Raman scattering for the first sample; calculating a net signal for the sample by comparing a normalized rate of change in the intensity of Resonant Raman scattering for the sample with a normalized rate of change in the irradiation intensity of the sample by the monochromatic light source; and determining the presence of a microorganism in the sample based on the net signal for the sample. In certain instances, a microorganism is determined to be present when the net signal of the sample is above a predetermined threshold. In other embodiments, determining the presence of a microorganism includes: irradiating a first sample over a plurality of intensities by a monochromatic light source for a period of time and calculating a rate of change in the intensity of Resonant Raman scattering for the first sample; calculating a net signal of the first sample by comparing a normalized rate of change in the intensity of Resonant Raman scattering for the first sample with a normalized rate of change in the irradiation intensity of the first sample by the monochromatic light source; irradiating a second sample over a plurality of intensities by the monochromatic light source for the period of time and determining a rate of change in the intensity of Resonant Raman scattering for the second sample; calculating a net signal of the second sample by comparing a normalized rate of change in the intensity of Resonant Raman scattering for the second sample with a normalized rate of change in the irradiation intensity of the second sample by the monochromatic light source; and determining the presence of a microorganism in one or more of the first sample or the second sample by comparing the net signal of the first sample with net signal of the second sample. In some instances, a microorganism is determined to be present in the second sample when the net signal of the second sample is greater than the net signal of the first sample. In other instances, a microorganism is determined to be present in the first sample when the net signal of the first sample is greater than the net signal of the second sample.

Aspects of the present disclosure also include determining the presence of a microorganism (e.g., an actively metabolizing microorganism) in a sample by fluorescence spectroscopy. Methods according to certain embodiments include irradiating a sample by a monochromatic light source for a period of time and detecting fluorescence from the sample over the period of time; calculating a rate of change of the fluorescence due to the presence of a microorganism by comparing a normalized rate of change in the intensity of the detected fluorescence produced by the sample with a normalized rate of change of fluorescence produced by a control; and determining the presence of a microorganism in the sample based on the calculated changes in the fluorescence of the sample compared to preset thresholds.

In determining the presence of a microorganism (e.g., an actively metabolizing microorganism) in a sample, methods include irradiating the sample in a sample holder. In some embodiments, the sample holder is a container, for example a cuvette, vial, planar substrate, or microfluidic device. The sample container is, in certain instances, a glass vial. In some embodiments, the glass vial has walls with a zwitterionic coating, such as a zwitterionic silane coating. In these embodiments, the sample may be irradiated at an interface between the sample and a surface of the sample holder (e.g., the container wall), such as by focusing the monochromatic light source at a position at the interface between the sample and the surface of the sample holder (e.g., container wall). In some instances, the monochromatic light is focused at a position of from 0.01 mm to 2 mm from the surface of the surface of the sample holder (e.g., container wall), such as at about 0.2 mm from the surface of the surface of the sample holder (e.g., container wall). The monochromatic light may be focused for example, with a collimating optics (e.g., including a collimating lens).

Aspects of the present disclosure also include a method for calculating signal-to-noise ratio. In some embodiments, methods include irradiating a first sample over a plurality of intensities by a monochromatic light source for a period of time and determining a rate of change in the intensity of Resonant Raman scattering for the first sample; calculating an average rate of change in the intensity of Resonant Raman scattering by the first sample to give a first average rate of change; calculating a standard deviation for the first average rate of change; irradiating a second sample over a range of intensities by the monochromatic light source for the period of time and determining a rate of change in the intensity of Resonant Raman scattering for the second sample; calculating an average rate of change in the intensity of Resonant Raman scattering by the second sample to give a second average rate of change; calculating a standard deviation for the second average rate of change; subtracting the second average rate of change from the first average rate of change to give a signal average rate of change; adding the first standard deviation and the second standard deviation to give a signal standard deviation; and dividing the signal average rate of change by the signal standard deviation to determine a signal-to-noise ratio for Resonant Raman response.

Aspects of the present disclosure further include a method for determining and correcting for variations in optical measurement instrumentation (e.g., thermal drift of a monochromatic light source, changes in positioning of optical components, etc.) as well as variations in the sample (e.g., fluorescence from non-target compounds). In some embodiments, methods include irradiating a reference composition over a plurality of intensities by the monochromatic light source for the period of time and determining one or more of a rate of change in the intensity of Resonant Raman scattering and a rate of change in the intensity of fluorescence scattering, wherein the reference composition comprises a reference compound that exhibits no change in the intensity of Resonant Raman scattering or fluorescence scattering in response to the change in irradiation intensity by the monochromatic light source; and calculating a net signal of the reference composition by comparing one or more of the rate of change in the intensity of Resonant Raman scattering and the rate of change in the intensity of fluorescence scattering for the reference composition with the rate of change in the irradiation intensity of the reference composition by the monochromatic light source. In certain instances, methods further include irradiating a sample over a range of intensities by a monochromatic light source for a period of time and determining one or more of a rate of change in the intensity of Resonant Raman scattering; and obtaining a net signal by correcting the determined rate of change in the intensity of Resonant Raman scattering of the sample with the rate of change of irradiation intensity of the sample by the monochromatic light source to produce a correction factor; and subtracting the correction factor from the determined rate of change in the intensity of Resonant Raman scattering for the sample.

Aspects of the present disclosure further include a method for determining the antimicrobial susceptibility of a microorganism to an antimicrobial agent with Resonant Raman scattering. In some embodiments, methods include irradiating a plurality of samples, each sample comprising a microorganism and an antimicrobial agent over a plurality of intensities by the monochromatic light source for a period of time and determining a rate of change in the intensity of Resonant Raman scattering for each irradiated sample, wherein each sample comprises the same concentration of microorganism and different concentrations of antimicrobial agent; calculating a net signal for each sample by comparing a normalized rate of change in the intensity of Resonant Raman scattering for each sample with a normalized rate of change in the irradiation intensity of each sample by the monochromatic light source; and determining the susceptibility of the microorganism to the antimicrobial agent based on the net signal of the plurality of samples. In some instances, methods further include plotting the net signal for each sample as a function of the log of the concentration of antimicrobial agent in each sample. In certain instances, methods may also include determining the minimum inhibitory concentration of antimicrobial agent by determining the concentration that first exhibits a decrease in the plotted net signal. In other instances, methods may also include determining the maximal bactericidal concentration of the antimicrobial agent by determining the concentration that first exhibits an increase in the plotted net signal. In other embodiments, methods further include determining the metabolic activity of the microorganism in each sample based on the net signal for each sample. In some instances, methods include determining the concentration of antimicrobial agent that exhibits a decrease in metabolic activity. In other instances, methods include determining the concentration of antimicrobial agent that exhibits an increase in metabolic activity.

Aspects of the present disclosure further include a method for determining the antimicrobial susceptibility of a microorganism to an antimicrobial agent by fluorescence spectroscopy. In some embodiments, methods include irradiating a plurality of samples each having a microorganism and an antimicrobial agent with a monochromatic light source for a period of time and detecting fluorescence from each of the irradiated samples over the period of time, where each sample has the same concentration of microorganism and different concentrations of antimicrobial agent; calculating a rate of change of the fluorescence in each sample by comparing a normalized rate of change in the intensity of the detected fluorescence produced by each sample with a normalized rate of change of fluorescence produced by a control; and determining the susceptibility of the microorganism to the antimicrobial agent based on the calculated rate of change of the fluorescence of the plurality of samples. In some embodiments, methods include irradiating each of the samples over a plurality of intensities of the monochromatic light source.

Each sample in these embodiments may include the same concentration of microorganism, for example, a concentration of microorganism of 10 colony forming units (CFUs) or more, such as 14 CFUs or more. In certain embodiments, the samples of microorganisms are prepared by preparing a composition having a predetermined concentration of microorganism (e.g., 100 CFUs) and aliquoting a predetermined volume of the microorganism composition into each sample such that each sample has the same concentration of microorganism. In embodiments, the concentration of antimicrobial agent in the plurality of samples ranges from a concentration that is below the minimum inhibitory concentration of the antimicrobial agent to a concentration that is greater than the minimum bactericidal concentration of the antimicrobial agent. The antimicrobial agent may be incubated with the microorganisms in the sample for a predetermined period of time before irradiating with the monochromatic light source, such as for 10 minutes or more, or 20 minutes or more.

Aspects of the present disclosure further include a method for characterizing a phenotype of an unknown microorganism with Resonant Raman scattering. In some embodiments, methods include irradiating with a monochromatic light source a sample comprising a microorganism, a crosslinking agent and an albumin protein over a plurality of intensities by the monochromatic light source for a period of time and determining a rate of change in the intensity of Resonant Raman scattering; calculating a net signal for the sample by comparing a normalized rate of change in the intensity of Resonant Raman scattering for the sample with a normalized rate of change in the irradiation intensity of the sample by the monochromatic light source; and determining crosslink cleavage of the albumin protein based on the net signal of the sample, wherein the extent of crosslink cleavage is indicative of the phenotype of the microorganism.

Aspects of the present disclosure further include a method for characterizing a phenotype of an unknown microorganism by fluorescence spectroscopy. In some embodiments, methods include irradiating with a monochromatic light source a sample comprising a microorganism, a crosslinking agent and an albumin protein for a period of time and detecting fluorescence from the sample over the period of time; calculating a rate of change of the fluorescence by comparing a normalized rate of change in the intensity of the detected fluorescence produced by the sample with a normalized rate of change of fluorescence produced by a control; and determining crosslink cleavage based on the calculated rate of change of fluorescence of the sample, wherein the extent of crosslink cleavage is indicative of the phenotype of the microorganism. In some embodiments, methods include irradiating the sample over a plurality of intensities of the monochromatic light source.

In embodiments, the crosslinking agent may be a disulfide crosslinker. In some instances, the crosslinking agent is a glutamic acid derivative. In certain embodiments, the crosslinking agent is a compound of Formula (I):

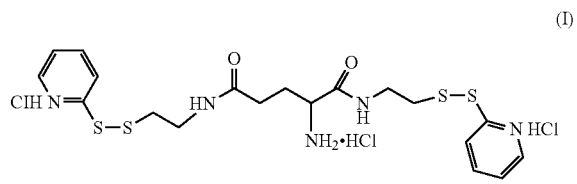

The crosslinking agent may be present in the sample in an amount where the molar ratio of crosslinking agent to albumin protein is from 1:10 to 10:1, for example a molar ratio of crosslinking agent to albumin protein of about 1:2. In embodiments, an increase over time in the net signal of the sample is indicative that the microorganism produces a metabolite that cleaves one or more crosslinks in the albumin protein. Based on this, the phenotype of the microorganism may be characterized.

Systems for practicing the subject methods having a monochromatic light source and a detector for detecting Resonant Raman scattering or fluorescence are also provided. In some embodiments, the monochromatic light source is a laser. For example, the laser may be a Nd:YAG laser, such as a frequency doubled Nd:YAG laser that outputs light at 532 nm. In some instances, the detector is a charged coupled device (CCD). In some embodiments, systems further include a sample container. The sample container, for example, may be a glass vial. In some embodiments, the glass vial has walls with a zwitterionic coating, such as a zwitterionic silane coating. In these embodiments, the subject systems are configured to irradiate the sample at an interface between the sample and the container wall, such as by focusing the monochromatic light source at a position at the interface between the sample and the container wall. In some instances, the monochromatic light is focused at a position of from 0.01 mm to 2 mm from the surface of the container wall, such as at about 0.2 mm from the surface of the container wall. These systems may also include an optical adjustment component to focus the monochromatic light source at the interface between the sample and the container wall, such as a collimating lens.

BRIEF DESCRIPTION OF THE FIGURES

The invention may be best understood from the following detailed description when read in conjunction with the accompanying drawings. Included in the drawings are the following figures:

FIG. 9A depicts the raw data values as measured. FIG. 9B depicts data values corrected for the observed drift in laser power.

SELECT DEFINITIONS

Figure 1:
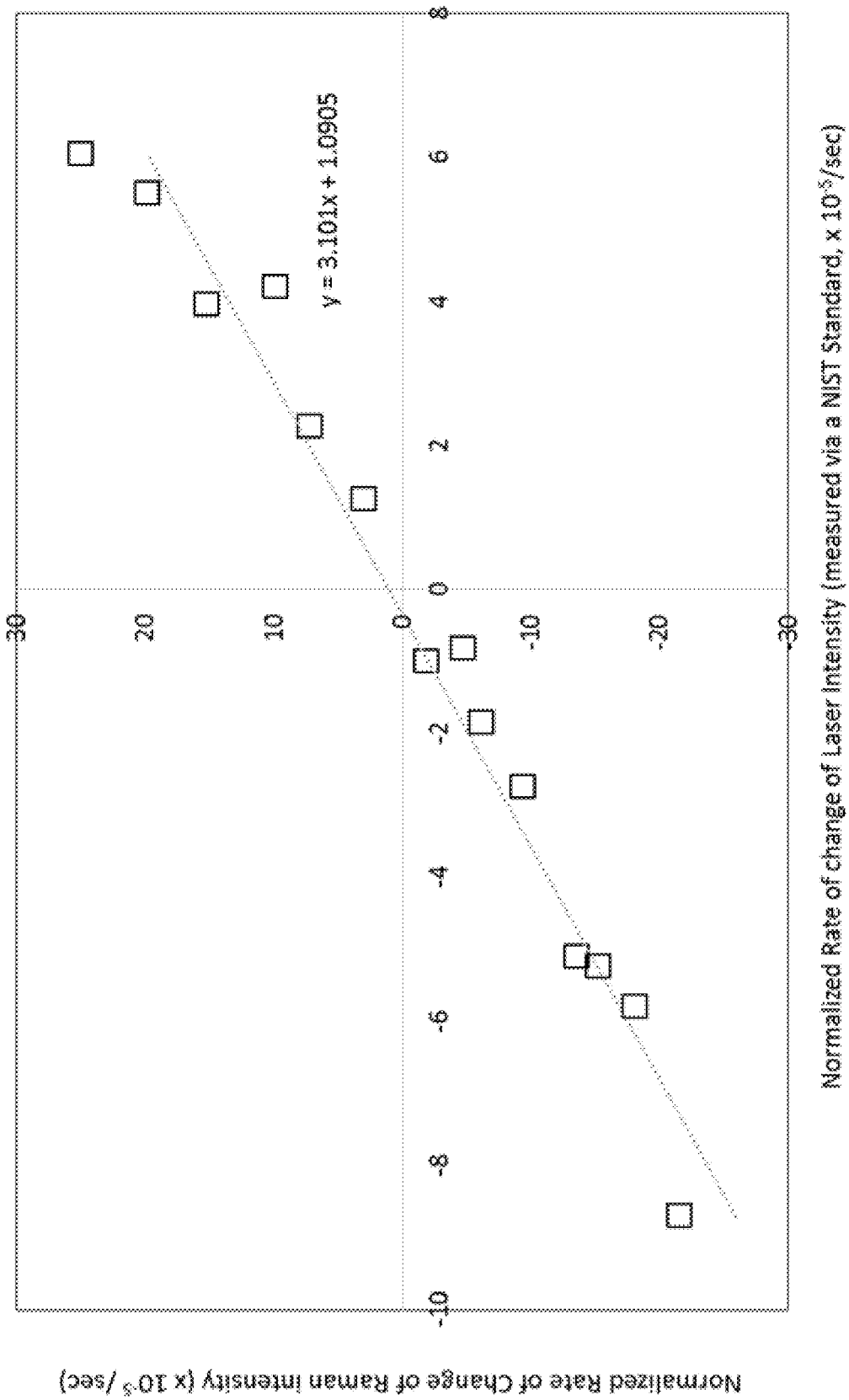
FIG. 1 depicts normalized rate of change of Resonant Raman intensity from lycopene plotted against the normalized rate of change of laser intensity according to certain embodiments.

As used herein, "Raman scattering" and other similar terms and/or phrases, refer to any method whereby light incident on a sample at a fixed wavelength is scattered at other wavelengths. The scattering may be by an incoherent process due to the absorption of the incident photon by the excitation of the structure from an initially lower (the ground state) to a higher vibrational level, and subsequent relaxation down to a different ground state level.

As used herein, the "Raman band" and similar terms and/or phrases refer to the spectral profile (e.g. intensity versus frequency) corresponding to the Raman scattering from a particular chemical bond within a molecule. It is understood that each chemical bond manifests as a Raman band at distinct frequencies and that in some cases, these Raman bands may overlap, making them difficult to distinguish. Further, it is understood that the Raman cross section of a chemical bond is a constant that defines the intensity of the corresponding Raman peak. Furthermore, it is understood that this cross section can change with wavelength and/or with resonance. Such a resonance change occurs during resonant Raman enhancement.

As used herein, it is understood that the "Raman spectrum" of a sample, and similar terms and/or phrases, refer to the sum of all the Raman bands, and the relative heights on individual Raman bands in a Raman spectrum is proportional to the relative abundance of the corresponding chemical bonds multiplied by their Raman cross section.

As used herein, "absorption" and similar terms and or phrases refer to any method wherein incident light is absorbed by a sample of interest. The incident photon may interact with a structure by any number of mechanisms, including the excitation of outer electrons (e.g. corresponding to the absorption of UV or visible radiation), or the excitation of the molecule into higher vibrational/rotational energy states.

As used herein, "Resonant Raman scattering" and similar phrases and/or terms, refers to a process that is understood to be a special type of Raman scattering that involves the excitation of a molecule from an initial ground state to a real excited state that corresponds to a real vibrational state. Thus, for the purpose of the present discussion, resonant "Raman enhancement" (or "resonance Raman"), and other similar terms and/or phrases, refer to any method whereby the Raman cross section of a particular band is enhanced by the strong optical absorption.

As used herein, "Resonant Raman Nonlinearity (RRNL)" refers to the slope of the trace between the rate at which the intensity of the Resonant Raman peak changes (plotted on the Y axis) and the rate at which the intensity of the incident laser beam changes (plotted on the X axis).

As used herein, "net signal" refers to the rate of change of the intensity of one or more of the Raman scattering or fluorescence scattering after correction for variations associated with the instrument (e.g., drift in the monochromatic light source, drift in optical components such as collimating optics) and/or in the sample vial (e.g., fluorescence from non-target compounds). In some embodiments, "net signal" is related to Resonant Raman Nonlinearity (RRNL) as defined above in that when the RRNL=1, Net Signal=0 and when Net Signal is less than 0, then RRNL is <1.

As used herein, "vial" and other similar terms and/or phrases refer to a test container that contains, e.g., the test sample, along with any other components of the assay. It is understood that the vial can be constructed out of any suitably transparent material, such as glass and plastics as described in greater detail below.

DETAILED DESCRIPTION

Aspects of the present disclosure include methods and systems for Resonant Raman spectroscopy. Methods according to certain embodiments include irradiating a sample with a monochromatic light source at a first irradiation intensity and a second irradiation intensity, determining the intensity of one or more of the Resonant Raman scattering and the intensity of fluorescence scattering at the first irradiation intensity and second irradiation intensity, calculating a rate of change of one or more of the intensity of Resonant Raman scattering and the intensity of fluorescence scattering in response to the change in irradiation intensity from the first irradiation intensity to the second irradiation intensity and comparing one or more of the rate of change in the intensity of Resonant Raman scattering and the rate of change in the intensity of fluorescence scattering with the rate of change in the irradiation intensity by the monochromatic light source to determine the spectroscopic response of the sample. Methods also include determining the presence or absence of a microorganism in a sample and correcting for variations associated with measurement instrumentation (e.g., monochromatic light source) and variations associated with the sample (e.g., fluorescence from non-target compounds). Also provided are methods for determining the antimicrobial susceptibility of a microorganism to an antimicrobial agent as well as methods for characterizing a phenotype of an unknown microorganism in a sample. Systems for practicing the subject methods are also provided.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Resonant Raman Spectroscopy

As summarized above, aspects of the present disclosure include methods for Resonant Raman spectroscopy. Methods according to certain embodiments include irradiating a sample with a monochromatic light source at a first irradiation intensity and a second irradiation intensity, determining the intensity of one or more of the Resonant Raman scattering and the intensity of fluorescence scattering at the first irradiation intensity and second irradiation intensity, calculating a rate of change of one or more of the intensity of Resonant Raman scattering and the intensity of fluorescence scattering in response to the change in irradiation intensity from the first irradiation intensity to the second irradiation intensity and comparing one or more of the rate of change in the intensity of Resonant Raman scattering and the rate of change in the intensity of fluorescence scattering with the rate of change in the irradiation intensity by the monochromatic light source to determine the spectroscopic response of the sample.

In practicing methods according to certain embodiments, a sample is irradiated with a monochromatic light source. The term "monochromatic" is used herein in its conventional sense to refer to a light source that outputs a narrow bandwidth of light irradiation. In embodiments, the monochromatic light source outputs light having a narrow range of wavelengths, such as a range of 25 nm or less, such as 20 nm or less, such as 15 nm or less, such as 10 nm or less, such as 5 nm or less and including 2 nm or less. In certain embodiments, the monochromatic light source outputs a single wavelength of light (e.g., 532 nm light). Any convenient monochromatic light source may be employed, such as a laser or a single wavelength light emitting diode. In certain embodiments, the light source is a broadband light source in optical communication with an optical adjustment component that narrows the irradiation bandwidth to a single wavelength. For example, monochromatic light irradiation of the sample for Resonant Raman spectroscopy according to the subject methods may be achieved using a broadband light source such as a broadband halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source or a multi-LED integrated white light source coupled to one or more optical bandpass filters, diffraction gratings, monochromators or any combination thereof.

In certain embodiments, the sample is irradiated with a laser. In some instances, the laser is a continuous wave laser. In other instances, the laser is a pulsed laser. In certain instances, the laser is a diode laser, such as an ultraviolet diode laser, a visible diode laser and a near-infrared diode laser. In some instances, the monochromatic light source is a diode laser that outputs light at a wavelength from 375 nm to 1000 nm, such as from 405 nm to 875 nm, such as from 450 nm to 800 nm, such as from 500 nm to 650 nm and including from 525 nm to 625 nm. In other instances, the laser is a pulsed laser, such as a solid state laser. In certain instances, the monochromatic light source is a solid-state laser that outputs light at a wavelength from 375 nm to 1000 nm, such as from 405 nm to 875 nm, such as from 450 nm to 800 nm, such as from 500 nm to 650 nm and including from 525 nm to 625 nm. Other suitable lasers may include, but are not limited to, helium-neon (HeNe) lasers, argon lasers, krypton lasers, xenon ion lasers, nitrogen lasers, carbon dioxide lasers, carbon monoxide lasers, excimer lasers, hydrogen fluoride lasers, deuterium fluoride lasers, oxyen-iodine lasers, gas-phase iodine lasers, helium cadium lasers, helium mercury lasers, helium silver lasers, strontium vapor lasers, neon copper lasers, copper vapor laser, gold vapor laser, manganese vapor lasers, ruby lasers, Nd:YAG lasers, NdCrYAG lasers, Er:YAG lasers, Nd:YLF lasers, Nd:YVO$_4$ lasers, Nd:YCa$_4$O(BO$_3$)$_3$ lasers, Nd:glass lasers, titanium sapphire lasers, thulium YAG lasers, ytterbium YAG lasers, Yb$_2$O$_3$ lasers, ytterbium doped glass lasers, holmium YAG lasers, chromium ZnSe lasers, cerium doped lithium strontium aluminum fluoride lasers, promethium 147 doped phosphate glass lasers, chromium doped chrysoberyl lasers, erbium doped and erbium-ytterbium codoped glass lasers, trivalent uranium doped calcium fluoride lasers, samarium doped calcium fluoride lasers, GaN lasers, InGaN lasers, AlGaInP lasers, AlGaAs lasers, InGaAsP lasers, among other laser types. In certain embodiments, the monochromatic light source is a frequency doubled neodymium-doped yttrium aluminium garnet that outputs light at 532 nm.

In some embodiments, the sample is irradiated continuously. In other embodiments, the sample is irradiated by the monochromatic light source in discrete intervals, such as for 0.001 milliseconds or more, such as for 0.005 milliseconds or more, such as for 0.01 milliseconds or more, such as for 0.05 milliseconds or more, such as for 0.1 milliseconds or more, such as for 0.5 milliseconds or more, such as for 1 millisecond or more, such as for 5 milliseconds or more, such as for 10 milliseconds or more, such as for 100 milliseconds or more, such as for 1000 milliseconds or more, such as for 5 seconds or more, such as from 15 seconds or more, such as for 30 seconds or more, such as for 60 seconds or more, such as from 100 seconds or more, such as for 200 seconds or more, such as for 300 seconds or more, such as for 400 seconds or more, such as for 500 seconds or more, such as for 1000 seconds or more and including for 1500 seconds or more, or some other interval. The time between each interval may vary, and may be 0.001 milliseconds or more, such as 0.005 milliseconds or more, such as 0.01 milliseconds or more, such as 0.05 milliseconds or more, such as 0.1 milliseconds or more, such as 0.5 milliseconds or more, such as 1 millisecond or more, such as 5 milliseconds or more, such as 10 milliseconds or more, such as 100 milliseconds or more and including 1000 milliseconds or more.

In certain embodiments, the monochromatic light source is a stroboscopic light source where the sample is illuminated with periodic flashes of light. For example, the frequency of light strobe may be 0.01 kHz or greater, such as 0.05 kHz or greater, such as 0.1 kHz or greater, such as 0.5 kHz or greater, such as 1 kHz or greater, such as 2.5 kHz or greater, such as 5 kHz or greater, such as 10 kHz or greater, such as 25 kHz or greater, such as 50 kHz or greater and including 100 kHz or greater.

The sample may be irradiated for any number of intervals to acquire sufficient Resonant Raman scattering and/or fluorescence scattering, such as irradiating the sample 1 time or more, such as 2 times or more, such as 3 times or more, such as 4 times or more, such as 5 times or more, such as 10 times or more, such as 25 times or more and including 50 times or more.

Depending on the type of light source, the optical components (e.g., lens, mirrors, collimators, etc.), the sample may be irradiated by the monochromatic light source from any suitable distance, such as at a distance that is 1 mm or more from the sample, such as 2.5 mm or more, such as 5 mm or more, such as 10 mm or more, such as 15 mm or more, such as 25 mm or more, such as 50 mm or more, such as 100 mm or more, such as 500 mm or more, such as 1000 mm or more, such as 2500 mm or more, such as 5000 mm or more and including 10000 mm or more from the sample. Likewise, the sample may be irradiated by the monochromatic light source from any suitable angle, such as from 5° to 90°, such as from 15° to 85°, such as from 20° to 80°, such as from 25° to 75° and including from 30° to 60°.

As summarized above, methods include determining the intensity of one or more of Resonant Raman scattering and fluorescence scattering at one or more wavenumbers. Resonant Raman scattering may be detected at any suitable wavenumber depending on the chromophore, ranging from 200 cm$^{-1}$ to 2000 cm$^{-1}$, such as from 250 cm$^{-1}$ to 1900 cm$^{-1}$, such as from 300 cm$^{-1}$ to 1800 cm$^{-1}$, such as from 350 cm$^{-1}$ to 1700 cm$^{-1}$ and including from 400 nm to 1600 cm$^{-1}$. In certain embodiments, the chromophore is lycopene and Resonant Raman scattering is detected and measured at one or more of 1512 cm$^{-1}$, 1515 cm$^{-1}$, 1525 cm$^{-1}$ and 1535 cm$^{-1}$. In other embodiments, methods also include detecting fluorescence at one or more wavenumbers, ranging from 1500 cm$^{-1}$ to 4000 cm$^{-1}$, such as from 1750 cm$^{-1}$ to 3750 cm$^{-1}$, such as from 2000 cm$^{-1}$ to 3500 cm$^{-1}$, including 3000 cm$^{-1}$.

The duration for detecting light from the sample (e.g., Resonant Raman scattering, fluorescence) in accordance with the subject method (as described in greater detail below) may range from 10 seconds to 2000 seconds, such as from 30 seconds to 1750 seconds, such as from 45 seconds to 1500 seconds, such as from 60 seconds to 1250 seconds, such as from 120 seconds to 1000 seconds, such as from 200 seconds to 800 seconds and including from 400 seconds to 600 seconds.

Light from the sample (e.g., Resonant Raman scattering, fluorescence) may be detected by any convenient detection protocol, including but not limited to photosensors or photodetectors, such as active-pixel sensors (APSs), quadrant photodiodes, wedge detectors image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, Light from the sample (e.g., Resonant Raman scattering, fluorescence) is detected with one or more CCDs.

Spectroscopy (e.g., non-linear Resonant Raman spectroscopy, fluorescence spectroscopy) as described herein may be conducted while maintaining a constant temperature, such as where the temperature during the subject methods changes by 5° C. or less, such as by 4.5° C. or less, such as by 4° C. or less, such as by 3.5° C. or less, such as by 3° C. or less, such as by 2.5° C. or less, such as by 2° C. or less, such as by 1.5° C. or less, such as 1° C. or less, such as by 0.5° C. or less, such as by 0.1° C. or less, such as by 0.05° C. or less, such as by 0.01° C. or less, such as by 0.005° C., such as by 0.001° C., such as by 0.0001° C., such as by 0.00001° C. or less and including by 0.000001° C. or less. Temperature may be controlled by any convenient protocol, including, but not limited to heat sinks, fans, exhaust pumps, vents, refrigeration, coolants, heat exchanges, Peltier or resistive heating elements and any combination thereof, among other types of temperature control protocols.

In some embodiments, the sample is irradiated through one or more optical adjustment components. By "optical adjustment" is meant that light from the monochromatic light source is changed or adjusted before being impinged onto the sample. For example, the optical adjustment may be to change the profile of the light beam, the focus of the light beam, the direction of beam propagation or to collimate the light beam. In some instances, optical adjustment includes collimating the light. The term "collimate" is used in its conventional sense to refer to the optically adjusting the collinearity of light propagation or reducing divergence by the light of from a common axis of propagation. In some instances, collimating includes narrowing the spatial cross section of a light beam. In other instances, optical adjustment includes changing the direction of the light beam, such as changing the propagation of the light beam by 1° or more, such as by 5° or more, such as by 10° or more, such as by 15° or more, such as by 20° or more, such as by 25° or more, such as by 30° or more, such as by 45° or more, such as by 60° or more, such as by 75° or more and including changing the direction of light propagation by 90° or more. In yet other instances, optical adjustment is a de-magnification protocol so as to decrease the dimensions of the light (e.g., beam spot), such as decreasing the dimensions by 5% or more, such as by 10% or more, such as by 25% or more, such as by 50% or more and including decreasing the dimensions by 75% or more.

Optical adjustment components may be any convenient device or structure which provides the desired change to the light beam and may include, but is not limited to, lenses, mirrors, beam splitters, collimating optics (e.g., lenses), pinholes, slits, gratings, light refractors, and any combinations thereof. The subject systems, as described in greater detail below, may include one or more optical adjustment components as needed, such as two or more, such as three or more, such as four or more and including five or more optical adjustment components.

In certain embodiments, light detection systems include a collimator positioned adjacent to the sample holder. The collimator may be any convenient collimating protocol, such as one or more mirrors or curved lenses or a combination thereof. For example, the collimator is in certain instances a single collimating lens. In other instances, the collimator is a collimating mirror. In yet other instances, the collimator includes two lenses. In still other instances, the collimator includes a mirror and a lens. Where the collimator includes one or more lenses, the focal length of each collimating lens may vary, ranging from 5 mm to 500 mm, such as from 6 mm to 475 mm, such as from 7 mm to 450 mm, such as from 8 mm to 425 mm, such as from 9 mm to 400 mm, such as from 10 mm to 375 mm, such as from 12.5 mm to 350 mm and including a focal length ranging from 15 mm to 300 mm. In certain embodiments, the focal length ranges from 400 mm to 500 mm, such as from 405 mm to 475 mm, such as from 410 mm to 450 mm and including from 410 mm to 425 mm, such as 410 mm or 420 mm.

In embodiments, the sample is irradiated in a sample holder, e.g., a sample container. The sample holder may be any suitable shaped substrate or container for irradiating a sample and detecting one or more of Resonant Raman scattering and fluorescence scattering. In some embodiments, the sample holder is a planar substrate (e.g., microscope slide). In other embodiments, the sample holder is a microfluidic device having one or more microfluidic channels. In yet other embodiments, the sample holder is a container having a cross-sectional shape, where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. The size of the sample holder may vary, depending on the volume of the samples being irradiated, where holders of interest have a length that ranges from 5 mm to 100 mm, such as from 10 mm to 90 mm, such as from 15 mm to 85 mm, such as from 20 mm to 80 mm, such as from 25 mm to 75 mm, such as from 30 mm to 70 mm and including from 35 mm to 65 mm and a width (or cross-section where the container is cylindrical) of from 5 mm to 100 mm, such as from 10 mm to 90 mm, such as from 15 mm to 85 mm, such as from 20 mm to 80 mm, such as from 25 mm to 75 mm, such as from 30 mm to 70 mm and including from 35 mm to 65 mm. In embodiments, the sample holder may have a volume of from 0.1 $cm^3$ to 10 $cm^3$, such as from 0.5 $cm^3$ to 9 $cm^3$, such as from 1 $cm^3$ to 8 $cm^3$, such as from 1.5 $cm^3$ to 7 $cm^3$, such as from 2 $cm^3$ to 6 $cm^3$, such as from 2.5 $cm^3$ to 5 $cm^3$ including from 3 $cm^3$ to 4 $cm^3$.

The sample holder may be formed from any transparent material which passes the desired range of wavelength, including but not limited to optical glass, borosilicate glass, Pyrex glass, ultraviolet quartz, infrared quartz, sapphire. In certain embodiments, the sample container is glass having walls with a zwitterionic coating, such as a zwitterionic silane coating (e.g., as described in the Experimental Section below). The sample container may also be formed from plastic, such as polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials, including polyester, where polyesters of interest may include, but are not limited to poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly(hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly($\varepsilon$-caprolactone) and poly($\beta$-propiolactone); poly(alkylene isophthalates) such as poly(ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediylalkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide); polyesters, e.g., polyethylene terephthalates, e.g., Mylar™ polyethylene terephthalate; etc.

In embodiments, the sample holder may pass light that ranges from 100 nm to 1500 nm, such as from 150 nm to 1400 nm, such as from 200 nm to 1300 nm, such as from 250 nm to 1200 nm, such as from 300 nm to 1100 nm, such as from 350 nm to 1000 nm, such as from 400 nm to 900 nm and including from 500 nm to 800 nm, for example 532 nm.

As summarized above, methods include irradiating the sample with a monochromatic light source at a first irradiation intensity and a second irradiation intensity and determining the intensity of Resonant Raman scattering at the first irradiation intensity and second irradiation intensity. To detect Resonant Raman scattering, samples of interest in the subject methods include a compound which exhibits Resonant Raman scattering in response to irradiation by a monochromatic light source. In some embodiments, the compound is a chromophore where the incident irradiation frequency of the monochromatic light source is close in energy to an electronic transition of the compound. For example, methods include in certain instances, irradiating a sample with a monochromatic light source having a frequency that is 100 cm$^{-1}$ or less from an electronic transition of a chromophore in the sample, such as 90 cm$^{-1}$ or less, such as 80 cm$^{-1}$ or less, such as 70 cm$^{-1}$ or less, such as 60 cm$^{-1}$ or less, such as 50 cm$^{-1}$ or less, such as 40 cm$^{-1}$ or less, such as 30 cm$^{-1}$ or less, such as 25 cm$^{-1}$ or less, such as 20 cm$^{-1}$ or less, such as 15 cm$^{-1}$ or less, such as 10 cm$^{-1}$ or less, such as 5 cm$^{-1}$ or less, such as 4 cm$^{-1}$ or less, such as 3 cm$^{-1}$ or less, such as 2 cm$^{-1}$ or less, such as 1 cm$^{-1}$ or less, such as 0.5 cm$^{-1}$ or less, such as 0.1 cm$^{-1}$ or less, such as 0.05 cm$^{-1}$ or less, such as 0.01 cm$^{-1}$ or less and including irradiating with a monochromatic light source having a frequency that is 0.001 cm$^{-1}$ or less from an electronic transition of a chromophore in the sample.

Depending on the wavelength of irradiation and the type of monochromatic light source (e.g., laser), chromophores in samples of the subject methods may vary. In some embodiments, the chromophore is a hydrophobic compound that exhibits Resonant Raman scattering in response to laser irradiation. In some instances, the chromophore is a carotene or carotenoid. For example, Carotenoids of interest include, but are not limited to, carotene (e.g., $\alpha$-carotene, $\beta$-carotene, $\gamma$-carotene, $\delta$-carotene, $\varepsilon$-carotene, lycopene, etc.) and xanthophylls (e.g., lutein, zeaxanthin, neoxanthin, violaxanthin, flavoxanthin, $\alpha$- and $\beta$-cryptoxanthin, etc.). In certain embodiments, the chromophore is lycopene.

In some embodiments, the chromophore is associated with another component in the sample, such as to increase solubility of the chromophore in the sample. In certain instances, the chromophore is hydrophobic and is non-covalently associated with an albumin protein. Albumin proteins of interest include, but are not limited to, human serum albumin (HSA; Gene ID: 213); bovine serum albumin (BSA; Gene ID: 280717); mouse albumin (Gene ID: 11657); rat albumin (Gene ID: 24186); goat albumin (Gene ID: 100860821); donkey albumin (Gene ID: 106835108); horse albumin (Gene ID: 100034206); camel albumin (Gene ID: 105080389 or 105091295), etc. or a protein having an amino acid sequence having at least about 80%, at least about 85%, at least about 90%, at least about 95%, at least about 98%, at least about 99%, or 100%, amino acid sequence identity to human serum albumin (HSA; Gene ID: 213); bovine serum albumin (BSA; Gene ID: 280717); mouse albumin (Gene ID: 11657); rat albumin (Gene ID: 24186); goat albumin (Gene ID: 100860821); donkey albumin (Gene ID: 106835108); horse albumin (Gene ID: 100034206); camel albumin (Gene ID: 105080389 or 105091295).

In certain embodiments, samples of the present disclosure include a hydrophobic compound (e.g., chromophore) that is non-covalently associated with an albumin protein, such as those described in the U.S. Patent Publication No. 2016/0324933, filed on May 6, 2016, the disclosure of which is herein incorporated by reference in its entirety.

Samples of the subject methods may also include a free radical scavenger. The term "free radical scavenger" is used herein in its conventional sense to refer to a compound that reacts, complexes or otherwise removes free radicals in a composition. Free radical scavengers of the subject methods may be antioxidants, oxygen scavengers, gas ion scavengers, hydroxyl radical scavengers and the like. In certain embodiments, the free radical scavenger is bilirubin or a derivative thereof, such as unconjugated bilirubin that is not water soluble at pH 7.2.

In some embodiments, the bilirubin or derivative thereof is non-covalently associated with a protein, such as an albumin protein as described above. The term "non-covalently" is used herein in its conventional sense to refer to interactions between the bilirubin or derivative thereof with the protein and may include dipole-dipole bonds, van der Waals interaction, ionic bonding, ion-dipole bonds, hydrogen bonding, among other types of non-covalent bonding. In some instances, the bilirubin or derivative thereof is positioned at least partially within the albumin protein. In certain instances, the bilirubin or derivative thereof is coupled to a binding site in the albumin protein.

The free radical scavenger may be present in the sample in an amount that varies, ranging from 0.001 µM to 5 µM, such as from 0.005 µM to 4.9 µM, such as from 0.01 µM to 4.8 µM, such as from 0.05 µM to 4.7 µM, such as from 0.1

μM to 4.6 μM, such as from 0.5 μM to 4.5 μM, such as from 0.75 μM to 4 μM and including from 0.75 μM to 1.5 μM, for example 0.75 μM to 1.25 μM. In certain instances, the free radical scavenger is bilirubin or a derivative thereof and is present in the sample in an amount of from 0.001 μM to 5 μM, such as from 0.005 μM to 4.9 μM, such as from 0.01 μM to 4.8 μM, such as from 0.05 μM to 4.7 μM, such as from 0.1 μM to 4.6 μM, such as from 0.5 μM to 4.5 μM, such as from 0.75 μM to 4 μM and including from 0.75 μM to 1.5 μM, for example 0.75 μM to 1.25 μM.

In some embodiments, samples include a reducing agent. The term "reducing agent" is used herein in its conventional sense to refer to a compound that loses ("or donates") an electron to another chemical species in a redox chemical reaction. In certain embodiments, the reducing agent is glutathione or a derivative thereof.

The reducing agent may be present in the sample in an amount that varies, ranging from 0.001 mg/mL to 10 mg/mL, such as from 0.005 mg/mL to 9 mg/mL, such as from 0.01 mg/mL to 8 mg/mL, such as from 0.05 mg/mL to 7 mg/mL, such as from 0.1 mg/mL to 6 mg/mL, for example from 0.1 mg/mL to 1 mg/mL. In certain instances, the reducing agent is glutathione or a derivative thereof and is present in the sample in an amount of from 0.001 mg/mL to 10 mg/mL, such as from 0.005 mg/mL to 9 mg/mL, such as from 0.01 mg/mL to 8 mg/mL, such as from 0.05 mg/mL to 7 mg/mL, such as from 0.1 mg/mL to 6 mg/mL, for example from 0.1 mg/mL to 1 mg/mL.

In some embodiments, samples include a crosslinking agent. In some instances, the crosslinking agent may be a disulfide crosslinker (e.g., a compound having disulfide linkages that exchanges disulfide bonds with a cysteine groups on proteins). In some instances, the crosslinking agent has a core that is a glutamic acid derivative, such as a glutamic acid derivative having one or more disulfide linkages. In certain embodiments, the crosslinking agent is a compound of Formula (I):

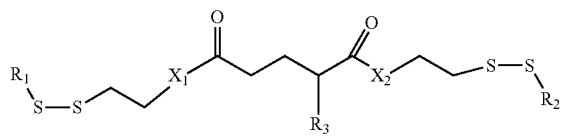

(I)

where:

$R_1$, and $R_2$ are independently selected from hydrogen, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl and substituted heteroaryl;

$X_1$ and $X_2$ are independently selected from N, O, or S; and $R_3$ is a hydrogen, alkyl, substituted alkyl, amino, halogen, cyano, alcohol or alkoxy.

In some embodiments, $R_1$, and $R_2$ are heteroaryl, $X_1$ and $X_2$ are N and $R_3$ is amino.

In certain embodiments, the crosslinking agent is a compound of Formula (DS-1)

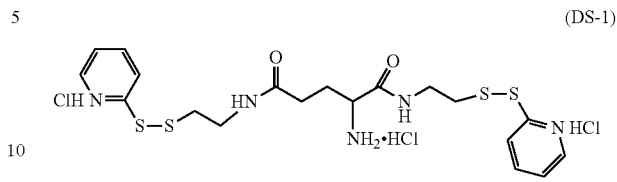

(DS-1)

The crosslinking agent may be present in the sample in an amount where the molar ratio of crosslinking agent to albumin protein is from 1:10 to 10:1, such as from 1:9 to 9:1, such as from 1:8 to 8:1, such as from 1:7 to 7:1, such as from 1:6 to 6:1, such as from 1:5 to 5:1, such as from 1:4 to 4:1, such as from 1:3 to 3:1, and including from 1:2 to 2:1. In certain embodiments, the molar ratio of crosslinking agent to albumin protein in samples of the subject methods is about 1:2. According to certain embodiments, methods include irradiating the sample over a plurality of intensities by the monochromatic light source over a period of time and determining a rate of change in the intensity of one or more of the Raman scattering and fluorescence scattering. The sample may be irradiated in these embodiments for any desired duration, such as from 10 seconds to 1500 seconds, such as from 30 seconds to 1400 seconds, such as from 45 seconds to 1300 seconds, such as from 60 seconds to 1200 seconds, such as from 120 seconds to 1000 seconds, such as from 200 seconds to 800 seconds and including from 400 seconds to 600 seconds. In some embodiments, a normalized rate of change of the intensity of Resonant Raman scattering is calculated. In other embodiments, a normalized rate of change of irradiation intensity by the monochromatic light source (e.g., laser) is also calculated.

In certain embodiments, methods include irradiating the sample at an interface (e.g., by focusing the monochromatic light source with a collimator as described above) between the sample and a surface of the sample holder (e.g., wall of the sample container). By "interface" is meant the space where the surface of the sample holder (e.g., container wall) comes into contact with the sample. In embodiments, the interface irradiated by the monochromatic light source in the subject methods may extend from about 0.01 mm to 2 mm from the surface of the container wall (i.e., where the sample comes into contact with the container), such as from 0.02 mm to 1.9 mm, such as from 0.03 mm to 1.8 mm, such as from 0.04 mm to 1.7 mm, such as from 0.05 mm to 1.6 mm, such as from 0.06 mm to 1.5 mm, such as from 0.07 mm to 1.4 mm, such as from 0.08 mm to 1.3 mm, such as from 0.09 mm to 1.2 mm, such as from 0.1 mm to 1 mm, for example 0.2 mm from the surface of the sample holder (e.g., container wall). In these embodiments, the sample holder (e.g., glass vial) is maintained substantially at rest (e.g., no vibration, agitation, etc.) and the velocity of the interfacial liquid layer irradiated by the monochromatic light source is near or at zero. For example, the liquid velocity of the interfacial sample layer irradiated by the monochromatic light source may be $10^{-2}$ cm$^3$/second or less, such as $10^{-3}$ cm$^3$/second or less, such as $10^{-4}$ cm$^3$/second or less, such as $10^{-5}$ cm$^3$/second, such as $10^{-6}$ cm$^3$/second, such as $10^{-7}$ cm$^3$/second or less, such as $10^{-8}$ cm$^3$/second or less, such as $10^{-9}$ cm$^3$/second or less and including $10^{-10}$ cm$^3$/second or less. In certain embodiments, the velocity of the sample at the interfacial layer irradiated by the monochromatic light source in the subject methods is zero cm$^3$/second.

Methods also include determining the spectroscopic response of a sample by calculating a rate of change of the intensity of one or more of the Resonant Raman scattering and fluorescence scattering in response to the change in irradiation intensity from the first irradiation intensity to the second irradiation intensity and comparing the rate of change in the intensity of one or more of the Resonant Raman scattering and fluorescence scattering with the rate of change in the irradiation intensity by the monochromatic light source. In some embodiments, the spectroscopic response of the sample is indicative of a physical change over time in the sample. In other embodiments, the spectroscopic response of the sample is indicative of a chemical change over time in the sample. In still other embodiments, the spectroscopic response of the sample is indicative of the presence of an actively metabolizing microorganism in the sample.

In embodiments, methods include irradiating the sample over a plurality of intensities by the monochromatic light source over a period of time and determining a rate of change in the intensity of one or more of the Resonant Raman scattering and fluorescence scattering and comparing the rate of change in the intensity of one or more of the Resonant Raman scattering and fluorescence scattering with the rate of change in the normalized irradiation intensity by the monochromatic light source to determine a net signal. In calculating the net signal, methods may further include calculating a normalized rate of change of the intensity of one or more of the Resonant Raman scattering and fluorescence scattering and a normalized rate of change of irradiation intensity and comparing the normalized rate of change of the intensity of one or more of the Resonant Raman scattering and fluorescence scattering to the normalized rate of change of irradiation intensity to determine the net signal.

In embodiments of the present disclosure, the term "normalized" is used herein in its conventional sense to refer to adjusting values measured on different scales to a notionally common scale. For example, normalized values may provide for the comparison of corresponding normalized values for different datasets which eliminates the effect of gross influences. In certain embodiments, determining the normalized rate of change includes dividing the slope (e.g., of the linear fit of the dataset) with the absolute value observed at time=0.

The range of normalized irradiation intensity may vary depending on the chromophore and the monochromatic light source. In some embodiments, the monochromatic light source is a laser and the normalized intensity of the laser is varied by 10% or more, such as by 15% or more, such as by 25% or more, such as by 50% or more, such as by 75% or more, such as by 90% or more and including by 99% or more. In these embodiments, the normalized rate of change of the laser intensity may vary, ranging from $-10\times10^{-5}$ sec$^{-1}$ to $10\times10^{-5}$ sec$^{-1}$, such as from $-9\times10^{-5}$ sec$^{-1}$ to $9\times10^{-5}$ sec$^{-1}$, such as from $-8\times10^{-5}$ sec$^{-1}$ to $8\times10^{-5}$ sec$^{-1}$, such as from $-7\times10^{-5}$ sec$^{-1}$ to $7\times10^{-5}$ sec$^{-1}$, such as from $-6\times10^{-5}$ sec$^{-1}$ to $6\times10^{-5}$ sec$^{-1}$, such as from $-5\times10^{-5}$ sec$^{-1}$ to $5\times10^{-5}$ sec$^{-1}$, such as from $-4\times10^{-5}$ sec$^{-1}$ to $4\times10^{-5}$ sec$^{-1}$, such as from $-3\times10^{-5}$ sec$^{-1}$ to $3\times10^{-5}$ sec$^{-1}$, such as from $-2\times10^{-5}$ sec$^{-1}$ to $2\times10^{-5}$ sec$^{-1}$ and including from $-1\times10^{-5}$ sec$^{-1}$ to $1\times10^{-5}$ sec$^{-1}$. The normalized rate of change in the intensity of Resonant Raman scattering may also vary, ranging from $-10\times10^{-5}$ sec$^{-1}$ to $10\times10^{-5}$ sec$^{-1}$, such as from $-9\times10^{-5}$ sec$^{-1}$ to $9\times10^{-5}$ sec$^{-1}$, such as from $-8\times10^{-5}$ sec$^{-1}$ to $8\times10^{-5}$ sec$^{-1}$, such as from $-7\times10^{-5}$ sec$^{-1}$ to $7\times10^{-5}$ sec$^{-1}$, such as from $-6\times10^{-5}$ sec$^{-1}$ to $6\times10^{-5}$ sec$^{-1}$, such as from $-5\times10^{-5}$ sec$^{-1}$ to $5\times10^{-5}$ sec$^{-1}$, such as from $-4\times10^{-5}$ sec$^{-1}$ to $4\times10^{-5}$ sec$^{-1}$, such as from $-3\times10^{-5}$ sec$^{-1}$ to $3\times10^{-5}$ sec$^{-1}$, such as from $-2\times10^{-5}$ sec$^{-1}$ to $2\times10^{-5}$ sec$^{-1}$ and including from $-1\times10^{-5}$ sec$^{-1}$ to $1\times10^{-5}$ sec$^{-1}$.

Methods according to certain embodiments include characterizing a sample composition with the net signal. For example, the net signal may be used to detect a change in a sample composition or for determining whether two compositions have equivalent or different makeup. In certain embodiments, the net signal is used to characterize the amount of gases present in the sample. In other embodiments, the net signal may be used to determine if actively metabolizing microorganisms are present in a sample.

In one embodiment, methods include irradiating a first sample over a plurality of intensities by the monochromatic light source (e.g., laser) for a period of time and determining a first rate of change in the intensity of one or more of Raman scattering and fluorescence scattering; irradiating a second sample over a plurality of intensities by the monochromatic light source for the period of time and determining a rate of change in the intensity of one or more of Raman scattering and fluorescence scattering for the second sample. The net signal the first sample is calculated by comparing the normalized rate of change in the intensity of one or more of Resonant Raman scattering and fluorescence scattering with the normalized rate of change in the irradiation intensity of the first sample by the monochromatic light source. The net signal of the second sample is determined by comparing the normalized rate of change in the intensity of one or more of Resonant Raman scattering and fluorescence scattering with the normalized rate of change in the irradiation intensity of the second sample by the monochromatic light source.

In some embodiments, the net signal of the first sample and the net signal of the second sample are the same. In other embodiments, the net signal of the first sample and the net signal of the second sample are different. In some instances, this difference is indicative that the amount of gases (e.g., carbon dioxide, oxygen, methane, nitrogen, etc.) present in the first sample and the second sample is different. In other instances, this difference is indicative that the type of gases present in the first sample and the second sample is different. In yet other instances, a difference between the first net signal and the second net signal is indicative that the amount of solubilized gases (i.e., gas dissolved into the sample solution) is different.

Methods of Determining the Presence of a Microorganism in a Sample by Resonant Raman Scattering Aspects of the present disclosure also include determining the presence of a microorganism (e.g., an actively metabolizing microorganism) in a sample by Resonant Raman scattering. Methods according to certain embodiments include irradiating a sample over a plurality of intensities by a monochromatic light source for a period of time and calculating a rate of change in the intensity of Resonant Raman scattering for the first sample; calculating a net signal of the sample by comparing a normalized rate of change in the intensity of Resonant Raman scattering for the sample with a normalized rate of change in the irradiation intensity of the sample by the monochromatic light source; and determining the presence of a microorganism in the sample based on the net signal of the sample.

Methods according to certain embodiments, include combining in a sample holder the sample with a reagent that contains albumin with an incorporated ligand; irradiating the sample with a monochromatic light source that is absorbed by the ligand, with either an invariant light intensity or one that varies over time focused at an interface between the sample and a surface of the sample holder; collecting scattered light from the irradiated sample and measuring a Raman signal and a fluorescence signal from the scattered light at a plurality of different times; calculating a rate of change in intensity of the Raman signal and fluorescence signal for the sample over time; correcting the calculated rates of change in the intensities of the Raman signal and the fluorescence signal to obtain a net signal; and determining the presence of a microorganism in the sample based on a comparison of the net signal versus one or more preset thresholds.

In some instances, correcting the rate of change in the intensities of the Raman signal and the fluorescence signal includes characterizing a spectral output from a standard sample. In other instances, correcting the rate of change in the intensities of the Raman signal includes characterizing a fluorescence output from the reagent.

In certain embodiments, correcting the rate of change in the intensities of the Raman signal and the fluorescence signal includes determining a rate of change in total output from a standard reference sample and calculating a net signal as the rate of change in the intensity of the Resonant Raman scattering minus the rate of change in the intensity of Resonant Raman scattering from the standard sample.

In other embodiments, correcting the rate of change in the intensities of the Raman signal and the fluorescence signal includes determining a rate of change in the intensity of fluorescent scattering from a standard reference sample and calculating a net signal as the rate of change in the intensity of the Resonant Raman scattering minus the rate of change in the intensity of fluorescent scattering from the standard sample.

In certain embodiments, a microorganism is determined to be present when the net signal of the sample is above a predetermined threshold. Depending on the chromophore in the sample (e.g., lycopene non-covalently associated with albumin) and the microorganism, the threshold may vary, ranging from $-0.5$ to $-4 \times 10^{-5}$/sec, such as from $-0.5$ to $-1.0 \times 10^{-5}$/sec, such as from $-1$ to $-2 \times 10^{-5}$/sec and including a predetermined threshold where the net signal is 1. In some embodiments, the one or more present thresholds are set by implementing the method above on one or more control samples that contains an inoculum in an amount at a lower limit of concentration in a clinically infected sample. In some embodiments, a microorganism is determined to be present in the sample when the net signal of the sample exceeds the threshold by 1% or more of the threshold value, such as 5% or more, such as 10% or more, such as 15% or more, such as 25% or more, such as 50% or more, such as 75% or more and including 90% or more. In certain instances, a microorganism is determined to be present in the sample when the net signal of the sample exceeds the threshold by 2-fold or more, such as 3-fold or more, such as 5-fold or more and including 10-fold or more.

In other embodiments, determining the presence of a microorganism includes comparing the net signal of two different samples. In some embodiments, one of the samples is a reference sample that does not contain a microorganism. In these embodiments, methods may include includes: irradiating a first sample over a plurality of intensities by a monochromatic light source for a period of time and calculating a rate of change in the intensity of Resonant Raman scattering for the first sample; calculating a net signal of the first sample by comparing a normalized rate of change in the intensity of Resonant Raman scattering for the first sample with a normalized rate of change in the irradiation intensity of the first sample by the monochromatic light source; irradiating a second sample over a plurality of intensities by the monochromatic light source for the period of time and determining a rate of change in the intensity of Resonant Raman scattering for the second sample; calculating a net signal of the second sample by comparing a normalized rate of change in the intensity of Resonant Raman scattering for the second sample with a normalized rate of change in the irradiation intensity of the second sample by the monochromatic light source; and determining the presence of a microorganism in one or more of the first sample or the second sample by comparing the net signal of the first sample with the net signal of the second sample.

In some instances, a microorganism is determined to be present in the second sample when the net signal of the second sample is greater than the net signal of the first sample. In other instances, a microorganism is determined to be present in the first sample when the net signal of the first sample is greater than the net signal of the second sample. Where the first sample is a reference sample, a microorganism is determined to be present in the second sample when the net signal of the second sample is greater than the net signal of the reference sample.

Methods of Determining the Presence of a Microorganism in a Sample by Fluorescence Aspects of the present disclosure also include determining the presence of a microorganism (e.g., an actively metabolizing microorganism) in a sample by fluorescence. Methods according to certain embodiments include irradiating a sample by a monochromatic light source for a period of time and detecting fluorescence from the sample over the period of time; calculating a rate of change of the fluorescence due to the presence of a microorganism by comparing a normalized rate of change in the intensity of the detected fluorescence produced by the sample with a normalized rate of change of fluorescence produced by a control; and determining the presence of a microorganism in the sample based on the calculated changes in the fluorescence of the sample compared to preset thresholds.

In some embodiments, the sample is irradiated over a plurality of intensities by the monochromatic light source. The fluorescence produced by the sample and the control is detected from $2500$ $cm^{-1}$ to $3500$ $cm^{-1}$, such as at $3000$ $cm^{-1}$. In embodiments, the control and sample include a reagent composition that includes a hydrophobic compound non-covalently associated with an albumin protein. The control sample is, in some instances, a composition that includes the reagent composition and does not include a microorganism. For example, the control is a composition that has the same components as the sample in the absence of microorganism. In some embodiments, the control includes only the components of the reagent composition. In other embodiments, the control includes the components of the reagent composition and microorganism-free plasma.

Methods of Calculating Signal-to-Noise Ratio

Aspects of the present disclosure also include methods for calculating signal-to-noise ratio in non-linear Resonant Raman spectroscopy. In some embodiments, the signal-to-noise ratio is calculated by: irradiating a first sample over a plurality of intensities by a monochromatic light source for a period of time and determining a rate of change in the intensity of Resonant Raman scattering for the first sample; calculating an average rate of change in the intensity of Resonant Raman scattering by the first sample to give a first average rate of change; calculating a standard deviation for the first average rate of change; irradiating a second sample over a range of intensities by the monochromatic light source for the period of time and determining a rate of change in the intensity of Resonant Raman scattering for the second sample; calculating an average rate of change in the intensity of Resonant Raman scattering by the second sample to give a second average rate of change; calculating a standard deviation for the second average rate of change; subtracting the second average rate of change from the first average rate of change to give a signal average rate of change; adding the first standard deviation and the second standard deviation to give a signal standard deviation; and dividing the signal average rate of change by the signal standard deviation to determine a signal-to-noise ratio for Resonant Raman response.

In some embodiments, the first sample includes a hydrophobic compound non-covalently associated with an albumin protein and the second sample includes a hydrophobic compound non-covalently associated with an albumin protein and a microorganism. For example, the first sample may include lycopene non-covalently associated with an albumin protein and the second sample includes lycopene non-covalently associated with an albumin protein and a microorganism.

In certain embodiments, methods include enhancing the signal-to-noise ratio by contacting the first sample and the second sample with a free radical scavenger, such as bilirubin or a derivative thereof. In certain embodiments, the free radical scavenger (e.g., bilirubin or derivative thereof) enhances the signal-to-noise ratio by 5% or greater, such as by 10% or greater, such as by 15% or greater, such as by 25% or greater, such as by 50% or greater, such as by 75% or greater, such as by 90% or greater, such as by 95% or greater, such as by 1.5-fold or greater, such as by 2-fold or greater, such as by 3-fold or greater, such as by 5-fold or greater and including by 10-fold or greater.

The free radical scavenger may be present in these embodiments in an amount that varies, ranging from 0.001 μM to 5 μM, such as from 0.005 μM to 4.9 μM, such as from 0.01 μM to 4.8 μM, such as from 0.05 μM to 4.7 μM, such as from 0.1 μM to 4.6 μM, such as from 0.5 μM to 4.5 μM, such as from 0.75 μM to 4 μM and including from 0.75 μM to 1.5 μM, for example 0.75 μM to 1.25 μM. In certain instances, bilirubin or a derivative thereof is contacted with the first sample and second sample in an amount of from 0.001 μM to 5 μM, such as from 0.005 μM to 4.9 μM, such as from 0.01 μM to 4.8 μM, such as from 0.05 μM to 4.7 μM, such as from 0.1 μM to 4.6 μM, such as from 0.5 μM to 4.5 μM, such as from 0.75 μM to 4 μM and including from 0.75 μM to 1.5 μM, for example 0.75 μM to 1.25 μM.

Depending on the amount of free radical scavenger (e.g., bilirubin or derivative thereof), the duration for irradiating the first and second samples varies, such as from 10 seconds to 2000 seconds, such as from 30 seconds to 1750 seconds, such as from 45 seconds to 1500 seconds, such as from 60 seconds to 1250 seconds, such as from 120 seconds to 1000 seconds, such as from 200 seconds to 800 seconds and including from 400 seconds to 600 seconds. In some embodiments, the free radical scavenger (e.g., bilirubin or a derivative thereof) is present in the first sample and the second sample in an amount that ranges from 0.75 μM to about 1.25 μM and the first sample and the second sample are irradiated for a duration of from 600 seconds to 900 seconds. In one example, the free radical scavenger (e.g., bilirubin or a derivative thereof) is present in the first sample and the second sample in an amount of about 1 μM, and the first sample and the second sample are irradiated for a duration of from 600 seconds to 900 seconds. In another example, the free radical scavenger (e.g., bilirubin or a derivative thereof) is present in the first sample and the second sample in an amount of about 1.5 μM, and the first sample and the second sample are irradiated for a duration of from 900 seconds to 1200 seconds.

Methods for Correcting for Thermal Drift

Aspects of the present disclosure also include methods for correcting for thermal drift in the monochromatic light source in non-linear Resonant Raman spectroscopy. In some embodiments, the monochromatic light source is a laser and the subject methods correct for thermal drift of the laser in non-linear Resonant Raman spectroscopy.

In certain embodiments, methods include first determining whether the monochromatic light source exhibits thermal drift. In these embodiments, methods include: irradiating a reference composition over a plurality of intensities by the monochromatic light source for the period of time and determining a rate of change in the intensity of Resonant Raman scattering, wherein the reference composition comprises a reference compound that exhibits no change in the intensity of Resonant Raman scattering in response to the change in irradiation intensity by the monochromatic light source; and determining a net signal of the reference composition by comparing the rate of change in the intensity of Resonant Raman scattering for the reference composition with the rate of change in the irradiation intensity of the reference composition by the monochromatic light source to determine if the monochromatic light source exhibits thermal drift.

In these embodiments, the reference composition includes a reference compound that exhibits no change in the intensity of Resonant Raman scattering in response to the change in irradiation intensity, such as the NIST calibration standard SRM 2242.

Methods may also include correcting for the thermal drift in the monochromatic light source. To correct for laser drift, methods may include irradiating a sample over a plurality of intensities by a monochromatic light source for a period of time and determining a rate of change in the intensity of Resonant Raman scattering; determining the rate of change of the output from the reference composition to produce a correction factor; and subtracting the correction factor from the determined rate of change in the intensity of Resonant Raman scattering for the sample to correct for the thermal drift of the monochromatic light source.

Methods for Characterizing the Susceptibility of a Microorganism to an Antimicrobial Agent with Resonant Raman Scattering Aspects of the present disclosure also include methods for determining the susceptibility of a microorganism to an antimicrobial agent with Resonant Raman scattering. In some embodiments, methods include determining the minimum inhibitory concentration (MIC) of the antimicrobial agent (i.e., the lowest concentration of antimicrobial agent that inhibits growth of the microorganism). In other embodiments, methods include determining the minimum bactericidal concentration (MBC) of the antimicrobial agent (i.e., the lowest concentration of antimicrobial agent required to kill the microorganism)

In embodiments, methods include irradiating a plurality of samples, each sample comprising a microorganism and an antimicrobial agent over a plurality of intensities by the monochromatic light source for a period of time and determining a rate of change in the intensity of Resonant Raman scattering for each irradiated sample, wherein each sample comprises the same concentration of microorganism and different concentrations of antimicrobial agent; determining a net signal for each sample by comparing a normalized rate of change in the intensity of Resonant Raman scattering for each sample with a normalized rate of change in the irradiation intensity of each sample by the monochromatic light source; and determining the susceptibility of the microorganism to the antimicrobial agent based on the net signal for the plurality of samples.

In some embodiments, methods further include comparing the net signal for each sample. For example, comparing the net signal for each sample may include plotting the net signal for each sample as a function of the log of the concentration of antimicrobial agent in each sample. In these embodiments, methods may further include determining one or more of the concentration of antimicrobial agent that exhibits a decrease in the net signal and the concentration of antimicrobial agent that exhibits an increase in the net signal. In some embodiments, the concentration of antimicrobial agent that first exhibits a decrease in the net signal on the plot is determined to be the minimum inhibitory concentration (MIC) of the antimicrobial agent for the microorganism. In other embodiments, the concentration of antimicrobial agent that exhibits an increase in the net signal on the plot is determined to be the minimum bactericidal concentration (MBC) of the antimicrobial agent for the microorganism. In some embodiments, methods include determining metabolic activity of the microorganism in each sample based on the net signal for each sample. For example, methods may include determining the concentration of antimicrobial agent that exhibits a decrease in metabolic activity or determining the concentration of antimicrobial agent that exhibits an increase in the metabolic activity. In these embodiments, the minimum inhibitory concentration of the antimicrobial agent may be determined to be the concentration of antimicrobial agent that exhibits a decrease in metabolic activity of the microorganism. The minimum bactericidal concentration of the antimicrobial agent may be determined to be the concentration of antimicrobial agent that exhibits an increase in metabolic activity of the microorganism.

Depending on the type of microorganism, antimicrobial agents of interest may include but are not limited to antibacterials, antifungals, antivirals, antiparasitics as well as antimicrobial pesticides. Suitable antibiotics include, but are not limited to, fluoroquinolones such as ciprofloxacin, norfloxacin, ofloxacin, enoxacin, perfloxacin, fleroxacin, enrofloxacin, marbofloxacin, sarafloxacin, orbifloxacin, danofloxacin; aminoglycosides such as streptomycin, netilmicin, kanamycin, neomycin, tobramycin, am ikacin, sisomicin, ribostamycin, dibekacin, framycetin, gentamycin, penicillins and aminopenicillins such as penicillin, ampicillin, amoxicillin, nafcillin, oxacillin and ticarcillin, cephalosporins such as ceftriaxone, cephalexin, cefadroxil and ceftiofur, β-lactams such as clavulanic acid which may be used in conjunction with penicillins or aminopenicillins, macrolides such as clarythromycin and erythromycin and other antibiotics such as dactinomycin, clindamycin, naladixic acid, chloramphenicol, rifamopin, clofazimine, spectinomycin, polymyxin B, colistin, minocycline, vancomycin, hygromycin B or C, fusidic acid, trimethoprim and cefotaxim. The concentration of antimicrobial agent in each sample vial may vary, depending on the type of antimicrobial agent, ranging from 0.001 µg/mL to 1000 µg/mL, such as 0.005 µg/mL to 900 µg/m L, such as from 0.01 µg/m L to 800 µg/m L, such as from 0.05 µg/mL to 700 µg/m L, such as from 0.1 µg/mL to 500 µg/m L, such as from 0.5 µg/mL to 250 µg/mL and including from 1 µg/mL to 100 µg/mL. In some embodiments, the amount of antimicrobial agent ranges across the samples, such as from a concentration that is below the minimum inhibitory concentration of the antimicrobial agent to a concentration that is greater than the minimum bactericidal concentration of the antimicrobial agent. For instance, the amount of antimicrobial agent may include increasing amounts in the sample vials being tested. For example, the sample vials may include antimicrobial agents with concentrations that range from 0.125 µg/mL to 8 µg/m L, such as concentrations of 0.125 µg/m L, 0.25 µg/m L, 0.5 µg/mL, 1 µg/m L, 2 µg/mL, 4 µg/m L and 8 µg/m L.

In methods for characterizing the susceptibility of a microorganism to an antimicrobial agent according to the present disclosure, the amount of microorganism in each sample may be the same and may be 10 colony forming unit (CFU) or more, such as 11 CFU or more, such as 12 CFU or more, such as 13 CFU or more, such as 14 CFU or more, such as 15 CFU or more, such as 20 CFU or more, such as 25 CFU or more and including 50 CFU or more. In certain embodiments, methods include preparing a microorganism-containing composition having a determined amount of microorganism (e.g., 100 CFU) and aliquoting an equivalent volume of the microorganism-containing composition into each of the samples.

The microorganism and antimicrobial agent is, in certain embodiments, incubated in the sample for a predetermined period of time before irradiating the sample the monochromatic light source, such as from 0.5 minutes or more, such as for 1 minute or more, such as for 2 minutes or more, such as for 5 minutes or more, such as for 10 minutes or more, such as for 15 minutes or more, such as for 20 minutes or more, such as from 30 minutes or more, such as for 45 minutes or more and including for 60 minutes or more. For example, the antimicrobial agent and the microorganism may be incubated in the sample before being irradiated by the monochromatic light source for a predetermined period of time that ranges from 0.5 minutes to 60 minutes, such as from 1 minute to 55 minutes, such as from 2 minutes to 50 minutes, such as from 3 minutes to 45 minutes, such as from 4 minutes to 40 minutes, such as from 5 minutes to 35 minutes and including from 10 minutes to 30 minutes, for example for 20 minutes.

Methods for Characterizing the Susceptibility of a Microorganism to an Antimicrobial Agent by Fluorescence Spectroscopy Aspects of the present disclosure also include methods for determining the susceptibility of a microorganism to an antimicrobial agent by fluorescence spectroscopy. In some embodiments, methods include determining the minimum inhibitory concentration (MIC) of the antimicrobial agent (i.e., the lowest concentration of antimicrobial agent that inhibits growth of the microorganism). In other embodiments, methods include determining the minimum bactericidal concentration (MBC) of the antimicrobial agent (i.e., the lowest concentration of antimicrobial agent required to kill the microorganism)

In embodiments, methods include irradiating a plurality of samples with a monochromatic light source, each sample having a microorganism and an antimicrobial agent, for a period of time and detecting fluorescence from each of the irradiated samples over the period of time, where each sample has the same concentration of microorganism and different concentrations of antimicrobial agent; calculating a rate of change of the fluorescence in each sample by comparing a normalized rate of change in the intensity of the detected fluorescence produced by each sample with a normalized rate of change of fluorescence produced by a control; and determining the susceptibility of the microorganism to the antimicrobial agent based on the calculated rate of change of the fluorescence of the plurality of samples.

In some embodiments, each sample is irradiated over a plurality of intensities by the monochromatic light source.

In some embodiments, methods further include comparing the calculated rate of change of fluorescence for each sample. In some instances, the comparing includes plotting the calculated rate of change of fluorescence for each sample as a function of the log of the concentration of antimicrobial agent in each sample. In other embodiments, methods further include determining the concentration of antimicrobial agent that exhibits a decrease or an increase in the rate of change of fluorescence. In still other embodiments, methods further include determining metabolic activity of the microorganism in each sample based on the calculated rate of change of fluorescence for each sample. For example, methods include determining the concentration of antimicrobial agent that exhibits an increase or decrease in metabolic activity.

The fluorescence produced by the sample and the control is detected from 2500 $cm^{-1}$ to 3500 $cm^{-1}$, such as at 3000 $cm^{-1}$. In embodiments, the control and sample include a reagent composition that includes a hydrophobic compound non-covalently associated with an albumin protein. The control sample is, in some instances, a composition that includes the reagent composition and does not include a microorganism. For example, the control is a composition that has the same components as the sample in the absence of microorganism. In some embodiments, the control includes only the components of the reagent composition. In other embodiments, the control includes the components of the reagent composition and microorganism-free plasma.

Methods for Determining the Phenotype of an Unknown Microorganism with Resonant Raman Scattering Aspects of the present disclosure also include methods for determining the phenotype of an unknown microorganism with Resonant Raman scattering. In some embodiments, methods include determining whether an unknown microorganism produces a reactive metabolite (e.g., a free radical-containing metabolite). In certain embodiments, the metabolite is a reactive species capable of reacting with or cleaving a crosslink.

In embodiments, methods include irradiating with a monochromatic light source a sample comprising a microorganism, a crosslinking agent and an albumin protein over a plurality of intensities by the monochromatic light source for a period of time and determining a rate of change in the intensity of Resonant Raman scattering; calculating a net signal for the sample by comparing a normalized rate of change in the intensity of Resonant Raman scattering for the sample with a normalized rate of change in the irradiation intensity of the sample by the monochromatic light source; and determining crosslink cleavage based on the net signal of the sample, wherein the extent of crosslink cleavage is indicative of the phenotype of the microorganism. In certain embodiments, an increase over time in the net signal of the sample is indicative that the microorganism produces a metabolite that cleaves one or more crosslinks in the albumin protein.

Any suitable reactive crosslinking agent may be employed depending on the type of microorganism being tested for, e.g., where the microorganisms of interest may in certain embodiments produce a peptidase enzyme (e.g., a peptidase that cleaves a glutamic acid peptide bond). In some embodiments, the crosslinking agent is a disulfide crosslinker (e.g., a compound having disulfide linkages that exchanges disulfide bonds with a protein). In certain instances, the crosslinking agent is also a glutamic acid derivative, such as a glutamic acid derivative having one or more disulfide linkages. In certain embodiments, the crosslinking agent is a compound of Formula (I):

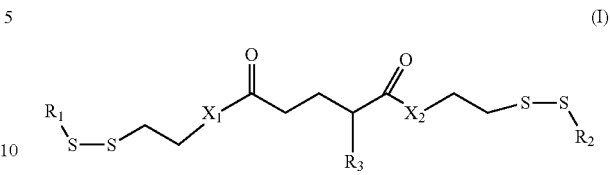

where:

$R_1$, and $R_2$ are independently selected from hydrogen, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl and substituted heteroaryl;

$X_1$ and $X_2$ are independently selected from N, O, or S; and $R_3$ is a hydrogen, alkyl, substituted alkyl, amino, halogen, cyano, alcohol or alkoxy.

In some embodiments, $R_1$, and $R_2$ are heteroaryl, $X_1$ and $X_2$ are N and $R_3$ is amino.

In certain embodiments, the crosslinking agent is a compound of Formula (DS-1)

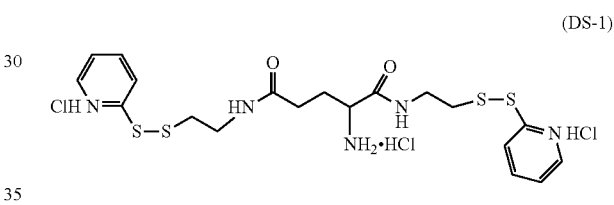

The crosslinking agent may be present in the sample in an amount where the molar ratio of crosslinking agent to albumin protein is from 1:10 to 10:1, such as from 1:9 to 9:1, such as from 1:8 to 8:1, such as from 1:7 to 7:1, such as from 1:6 to 6:1, such as from 1:5 to 5:1, such as from 1:4 to 4:1, such as from 1:3 to 3:1, and including from 1:2 to 2:1. In certain embodiments, the molar ratio of crosslinking agent to albumin protein in samples of the subject methods is about 1:2.

Methods for Determining the Phenotype of an Unknown Microorganism with Fluorescence Spectroscopy Aspects of the present disclosure also include methods for determining the phenotype of an unknown microorganism with fluorescence spectroscopy. In some embodiments, methods include determining whether an unknown microorganism produces a reactive metabolite (e.g., a free radical-containing metabolite). In certain embodiments, the metabolite is a reactive species capable of reacting with or cleaving a crosslink.

In embodiments, methods include irradiating with a monochromatic light source a sample comprising a microorganism, a crosslinking agent and an albumin protein for a period of time and detecting fluorescence from the sample over the period of time; calculating a rate of change of the fluorescence by comparing a normalized rate of change in the intensity of the detected fluorescence produced by the sample with a normalized rate of change of fluorescence produced by a control; and determining crosslink cleavage based on the calculated rate of change of fluorescence of the sample, wherein the extent of crosslink cleavage is indicative of the phenotype of the microorganism. In some embodiments, the sample is irradiated over a plurality of intensities by the monochromatic light source.

The fluorescence produced by the sample and the control is detected from 2500 cm$^{-1}$ to 3500 cm$^{-1}$, such as at 3000 cm$^{-1}$. In embodiments, the control and sample include a reagent composition that includes a hydrophobic compound non-covalently associated with an albumin protein. The control sample is, in some instances, a composition that includes the reagent composition and does not include a microorganism. For example, the control is a composition that has the same components as the sample in the absence of microorganism. In some embodiments, the control includes only the components of the reagent composition. In other embodiments, the control includes the components of the reagent composition and microorganism-free plasma.

Systems for Non-Linear Resonant Raman Spectroscopy

Aspects of the present disclosure also include systems for non-linear Resonant Raman spectroscopy. Systems according to certain embodiments include a monochromatic light source, a detector for detecting Resonant Raman scattering and a processor having memory operably coupled to the processor, the memory having instructions stored thereon, which when executed by the processor, cause the processor to: irradiate a sample with a monochromatic light source at a first irradiation intensity and a second irradiation intensity; determine the intensity of Resonant Raman scattering at the first irradiation intensity and the second irradiation intensity; calculate a rate of change of the intensity of Resonant Raman scattering in response to the change in irradiation intensity from the first irradiation intensity to the second irradiation intensity; and compare the rate of change in the intensity of Resonant Raman scattering with the rate of change in the irradiation intensity by the monochromatic light source to determine the Resonant Raman response of the sample. Systems of interest also include (a) a monochromatic light source; (b) an optical adjustment component; (c) a photodetector; and (d) a processor comprising memory operably coupled to the processor wherein the memory comprises instructions stored thereon, which when executed by the processor, cause the processor to: irradiate a sample in a sample holder with the monochromatic light source at a first irradiation intensity and a second irradiation intensity for preset durations; measure scattered light from the sample with the photodetector; determine the intensity of Resonant Raman scattering and fluorescence scattering at the first irradiation intensity and the second irradiation intensity; calculate a rate of change in the intensity of Resonant Raman scattering and the intensity of fluorescence scattering; and correct the rate of change of the intensity of Resonant Raman scattering and the intensity of fluorescence scattering to obtain a net signal.

As summarized above, systems include one or more monochromatic light sources. In embodiments, monochromatic light sources of interest output light having a narrow range of wavelengths, such as a range of 25 nm or less, such as 20 nm or less, such as 15 nm or less, such as 10 nm or less, such as 5 nm or less and including 2 nm or less. In certain embodiments, the monochromatic light source outputs a single wavelength of light. In some instances, the monochromatic light source is a single wavelength laser. In other instances, the monochromatic light source is a single wavelength LED.

In certain embodiments, the light source is a broadband light source in optical communication with an optical adjustment component that narrows the irradiation bandwidth to a single wavelength. For example, monochromatic light irradiation of the sample for Resonant Raman spectroscopy according to the subject methods may be achieved using a broadband light source such as a broadband halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source or a multi-LED integrated white light source coupled to one or more optical bandpass filters, diffraction gratings, monochromators or any combination thereof.

In certain embodiments, systems include a laser. In some instances, the laser is a continuous wave laser. In other instances, the laser is a pulsed laser. In certain instances, the laser is a diode laser, such as an ultraviolet diode laser, a visible diode laser and a near-infrared diode laser. In some instances, the monochromatic light source is a diode laser that outputs light at a wavelength from 375 nm to 1000 nm, such as from 405 nm to 875 nm, such as from 450 nm to 800 nm, such as from 500 nm to 650 nm and including from 525 nm to 625 nm. In other instances, the laser is a pulsed laser, such as a solid state laser. In certain instances, the monochromatic light source is a solid-state laser that outputs light at a wavelength from 375 nm to 1000 nm, such as from 405 nm to 875 nm, such as from 450 nm to 800 nm, such as from 500 nm to 650 nm and including from 525 nm to 625 nm. Other suitable lasers may include, but are not limited to, helium-neon (HeNe) lasers, argon lasers, krypton lasers, xenon ion lasers, nitrogen lasers, carbon dioxide lasers, carbon monoxide lasers, excimer lasers, hydrogen fluoride lasers, deuterium fluoride lasers, oxyen-iodine lasers, gas-phase iodine lasers, helium cadium lasers, helium mercury lasers, helium silver lasers, strontium vapor lasers, neon copper lasers, copper vapor laser, gold vapor laser, manganese vapor lasers, ruby lasers, Nd:YAG lasers, NdCrYAG lasers, Er:YAG lasers, Nd:YLF lasers, Nd:YVO$_4$ lasers, Nd:YCa$_4$O(BO$_3$)$_3$ lasers, Nd:glass lasers, titanium sapphire lasers, thulium YAG lasers, ytterbium YAG lasers, Yb$_2$O$_3$ lasers, ytterbium doped glass lasers, holmium YAG lasers, chromium ZnSe lasers, cerium doped lithium strontium aluminum fluoride lasers, promethium 147 doped phosphate glass lasers, chromium doped chrysoberyl lasers, erbium doped and erbium-ytterbium codoped glass lasers, trivalent uranium doped calcium fluoride lasers, samarium doped calcium fluoride lasers, GaN lasers, InGaN lasers, AlGaInP lasers, AlGaAs lasers, InGaAsP lasers, among other laser types. In certain embodiments, the monochromatic light source is a frequency doubled neodymium-doped yttrium aluminium garnet that outputs light at 532 nm.

In some embodiments, systems include an optical adjustment component that is optically coupled to the laser. By "optical adjustment" is meant that the laser light is change as desired before being conveyed to the sample. For example, systems may include one or more lenses, collimators, pinholes, mirrors, beam choppers, slits, gratings, filters, light refractors, and any combinations thereof. In certain embodiments, the optical adjustment component is a wavelength separator. The term "wavelength separator" is used herein in its conventional sense to refer to an optical protocol for separating polychromatic light into its component wavelengths. Wavelength separation, according to certain embodiments, may include selectively passing or blocking specific wavelengths or wavelength ranges of the polychromatic light. Wavelength separation protocols of interest which may be a part of or combined with the subject connector, include but are not limited to, colored glass, bandpass filters, interference filters, dichroic mirrors, diffraction gratings, monochromators and combinations thereof, among other wavelength separating protocols.

In some instances, the monochromatic light source for irradiating the sample is coupled to a collimator. The term "collimate" is used in its conventional sense to refer to the optically adjusting the collinearity of light propagation or reducing divergence by the light of from a common axis of propagation. In some instances, collimators are configured to narrow the spatial cross section of a light beam from the monochromatic light source. In other instances, the optical adjustment component is configured to change the direction of the light beam from the monochromatic light source, such as changing the propagation of the light beam from the monochromatic light source by 1° or more, such as by 5° or more, such as by 10° or more, such as by 15° or more, such as by 20° or more, such as by 25° or more, such as by 30° or more, such as by 45° or more, such as by 60° or more, such as by 75° or more and including changing the direction of light propagation by 90° or more. In yet other instances, optical adjustment is a de-magnification protocol so as to decrease the dimensions of the light (e.g., beam spot), such as decreasing the dimensions by 5% or more, such as by 10% or more, such as by 25% or more, such as by 50% or more and including decreasing the dimensions by 75% or more.

In certain embodiments, systems are configured for irradiating the sample at an interface (e.g., by focusing the monochromatic light source with a collimator as described above) between the sample and a wall of the sample container. By "interface" is meant the space where the surface of the container wall comes into contact with the sample in the container. In embodiments, the subject systems may be configured such that the monochromatic light source irradiates the interface at a point from about 0.01 mm to 2 mm from the surface of the container wall (i.e., where the sample comes into contact with the container), such as from 0.02 mm to 1.9 mm, such as from 0.03 mm to 1.8 mm, such as from 0.04 mm to 1.7 mm, such as from 0.05 mm to 1.6 mm, such as from 0.06 mm to 1.5 mm, such as from 0.07 mm to 1.4 mm, such as from 0.08 mm to 1.3 mm, such as from 0.09 mm to 1.2 mm, such as from 0.1 mm to 1 mm, for example 0.2 mm from the surface of the container wall. In these embodiments, the subject systems are configured to maintain the sample container (e.g., glass vial as described below) substantially at rest (e.g., no vibration, agitation, etc.) so that the velocity of the interfacial liquid layer irradiated by the monochromatic light source is near or at zero. For example, the liquid velocity of the interfacial sample layer irradiated by the monochromatic light source may be $10^{-2}$ $cm^3$/second or less, such as $10^{-3}$ $cm^3$/second or less, such as $10^{-4}$ $cm^3$/second or less, such as $10^{-5}$ $cm^3$/second, such as $10^{-6}$ $cm^3$/second, such as $10^{-7}$ $cm^3$/second or less, such as $10^{-8}$ $cm^3$/second or less, such as $10^{-9}$ $cm^3$/second or less and including $10^{-10}$ $cm^3$/second or less. In certain embodiments, the subject systems are configured such that the velocity of the sample at the interfacial layer when irradiated by the monochromatic light source in the subject methods is 0 $cm^3$/second.

As described above, methods include irradiating a sample with the monochromatic light and determining the intensity of Resonant Raman scattering and fluorescence. Systems for practicing the subject methods include one or more detectors for detecting fluorescence and Resonant Raman scattering. Any convenient light detection protocol may be employed, including but not limited to photosensors or photodetectors such as active-pixel sensors (APSs), quadrant photodiodes, wedge detectors image sensors, charge-coupled devices (CCDs), intensified charge-coupled devices (ICCDs), light emitting diodes, photon counters, bolometers, pyroelectric detectors, photoresistors, photovoltaic cells, photodiodes, photomultiplier tubes, phototransistors, quantum dot photoconductors or photodiodes and combinations thereof, among other photodetectors. In certain embodiments, systems include one or more CCDs.

Where the subject systems include more than one photodetector, each photodetector may be the same or a combination of different types of photodetectors. For example, where the subject systems include two photodetectors, in some embodiments the first photodetector is a CCD-type device and the second photodetector is a CMOS-type device. In other embodiments, both the first and second photodetectors are CCD-type devices. In yet other embodiments, both the first and second photodetctors are CMOS-type devices. In yet other embodiments, the first photodetector is a CCD-type photodetector or CMOS-type device and the second photodetector is a photomultiplier tube. In still other embodiments, the first photodetector and the second photodetector are photomultiplier tubes.

The detector may be optically coupled to one or more optical adjustment components. For example, systems may include one or more lenses, collimators, pinholes, mirrors, beam choppers, slits, gratings, filters, light refractors, and any combinations thereof. In some embodiments, the detector is coupled to a wavelength separator, such as colored glass, bandpass filters, interference filters, dichroic mirrors, diffraction gratings, monochromators and combinations thereof. In certain embodiments, Resonant Raman scattering from the sample is collected with fiber optics (e.g., fiber optics relay bundle) and the Resonant Raman scattering is conveyed to the detector surface through the fiber optics. Any fiber optics light relay system may be employed to propagate the scattered light onto the active surface of the detector.

In certain embodiments, light detection systems include a collimator positioned adjacent to the sample container. The collimator may be any convenient collimating device, such as one or more mirrors or curved lenses or a combination thereof. For example, the collimator is in certain instances a single collimating lens. In other instances, the collimator is a collimating mirror. In yet other instances, the collimator includes two lenses. In still other instances, the collimator includes a mirror and a lens. Where the collimator includes one or more lenses, the focal length of each collimating lens may vary, ranging from 5 mm to 500 mm, such as from 6 mm to 475 mm, such as from 7 mm to 450 mm, such as from 8 mm to 425 mm, such as from 9 mm to 400 mm, such as from 10 mm to 375 mm, such as from 12.5 mm to 350 mm and including a focal length ranging from 15 mm to 300 mm. In certain embodiments, the focal length ranges from 400 mm to 500 mm, such as from 405 mm to 475 mm, such as from 410 mm to 450 mm and including from 410 mm to 425 mm, such as 410 mm or 420 mm.

In embodiments, spectroscopy (e.g., non-linear Resonant Raman, fluorescence, etc.) is conducted at a substantially constant temperature. As such, the subject systems are configured to maintain a substantially constant temperature, such as where the temperature of the system changes by 5° C. or less, such as by 4.5° C. or less, such as by 4° C. or less, such as by 3.5° C. or less, such as by 3° C. or less, such as by 2.5° C. or less, such as by 2° C. or less, such as by 1.5° C. or less, such as 1° C. or less, such as by 0.5° C. or less, such as by 0.1° C. or less, such as by 0.05° C. or less, such as by 0.01° C. or less, such as by 0.005° C., such as by 0.001° C., such as by 0.0001° C., such as by 0.00001° C. or less and including by 0.000001° C. or less. In embodiments, the temperature of the system may be controlled by a temperature control subsystem which measures the system temperature and if necessary, controls the ambient conditions to maintain a desired system temperature. Temperature subsystems may include any convenient temperature control protocol, including, but not limited to heat sinks, fans, exhaust pumps, vents, refrigeration, coolants, heat exchanges, Peltier or resistive heating elements, among other types of temperature control protocols. As described in greater detail below, in some embodiments, systems include a processor having memory with instructions that include algorithm that measures the spectral drift of the laser at predetermined times and calculates the thermal drift of the laser in response to the changes in temperature. Systems according to these embodiments, also include algorithm for calculating a correction factor for Resonant Raman spectroscopy for the measured thermal drift of the laser.

Systems of interest may also include a sample holder for irradiating the sample with the monochromatic light source. The sample holder may be any suitable shaped substrate or container for irradiating a sample and detecting one or more of Resonant Raman scattering and fluorescence scattering. In some embodiments, the sample holder is a planar substrate (e.g., microscope slide). In other embodiments, the sample holder is a microfluidic device having one or more microfluidic channels. In yet other embodiments, the sample holder is a container having a cross-sectional shape, where cross-sectional shapes of interest include, but are not limited to: rectilinear cross sectional shapes, e.g., squares, rectangles, trapezoids, triangles, hexagons, etc., curvilinear cross-sectional shapes, e.g., circles, ovals, etc., as well as irregular shapes, e.g., a parabolic bottom portion coupled to a planar top portion, etc. The size of the sample holder may vary, depending on the volume of the samples being irradiated, where holders of interest have a length that ranges from 5 mm to 100 mm, such as from 10 mm to 90 mm, such as from 15 mm to 85 mm, such as from 20 mm to 80 mm, such as from 25 mm to 75 mm, such as from 30 mm to 70 mm and including from 35 mm to 65 mm and a width (or cross-section where the container is cylindrical) of from 5 mm to 100 mm, such as from 10 mm to 90 mm, such as from 15 mm to 85 mm, such as from 20 mm to 80 mm, such as from 25 mm to 75 mm, such as from 30 mm to 70 mm and including from 35 mm to 65 mm. In embodiments, the sample holder may have a volume of from 0.1 $cm^3$ to 10 $cm^3$, such as from 0.5 $cm^3$ to 9 $cm^3$, such as from 1 $cm^3$ to 8 $cm^3$, such as from 1.5 $cm^3$ to 7 $cm^3$, such as from 2 $cm^3$ to 6 $cm^3$, such as from 2.5 $cm^3$ to 5 $cm^3$ including from 3 $cm^3$ to 4 $cm^3$.

The sample holder may be formed from any transparent material which passes the desired range of wavelength, including but not limited to optical glass, borosilicate glass, Pyrex glass, ultraviolet quartz, infrared quartz, sapphire. In certain embodiments, the sample container is glass having walls with a zwitterionic coating, such as a zwitterionic silane coating (e.g., as described in the Experimental Section below). The sample container may also be formed from plastic, such as polycarbonates, polyvinyl chloride (PVC), polyurethanes, polyethers, polyamides, polyimides, or copolymers of these thermoplastics, such as PETG (glycol-modified polyethylene terephthalate), among other polymeric plastic materials, including polyester, where polyesters of interest may include, but are not limited to poly(alkylene terephthalates) such as poly(ethylene terephthalate) (PET), bottle-grade PET (a copolymer made based on monoethylene glycol, terephthalic acid, and other comonomers such as isophthalic acid, cyclohexene dimethanol, etc.), poly(butylene terephthalate) (PBT), and poly (hexamethylene terephthalate); poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(ε-caprolactone) and poly(β-propiolactone); poly(alkylene isophthalates) such as poly (ethylene isophthalate); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediylalkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly ([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly (tetramethylglycolide), and poly(lactide-co-glycolide); and polycarbonates of bisphenol A, 3,3'-dimethylbisphenol A, 3,3',5,5'-tetrachlorobisphenol A, 3,3',5,5'-tetramethylbisphenol A; polyamides such as poly(p-phenylene terephthalamide); polyesters, e.g., polyethylene terephthalates, e.g., Mylar™ polyethylene terephthalate; etc.

In embodiments, the sample holder may pass light that ranges from 100 nm to 1500 nm, such as from 150 nm to 1400 nm, such as from 200 nm to 1300 nm, such as from 250 nm to 1200 nm, such as from 300 nm to 1100 nm, such as from 350 nm to 1000 nm, such as from 400 nm to 900 nm and including from 500 nm to 800 nm, for example 532 nm. As summarized above, systems include one or more processors having memory that includes instructions stored for practicing the methods described above. In some embodiments, the memory includes instructions stored thereon, which when executed by the processor, cause the processor to: irradiate a sample with a monochromatic light source at a first irradiation intensity and a second irradiation intensity; determine the intensity of Resonant Raman scattering at the first irradiation intensity and the second irradiation intensity; calculate a rate of change of the intensity of Resonant Raman scattering in response to the change in irradiation intensity from the first irradiation intensity to the second irradiation intensity; and compare the rate of change in the intensity of Resonant Raman scattering with the rate of change in the irradiation intensity by the monochromatic light source to determine the Resonant Raman response of the sample.

In other embodiments, the memory includes instructions, which when executed by the processor, cause the processor to irradiate the sample over a plurality of intensities by the monochromatic light source over a period of time and determine a rate of change in the intensity of Resonant Raman scattering. In certain instances, the memory includes instructions which when executed by the processor, cause the processor to: irradiate a first sample over a plurality of intensities by the monochromatic light source for a period of time and determine a rate of change in the intensity of Resonant Raman scattering for the first sample; calculate a net signal of the first sample by comparing a normalized rate of change in the intensity of Resonant Raman scattering for the first sample with a normalized rate of change in the irradiation intensity of the first sample by the monochromatic light source; irradiate a second sample over a plurality of intensities by the monochromatic light source for the period of time and determine a rate of change in the intensity of Resonant Raman scattering for the second sample; and calculate a net signal of the second sample by comparing a normalized rate of change in the intensity of Resonant Raman scattering for the second sample with a normalized rate of change in the irradiation intensity of the second sample by the monochromatic light source. The memory may also include instructions, in certain embodiments, which when executed by the processor, cause the processor to determine that the first sample comprises a different gaseous composition from the second sample based on the compared net signals. In other embodiments, the memory includes instructions which when executed by the processor, cause the processor to determine that the first sample or the second sample comprises actively metabolizing microorganisms based on the compared net signals.

Aspects also include systems for determining the presence of absence of a microorganism in a sample. Systems according to certain embodiments, include a processor comprising memory operably coupled to the processor wherein the memory includes instructions stored thereon, which when executed by the processor, cause the processor to: irradiate a sample over a plurality of intensities by a monochromatic light source for a period of time and calculating a rate of change in the intensity of Resonant Raman scattering for the first sample; calculate a net signal of the sample by comparing a normalized rate of change in the intensity of Resonant Raman scattering for the sample with a normalized rate of change in the irradiation intensity of the sample by the monochromatic light source; and determine the presence or absence of a microorganism in the sample based on the net signal of the sample. In some instances, the memory further includes instructions, which when executed by the processor, cause the processor to determine that a microorganism is present when the net signal of the sample is above a predetermined threshold. The threshold may vary, ranging from $-0.5$ to $-4 \times 10^{-5}$/sec, such as from $-0.5$ to $-1 \times 10^{-5}$/sec, such as from $-1$ to $-2 \times 10^{-5}$/sec and including a predetermined threshold where the net signal is $-1 \times 10^{-5}$/sec. In some embodiments, the one or more present thresholds are set by implementing the method above on one or more control samples that contains an inoculum in an amount at a lower limit of concentration in a clinically infected sample. In some embodiments, the memory includes instructions which when executed by the processor, cause the processor to determine that a microorganism is present when the net signal of the sample exceeds the threshold by 1% or more of the threshold value, such as 5% or more, such as 10% or more, such as 15% or more, such as 25% or more, such as 50% or more, such as 75% or more and including 90% or more, for example, by 2-fold or more, such as 3-fold or more, such as 5-fold or more and including 10-fold or more.

In certain embodiments, systems include a processor comprising memory operably coupled to the processor wherein the memory includes instructions stored thereon, which when executed by the processor, cause the processor to determine the presence of a microorganism by comparing the net signal of two different samples. In some embodiments, one of the samples is a reference sample that does not contain a microorganism. In these embodiments, the memory may include instructions which when executed by the processor, cause the processor to: irradiate a first sample over a plurality of intensities by a monochromatic light source for a period of time and calculate a rate of change in the intensity of Resonant Raman scattering for the first sample; calculate a net signal of the first sample by comparing a normalized rate of change in the intensity of Resonant Raman scattering for the first sample with a normalized rate of change in the irradiation intensity of the first sample by the monochromatic light source; irradiate a second sample over a plurality of intensities by the monochromatic light source for the period of time and determining a rate of change in the intensity of Resonant Raman scattering for the second sample; calculate a net signal of the second sample by comparing a normalized rate of change in the intensity of Resonant Raman scattering for the second sample with a normalized rate of change in the irradiation intensity of the second sample by the monochromatic light source; and determine the presence or absence of a microorganism in one or more of the first sample or the second sample by comparing the net signal of the first sample with the net signal of the second sample. In some instances, the memory includes instructions, which when executed by the processor, cause the processor to determine that a microorganism is present in the second sample when the net signal of the second sample is greater than the net signal of the first sample. In other instances, the memory includes instructions, which when executed by the processor, cause the processor to determine that a microorganism is present in the first sample when the net signal of the first sample is greater than the net signal of the second sample. Where the first sample is a reference sample, the memory includes instructions, which when executed by the processor, cause the processor to determine that a microorganism is present in the second sample when the net signal of the second sample is greater than the net signal of the reference sample.

Aspects also include systems for calculating signal-to-noise ratio in non-linear Resonant Raman spectroscopy. Systems according to certain embodiments, include a processor comprising memory operably coupled to the processor wherein the memory includes instructions stored thereon, which when executed by the processor, cause the processor to: irradiate a first sample over a plurality of intensities by a monochromatic light source for a period of time and determining a rate of change in the intensity of Resonant Raman scattering for the first sample; calculate an average rate of change in the intensity of Resonant Raman scattering by the first sample to give a first average rate of change; calculate a standard deviation for the first average rate of change; irradiate a second sample over a range of intensities by the monochromatic light source for the period of time and determine a rate of change in the intensity of Resonant Raman scattering for the second sample; calculate an average rate of change in the intensity of Resonant Raman scattering by the second sample to give a second average rate of change; calculate a standard deviation for the second average rate of change; subtract the second average rate of change from the first average rate of change to give a signal average rate of change; add the first standard deviation and the second standard deviation to give a signal standard deviation; and divide the signal average rate of change by the signal standard deviation to determine a signal-to-noise ratio for Resonant Raman response.

Aspects of the present disclosure also include subsystems for correcting for thermal drift in the monochromatic light source in non-linear Resonant Raman spectroscopy. Where the subject systems include a laser, subsystems of interest are configured to correct for thermal drift in a laser. Systems according to certain embodiments, include a processor comprising memory operably coupled to the processor wherein the memory includes instructions stored thereon, which when executed by the processor, cause the processor to: irradiate a reference composition over a plurality of intensities by the monochromatic light source for the period of time and determining a rate of change in the intensity of Resonant Raman scattering, wherein the reference composition comprises a reference compound that exhibits no change in the intensity of Resonant Raman scattering in response to the change in irradiation intensity by the monochromatic light source; and calculate a net signal of the reference composition by comparing the rate of change in the intensity of Resonant Raman scattering for the reference composition with the rate of change in the irradiation intensity of the reference composition by the monochromatic light source to determine if the monochromatic light source exhibits thermal drift.

Where the system determines that the monochromatic light source (e.g., laser) exhibits thermal drift, the system may be configured to correct for the thermal drift in non-linear Resonant Raman spectroscopy. In these embodiments, the subject systems may include memory with instructions, which when executed by the processor, cause the processor to: irradiate a sample over a range of intensities by a monochromatic light source for a period of time and determining a rate of change in the intensity of Resonant Raman scattering; multiply the net signal of the reference composition with the rate of change of irradiation intensity of the sample by the monochromatic light source to produce a correction factor; and subtract the correction factor from the determined rate of change in the intensity of Resonant Raman scattering for the sample to correct for the thermal drift of the monochromatic light source.

Aspects also include systems for characterizing the antimicrobial susceptibility of a microorganism to an antimicrobial agent with Resonant Raman scattering. Systems according to certain embodiments, include a processor comprising memory operably coupled to the processor wherein the memory includes instructions stored thereon, which when executed by the processor, cause the processor to: irradiate a plurality of samples, each sample comprising a microorganism and an antimicrobial agent over a plurality of intensities by the monochromatic light source for a period of time and determining a rate of change in the intensity of Resonant Raman scattering for each irradiated sample, wherein each sample comprises the same concentration of microorganism and different concentrations of antimicrobial agent; calculate a net signal for each sample by comparing a normalized rate of change in the intensity of Resonant Raman scattering for each sample with a normalized rate of change in the irradiation intensity of each sample by the monochromatic light source; and determine the susceptibility of the microorganism to the antimicrobial agent based on the net signals the plurality of samples. In some embodiments, the memory includes instructions stored thereon, which when executed by the processor, cause the processor to compare the net signal for each sample. In some instances, the memory further includes instructions stored thereon, which when executed by the processor, cause the processor to plot the net signal for each sample as a function of the log of the concentration of antimicrobial agent in each sample. In some instances, the memory includes instructions stored thereon, which when executed by the processor, cause the processor to determine the concentration of antimicrobial agent that exhibits a decrease in the net signal. For example, the memory may include instructions stored thereon, which when executed by the processor, cause the processor to determine the concentration of antimicrobial agent that exhibits an increase in the net signal.

In other embodiments, the memory includes instructions stored thereon, which when executed by the processor, cause the processor to determine metabolic activity of the microorganism in each sample based on the net signal for each sample. For instance, the memory may include instructions stored thereon, which when executed by the processor, cause the processor to determine the concentration of antimicrobial agent that exhibits a decrease in metabolic activity or cause the processor to determine the concentration of antimicrobial agent that exhibits an increase in metabolic activity.

Aspects also include systems for characterizing the antimicrobial susceptibility of a microorganism to an antimicrobial agent with fluorescence spectroscopy. Systems according to certain embodiments, include a processor comprising memory operably coupled to the processor wherein the memory includes instructions stored thereon, which when executed by the processor, cause the processor to: irradiate a plurality of samples comprising a microorganism, each sample comprising a microorganism and an antimicrobial agent by the monochromatic light source for a period of time and detecting fluorescence from each of the irradiated samples over the period of time, wherein each sample comprises the same concentration of microorganism and different concentrations of antimicrobial agent; calculate a rate of change of the fluorescence in each sample by comparing a normalized rate of change in the intensity of the detected fluorescence produced by each sample with a normalized rate of change of fluorescence produced by a control; and determine the susceptibility of the microorganism to the antimicrobial agent based on the calculated rate of change of the fluorescence of the plurality of samples. In some embodiments, the system is configured to irradiate each sample over a plurality of intensities by the monochromatic light source. In some embodiments, the memory further includes instructions, which when executed by the processor, cause the processor to compare the calculated rate of change of fluorescence for each sample. In these instances, comparing may include plotting the calculated rate of change of fluorescence for each sample as a function of the log of the concentration of antimicrobial agent in each sample. In other embodiments, the memory further includes instructions, which when executed by the processor, cause the processor to determine the concentration of antimicrobial agent that exhibits a decrease or increase in the rate of change of fluorescence. In still other embodiments, the memory further includes instructions, which when executed by the processor, cause the processor to determine the concentration of antimicrobial agent that exhibits a decrease or increase in metabolic activity.

Aspects also include systems for determining the phenotype of an unknown microorganism in a sample with Resonant Raman scattering. Systems according to certain embodiments, include a processor comprising memory operably coupled to the processor wherein the memory includes instructions stored thereon, which when executed by the processor, cause the processor to: irradiate with a monochromatic light source a sample comprising a microorganism, a crosslinking agent and a protein over a plurality of intensities by the monochromatic light source for a period of time and determining a rate of change in the intensity of Resonant Raman scattering; calculate a net signal for the sample by comparing a normalized rate of change in the intensity of Resonant Raman scattering for the sample with a normalized rate of change in the irradiation intensity of the sample by the monochromatic light source; and determine crosslink cleavage based on the net signal of the sample, wherein the extent of crosslink cleavage is indicative of the phenotype of the microorganism.

Aspects also include systems for determining the phenotype of an unknown microorganism in a sample with fluorescence spectroscopy. Systems according to certain embodiments, include a processor comprising memory operably coupled to the processor wherein the memory includes instructions stored thereon, which when executed by the processor, cause the processor to: irradiate with a monochromatic light source a sample comprising a microorganism, a crosslinking agent and an albumin protein for a period of time and detect fluorescence from the sample over the period of time; calculate a rate of change of the fluorescence by comparing a normalized rate of change in the intensity of the detected fluorescence produced by the sample with a normalized rate of change of fluorescence produced by a control; and determine crosslink cleavage based on the calculated rate of change of fluorescence of the sample, wherein the extent of crosslink cleavage is indicative of the phenotype of the microorganism. In some embodiments, the system is configured to irradiate the sample over a plurality of intensities by the monochromatic light source.

In some embodiments, the crosslinking agent is a disulfide crosslinker (e.g., a compound having disulfide linkages that exchanges disulfide bonds with a protein). In certain instances, the crosslinking agent is also a glutamic acid derivative, such as a glutamic acid derivative having one or more disulfide linkages. In certain embodiments, the crosslinking agent is a compound of Formula (I):

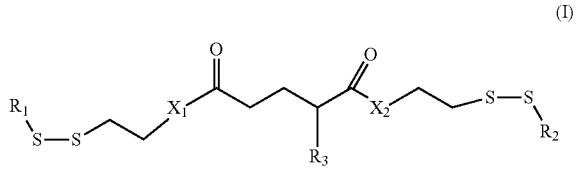

(I)

where:
R$_1$, and R$_2$ are independently selected from hydrogen, alkyl, substituted alkyl, cycloalkyl, substituted cycloalkyl, aryl, substituted aryl, heteroalkyl, substituted heteroalkyl, heterocycloalkyl, substituted heterocycloalkyl, heteroaryl and substituted heteroaryl;
X$_1$ and X$_2$ are independently selected from N, O, or S; and
R$_3$ is a hydrogen, alkyl, substituted alkyl, amino, halogen, cyano, alcohol or alkoxy.

In some embodiments, R$_1$, and R$_2$ are heteroaryl, X$_1$ and X$_2$ are N and R$_3$ is amino.

In certain embodiments, the crosslinking agent is a compound of Formula (DS-1)

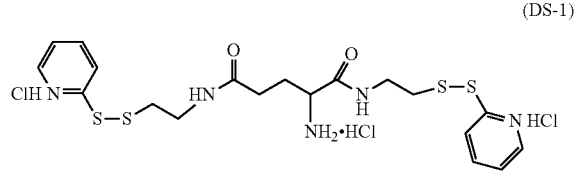

(DS-1)

The crosslinking agent may be present in the sample in an amount where the molar ratio of crosslinking agent to albumin protein is from 1:10 to 10:1, such as from 1:9 to 9:1, such as from 1:8 to 8:1, such as from 1:7 to 7:1, such as from 1:6 to 6:1, such as from 1:5 to 5:1, such as from 1:4 to 4:1, such as from 1:3 to 3:1, and including from 1:2 to 2:1. In certain embodiments, the molar ratio of crosslinking agent to albumin protein in samples of the subject methods is about 1:2. As described above, the subject systems include a processor with memory operably coupled to the processor having instructions for practicing the methods described herein. Systems may include non-transitory computer readable storage mediums for storing the above-described instructions. Computer readable storage mediums may be employed on one or more computers for complete automation or partial automation of a system for practicing methods described herein. In certain embodiments, instructions in accordance with the methods described herein can be coded onto a computer-readable medium in the form of "programming", where the term "computer readable medium" as used herein refers to any non-transitory storage medium that participates in providing instructions and data to a computer for execution and processing. Examples of suitable non-transitory storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

The computer readable storage medium may be employed on one or more computer systems having a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

Technical Features

Certain technical features of the subject methods are provided below.

Rate of change of Resonant Raman Peaks

In Resonant Raman spectroscopy, the intensity of the observed Raman band can be described by Equation 1:

$$I_R = I_o(v_o - v_{mn})^4 \Sigma |(\alpha_{ij})_{mn}|^2 \qquad \text{Equation 1}$$

where $I_o$ & $v_o$ are the Intensity and frequency of the laser, $I_R$ is the intensity of the Raman band observed at frequency $v_{mn}$. And the polarizability can be defined by the difference between the laser frequency and the energy difference between the ground and excited states.

$$(\alpha_{ij})_{mn} \propto (v_{em} - v_o)^{-1}.$$

Using these fundamental terms, it can be seen that the rate of change of the intensity of the Raman band scales with the rate of change of the intensity of the laser and the rate of change of the polarizability term $$\frac{1}{I_R}\frac{\delta I_R}{\delta t} = \frac{1}{I_o}\frac{\delta I_o}{\delta t} + \frac{\delta \ln \sum |(\alpha_{ij})_{mn}|^2}{\delta t} \quad \text{Equation 2}$$

Absent changes in the polarizability terms (the $2^{nd}$ term in Equation 2 above), the normalized rate of change of Raman bands will be equal to the normalized rate of change laser intensity. If the polarizability terms change with laser intensity (for instance, if the excited state is being altered by changes in laser intensity), or if the polarizability term is changing by itself (for instance, if the excited state is being changed by an ongoing chemical/physical reaction) then the two terms will not be equal. In this scenario, the rate of change of Raman peak intensity can be used to characterize any changes that can affect the polarizability terms.

$$\frac{1}{I_R}\frac{\delta I_R}{\delta t} = \frac{1}{I_o}\frac{\delta I_o}{\delta t} + \frac{\delta \ln \sum |(\alpha_{ij})_{mn}|^2}{\delta t}$$

Aspects, including embodiments, of the subject matter described herein may be beneficial alone or in combination, with one or more other aspects or embodiments. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A method of determining a Resonant Raman response of a sample, the method comprising:
   irradiating a sample with a monochromatic light source at a first irradiation intensity and a second irradiation intensity;
   determining the intensity of Resonant Raman scattering at the first irradiation intensity and the second irradiation intensity;
   calculating a rate of change of the intensity of Resonant Raman scattering in response to the change in irradiation intensity from the first irradiation intensity to the second irradiation intensity; and
   comparing the rate of change in the intensity of Resonant Raman scattering with the rate of change in the irradiation intensity by the monochromatic light source to determine changes to the Resonant Raman response of the sample.
2. The method according to 1, wherein the Resonant Raman response of the sample is indicative of a physical change over time in the sample.
3. The method according to 1, wherein the Resonant Raman response of the sample is indicative of a chemical change over time in the sample.
4. The method according to 1, wherein the Resonant Raman response of the sample is indicative of the presence of an actively metabolizing microorganism in the sample.
5. The method according to any one of 1-4, wherein the monochromatic light source is a laser.
6. The method according to any one of 1-5, wherein the sample comprises a hydrophobic compound and an albumin protein.
7. The method according to 6, wherein the hydrophobic compound is a carotenoid.
8. The method according to 7, wherein the hydrophobic compound is lycopene.
9. The method according to any one of 6-8, wherein the hydrophobic compound is non-covalently associated with the albumin protein.
10. The method according to any one of 1-9, wherein the sample comprises a free radical scavenger.
11. The method according to 10, wherein the free radical scavenger is non-covalently associated with an albumin protein.
12. The method according to any one of 10-11 wherein the free-radical scavenger comprises bilirubin or a derivative thereof.
13. The method according to 12, wherein bilirubin or a derivative thereof is present in the sample at a concentration of from 0.5 µM to 2 µM.
14. The method according to 12, wherein bilirubin or a derivative thereof is present in the sample at a concentration of from 0.25 µM to 1.75 µM.
15. The method according to any one of 1-9, wherein the sample comprises a reducing agent.
16. The method according to 15, wherein the reducing agent is glutathione or a derivative thereof.
17. The method according to any one of 15-16, wherein the reducing agent is present in the sample at a concentration of 0.1 mg/mL to 1 mg/m L.
18. The method according to any one of 1-17, wherein the method comprises irradiating the sample over a plurality of irradiation intensities by the monochromatic light source over a period of time and determining a rate of change in the intensity of Resonant Raman scattering.
19. The method according to any one of 1-17, wherein the method comprises:
   irradiating a first sample over a plurality of intensities by the monochromatic light source for a period of time and determining a rate of change in the intensity of Resonant Raman scattering for the first sample;
   calculating a net signal of the first sample by comparing a normalized rate of change in the intensity of Resonant Raman scattering for the first sample with a normalized rate of change in the irradiation intensity of the first sample by the monochromatic light source;
   irradiating a second sample over a plurality of intensities by the monochromatic light source for the period of time and determining a rate of change in the intensity of Resonant Raman scattering for the second sample; and
   calculating a net signal of the second sample by comparing a normalized rate of change in the intensity of Resonant Raman scattering for the second sample with a normalized rate of change in the irradiation intensity of the second sample by the monochromatic light source.
20. The method according to 18, further comprising comparing the calculated net signal of the first sample with the calculated net signal of the second sample.
21. The method according to 20, further comprising determining that the first sample and the second sample are different based on the compared calculated net signals.
22. The method according to 20, further comprising determining that the first sample comprises a different gaseous composition from the second sample based on the compared calculated net signals.

23. The method according to 20, further comprising determining that the first sample or the second sample comprises actively metabolizing microorganisms based on the compared calculated net signals.
24. The method according to any one of 1-23, wherein the sample is irradiated in a sample container.
25. The method according to 24, wherein the sample container is a glass vial.
26. The method according to 25, wherein the glass vial comprises walls having a zwitterionic coating.
27. The method according to 26, wherein the glass vial comprises walls having a zwitterionic silane coating.
28. The method according to any one of 25-27, wherein the sample is irradiated at an interface between the sample and the container wall.
29. The method according to 28, wherein the monochromatic light source is focused at a position at the interface between the sample and the container wall.
30. The method according to 29, wherein the monochromatic light source is focused in the sample at a position of from 0.01 mm to 2 mm from the surface of the container wall.
31. The method according to 30, wherein the monochromatic light source is focused in the sample at a position of about 0.2 mm from the surface of the container wall.
32. The method according to any one of 29-31, wherein the monochromatic light source is focused with a collimating lens.
33. The method according to any one of 1-32, wherein the sample further comprises a crosslinking agent.
34. The method according to 33, wherein the crosslinking agent is a disulfide crosslinker.
35. The method according to any one of 33-34, wherein the crosslinking agent is a glutamic acid derivative.
36. The method according to 35, wherein the crosslinking agent comprises a compound of Formula (I):

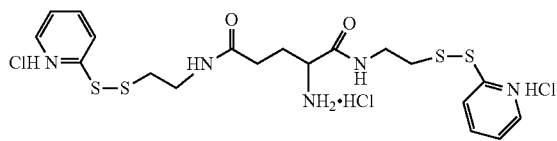

37. The method according to any one of 33-36, wherein the crosslinking agent is present in the sample in an amount such that the molar ratio of crosslinking agent to albumin protein is from 1:10 to 10:1.
38. The method according to 37, wherein the crosslinking agent is present in the sample in an amount such that the molar ratio of crosslinking agent to albumin protein is about 1:2.

Methods for Detecting a Microorganism in a Sample
1. A method for determining the presence of a microorganism in a sample, the method comprising:
   irradiating a sample over a plurality of intensities by a monochromatic light source for a period of time and calculating a rate of change in the intensity of Resonant Raman scattering for the sample;
   calculating a net signal of the sample by comparing a normalized rate of change in the intensity of Resonant Raman scattering for the sample with a normalized rate of change in the irradiation intensity of the sample by the monochromatic light source; and
   determining the presence of a microorganism in the sample based on the calculated net signal of the sample.
2. The method according to 1, wherein a microorganism is determined to be present when the calculated net signal of the sample is above a predetermined threshold.
3. The method according to 2, wherein the predetermined threshold is a net signal of 1.
4. The method according to any one of 1-3, wherein the monochromatic light source is a laser.
5. The method according to any one of 1-4, wherein the sample comprises a hydrophobic compound non-covalently associated with an albumin protein.
6. The method according to any one of 1-5, further comprising a free radical scavenger.
7. The method according to 6, wherein the free radical scavenger comprises bilirubin or a derivative thereof.
8. The method according to 7, wherein the bilirubin or derivative thereof is present at a concentration of from 0.5 μM to 2 μM.
9. The method according to 7, wherein the bilirubin is present at a concentration of from 0.25 μM to 1.75 μM.
10. The method according to any one of 1-9, wherein the sample comprises a reducing agent.
11. The method according to 10, wherein the reducing agent is glutathione or a derivative thereof.
12. The method according to any one of 10-11, wherein the reducing agent is present in the sample at a concentration of 0.1 mg/mL to 1 mg/m L.
13. The method according to any one of 1-12, wherein the sample is irradiated in a sample container.
14. The method according to 13, wherein the sample container is a glass vial.
15. The method according to 14, wherein the glass vial comprises walls having a zwitterionic coating.
16. The method according to 15, wherein the glass vial comprises walls having a zwitterionic silane coating.
17. The method according to any one of 14-16, wherein the sample is irradiated at an interface between the sample and the container wall.
18. The method according to 17, wherein the monochromatic light source is focused at a position at the interface between the sample and the container wall.
19. The method according to 18, wherein the monochromatic light source is focused in the sample at a position of from 0.01 mm to 2 mm from the surface of the container wall.
20. The method according to 19, wherein the monochromatic light source is focused in the sample at a position of about 0.2 mm from the surface of the container wall.
21. The method according to any one of 18-20, wherein the monochromatic light source is focused with a collimating lens.
22. A method for determining the presence of a microorganism in a sample, the method comprising:
   irradiating a first sample over a plurality of intensities by a monochromatic light source for a period of time and calculating a rate of change in the intensity of Resonant Raman scattering for the first sample;
   calculating a net signal of the first sample by comparing a normalized rate of change in the intensity of Resonant Raman scattering for the first sample with a normalized rate of change in the irradiation intensity of the first sample by the monochromatic light source;
   irradiating a second sample over a plurality of intensities by the monochromatic light source for the period of time and determining a rate of change in the intensity of Resonant Raman scattering for the second sample;

calculating a net signal of the second sample by comparing a normalized rate of change in the intensity of Resonant Raman scattering for the second sample with a normalized rate of change in the irradiation intensity of the second sample by the monochromatic light source; and determining the presence of a microorganism in one or more of the first sample or the second sample by comparing the net signal of the first sample with the net signal of the second sample.

23. The method according to any one of 22, wherein a microorganism is determined to be present in the second sample when the calculated net signal of the second sample is greater than the calculated net signal of the first sample.

24. The method according to any one of 22, wherein a microorganism is determined to be present in the first sample when the calculated net signal of the first sample is greater than the calculated net signal of the second sample.

25. The method according to any one of 22-24, wherein the monochromatic light source is a laser.

26. The method according to any one of 22-25, wherein the sample comprises a hydrophobic compound non-covalently associated with an albumin protein.

27. The method according to 26, further comprising a free radical scavenger.

28. The method according to 27, wherein the free radical scavenger comprises bilirubin or a derivative thereof.

29. The method according to 28, wherein the bilirubin or derivative thereof is present at a concentration of from 0.5 µM to 2 µM.

30. The method according to 28, wherein the bilirubin is present at a concentration of from 0.25 µM to 1.75 µM.

31. The method according to any one of 22-30, wherein the sample comprises a reducing agent.

32. The method according to 31, wherein the reducing agent is glutathione or a derivative thereof.

33. The method according to any one of 31-32, wherein the reducing agent is present in the sample at a concentration of 0.1 mg/mL to 1 mg/m L.

34. The method according to any one of 22-33, wherein the sample is irradiated in a sample container.

35. The method according to 34, wherein the sample container is a glass vial.

36. The method according to 35, wherein the glass vial comprises walls having a zwitterionic coating.

37. The method according to 36, wherein the glass vial comprises walls having a zwitterionic silane coating.

38. The method according to any one of 34-37, wherein the sample is irradiated at an interface between the sample and the container wall.

39. The method according to claim 38, wherein the monochromatic light source is focused at a position at the interface between the sample and the container wall.

40. The method according to 39, wherein the monochromatic light source is focused in the sample at a position of from 0.01 mm to 2 mm from the surface of the container wall.

41. The method according to 39, wherein the monochromatic light source is focused in the sample at a position of about 0.2 mm from the surface of the container wall.

42. The method according to any one of 39-41, wherein the monochromatic light source is focused with a collimating lens.

Methods for Determining the Presence of Microorganism in a Sample

1. A method for determining the presence of a microorganism in a sample, the method comprising:

(a) combining in a sample holder the sample with a reagent that contains albumin with an incorporated ligand;

(b) irradiating the sample with a monochromatic light source that is absorbed by the ligand, with either an invariant light intensity or one that varies over time focused at an interface between the sample and a surface of the sample holder; and (c) collecting scattered light from the irradiated sample and measuring a Raman signal and a fluorescence signal from the scattered light at a plurality of different times; and (d) calculating a rate of change in intensity of the Raman signal and fluorescence signal for the sample over time; and (e) correcting the calculated rates of change in the intensities of the Raman signal and the fluorescence signal to obtain a net signal; and (f) determining the presence of a microorganism in the sample based on a comparison of the net signal versus one or more preset thresholds.

2. The method according to 1, wherein the one or more present thresholds of 1f are set by implementing the method of claim 1 on one or more control samples that contains an inoculum in an amount at a lower limit of concentration in a clinically infected sample.

3. The method according to 1, wherein the ligand islycopene.

4. The method according to 1, wherein the monochromatic light source is a laser.

5. The method according to 4, wherein the laser irradiates the sample at 532 nm.

6. The method according to 1, wherein correcting the rate of change in the intensities of the Raman signal and the fluorescence signal comprises characterizing a spectral output from a standard sample.

7. The method according to 6, wherein the standard is a NIST SRM 2242.

8. The method according to claim 1, wherein correcting the rate of change in the intensities of the Raman signal comprises characterizing a fluorescence output from the reagent.

9. The method according to 1, further comprising pretreating the albumin of the reagent with a reducing agent prior to incorporating the ligand.

10. The method according to 9, wherein pretreating the albumin with the reducing agent is sufficient to reduce disulfide bonds.

11. The method according to 9, wherein the reducing agent is glutathione or bilirubin.

12. The method according to 10, further comprising contacting the pretreated albumin with a disulfide crosslinking agent.

13. The method according to 12, where the disulfide crosslinking agent comprises a core that is cleaved by enzymes or a metabolite produced by the microorganism in the sample.

14. The method according to 10, wherein the crosslinking agent comprises a compound of Formula (I):

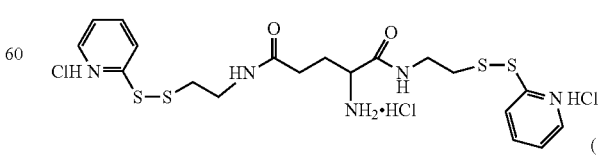

15. The method according to 1, wherein the sample holder is a glass vial.

16. The method according to 15, wherein a surface of the glass vial comprises a coating that modifies the absorption of albumin on the glass surface.
17. The method according to 16, wherein the coating is a zwitterionic coating.
18. The method according to 1, where the reagent comprises an antimicrobial composition.
19. The method according to 18, further comprising plotting the net signal against antimicrobial concentration,
   wherein a minima in the plot is used to estimate minimum bactericidal concentration of the antimicrobial composition; and
   wherein a breakpoint in the plot is used to estimate minimum inhibitory concentration of the antimicrobial composition.

Methods for Correcting for Drifts in Laser Power During Non-Linear Raman Spectroscopy 1. A method comprising:
   irradiating a reference composition over a plurality of intensities by a monochromatic light source for the period of time and determining a rate of change in the intensity of Resonant Raman scattering, wherein the reference composition comprises a reference compound that exhibits no change in the intensity of Resonant Raman scattering in response to the change in irradiation intensity by the monochromatic light source; and
   calculating a net signal of the reference composition by comparing the rate of change in the intensity of Resonant Raman scattering for the reference composition with the rate of change in the irradiation intensity of the reference composition by the monochromatic light source to determine if the monochromatic light source exhibits thermal drift.
2. The method according to 1, further comprising:
   irradiating a sample over a range of intensities by a monochromatic light source for a period of time and determining a rate of change in the intensity of Resonant Raman scattering;
   multiplying the net signal of the reference composition with the rate of change of irradiation intensity of the sample by the monochromatic light source to produce a correction factor; and
   subtracting the correction factor from the determined rate of change in the intensity of Resonant Raman scattering for the sample to correct for the thermal drift of the monochromatic light source.
3. The method according to any one of 1-2, wherein the monochromatic light source is a laser.
4. The method according to 3, wherein the laser is a solid-state laser that irradiates at 532 nm.
5. The method according to any one of 1-4, wherein the sample comprises a hydrophobic compound non-covalently associated with an albumin protein.
6. The method according to 5, further comprising a free radical scavenger.
7. The method according to 6, wherein the free radical scavenger comprises bilirubin or a derivative thereof.
8. The method according to 7, wherein bilirubin or derivative thereof is present at a concentration of from 0.5 µM to 2 µM.
9. The method according to 7, wherein the bilirubin is present at a concentration of from 0.25 µM to 1.75 µM.
10. The method according to any one of 1-9, wherein the period of time is from 200 seconds to 1500 seconds.
11. The method according to 10, wherein the period of time is 600 seconds.
12. The method according to any one of 1-11, wherein the sample comprises a reducing agent.
13. The method according to 12, wherein the reducing agent is glutathione or a derivative thereof.
14. The method according to any one of 12-13, wherein the reducing agent is present in the sample at a concentration of 0.1 mg/mL to 1 mg/m L.

Methods for Characterizing the Antimicrobial Susceptibility

1. A method of determining antimicrobial susceptibility of a microorganism to an antimicrobial agent, the method comprising:
   irradiating a plurality of samples with a monochromatic light source, each sample comprising a microorganism and an antimicrobial agent, over a plurality of intensities by the monochromatic light source for a period of time, and determining a rate of change in the intensity of Resonant Raman scattering for each irradiated sample, wherein each sample comprises the same concentration of microorganism and different concentrations of antimicrobial agent;
   calculating a net signal for each sample by comparing a normalized rate of change in the intensity of Resonant Raman scattering for each sample with a normalized rate of change in the irradiation intensity of each sample by the monochromatic light source; and
   determining the susceptibility of the microorganism to the antimicrobial agent based on the calculated net signals of the plurality of samples.
2. The method according to 1, further comprising comparing the calculated net signal for each sample.
3. The method according to 2, wherein comparing comprises plotting the calculated net signal for each sample as a function of the log of the concentration of antimicrobial agent in each sample.
4. The method according to any one of 2-3, further comprising determining the concentration of antimicrobial agent that exhibits a decrease in the net signal.
5. The method according to 4, further comprising determining the concentration of antimicrobial agent that exhibits an increase in the net signal.
6. The method according to 1, further comprising determining metabolic activity of the microorganism in each sample based on the calculated net signal for each sample.
7. The method according to 6, further comprising determining the concentration of antimicrobial agent that exhibits a decrease in metabolic activity.
8. The method according to 6, further comprising determining the concentration of antimicrobial agent that exhibits an increase in metabolic activity.
9. The method according to any one of 1-8, wherein each sample comprises a concentration of microorganism of 10 colony forming units (CFU) or more.
10. The method according to 9, wherein each sample comprises a concentration of microorganism of 14 CFU or more.
11. The method according to 9, wherein the method comprises aliquoting each sample from a microorganism composition having a concentration of microorganism of 100 colony forming units (CFU) or more.
12. The method according to any one of 1-11, wherein the concentration of antimicrobial agent in the plurality of samples ranges from a concentration that is below the minimum inhibitory concentration of the antimicrobial agent to a concentration that is greater than the minimum bactericidal concentration of the antimicrobial agent.
13. The method according to any one of 1-12, further comprising incubating the antimicrobial agent with the microorganism for a predetermined period of time before irradiating the sample.

14. The method according to 13, wherein the antimicrobial agent is incubated with the microorganism for 10 minutes or more.

15. The method according to 13, wherein the antimicrobial agent is incubated with the microorganism for 20 minutes or more.

16. The method according to any one of 1-15, wherein the sample comprises a reducing agent.

17. The method according to 16, wherein the reducing agent is glutathione or a derivative thereof.

18. The method according to any one of 16-17, wherein the reducing agent is present in the sample at a concentration of 0.1 mg/mL to 1 mg/m L.

19. The method according to any one of 1-18, wherein the sample is irradiated in a sample container.

20. The method according to 19, wherein the sample container is a glass vial.

21. The method according to 20, wherein the glass vial comprises walls having a zwitterionic coating.

22. The method according to 21, wherein the glass vial comprises walls having a zwitterionic silane coating.

23. The method according to any one of claims 19-22, wherein the sample is irradiated at an interface between the sample and the container wall.

24. The method according to 23, wherein the monochromatic light source is focused at a position at the interface between the sample and the container wall.

25. The method according to 24, wherein the monochromatic light source is focused in the sample at a position of from 0.01 mm to 2 mm from the surface of the container wall.

26. The method according to 24, wherein the monochromatic light source is focused in the sample at a position of about 0.2 mm from the surface of the container wall.

27. The method according to any one of 24-27, wherein the monochromatic light source is focused with a collimating lens.

Methods for Phenotyping an Unknown Microorganism

1. A method of characterizing a phenotype of a microorganism, the method comprising:

irradiating with a monochromatic light source a sample comprising a microorganism, a crosslinking agent and an albumin protein over a plurality of intensities by the monochromatic light source for a period of time and determining a rate of change in the intensity of Resonant Raman scattering;

calculating a net signal for the sample by comparing a normalized rate of change in the intensity of Resonant Raman scattering for the sample with a normalized rate of change in the irradiation intensity of the sample by the monochromatic light source; and determining crosslink cleavage based on the calculated net signal of the sample, wherein the extent of crosslink cleavage is indicative of the phenotype of the microorganism.

2. The method according to 1, wherein the crosslinking agent is a disulfide crosslinker.

3. The method according to any one of 1-2, wherein the crosslinking agent is a glutamic acid derivative.

4. The method according to 3, wherein the crosslinking agent comprises a compound of Formula (I):

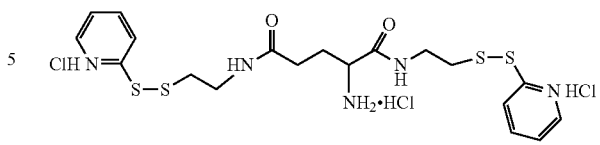

5. The method according to any one of 1-4, wherein the crosslinking agent is present in the sample in an amount such that the molar ratio of crosslinking agent to albumin protein is from 1:10 to 10:1.

6. The method according to 5, wherein the crosslinking agent is present in the sample in an amount such that the molar ratio of crosslinking agent to albumin protein is about 1:2.

7. The method according any one of 1-6, wherein an increase over time in the calculated net signal of the sample is indicative that the microorganism produces a metabolite that cleaves one or more crosslinks in the albumin protein.

8. The method according to any one of 1-7, wherein the monochromatic light source is a laser.

9. The method according to 8, wherein the laser is a solid-state laser that irradiates at 532 nm.

10. The method according to any one of 1-9, wherein the sample comprises a hydrophobic compound and an albumin protein.

11. The method according to 10, wherein the hydrophobic compound is a carotenoid.

12. The method according to 11, wherein the hydrophobic compound is lycopene.

13. The method according to any one of 10-12, wherein the hydrophobic compound is non-covalently associated with the albumin protein.

14. The method according to any one of 1-13, wherein the sample comprises a reducing agent.

15. The method according to 14, wherein the reducing agent is glutathione or a derivative thereof.

16. The method according to any one of 14-15, wherein the reducing agent is present in the sample at a concentration of 0.1 mg/mL to 1 mg/m L.

17. The method according to any one of 1-16, wherein the sample is irradiated in a sample container.

18. The method according to 17, wherein the sample container is a glass vial.

19. The method according to 18, wherein the glass vial comprises walls having a zwitterionic coating.

20. The method according to 19, wherein the glass vial comprises walls having a zwitterionic silane coating.

21. The method according to any one of 17-20, wherein the sample is irradiated at an interface between the sample and the container wall.

22. The method according to 21, wherein the monochromatic light source is focused at a position at the interface between the sample and the container wall.

23. The method according to 22, wherein the monochromatic light source is focused in the sample at a position of from 0.01 mm to 2 mm from the surface of the container wall.

24. The method according to 22, wherein the monochromatic light source is focused in the sample at a position of about 0.2 mm from the surface of the container wall.

25. The method according to any one of 22-24, wherein the monochromatic light source is focused with a collimating lens.

Methods for Detecting a Microorganism in a Sample Using Fluorescence

1. A method for determining the presence of a microorganism in a sample, the method comprising:
    irradiating a sample with a monochromatic light source for a period of time and detecting fluorescence from the sample over the period of time;
    calculating a rate of change of the fluorescence due to the presence of a microorganism by comparing a normalized rate of change in the intensity of the detected fluorescence produced by the sample with a normalized rate of change of fluorescence produced by a control; and
    determining the presence of a microorganism in the sample based on the calculated changes in the fluorescence of the sample compared to preset thresholds.
2. The method according to 1, comprising irradiating the sample over a plurality of intensities with the monochromatic light source.
3. The method according to any one of 1-2, wherein fluorescence produced by the sample and the control is detected from 2500 $cm^{-1}$ to 3500 $cm^{-1}$.
4. The method according to 3, wherein fluorescence produced by the sample and the control is detected at 3000 $cm^{-1}$.
5. The method according to any one of 1-4, wherein the control is a composition that does not include a microorganism.
6. The method according to any one of 1-5, wherein the microorganism is a pathogenic microorganism.
7. The method according to any one of 1-6, wherein the monochromatic light source is a laser.
8. The method according to any one of 1-7, wherein the sample comprises a hydrophobic compound non-covalently associated with an albumin protein.
9. The method according to any one of 1-8, further comprising a free radical scavenger.
10. The method according to 9, wherein the free radical scavenger comprises bilirubin or a derivative thereof.
11. The method according to 10, wherein the bilirubin or derivative thereof is present at a concentration of from 0.5 µM to 2 µM.
12. The method according to 11, wherein the bilirubin is present at a concentration of from 0.25 µM to 1.75 µM.
13. The method according to any one of 1-12, wherein the sample comprises a reducing agent.
14. The method according to 13, wherein the reducing agent is glutathione or a derivative thereof.
15. The method according to any one of 13-14, wherein the reducing agent is present in the sample at a concentration of 0.1 mg/mL to 1 mg/mL.
16. The method according to any one of 1-15, wherein the sample is irradiated in a sample container.
17. The method according to 16, wherein the sample container is a glass vial.
18. The method according to 17, wherein the glass vial comprises walls having a zwitterionic coating.
19. The method according to 18, wherein the glass vial comprises walls having a zwitterionic silane coating.
20. The method according to any one of 17-19, wherein the sample is irradiated at an interface between the sample and the container wall.
21. The method according to 20, wherein the monochromatic light source is focused at a position at the interface between the sample and the container wall.
22. The method according to 20, wherein the monochromatic light source is focused in the sample at a position of from 0.01 mm to 2 mm from the surface of the container wall.
23. The method according to 22, wherein the monochromatic light source is focused in the sample at a position of about 0.2 mm from the surface of the container wall.
24. The method according to any one of 21-23, wherein the monochromatic light source is focused with a collimating lens.
25. The method according to any one of 1-24, wherein the control is a composition that has the same components as the sample in the absence of microorganism.

Methods for Characterizing the Antimicrobial Susceptibility

1. A method of determining antimicrobial susceptibility of microorganism to an antimicrobial agent, the method comprising:
    irradiating a plurality of samples with a monochromatic light source, each sample comprising a microorganism and an antimicrobial agent, for a period of time and detecting fluorescence from each of the irradiated samples over the period of time, wherein each sample comprises the same concentration of microorganism and different concentrations of antimicrobial agent;
    calculating a rate of change of the fluorescence in each sample by comparing a normalized rate of change in the intensity of the detected fluorescence produced by each sample with a normalized rate of change of fluorescence produced by a control; and
    determining the susceptibility of the microorganism to the antimicrobial agent based on the calculated rate of change of the fluorescence of the plurality of samples.
2. The method according to 1, further comprising comparing the calculated rate of change of fluorescence for each sample.
3. The method according to 2, wherein comparing comprises plotting the calculated rate of change of fluorescence for each sample as a function of the log of the concentration of antimicrobial agent in each sample.
4. The method according to any one of 2-3, further comprising determining the concentration of antimicrobial agent that exhibits a decrease in the rate of change of fluorescence.
5. The method according to 4, further comprising determining the concentration of antimicrobial agent that exhibits an increase in the rate of change of fluorescence.
6. The method according to 1, further comprising determining metabolic activity of the microorganism in each sample based on the calculated rate of change of fluorescence for each sample.
7. The method according to 6, further comprising determining the concentration of antimicrobial agent that exhibits a decrease in metabolic activity.
8. The method according to 6, further comprising determining the concentration of antimicrobial agent that exhibits an increase in metabolic activity.
9. The method according to any one of 1-8, wherein each sample comprises a concentration of microorganism of 10 colony forming units (CFU) or more.
10. The method according to 9, wherein each sample comprises a concentration of microorganism of 14 CFU or more.
11. The method according to 9, wherein the method comprises aliquoting each sample from a microorganism composition having a concentration of microorganism of 100 colony forming units (CFU) or more.
12. The method according to any one of 1-11, wherein the concentration of antimicrobial agent in the plurality of samples ranges from a concentration that is below the minimum inhibitory concentration of the antimicrobial agent to a concentration that is greater than the minimum bactericidal concentration of the antimicrobial agent.

13. The method according to any one of 1-12, further comprising incubating the antimicrobial agent with the microorganism for a predetermined period of time before irradiating the sample.

14. The method according to 13, wherein the antimicrobial agent is incubated with the microorganism for 10 minutes or more.

15. The method according to 13, wherein the antimicrobial agent is incubated with the microorganism for 20 minutes or more.

16. The method according to any one of 1-15, wherein the sample comprises a reducing agent.

17. The method according to 16, wherein the reducing agent is glutathione or a derivative thereof.

18. The method according to any one of 16-17, wherein the reducing agent is present in the sample at a concentration of 0.1 mg/mL to 1 mg/m L.

19. The method according to any one of 1-18, wherein the sample is irradiated in a sample container.

20. The method according to 19, wherein the sample container is a glass vial.

21. The method according to 20, wherein the glass vial comprises walls having a zwitterionic coating.

22. The method according to 21, wherein the glass vial comprises walls having a zwitterionic silane coating.

23. The method according to any one of 19-22, wherein the sample is irradiated at an interface between the sample and the container wall.

24. The method according to 23, wherein the monochromatic light source is focused at a position at the interface between the sample and the container wall.

25. The method according to 24, wherein the monochromatic light source is focused in the sample at a position of from 0.01 mm to 2 mm from the surface of the container wall.

26. The method according to 24, wherein the monochromatic light source is focused in the sample at a position of about 0.2 mm from the surface of the container wall.

27. The method according to any one of 24-27, wherein the monochromatic light source is focused with a collimating lens.

28. The method according to any one of 1-27, wherein fluorescence produced by the sample and the control is detected from 2500 cm$^{-1}$ to 3500 cm$^{-1}$.

29. The method according to 28, wherein fluorescence produced by the sample and the control is detected at 3000 cm$^{-1}$.

30. The method according to any one of 1-29, wherein the control is a composition that does not include a microorganism.

31. The method according to any one of 1-30, wherein the control is a composition that has the same components as the sample in the absence of microorganism.

32. The method according to any one of 1-31, comprising irradiating each sample over a plurality of intensities with the monochromatic light source.

Methods for Phenotyping an Unknown Microorganism

1. A method of characterizing a phenotype of a microorganism, the method comprising:
    irradiating with a monochromatic light source, a sample comprising a microorganism, a crosslinking agent and an albumin protein, for a period of time and detecting fluorescence from the sample over the period of time;
    calculating a rate of change of the fluorescence by comparing a normalized rate of change in the intensity of the detected fluorescence produced by the sample with a normalized rate of change of fluorescence produced by a control; and
    determining crosslink cleavage based on the calculated rate of change of fluorescence of the sample, wherein the extent of crosslink cleavage is indicative of the phenotype of the microorganism.

2. The method according to 1, wherein the crosslinking agent is a disulfide crosslinker.

3. The method according to any one of 1-2, wherein the crosslinking agent is a glutamic acid derivative.

4. The method according to 3, wherein the crosslinking agent comprises a compound of Formula (I):

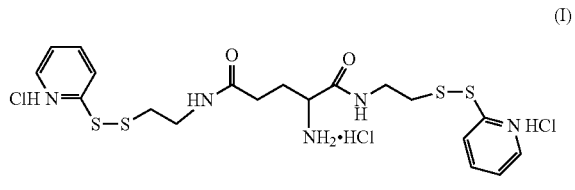

5. The method according to any one of 1-4, wherein the crosslinking agent is present in the sample in an amount such that the molar ratio of crosslinking agent to albumin protein is from 1:10 to 10:1.

6. The method according to 5, wherein the crosslinking agent is present in the sample in an amount such that the molar ratio of crosslinking agent to albumin protein is about 1:2.

7. The method according any one of 1-6, wherein an increase in the calculated rate of change in the fluorescence of the sample is indicative that the microorganism produces a metabolite that cleaves one or more crosslinks in the albumin protein.

8. The method according to any one of 1-7, wherein the monochromatic light source is a laser.

9. The method according to 8, wherein the laser is a solid-state laser that irradiates at 532 nm.

10. The method according to any one of 1-9, wherein the sample comprises a hydrophobic compound and an albumin protein.

11. The method according to 10, wherein the hydrophobic compound is a carotenoid.

12. The method according to 11, wherein the hydrophobic compound is lycopene.

13. The method according to any one of 10-12, wherein the hydrophobic compound is non-covalently associated with the albumin protein.

14. The method according to any one of 1-13, wherein the sample comprises a reducing agent.

15. The method according to 14, wherein the reducing agent is glutathione or a derivative thereof.

16. The method according to any one of 14-15, wherein the reducing agent is present in the sample at a concentration of 0.1 mg/mL to 1 mg/m L.

17. The method according to any one of 1-16, wherein the sample is irradiated in a sample container.

18. The method according to 17, wherein the sample container is a glass vial.

19. The method according to 18, wherein the glass vial comprises walls having a zwitterionic coating.

20. The method according to 19, wherein the glass vial comprises walls having a zwitterionic silane coating.

21. The method according to any one of 17-20, wherein the sample is irradiated at an interface between the sample and the container wall.

22. The method according to 21, wherein the monochromatic light source is focused at a position at the interface between the sample and the container wall.

23. The method according to claim 22, wherein the monochromatic light source is focused in the sample at a position of from 0.01 mm to 2 mm from the surface of the container wall.

24. The method according to 22, wherein the monochromatic light source is focused in the sample at a position of about 0.2 mm from the surface of the container wall.

25. The method according to any one of 22-24, wherein the monochromatic light source is focused with a collimating lens.

26. The method according to any one of 1-25, wherein fluorescence produced by the sample and the control is detected from 2500 $cm^{-1}$ to 3500 $cm^{-1}$.

27. The method according to 26, wherein fluorescence produced by the sample and the control is detected at 3000 $cm^{-1}$.

28. The method according to any one of 1-27, wherein the control is a composition that does not include a microorganism.

29. The method according to any one of 1-28, wherein the control is a composition that has the same components as the sample in the absence of microorganism.

30. The method according to any one of 1-29, comprising irradiating each sample over a plurality of intensities with the monochromatic light source.

Systems for Resonant Raman Spectroscopy

1. A system comprising:
   a monochromatic light source;
   a detector; and
   a processor comprising memory operably coupled to the processor wherein the memory comprises instructions stored thereon, which when executed by the processor, cause the processor to:
   irradiate a sample with a monochromatic light source at a first irradiation intensity and a second irradiation intensity;
   determine the intensity of Resonant Raman scattering at the first irradiation intensity and the second irradiation intensity;
   calculate a rate of change of the intensity of Resonant Raman scattering in response to the change in irradiation intensity from the first irradiation intensity to the second irradiation intensity; and
   compare the rate of change in the intensity of Resonant Raman scattering with the rate of change in the irradiation intensity by the monochromatic light source to determine the changes to Resonant Raman response of the sample.

2. The system according to 1, wherein the monochromatic light source is a laser.

3. The system according to 2, wherein the laser is a Nd:YAG laser.

4. The system according to 3, wherein the laser is a frequency-doubled Nd:YAG laser.

5. The system according to any one of 1-4, wherein the detector is a charged coupled device (CCD) detector.

6. The system according to any one of 1-5, wherein the memory further comprises instructions, which when executed by the processor, cause the processor to irradiate the sample over a plurality of intensities by the monochromatic light source over a period of time and determine a rate of change in the intensity of Resonant Raman scattering.

7. The system according to any one of 1-6, wherein the memory further comprises instructions which when executed by the processor, cause the processor to:
   irradiate a first sample over a plurality of intensities by the monochromatic light source for a period of time and determine a rate of change in the intensity of Resonant Raman scattering for the first sample;
   calculate a net signal of the first sample by comparing a normalized rate of change in the intensity of Resonant Raman scattering for the first sample with a normalized rate of change in the irradiation intensity of the first sample by the monochromatic light source;
   irradiate a second sample over a plurality of intensities by the monochromatic light source for the period of time and determine a rate of change in the intensity of Resonant Raman scattering for the second sample; and
   calculate a net signal of the second sample by comparing a normalized rate of change in the intensity of Resonant Raman scattering for the second sample with a normalized rate of change in the irradiation intensity of the second sample by the monochromatic light source.

8. The system according to 7, wherein the memory further comprises instructions which when executed by the processor, cause the processor to determine that the first sample comprises a different gaseous composition from the second sample based on the compared calculated net signals.

9. The system according to 8, wherein the memory further comprises instructions which when executed by the processor, cause the processor to determine that the first sample or the second sample comprises actively metabolizing microorganisms based on the compared calculated net signals.

Systems for Detecting a Microorganism in a Sample

1. A system comprising:
   a monochromatic light source;
   a detector; and
   a processor comprising memory operably coupled to the processor wherein the memory includes instructions stored thereon, which when executed by the processor, cause the processor to:
   irradiate a sample over one or more intensities by a monochromatic light source for a period of time and calculate a rate of change in the intensity of Resonant Raman scattering for the sample;
   calculate a net signal of the sample by comparing a normalized rate of change in the intensity of Resonant Raman scattering for the sample with a normalized rate of change in the irradiation intensity of the sample by the monochromatic light source; and
   determine the presence or absence of a microorganism in the sample based on the calculated net signal of the sample.

2. The system according to 1, wherein the memory further comprises instructions, which when executed by the processor, cause the processor to determine that a microorganism is present when the calculated net signal of the sample is above a predetermined threshold.

2. The system according to 2, wherein the predetermined threshold is a net signal of 1.

3. The system according to any one of 1-2, wherein the monochromatic light source is a laser.

4. The system according to 3, wherein the laser is a solid-state laser that irradiates at 532 nm.

5. The system according to any one of 1-4, wherein the sample comprises a hydrophobic compound non-covalently associated with an albumin protein.

6. The system according to any one of 1-5, wherein the sample comprises a reducing agent.

7. The system according to 6, wherein the reducing agent is glutathione or a derivative thereof.

8. The system according to any one of 6-7, wherein the reducing agent is present in the sample at a concentration of 0.1 mg/mL to 1 mg/m L.

9. The system according to any one of 1-8, further comprising a free radical scavenger.

10. The system according to 9, wherein the free radical scavenger comprises bilirubin or a derivative thereof.

11. The system according to 10, wherein the bilirubin or derivative thereof is present at a concentration of from 0.5 µM to 2 µM.

12. The system according to 11, wherein the bilirubin is present at a concentration of from 0.25 µM to 1.75 µM.

13. The system according to any one of 1-12, wherein the detector is a charge couple device (CCD) detector.

14. The system according to any one of 1-13, wherein further comprising a sample container.

15. The system according to 14, wherein the sample container is a glass vial.

16. The system according to 15, wherein the glass vial comprises walls having a zwitterionic coating.

17. The system according to 16, wherein the glass vial comprises walls having a zwitterionic silane coating.

18. The system according to any one of 14-17, wherein the system is configured to irradiate the sample at an interface between the sample and the container wall.

19. The system according to 18, wherein the monochromatic light source is focused at a position at the interface between the sample and the container wall.

20. The system according to 19, wherein the monochromatic light source is focused in the sample at a position of from 0.01 mm to 2 mm from the surface of the container wall.

21. The system according to 20, wherein the monochromatic light source is focused in the sample at a position of about 0.2 mm from the surface of the container wall.

22. The system according to any one of 19-21, wherein the monochromatic light source is focused with a collimating lens.

23. A system comprising:
   a monochromatic light source;
   a detector; and
   a processor comprising memory operably coupled to the processor wherein the memory includes instructions stored thereon, which when executed by the processor, cause the processor to:
      irradiate a first sample over a plurality of intensities by a monochromatic light source for a period of time and calculate a rate of change in the intensity of Resonant Raman scattering for the first sample;
      calculate a net signal of the first sample by comparing a normalized rate of change in the intensity of Resonant Raman scattering for the first sample with a normalized rate of change in the irradiation intensity of the first sample by the monochromatic light source;
      irradiate a second sample over a plurality of intensities by the monochromatic light source for the period of time and determine a rate of change in the intensity of Resonant Raman scattering for the second sample;
      calculate a net signal of the second sample by comparing a normalized rate of change in the intensity of Resonant Raman scattering for the second sample with a normalized rate of change in the irradiation intensity of the second sample by the monochromatic light source; and
      determine the presence or absence of a microorganism in one or more of the first sample or the second sample by comparing the net signal of the first sample with the net signal of the second sample.

24. The system according to 23, wherein the memory further comprises instructions, which when executed by the processor, cause the processor to determine that a microorganism is present in the second sample when the calculated net signal of the second sample is greater than the calculated net signal of the first sample.

25. The system according to 24, wherein the memory further comprises instructions, which when executed by the processor, cause the processor to determine that a microorganism is present in the first sample when the calculated net signal of the first sample is greater than the calculated net signal of the second sample.

26. The system according to any one of 23-25, wherein the monochromatic light source is a laser.

27. The system according to 26, wherein the laser is a solid-state laser that irradiates at 532 nm.

28. The system according to any one of 23-27, wherein the sample comprises a hydrophobic compound non-covalently associated with an albumin protein.

29. The system according to any one of 23-28, wherein the sample comprises a reducing agent.

30. The system according to 29, wherein the reducing agent is glutathione or a derivative thereof.

31. The system according to any one of 29-30, wherein the reducing agent is present in the sample at a concentration of 0.1 mg/mL to 1 mg/m L.

32. The system according to any one of 23-31, further comprising a free radical scavenger.

33. The system according to 32, wherein the free radical scavenger comprises bilirubin or a derivative thereof.

34. The system according to 33, wherein the bilirubin or derivative thereof is present at a concentration of from 0.5 µM to 2 µM.

35. The system according to 33, wherein the bilirubin is present at a concentration of from 0.25 µM to 1.75 µM.

36. The system according to any one of 70-79, wherein the detector is a charge couple device (CCD) detector.

37. The system according to any one of 23-36, further comprising a sample container.

38. The system according to 37, wherein the sample container is a glass vial.

39. The system according to 38, wherein the glass vial comprises walls having a zwitterionic coating.

40. The system according to 39, wherein the glass vial comprises walls having a zwitterionic silane coating.

41. The system according to any one of 37-40, wherein the system is configured to irradiate the sample at an interface between the sample and the container wall.

42. The system according to 41, wherein the monochromatic light source is focused at a position at the interface between the sample and the container wall.

43. The system according to 42, wherein the monochromatic light source is focused in the sample at a position of from 0.01 mm to 2 mm from the surface of the container wall.

44. The system according to 42, wherein the monochromatic light source is focused in the sample at a position of about 0.2 mm from the surface of the container wall.

45. The system according to any one of 42-44, wherein the monochromatic light source is focused with a collimating lens.

46. A system comprising:
 (a) a monochromatic light source;
 (b) an optical adjustment component;
 (c) a photodetector; and
 (d) a processor comprising memory operably coupled to the processor wherein the memory comprises instructions stored thereon, which when executed by the processor, cause the processor to:
  irradiate a sample in a sample holder with the monochromatic light source at a first irradiation intensity and a second irradiation intensity for preset durations;
  measure scattered light from the sample with the photodetector;
  determine the intensity of Resonant Raman scattering and fluorescence scattering at the first irradiation intensity and the second irradiation intensity;
   calculate a rate of change in the intensity of Resonant Raman scattering and the intensity of fluorescence scattering; and
   correct the rate of change of the intensity of Resonant Raman scattering and the intensity of fluorescence scattering to obtain a net signal.
47. The system according to 46, wherein the optical adjustment component comprises collimating optics mounted on a linear table that is configured to produce an adjustable focal spot.
48. The system according to 46, wherein the optical adjustment component comprises a mechanical shutter.
49. The system according to 46, further comprising a rotary table with a plurality of sample chambers.
50. The system according to 49, wherein the rotary table comprises 8 sample chambers.
51. The system according to 50, further comprising a subsystem for characterizing incoherently scattered light, wherein the subsystem comprises:
 collimating optics; and
 optical adjustment components configured to spread the incoherently scattered light onto a linear array of photodetectors.
52. The system according to 51, wherein the processor further comprises memory with instructions stored thereon, which when executed by the processor, cause the processor to move the collimating optics to focus light on each of the sample chambers.
53. The system according to 46, wherein the sample comprises an albumin with an incorporated ligand.
54. The system according to 1, wherein the memory further comprises instructions which when executed by the processor, cause the processor to:
 determine a rate of change in the intensity of fluorescent scattering from a standard reference sample;
 calculate a net signal as the rate of change in the intensity of the Resonant Raman scattering minus the rate of change in the intensity of fluorescent scattering from the standard sample.
55. The system according to 53 or 54, wherein the memory further comprises instructions which when executed by the processor, cause the processor to:
 determine a rate of change in total output from a standard reference sample;
 calculate a net signal as the rate of change in the intensity of the Resonant Raman scattering minus the rate of change in the intensity of Resonant Raman scattering from the standard sample.
56. The system according to 53 or 54, wherein the memory further comprises instructions which when executed by the processor, cause the processor to compare the net signal with preset thresholds, and to determine that the first sample includes actively metabolizing microorganisms based on the comparison.
57. The system according to 46, wherein the sample comprises a reducing agent.
58. The system according to 57, wherein the sample comprises a disulfide crosslinking agent.
59. The system according to 58, where the disulfide crosslinking agent comprises a core that is cleaved by enzymes or a metabolite produced by the microorganism in the sample.
60. The method according to 59, wherein the crosslinking agent comprises a compound of Formula (I):

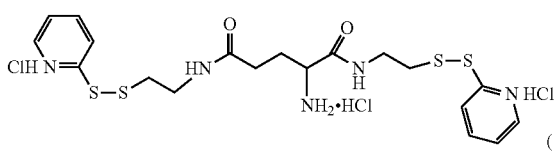

61. The system according to 46, wherein the sample holder is a glass vial.
62. The system according to 46, wherein the sample holder comprises a coating that modifies albumin absorption.
63. The system according to claim 62, wherein the coating comprises a Zwitterionic coating
64. The system according to 46, wherein the processor is configured to expose the sample to the monochromatic light source to minimize the net signal.
65. The system according to 46, wherein the system is configured to irradiate the sample at an interface between the sample and a surface of the sample holder.
66. The system according to 65, wherein the system is configured to maximize the net signal.

Systems for Correcting for Drifts in Laser Power During Non-Linear Raman Spectroscopy 1. A system comprising:
 a monochromatic light source;
 a detector; and
 a processor comprising memory operably coupled to the processor wherein the memory includes instructions stored thereon, which when executed by the processor, cause the processor to:
  irradiate a reference composition over a plurality of intensities by the monochromatic light source for the period of time and determine a rate of change in the intensity of Resonant Raman scattering, wherein the reference composition comprises a reference compound that exhibits no change in the intensity of Resonant Raman scattering in response to the change in irradiation intensity by the monochromatic light source; and
  calculate a net signal of the reference composition by comparing the rate of change in the intensity of Resonant Raman scattering for the reference composition with the rate of change in the irradiation intensity of the reference composition by the monochromatic light source to determine if the monochromatic light source exhibits thermal drift.
2. The system according to 1, wherein the memory further comprises instructions, which when executed by the processor, cause the processor to:
 irradiate a sample over a range of intensities by a monochromatic light source for a period of time and determine a rate of change in the intensity of Resonant Raman scattering;

multiply the net signal of the reference composition with the rate of change of irradiation intensity of the sample by the monochromatic light source to produce a correction factor; and subtract the correction factor from the determined rate of change in the intensity of Resonant Raman scattering for the sample to correct for the thermal drift of the monochromatic light source.

3. The system according to any one of 1-2, wherein the monochromatic light source is a laser.

4. The system according to 3, wherein the laser is a solid-state laser that irradiates at 532 nm.

5. The system according to any one of 1-4, wherein the sample comprises a hydrophobic compound non-covalently associated with an albumin protein.

6. The system according to any one of 1-5, wherein the sample comprises a reducing agent.

7. The system according to 6, wherein the reducing agent is glutathione or a derivative thereof.

8. The system according to any one of 6-7, wherein the reducing agent is present in the sample at a concentration of 0.1 mg/mL to 1 mg/m L.

9. The system according to any one of 1-8, further comprising a free radical scavenger.

10. The system according to 9, wherein the free radical scavenger comprises bilirubin or a derivative thereof.

11. The system according to 10, wherein bilirubin or derivative thereof is present at a concentration of from 0.5 µM to 2 µM.

12. The system according to 10, wherein the bilirubin is present at a concentration of from 0.25 µM to 1.75 µM.

13. The system according to any one of 1-12, wherein the period of time is from 200 seconds to 1500 seconds.

14. The system according to 13, wherein the period of time is 600 seconds.

15. The system according to any one of 1-14, wherein the detector is a charge couple device (CCD) detector.

Systems for Characterizing the Antimicrobial Susceptibility

1. A system comprising:
    a monochromatic light source;
    a detector; and
    a processor comprising memory operably coupled to the processor wherein the memory comprises instructions stored thereon, which when executed by the processor, cause the processor to:
    irradiate a plurality of samples, each sample comprising a microorganism and an antimicrobial agent over a plurality of intensities by the monochromatic light source for a period of time and determine a rate of change in the intensity of Resonant Raman scattering for each irradiated sample, wherein each sample comprises the same concentration of microorganism and different concentrations of antimicrobial agent;
    calculate a net signal for each sample by comparing a normalized rate of change in the intensity of Resonant Raman scattering for each sample with a normalized rate of change in the irradiation intensity of each sample by the monochromatic light source; and
    determine the susceptibility of the microorganism to the antimicrobial agent based on the calculated net signals the plurality of samples.

2. The system according to 1, wherein the memory comprises instructions stored thereon, which when executed by the processor, cause the processor to compare the calculated net signal for each sample.

3. The system according to 2, wherein the memory comprises instructions stored thereon, which when executed by the processor, cause the processor to plot the calculated net signal for each sample as a function of the log of the concentration of antimicrobial agent in each sample.

4. The system according to any one of 2-3, wherein the memory comprises instructions stored thereon, which when executed by the processor, cause the processor to determine the concentration of antimicrobial agent that exhibits a decrease in the net signal.

5. The system according to 4, wherein the memory comprises instructions stored thereon, which when executed by the processor, cause the processor to determine the concentration of antimicrobial agent that exhibits an increase in the net signal.

6. The system according to 1, wherein the memory comprises instructions stored thereon, which when executed by the processor, cause the processor to determine metabolic activity of the microorganism in each sample based on the calculated net signal for each sample.

7. The system according to 6, wherein the memory comprises instructions stored thereon, which when executed by the processor, cause the processor to determine the concentration of antimicrobial agent that exhibits a decrease in metabolic activity.

8. The system according to 6, wherein the memory comprises instructions stored thereon, which when executed by the processor, cause the processor to determine the concentration of antimicrobial agent that exhibits an increase in metabolic activity.

9. The system according to any one of 1-8, wherein each sample comprises a concentration of microorganism of 10 colony forming units (CFU) or more.

10. The system according to 9, wherein each sample comprises a concentration of microorganism of 14 CFU or more.

11. The system according to any one of 1-10, wherein the concentration of antimicrobial agent in the plurality of samples ranges from a concentration that is below the minimum inhibitory concentration of the antimicrobial agent to a concentration that is greater than the minimum bactericidal concentration of the antimicrobial agent.

12. The system according to any one of 1-11, wherein the sample comprises a reducing agent.

13. The system according to 12, wherein the reducing agent is glutathione or a derivative thereof.

14. The system according to any one of 12-13, wherein the reducing agent is present in the sample at a concentration of 0.1 mg/mL to 1 mg/m L.

15. The system according to any one of 1-14, wherein further comprising a sample container.

16. The system according to 15, wherein the sample container is a glass vial.

17. The system according to 16, wherein the glass vial comprises walls having a zwitterionic coating.

18. The system according to 17, wherein the glass vial comprises walls having a zwitterionic silane coating.

19. The system according to any one of 15-18, wherein the system is configured to irradiate the sample at an interface between the sample and the container wall.

20. The system according to 19, wherein the monochromatic light source is focused at a position at the interface between the sample and the container wall.

21. The system according to 20, wherein the monochromatic light source is focused in the sample at a position of from 0.01 mm to 2 mm from the surface of the container wall.

22. The system according to 20, wherein the monochromatic light source is focused in the sample at a position of about 0.2 mm from the surface of the container wall.

23. The system according to any one of 20-22, wherein the monochromatic light source is focused with a collimating lens.
24. The system according to any one of 1-23, wherein the detector is a charge couple device (CCD) detector.

Systems for Phenotyping an Unknown Microorganism

1. A system comprising:
    a monochromatic light source;
    a detector; and
    a processor comprising memory operably coupled to the processor wherein the memory comprises instructions stored thereon, which when executed by the processor, cause the processor to:
        irradiate with a monochromatic light source a sample comprising a microorganism, a crosslinking agent and an albumin protein over a plurality of intensities by the monochromatic light source for a period of time and determine a rate of change in the intensity of Resonant Raman scattering;
        calculate a net signal for the sample by comparing a normalized rate of change in the intensity of Resonant Raman scattering for the sample with a normalized rate of change in the irradiation intensity of the sample by the monochromatic light source; and
        determine crosslink cleavage based on the calculated net signal of the sample, wherein the extent of crosslink cleavage is indicative of the phenotype of the microorganism.
2. The system according to 1, wherein the crosslinking agent is a disulfide crosslinker.
3. The system according to any one of 1-2, wherein the crosslinking agent is a glutamic acid derivative.
4. The system according to 3, wherein the crosslinking agent comprises a compound of Formula (I):

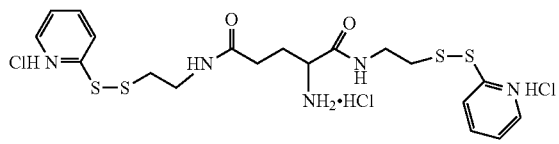

5. The system according to any one of 1-4, wherein the crosslinking agent is present in the sample in an amount such that the molar ratio of crosslinking agent to albumin protein is from 1:10 to 10:1.
6. The system according to 5, wherein the crosslinking agent is present in the sample in an amount such that the molar ratio of crosslinking agent to albumin protein is about 1:2.
7. The system according any one of 1-6, wherein an increase over time in the calculated net signal of the sample is indicative that the microorganism produces a metabolite that cleaves one or more crosslinks in the albumin protein.
8. The system according to any one of 1-7, wherein the monochromatic light source is a laser.
9. The system according to 8, wherein the laser is a solid-state laser that irradiates at 532 nm.
10. The system according to any one of 1-9, wherein the sample comprises a hydrophobic compound and an albumin protein.
11. The system according to 10, wherein the hydrophobic compound is a carotenoid.
12. The system according to 11, wherein the hydrophobic compound is lycopene.
13. The system according to any one of 10-12, wherein the hydrophobic compound is non-covalently associated with the albumin protein.
14. The system according to any one of 1-13, wherein the sample comprises a reducing agent.
15. The system according to 14, wherein the reducing agent is glutathione or a derivative thereof.
16. The system according to any one of 14-15, wherein the reducing agent is present in the sample at a concentration of 0.1 mg/mL to 1 mg/m L.
17. The system according to any one of 1-16, further comprising a sample container.
18. The system according to 17, wherein the sample container is a glass vial.
19. The system according to 18, wherein the glass vial comprises walls having a zwitterionic coating.
20. The system according to 19, wherein the glass vial comprises walls having a zwitterionic silane coating.
21. The system according to any one of 17-20, wherein the system is configured to irradiate the sample at an interface between the sample and the container wall.
22. The system according to 21, wherein the monochromatic light source is focused at a position at the interface between the sample and the container wall.
23. The system according to 22, wherein the monochromatic light source is focused in the sample at a position of from 0.01 mm to 2 mm from the surface of the container wall.
24. The system according to 22, wherein the monochromatic light source is focused in the sample at a position of about 0.2 mm from the surface of the container wall.
25. The system according to any one of 22-24, wherein the monochromatic light source is focused with a collimating lens.
26. The system according to any one of 1-25, wherein the detector is a charge couple device (CCD) detector.

Systems for Detecting a Microorganism in a Sample Via Fluorescence

1. A system comprising:
    a monochromatic light source;
    a detector; and
    a processor comprising memory operably coupled to the processor wherein the memory includes instructions stored thereon, which when executed by the processor, cause the processor to:
        irradiate a sample by a monochromatic light source for a period of time and detect fluorescence from the sample over the period of time;
        calculate a rate of change of the fluorescence due to the presence of microorganisms by comparing a normalized rate of change in the intensity of the detected fluorescence produced by the sample with a normalized rate of change in fluorescence from a control; and
        determine the presence or absence of a microorganism in the sample based on the calculated rate of change of fluorescence of the sample.
2. The system according to 1, wherein the memory further comprises instructions, which when executed by the processor, cause the processor to determine that a microorganism is present when the calculated rate of change of fluorescence is above a predetermined threshold.
3. The system according to any one of 1-2, wherein the monochromatic light source is a laser.
4. The system according to 3, wherein the laser is a solid-state laser that irradiates at 532 nm.
5. The system according to any one of 1-4, wherein the sample comprises a hydrophobic compound non-covalently associated with an albumin protein.

6. The system according to any one of 1-5, wherein the sample comprises a reducing agent.

7. The system according to 6, wherein the reducing agent is glutathione or a derivative thereof.

8. The system according to any one of 6-7, wherein the reducing agent is present in the sample at a concentration of 0.1 mg/mL to 1 mg/mL.

9. The system according to any one of 1-8, wherein the detector is a charge couple device (CCD) detector.

10. The system according to any one of 1-9, wherein further comprising a sample container.

11. The system according to 10, wherein the sample container is a glass vial.

12. The system according to 11, wherein the glass vial comprises walls having a zwitterionic coating.

13. The system according to 12, wherein the glass vial comprises walls having a zwitterionic silane coating.

14. The system according to any one of 11-13, wherein the system is configured to irradiate the sample at an interface between the sample and the container wall.

15. The system according to 14, wherein the monochromatic light source is focused at a position at the interface between the sample and the container wall.

16. The system according to 15, wherein the monochromatic light source is focused in the sample at a position of from 0.01 mm to 2 mm from the surface of the container wall.

17. The system according to 16, wherein the monochromatic light source is focused in the sample at a position of about 0.2 mm from the surface of the container wall.

18. The system according to any one of 15-17, wherein the monochromatic light source is focused with a collimating lens.

19. The system according to any one of 1-18, wherein fluorescence produced by the sample and the control is detected from 2500 cm$^{-1}$ to 3500 cm$^{-1}$.

20. The system according to 19, wherein fluorescence produced by the sample and the control is detected at 3000 cm$^{-1}$.

21. The system according to any one of 1-20, wherein the control is a composition that does not include a microorganism.

22. The system according to any one of 1-21, wherein the microorganism is a pathogenic microorganism.

23. The system according to any one of 1-22, wherein the control is a composition that has the same components as the sample in the absence of microorganism.

24. The system according to any one of 1-23, wherein the system is configured to irradiate a sample over a plurality of intensities with the monochromatic light source.

Systems for Characterizing the Antimicrobial Susceptibility

1. A system comprising:
    a monochromatic light source;
    a detector; and
    a processor comprising memory operably coupled to the processor wherein the memory includes instructions stored thereon, which when executed by the processor, cause the processor to:
        irradiate a plurality of samples comprising a microorganism, each sample comprising a microorganism and an antimicrobial agent, with the monochromatic light source for a period of time and detecting fluorescence from each of the irradiated samples over the period of time, wherein each sample comprises the same concentration of microorganism and different concentrations of antimicrobial agent;
        calculate a rate of change of the fluorescence in each sample by comparing a normalized rate of change in the intensity of the detected fluorescence produced by each sample with a normalized rate of change of fluorescence produced by a control; and
        determine the susceptibility of the microorganism to the antimicrobial agent based on the calculated rate of change of the fluorescence of the plurality of samples.

2. The system according to 1, wherein the memory further comprises instructions, which when executed by the processor, cause the processor to compare the calculated rate of change of fluorescence for each sample.

3. The system according to 2, wherein comparing comprises plotting the calculated rate of change of fluorescence for each sample as a function of the log of the concentration of antimicrobial agent in each sample.

4. The system according to 1, wherein the memory further comprises instructions, which when executed by the processor, cause the processor to determine the concentration of antimicrobial agent that exhibits a decrease in the rate of change of fluorescence.

5. The system according to 1, wherein the memory further comprises instructions, which when executed by the processor, cause the processor to determine the concentration of antimicrobial agent that exhibits an increase in the rate of change of fluorescence.

6. The system according to 1, wherein the memory further comprises instructions, which when executed by the processor, cause the processor to determine metabolic activity of the microorganism in each sample based on the calculated rate of change of fluorescence for each sample.

7. The system according to 1, wherein the memory further comprises instructions, which when executed by the processor, cause the processor to determine the concentration of antimicrobial agent that exhibits a decrease in metabolic activity.

8. The system according to 1, wherein the memory further comprises instructions, which when executed by the processor, cause the processor to determine the concentration of antimicrobial agent that exhibits an increase in metabolic activity.

9. The system according to any one of 1-8, wherein each sample comprises a concentration of microorganism of 10 colony forming units (CFU) or more.

10. The system according to 9, wherein each sample comprises a concentration of microorganism of 14 CFU or more.

11. The system according to 9, wherein each sample is aliquoted from a microorganism composition having a concentration of microorganism of 100 colony forming units (CFU) or more.

12. The system according to any one of 1-11, wherein the concentration of antimicrobial agent in the plurality of samples ranges from a concentration that is below the minimum inhibitory concentration of the antimicrobial agent to a concentration that is greater than the minimum bactericidal concentration of the antimicrobial agent.

13. The system according to any one of 1-12, wherein the antimicrobial agent is incubated with the microorganism for a predetermined period of time before irradiating the sample.

14. The system according to 13, wherein the antimicrobial agent is incubated with the microorganism for 10 minutes or more.

15. The system according to 13, wherein the antimicrobial agent is incubated with the microorganism for 20 minutes or more.

16. The system according to any one of 1-15, wherein the sample comprises a reducing agent.

17. The system according to 16, wherein the reducing agent is glutathione or a derivative thereof.

18. The system according to any one of 16-17, wherein the reducing agent is present in the sample at a concentration of 0.1 mg/mL to 1 mg/m L.
19. The system according to any one of 1-18, wherein the sample is irradiated in a sample container.
20. The system according to 19, wherein the sample container is a glass vial.
21. The system according to 20, wherein the glass vial comprises walls having a zwitterionic coating.
22. The system according to 21, wherein the glass vial comprises walls having a zwitterionic silane coating.
23. The system according to any one of 19-22, wherein the system is configured to irradiate the sample at an interface between the sample and the container wall.
24. The system according to 23, wherein the monochromatic light source is focused at a position at the interface between the sample and the container wall.
25. The system according to 24, wherein the monochromatic light source is focused in the sample at a position of from 0.01 mm to 2 mm from the surface of the container wall.
26. The system according to 24, wherein the monochromatic light source is focused in the sample at a position of about 0.2 mm from the surface of the container wall.
27. The system according to any one of 24-27, wherein the monochromatic light source is focused with a collimating lens.
28. The system according to any one of 1-27, wherein the system is configured to detect fluorescence produced by the sample and the control from 2500 cm$^{-1}$ to 3500 cm$^{-1}$.
29. The system according to 28, wherein the system is configured to detect fluorescence produced by the sample and the control at 3000 cm$^{-1}$.
30. The system according to any one of claims 1-29, wherein the control is a composition that does not include a microorganism.
31. The system according to any one of 1-30, wherein the control is a composition that has the same components as the sample in the absence of microorganism.
32. The system according to any one of 1-31, wherein the system is configured to irradiate each sample over a plurality of intensities with the monochromatic light source.

Systems for Phenotyping an Unknown Microorganism
1. A system comprising:
 a monochromatic light source;
 a detector; and
 a processor comprising memory operably coupled to the processor wherein the memory includes instructions stored thereon, which when executed by the processor, cause the processor to:
  irradiate with a monochromatic light source a sample comprising a microorganism, a crosslinking agent and an albumin protein for a period of time and detect fluorescence from the sample over the period of time;
  calculate a rate of change of the fluorescence by comparing a normalized rate of change in the intensity of the detected fluorescence produced by the sample with a normalized rate of change of fluorescence produced by a control; and
  determine crosslink cleavage based on the calculated rate of change of fluorescence of the sample, wherein the extent of crosslink cleavage is indicative of the phenotype of the microorganism.
2. The system according to 1, wherein the crosslinking agent is a disulfide crosslinker.
3. The system according to any one of 1-2, wherein the crosslinking agent is a glutamic acid derivative.

4. The system according to 3, wherein the crosslinking agent comprises a compound of Formula (I):

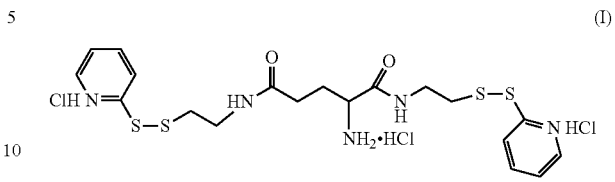

5. The system according to any one of 1-4, wherein the crosslinking agent is present in the sample in an amount such that the molar ratio of crosslinking agent to albumin protein is from 1:10 to 10:1.
6. The system according to 5, wherein the crosslinking agent is present in the sample in an amount such that the molar ratio of crosslinking agent to albumin protein is about 1:2.
7. The system according any one of 1-6, wherein an increase in the calculated rate of change in the fluorescence of the sample causes the processor to indicate that the microorganism produces a metabolite that cleaves one or more crosslinks in the albumin protein.
8. The system according to any one of 1-7, wherein the monochromatic light source is a laser.
9. The system according to 8, wherein the laser is a solid-state laser that irradiates at 532 nm.
10. The system according to any one of 1-9, wherein the sample comprises a hydrophobic compound and an albumin protein.
11. The system according to 10, wherein the hydrophobic compound is a carotenoid.
12. The system according to 11, wherein the hydrophobic compound is lycopene.
13. The system according to any one of 10-12, wherein the hydrophobic compound is non-covalently associated with the albumin protein.
14. The system according to any one of 1-13, wherein the sample comprises a reducing agent.
15. The system according to 14, wherein the reducing agent is glutathione or a derivative thereof.
16. The system according to any one of 14-15, wherein the reducing agent is present in the sample at a concentration of 0.1 mg/mL to 1 mg/m L.
17. The system according to any one of 1-16, wherein the system is configured to irradiate the sample in a sample container.
18. The system according to 17, wherein the sample container is a glass vial.
19. The system according to 18, wherein the glass vial comprises walls having a zwitterionic coating.
20. The system according to 19, wherein the glass vial comprises walls having a zwitterionic silane coating.
21. The system according to any one of 17-20, wherein the system is configured to irradiate the sample at an interface between the sample and the container wall.
22. The system according to 21, wherein the monochromatic light source is focused at a position at the interface between the sample and the container wall.
23. The system according to 22, wherein the monochromatic light source is focused in the sample at a position of from 0.01 mm to 2 mm from the surface of the container wall.
24. The system according to 22, wherein the monochromatic light source is focused in the sample at a position of about 0.2 mm from the surface of the container wall.

25. The system according to any one of 22-24, wherein the monochromatic light source is focused with a collimating lens.
26. The system according to any one of 1-25, wherein the system is configured to detect fluorescence produced by the sample and the control from 2500 cm$^{-1}$ to 3500 cm$^{-1}$.
27. The system according to 26, wherein the system is configured to detect fluorescence produced by the sample and the control at 3000 cm$^{-1}$.
28. The system according to any one of 1-27, wherein the control is a composition that does not include a microorganism.
29. The system according to any one of 1-28, wherein the control is a composition that has the same components as the sample in the absence of microorganism.
30. The system according to any one of 1-29, wherein the system is configured to irradiate a sample over a plurality of intensities with the monochromatic light source.

EXPERIMENTAL

As can be appreciated from the disclosure provided above, the present disclosure has a wide variety of applications. The following examples are put forth so as to provide those of ordinary skill in the art with a complete disclosure and description of how to make and use the present invention, and are not intended to limit the scope of the invention nor are they intended to represent that the experiments below are all or the only experiments performed. Those of skill in the art will readily recognize a variety of noncritical parameters that could be changed or modified to yield essentially similar results. Efforts have been made to ensure accuracy with respect to numbers used (e.g. amounts, temperature, etc.) but some experimental errors and deviations should be accounted for.

Methods

An example of the subject methods includes a Raman spectrometer built around a laser whose wavelength is close to an absorption bandgap that is affected by changes in the excited state of the molecule being probed. With respect to a system that comprises lycopene incorporated into albumin, a laser with wavelength 532 nm is used because this wavelength is at the tail of the lycopene absorption triplet, and is affected by changes in the excited state. The system also includes a component that modulates the laser intensity over time by small amounts.

Laser light at 532 nm is generated with an optical pump at 808 nm that pumps a cavity at 1064 nm, and which is Q-switched to 532 nm in an external cavity. The output of the final Q-switching cavity is very sensitive to pointing direction, which in turn is very sensitive to temperature. In turn, the temperature changes with heat buildup (and dissipation) from within the cavity. Thus, changes to the current applied in the pump laser do not always manifest as changes in the 532 nm laser light output from the external cavity.

It was found that slight changes in the temperature of the external cavity can affect the power output from the laser, and so any mechanism that affects this can be used to modulate the laser power. In one embodiment, it was determined that varying the CCD shutter time (i.e., the time used to acquire data in the CCD) affects the laser power. In this example, the frequency with which data is shifted out of the CCD affects the heat buildup within the CCD, which then affects the temperature of the external laser cavity that is in thermal proximity with the CCD.

The subject systems were configured to measure the time dependent changes in the Resonant Raman intensity, as the laser intensity is being modulated. The rate of change of the normalized Resonant Raman intensity is compared against the rate of change of normalized laser intensity. In order to minimize measurement errors, this comparison can be made at multiple normalized rates of changes of laser intensity. To eliminate any systematic differences between the control parameter used to modulate laser intensity and the resultant laser modulation, the laser power was characterized by using a reference composition that provides a characteristic Raman spectrum whose intensity does not change with laser power. In one example, NIST SRM 2242 was used which provides a broad Raman spectrum with 532 nm light. An example of non-linear Resonant Raman spectroscopy according to the present disclosure is depicted in FIG. 1.

The slope of the trace in FIG. 1 is the calculated net signal. If the slope is not equal to 1, then it indicates that the 2$^{nd}$ term in $$\frac{1}{I_R}\frac{\delta I_R}{\delta t} = \frac{1}{I_o}\frac{\delta I_o}{\delta t} + \frac{\delta \ln \sum |(\alpha_{ij})_{mn}|^2}{\delta t}$$

Equation 2 (the polarizability terms) is not equal to zero. This can either indicate a change being brought about by the laser itself, or a change being brought about by a physical or chemical change in the sample.

Example 1

Figure 2:
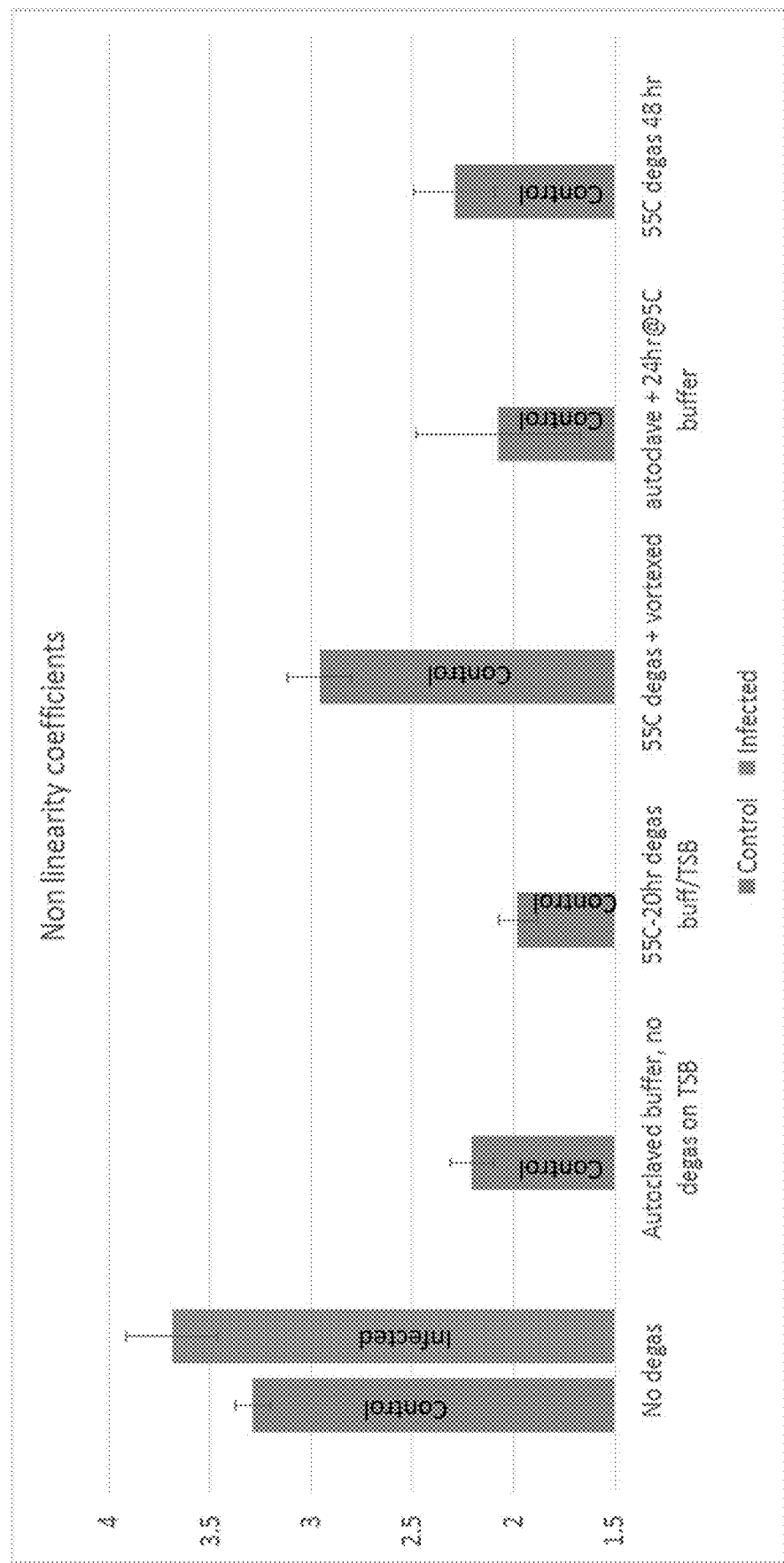
FIG. 2 depicts variation in the nonlinearity coefficient with the amount of dissolved gases (and super saturated gases) present in the liquid according to certain embodiments.

FIG. 2 depicts an example of non-linear Resonant Raman spectroscopy for characterizing small changes in a composition. The samples contain lycopene that is non-covalently associated into albumin (as described in U.S. Patent Publication No. 2016/0324933, the disclosure of which is herein incorporated by reference), to which a nutritional buffer was added to support microbial metabolism, and a buffer that maintains the pH at 7.2.

In these examples, non-linear Resonant Raman spectroscopy measures the Resonant Raman spectrum of lycopene and the magnitude of the Raman peaks are a sensitive function of small changes in the composition. Since the lycopene is incorporated into albumin, the non-linearity of the Resonant Raman response (i.e., the calculated non-linear Resonant Raman coefficient) characterizes the environment provided by albumin, and since albumin is designed to solubilize molecules that are insoluble in water, the non-linearity of the Resonant Raman will respond to the amount of insoluble molecules present in the solution.

In this example, the amount of gases present in the sample is characterized by the non-linearity of the Resonant Raman response. Common gases (like oxygen, nitrogen and carbon dioxide) are somewhat soluble in water, with the solubility decreasing as temperature increases. Thus, when one, or more parts of the test sample are heated to a high temperature (such as 55° C.) for long enough, then the dissolved gases become supersaturated and nucleate out via a time dependent process. When this liquid is then cooled to 37° C., the liquid becomes undersaturated with respect to the dissolved gases. If this undersaturated liquid is mixed in with the album in/lycopene reagent that is nominally stored at 4° C. (and is therefore saturated with gases at 4° C., and supersaturated at 37° C.), then the mixture can become undersaturated with respect to the dissolved gases. In this scenario, some of the dissolved gases that had partitioned into albumin will migrate to the solution, and reduce the amount of gases incorporated into albumin. Thus, by varying the amount of the undersaturated liquid (and the degree of undersaturation), the environment around the lycopene is varied, and is characterized by changes in the Resonant Raman non-linearity.

FIG. 2 illustrates the non-linearity of the Resonant Raman non linearity coefficient with respect to different liquid formulations that all contain the album in/lycopene reagent. The first example depicts a comparison between the reagent that has been stored at 5° C. for several weeks, and tested at 37° C. (and is therefore supersaturated with gases at 37° C.). The non-linearity coefficient of the reagent itself is 3.3. When bacteria (at a concentration of 10 CFU/mL) is added to the solution, the non-linearity coefficient increases to 3.7

Example 2

Bilirubin is a powerful antioxidant present in serum and has very weak optical absorption at 532 nm. In this example, bilirubin is used to control the signal in non-linear Resonant Raman spectroscopy and is used to improve signal-to-noise ratio when characterizing test samples.

Figure 3:
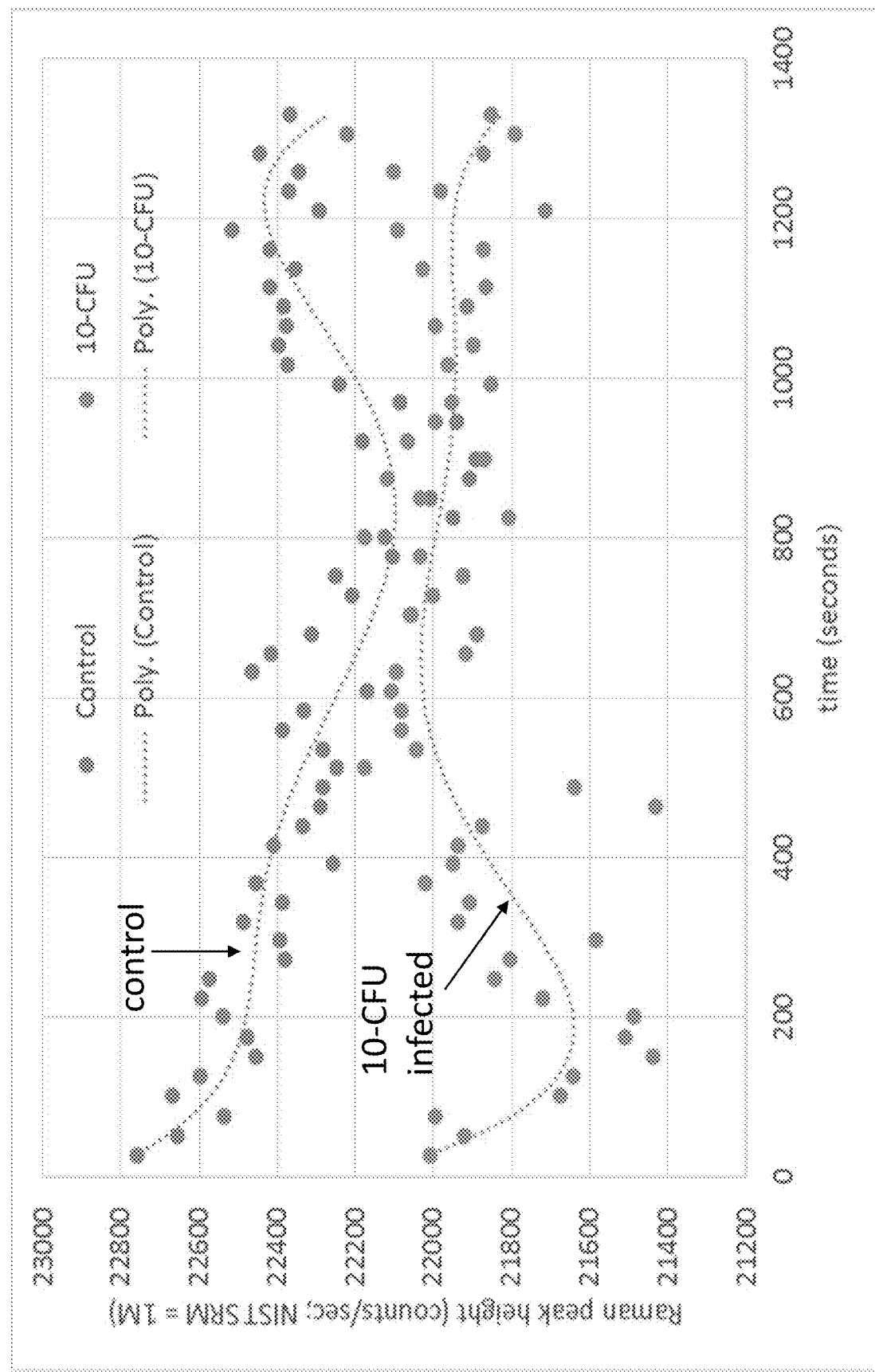
FIG. 3 depicts average Resonant Raman scattering peak height from 4 uninfected control samples and 3 samples infected with 10 CFUs of S. aureus.
Figure 4:
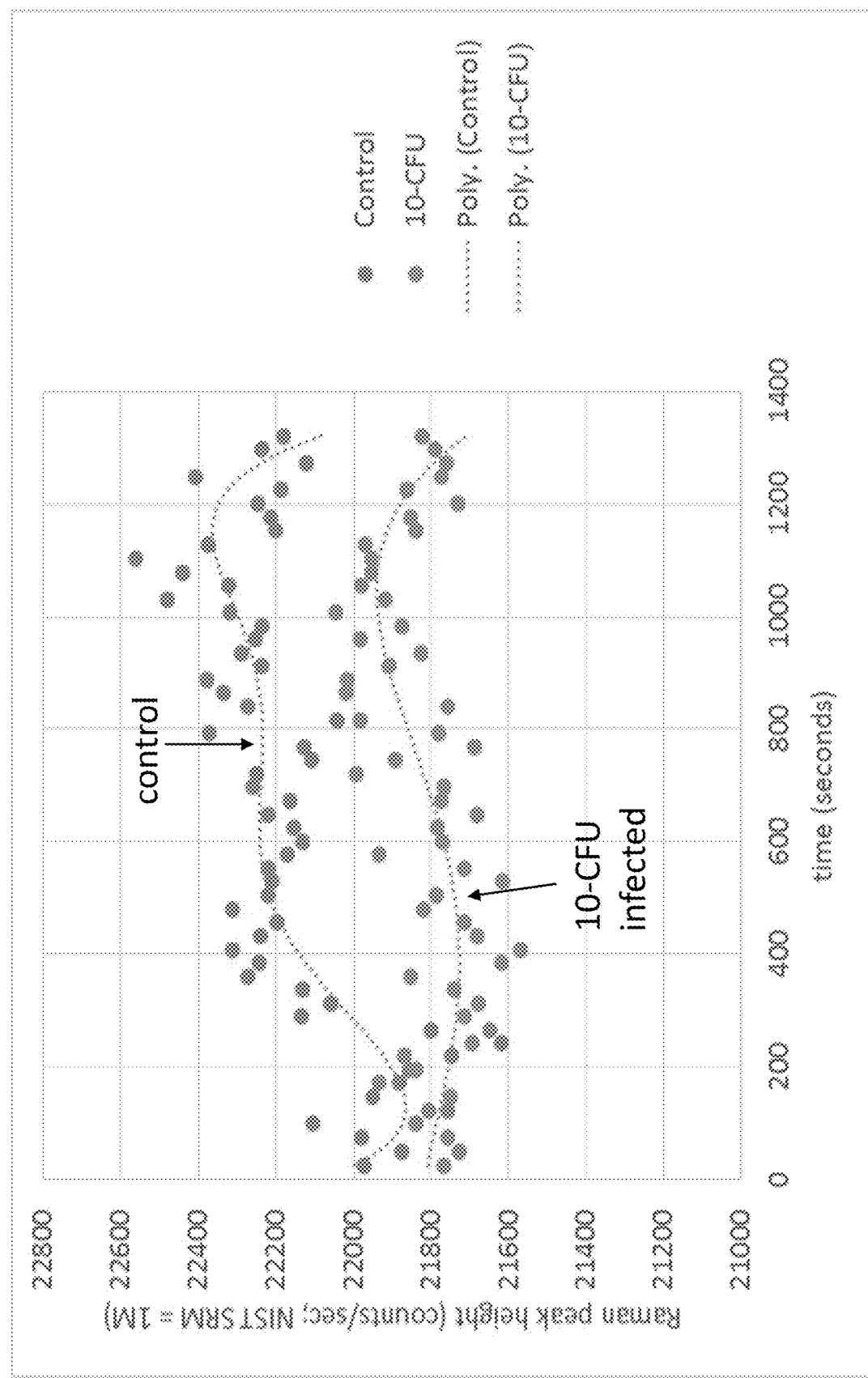
FIG. 4 depicts average Resonant Raman scattering peak height from 4 uninfected control samples and 3 samples infected with 10 CFUs of S. aureus, each composition including 1 μM of bilirubin.

In the samples described, bilirubin is added and is non-covalently associated with an albumin protein. FIGS. 3 and 4 depict the effect of bilirubin on the average Resonant Raman peak intensity. FIG. 3 depicts the average Raman peak height from 4 uninfected control samples and 3 samples infected with 10 CFUs of S. aureus. In all cases, the reagent includes lycopene incorporated into albumin and diluted into 4 mL of buffer medium and containing 0.5× of a nutritional broth to enable bacteria metabolism. FIG. 4 depicts the average Raman peak height from 4 uninfected control samples and 3 samples infected with 10 CFUs of S. aureus with 1 µM of added bilirubin. By comparison with FIG. 3, the dip in the infected samples has moved out to longer timescales (450 vs 200 seconds), and the uninfected control sample does not show a dip any longer.

Figure 5:
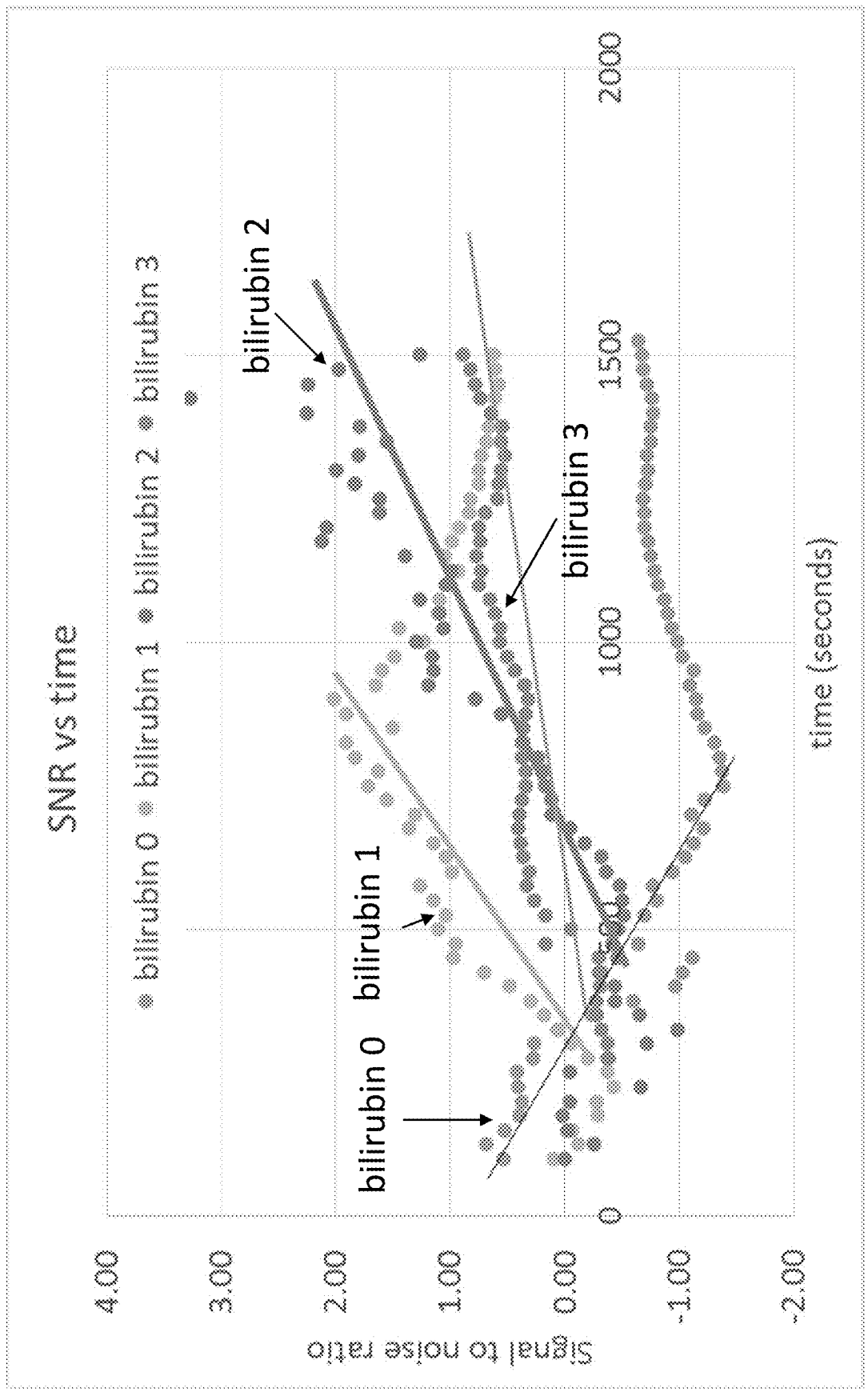
FIG. 5 depicts the signal-to-noise ratio of control samples and those with 10 CFU of S. aureus according to certain embodiments.

FIG. 5 depicts determining the signal-to-noise ratio for the above described samples. In this example, the "signal" is the difference in the average rates of change of the intensity of Resonant Raman peaks, computed using a linear fit from t=0 to the time denoted on the X axis, for the uninfected control samples and those with 10 CFU of S. aureus; and "noise" is the sum of the standard deviations around the average rates of change for the control and 10 CFU samples. The signal-to-noise ratio is plotted as a function of time (on the X axis) and the amount of added bilirubin in µM, denoted in the legend). As more bilirubin is added, the signal builds up more slowly, and is also less likely to revert to a negative value.

Figure 6:
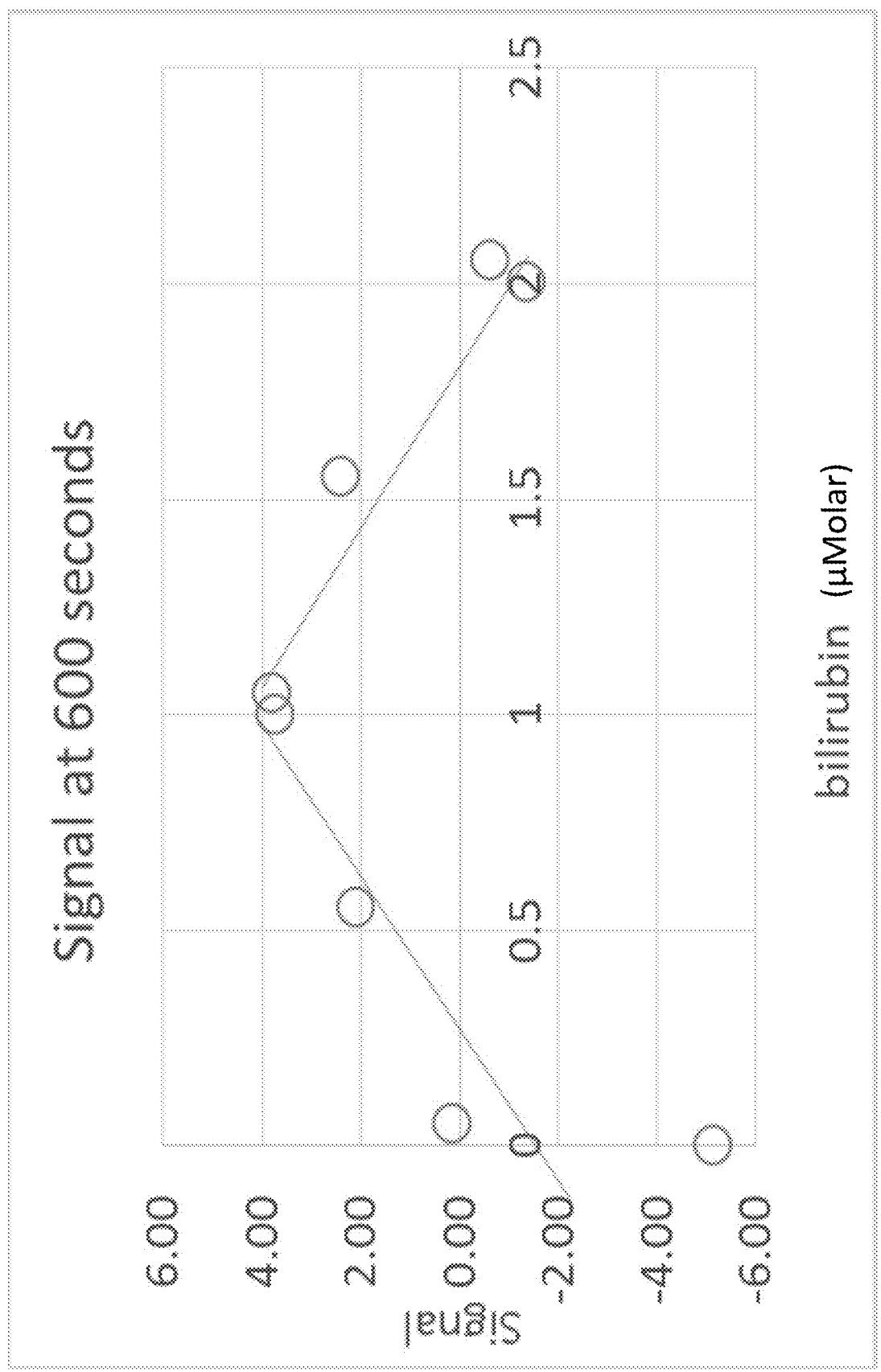
FIG. 6 depicts a plot of the signal for Resonant Raman scattering estimated at t=600 seconds, plotted as a function of added bilirubin according to certain embodiments.

FIG. 6 depicts the signal from the above described samples, estimated at time=600 seconds, plotted as a function of added bilirubin (in µM, denoted in the legend). For this timescale, 1 µM bilirubin is determined to be an optimized amount of bilirubin. At higher bilirubin levels, the signal does not have sufficient time to build up, and at lower bilirubin levels, the signal has already built up to it's maximum value and is decaying down to lower levels.

Example 3

Without being bound to any particular theory or mechanism of action, bilirubin in the subject methods enhances the signal in non-linear Resonant Raman spectroscopy by: (a) scavenging free radicals generated by the laser light. This reduces the artifact that can interfere with the signal, and so reduces the standard deviation around the control samples. Thus, the standard deviation around the average rates of change of the lycopene peaks in uninfected samples decreases as bilirubin is added to the assay (b) scavenging free radicals generated by the metabolic activity of the microorganism present in the sample. This can slow down the changes caused by the microorganism, in particular when changes to the sample are too rapid to observe cleanly in the absence of bilirubin.

Figure 7:
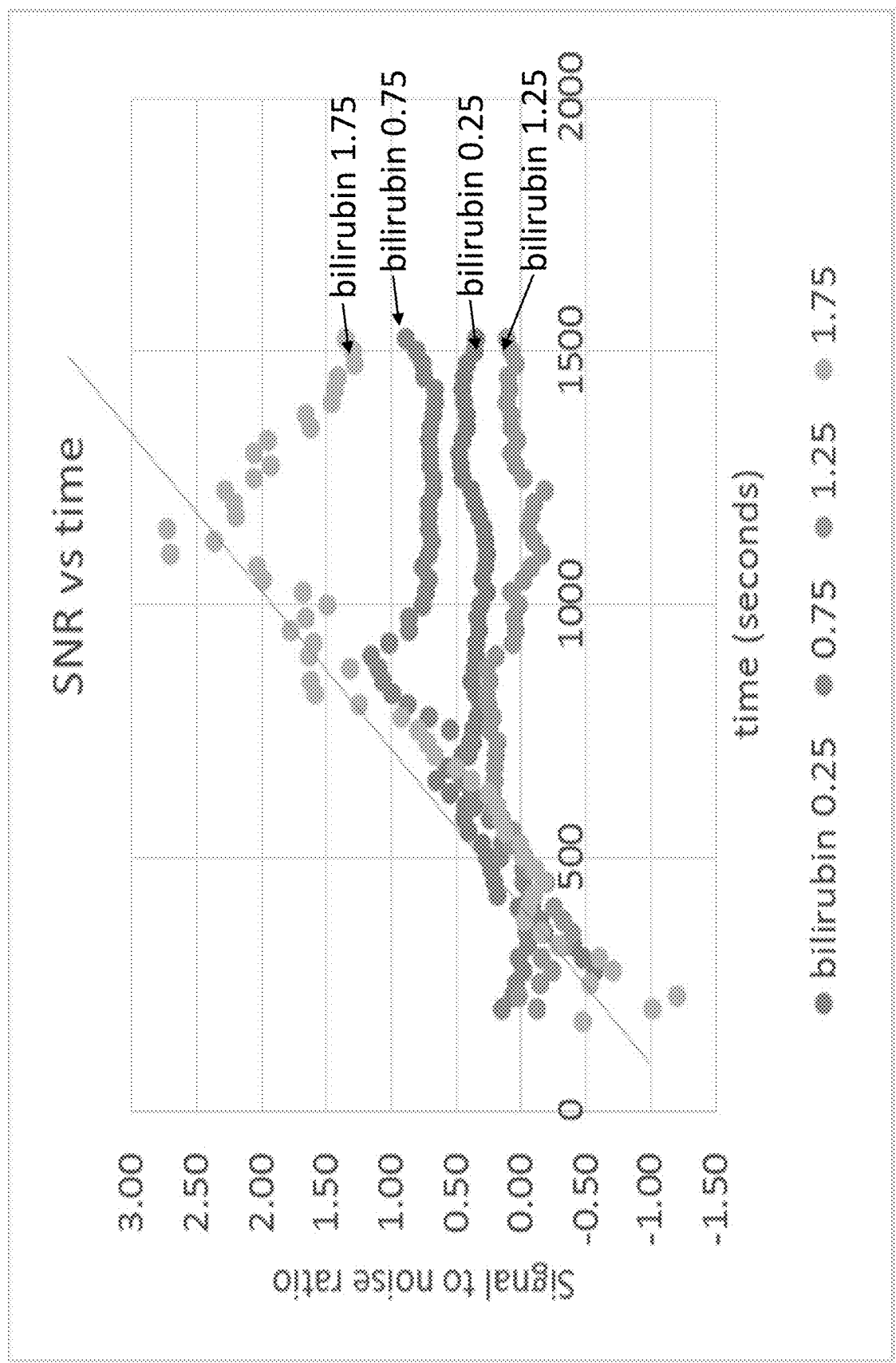
FIG. 7 depicts the variation of the signal to noise ratio for compositions having different amounts of bilirubin plotted as a function of time of experiment according to certain embodiments.

FIG. 7 shows a plot of the signal-to-noise ratio of samples that contain lycopene non-covalently associated with an albumin protein and different amounts of bilirubin as a function of data collection time. The signal-to-noise ratio is maximized along various points along the line depicted in the figure, and attains a maximum value at different points along the line. Variation of the signal to noise ratio SNR (where "Signal" is the difference between the average rate of change of the lycopene peaks for an uninfected control sample, and that in a sample infected with 10 CFUs of S aureus & "Noise" is the sum of the standard deviations around the two averages) with the time of experiment. In all cases, the slopes are calculated from t=0 to the time indicated on the X axis, so an increase in the SNR reflects a decrease in the standard deviations (which is due to a decrease in the confidence interval around the estimated slopes). The signal to noise ratio is plotted against time (on the X axis) and for a varying amount of bilirubin present in the assay (in the legend, in µM). The signal to noise ratio decreases when the signal starts to decrease because the time dependent Raman profile in the infected samples show a dip~for experiments conducted beyond the timescale of this tip, the magnitude of the signal decreases.

Figure 8:
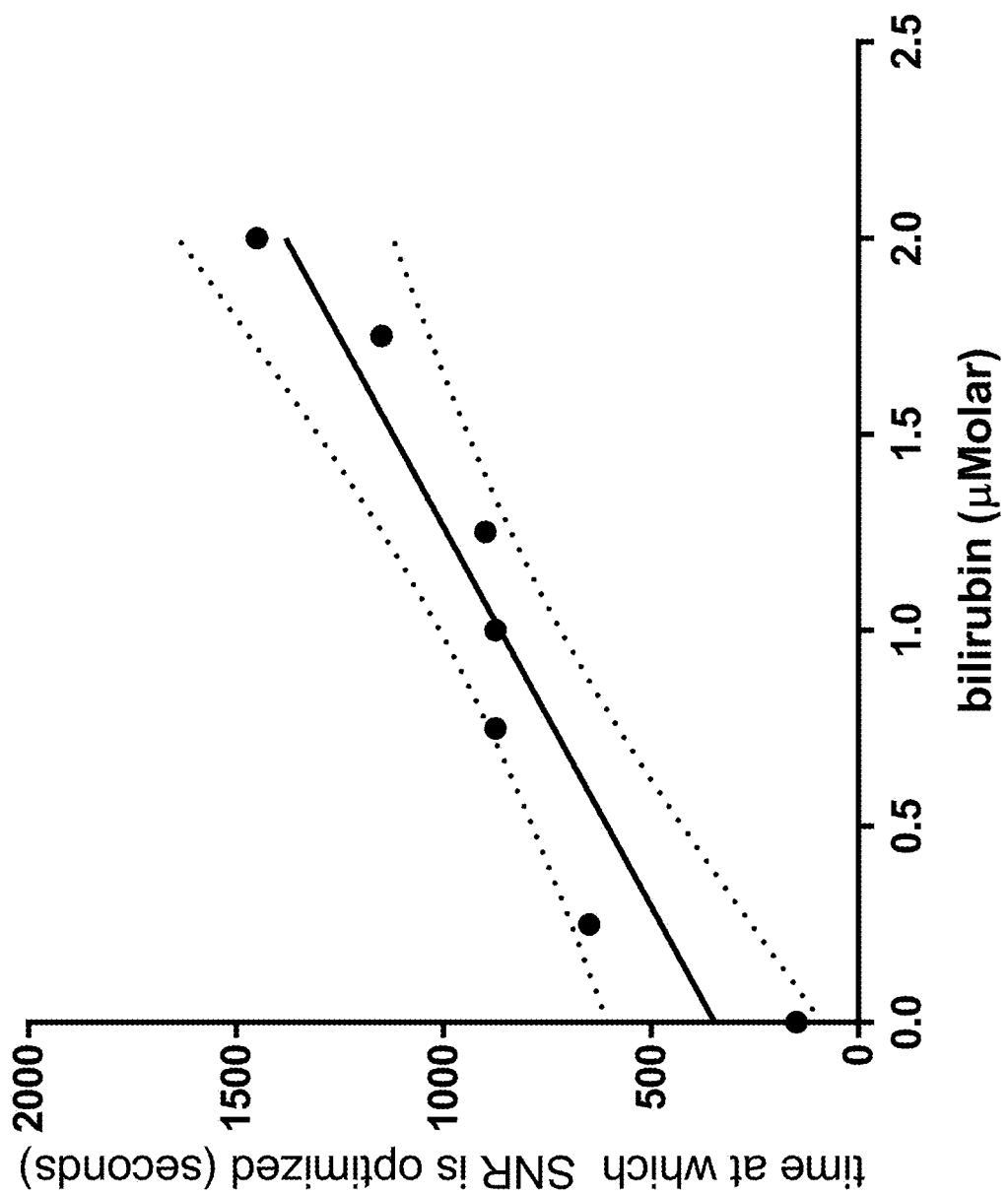
FIG. 8 depicts the variation in the timescale at which the signal-to-noise ratio is optimized with the amount of bilirubin present in the assay according to certain embodiments.

FIG. 8 plots the time points at which signal to noise ratio is maximized against the added bilirubin concentration. As the bilirubin concentration is increased, the optimal time-point increases, which makes the diagnostic test more reliable. Bilirubin has an absorption spectrum that is just slightly blue shifted for absorption at 532 nm. This means that while it does not contribute to the Raman signal in a significant manner, it could have a $2^{nd}$ order effect via the Raman enhancement or deenhancement effect. The intensity of a resonance Raman peak is proportional to the square of the scattering cross section. The scattering cross section, in turn, is related to the square of the transition dipole moment and thus usually follows the absorption spectrum. However, if there is another electronic state nearby, the Raman intensity is proportional to the square of the sum of the cross sections. If the cross sections are of opposite sign, destructive interference can occur, resulting in resonance deenhancement. If both bilirubin and lycopene are present in the albumin, then it is possible that destructive/constructive interference is occurring between the excited states, and this interference is altered as bilirubin degrades by scavenging free radicals. It has been found that other free radical scavengers (including hydrophilic ones such as glutathione and ascorbic acid and hydrophobic ones such as butylated hydroxytoulene incorporated into albumin) do not have a similar effect on the diagnostic signal.

Example 4

Figure 9A:
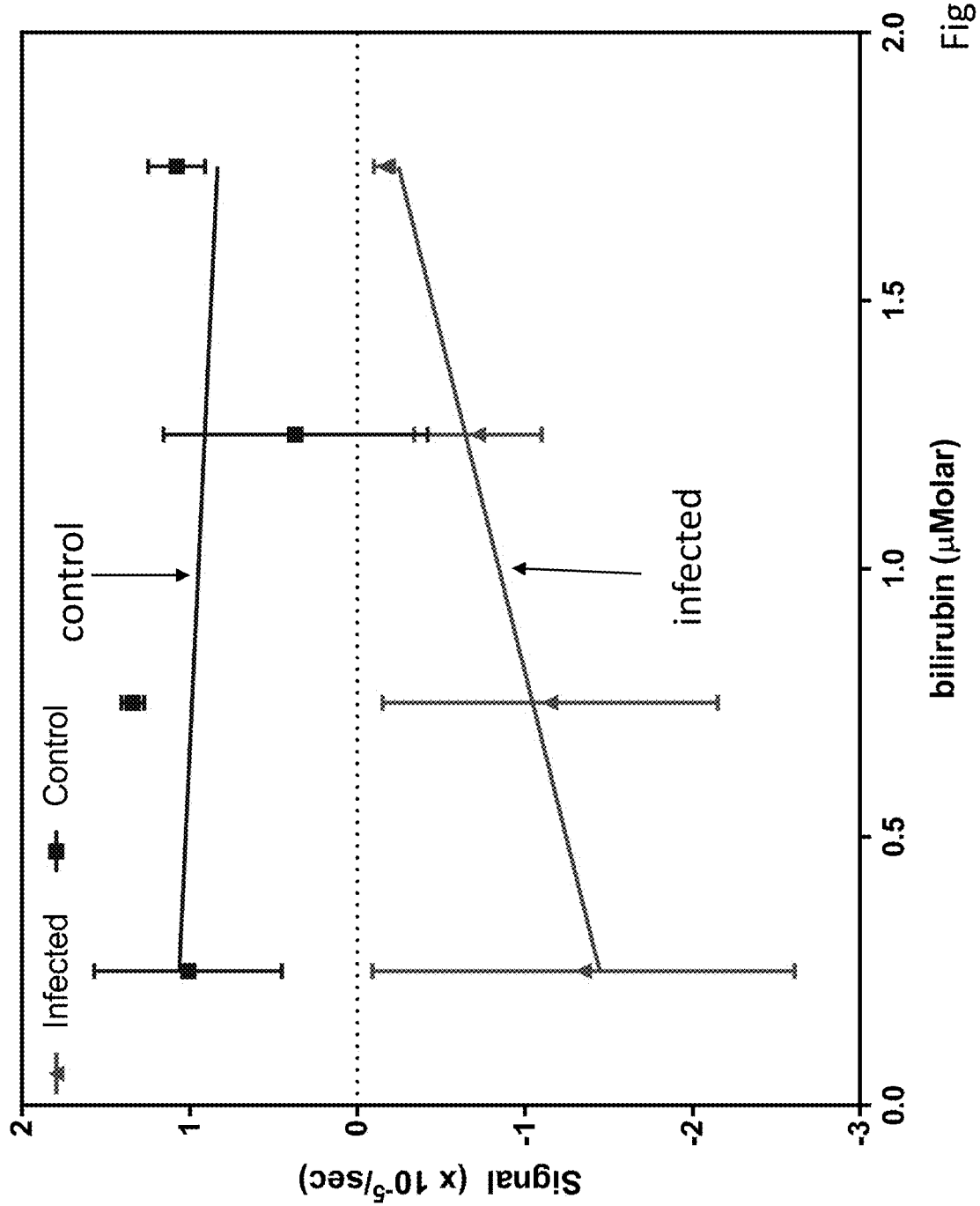
FIGS. 9A-9B depict the variation in the measured values for 4 uninfected and 3 infected samples, as a function of bilirubin content.
Figure 9B:
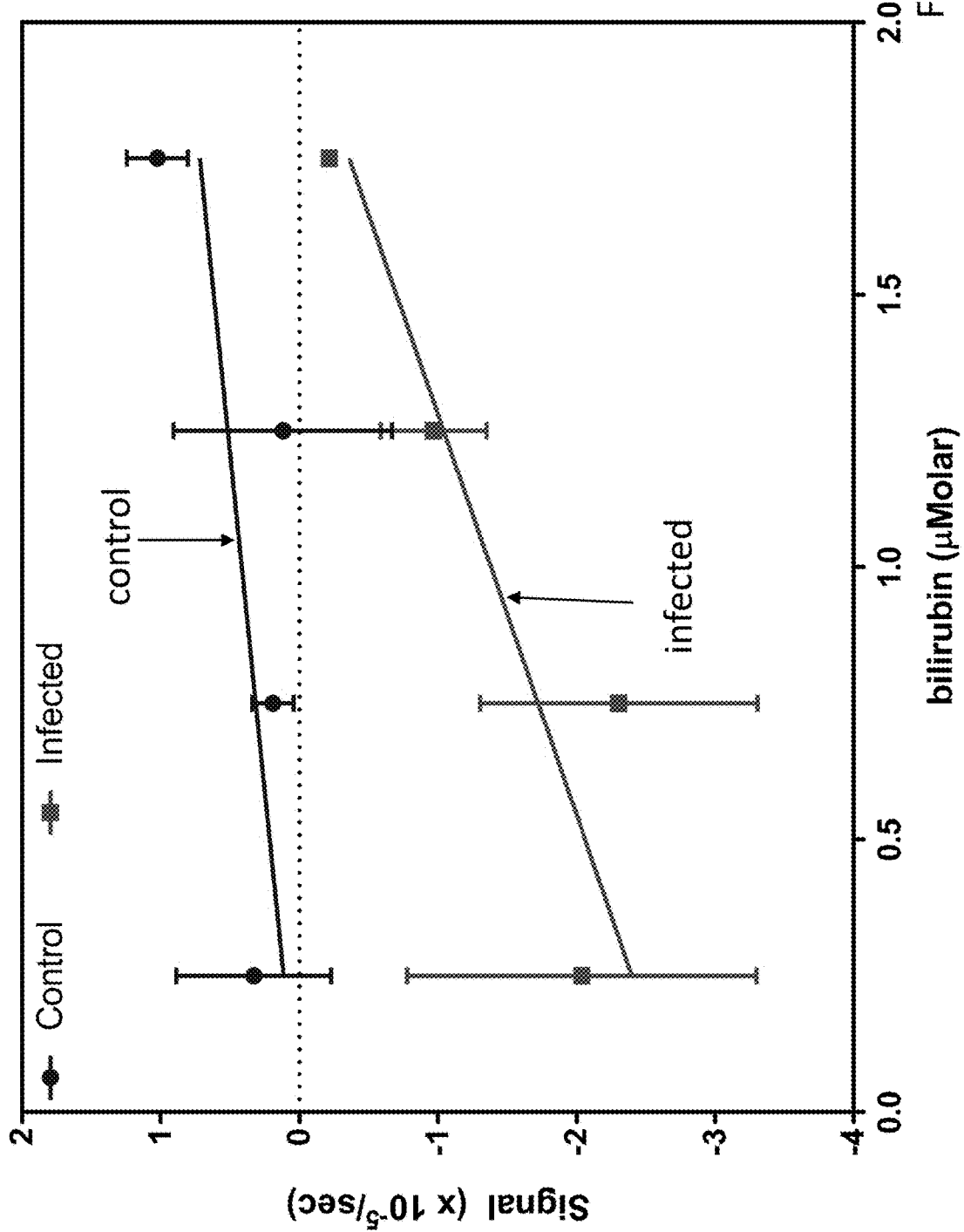

Uncontrolled variations in the laser power (or a drift in the laser power) can bias the observed rates of change. To correct for this, a reference standard (one whose normalized spectrum is not expected to change with laser power) was incorporated into the instrument and monitored concurrently with the samples being tested. This method can be used to characterize the actual drift in the laser power, which can be multiplied with the previously calibrated nonlinearity coefficient to subtract out the biasing error in the observed slopes. An example of this correction is illustrated in FIGS. 9a and 9b. FIGS. 9a and 9b depicts the Variation in the measured values for 4 uninfected and 3 infected samples, as a function of bilirubin content. FIG. 9a depicts the values as they are measured, and FIG. 9b depicts the values after they have been corrected for the observed drift in laser power.

An example system includes 8 sample chambers, one chamber is to be reserved for a calibration standard, such as NIST Raman Calibration Standard SRM 2242. The instrument monitors the spectrum from this calibration standard using the same optical components (spectrometers, fibers etc) and algorithms as that used to monitor the Raman spectrum from the test samples. From the measured spectra of the standard sample, we compute the rate of change of Raman intensity as a function of time. This is then multiplied by the RRNL coefficient that has been previously estimated for the reagent liquid. This is the offset factor. From the rate of change of the Raman peaks, the offset factor is subtracted.

Additional control steps are also implemented to ensure that the laser power performance is closer to the desired specifications. For the 532 nm laser, the laser power output can drift due to small changes in heat dissipation and buildup. These changes can affect performance. These limitations can be mitigated with control schemes that limit the drift in laser performance, and that can also flag when the laser is drifting outside of a specified range.

Figure 10:
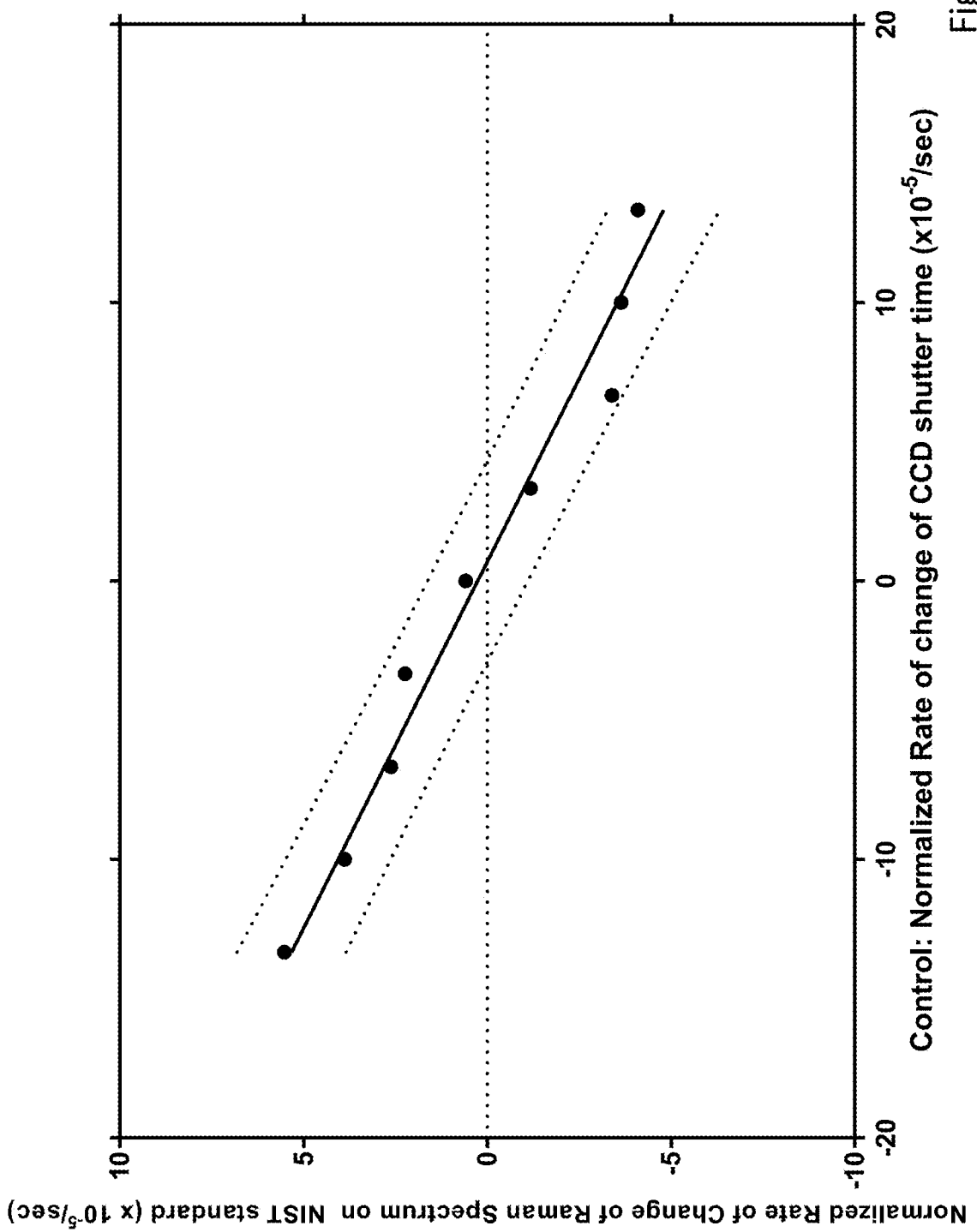
FIG. 10 depicts determining instrument stability using normalized rate of change of Resonant Raman scattering of a reference composition as compared to the normalized rate of change of the photodetector shutter time according to certain embodiments.

FIG. 10 depicts the normalized rate of change of the Raman spectrum from the NIST standard as a function of the normalized rate of change of the CCD shutter time (which affects laser power via thermal buildup within the external laser cavity). This control can be used to vary the laser power, but it can also be used to check if the instrument is behaving with respect to thermal buildup issues. If the observed rate of change of the Raman spectrum from the NIST standard is outside of the 90% confidence band depicted in FIG. 10, then it implies that the thermal management issues have not been sufficiently mitigated.

Example 5

Figure 11:
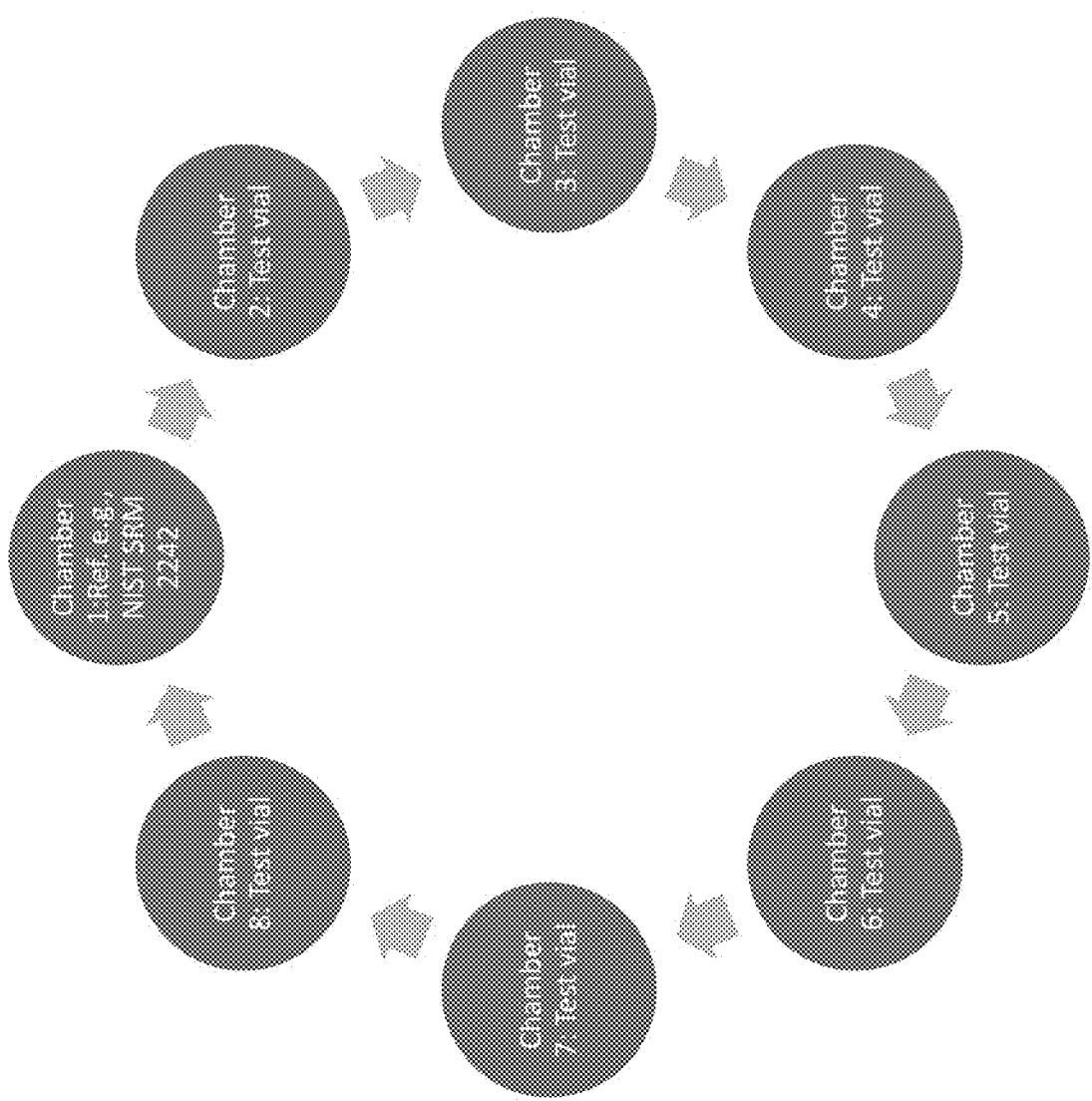
FIG. 11 depicts a layer of a sample chamber according to certain embodiments.

An example system is illustrated in FIG. 11. The layout shown in FIG. 11 depicts 8 chambers, each maintained at 35° C.-37° C. Chamber 1 includes a reference composition, such as NIST Standard SRM 2242. The system collects the spectrum for each chamber, and then rotates a circular stage to the next chamber. It collects one cycle of Raman spectra for all 8 chambers in 15-25 seconds, and then repeats the process for the next cycle until it has acquired data over about 600 seconds. Alternatively, if sampling rates faster than 15 seconds are desired, then the system can collect data on one chamber for the full time period required, and then move onto the next chamber.

Figure 12:
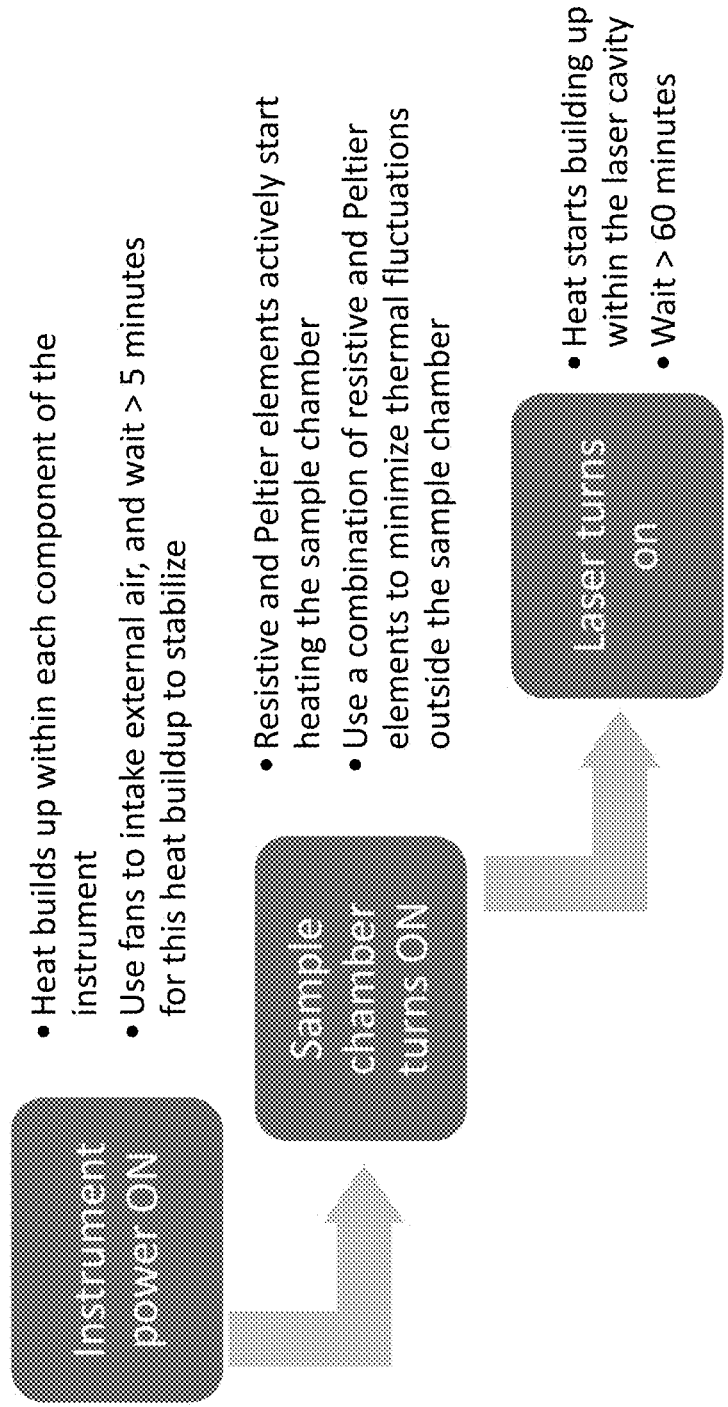
FIG. 12 depicts a flowchart for minimizing thermal effects on laser power according to certain embodiments.

FIG. 12 describes various subsystems that are designed to minimize thermal fluctuations in the laser cavity. These include (a) the use of fans for blowing in external air, circulating it within the instrument and then exhausting it (b) the use of a combination of resistive and Peltier heating elements that maintains the sample chamber at 35-37° C. without unduly affecting changes in the instrument chamber outside of the sample chamber (the Peltier elements move heat from the instrument chamber to the sample chamber while the resistive elements adds heat to both sample and instrument chambers) and (c) use of an appropriately long delay (about 1 hour) after the laser has been turned on before operations.

Figure 13:
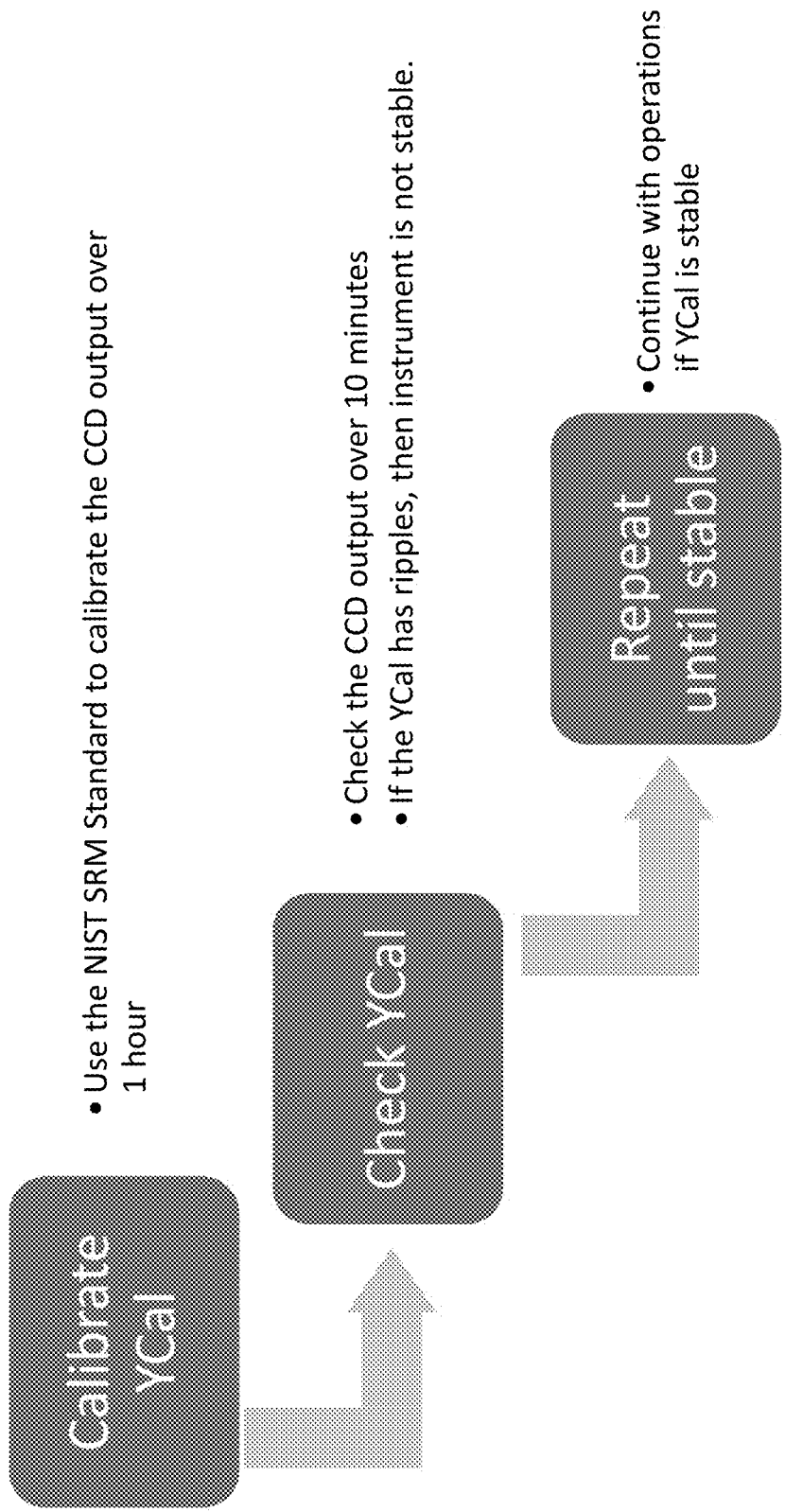
FIG. 13 depicts a flowchart for checking a system for thermal instability according to certain embodiments.
Figure 14:
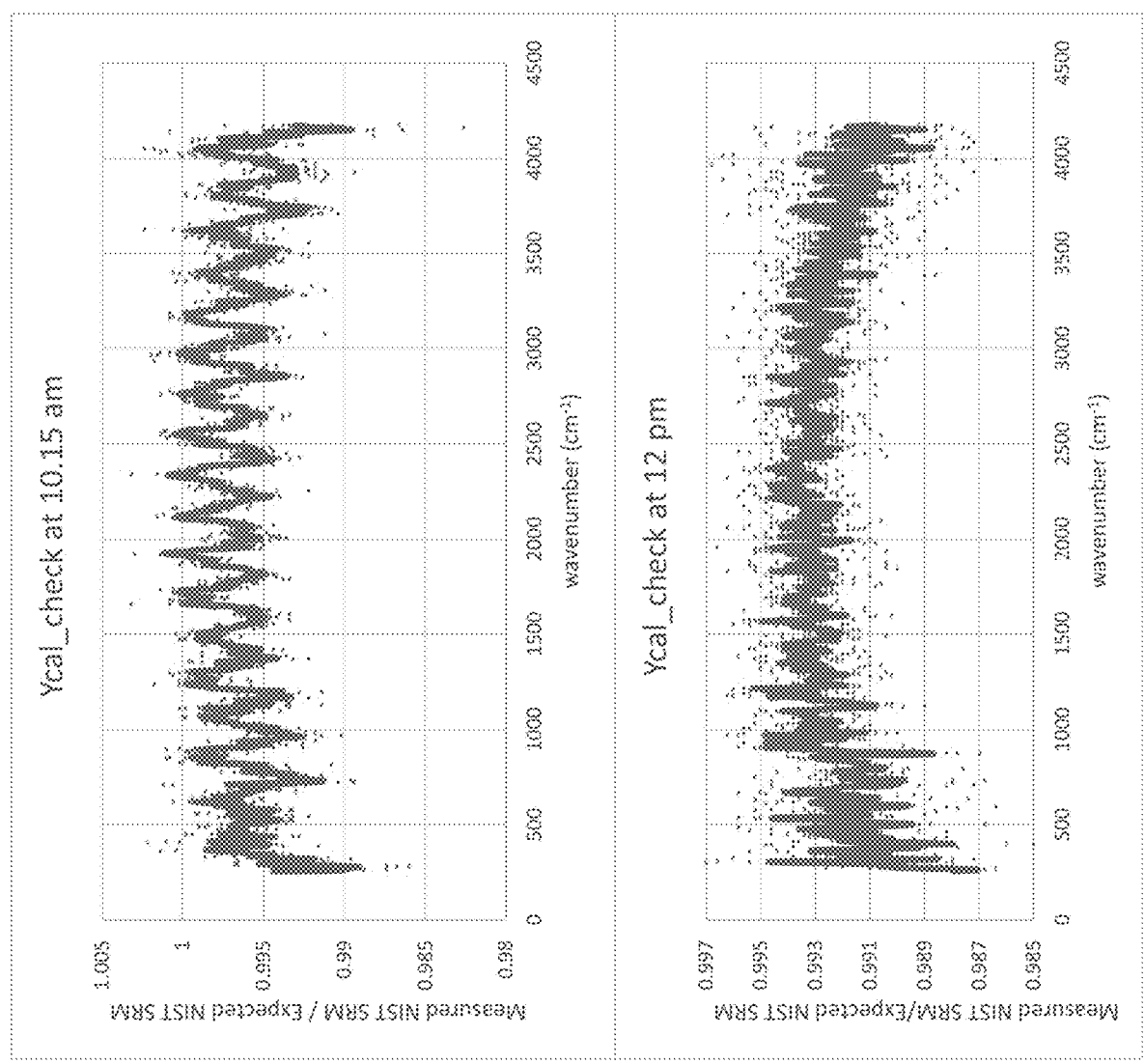
FIG. 14 depicts a YCAL test for checking a system for thermal instability according to certain embodiments.

In order to further minimize the thermal effects, additional controls are implemented to check for instrument stabilization. FIG. 13 depicts one setup algorithm that checks for instrument stabilization. The NIST Standard SRM 2242 was used to calibrate the CCD in the spectrometer over 1 hour. Briefly, this calibration involves collecting the spectrum for the NIST Standard SRM 2242, and dividing the measured output against the output expected for this standard. This calibration was performed over 1 hour. The ratio between the measured CCD output and the expected output is the YCAL. Subsequent to this, all output from the CCD is divided by YCAL to provide an output that should be independent of instrumental variations. The YCAL was checked by repeating the measurement on the same NIST SRM 2242 sample over 10 minutes. If the ratio between the measured spectra for the NIST SRM 2242 (after calibrating with YCAL) and the expected spectrum demonstrates any ripples, then it implies that the instrument has drifted in the 1 hour and 10 minute timescale. This is illustrated in FIG. 14. In some instances, the instrument stabilizes itself about 1-2 hours after the laser has been turned on.

Figure 15:
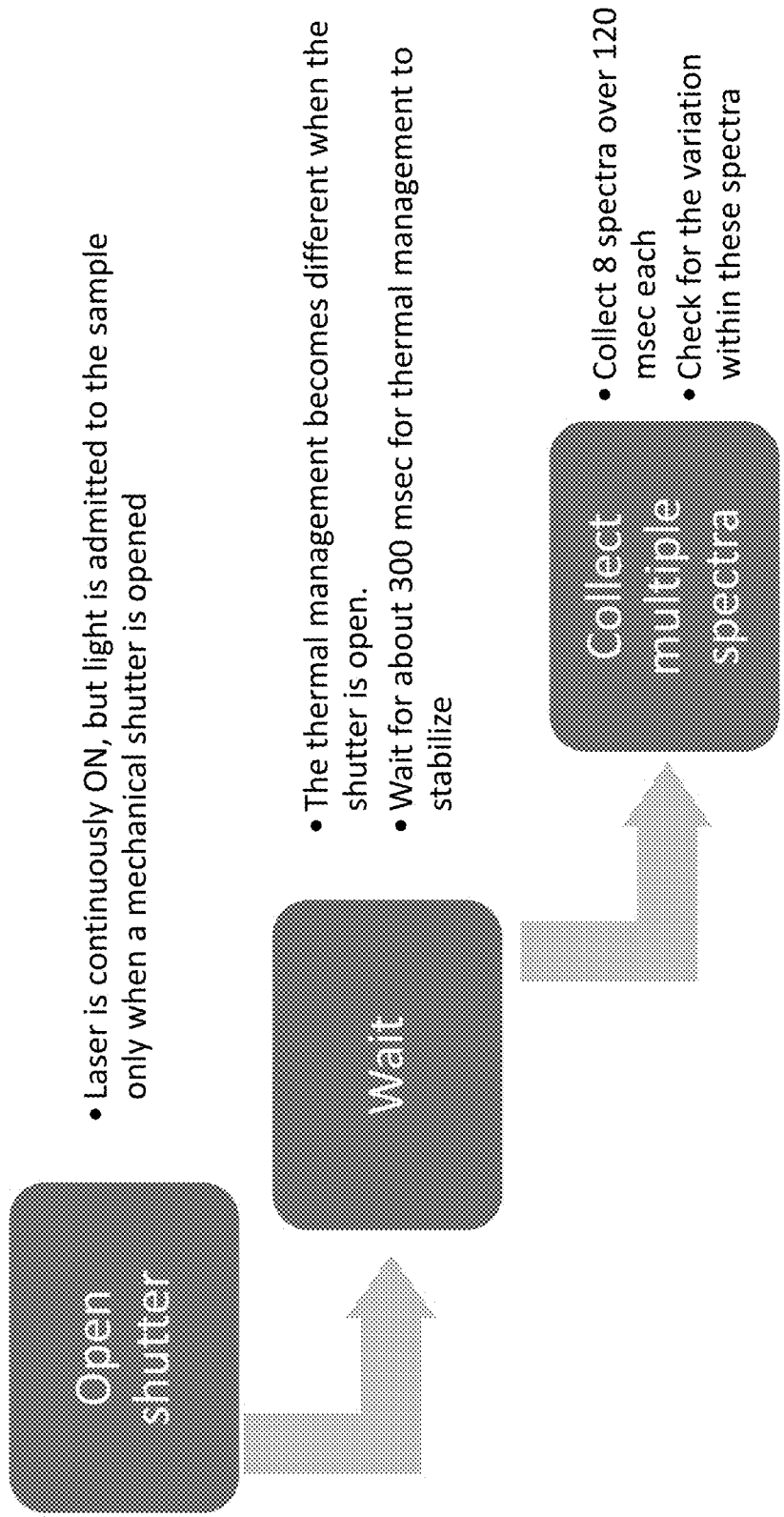
FIG. 15 depicts a flowchart for control steps to minimize thermal fluctuations during system operation according to certain embodiments.

In order to further minimize thermal management issues during instrument operation, one example includes utilization of control methods and algorithms as depicted in FIG. 15. Light is admitted to the sample chamber via a mechanical shutter that is normally closed. When this shutter is opened, the thermal management within the optical train changes. A short duration of time (e.g., ~300 msec) elapses for the changes to stabilize. Eight discrete spectra are acquired over 120 msec each (for a total data collection time of about 1 sec), instead of acquiring 1 spectrum over 1 sec. Variations within these 8 spectra are checked and if the individual time periods have been properly adjusted, then the 8 spectra will demonstrate small systematic changes between them.

Example 6

Experimental details for non-linear Resonant Raman spectroscopy according to certain embodiments of the subject methods are provided below.

Sample Preparation

Figure 16:
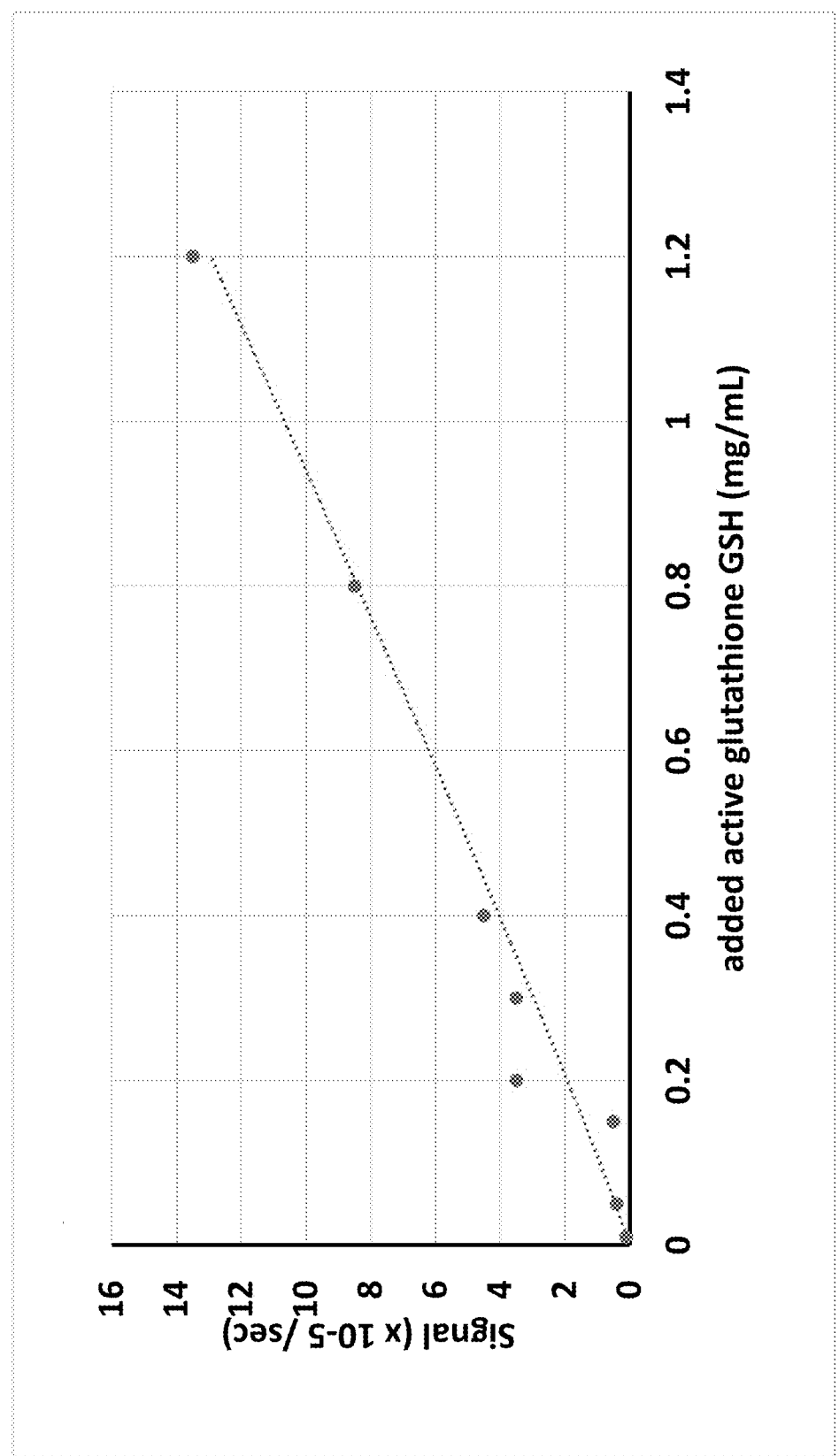
FIG. 16 depicts the relationship of signal magnitude from samples having different concentrations of reducing agent according to certain embodiments.
Figure 17:
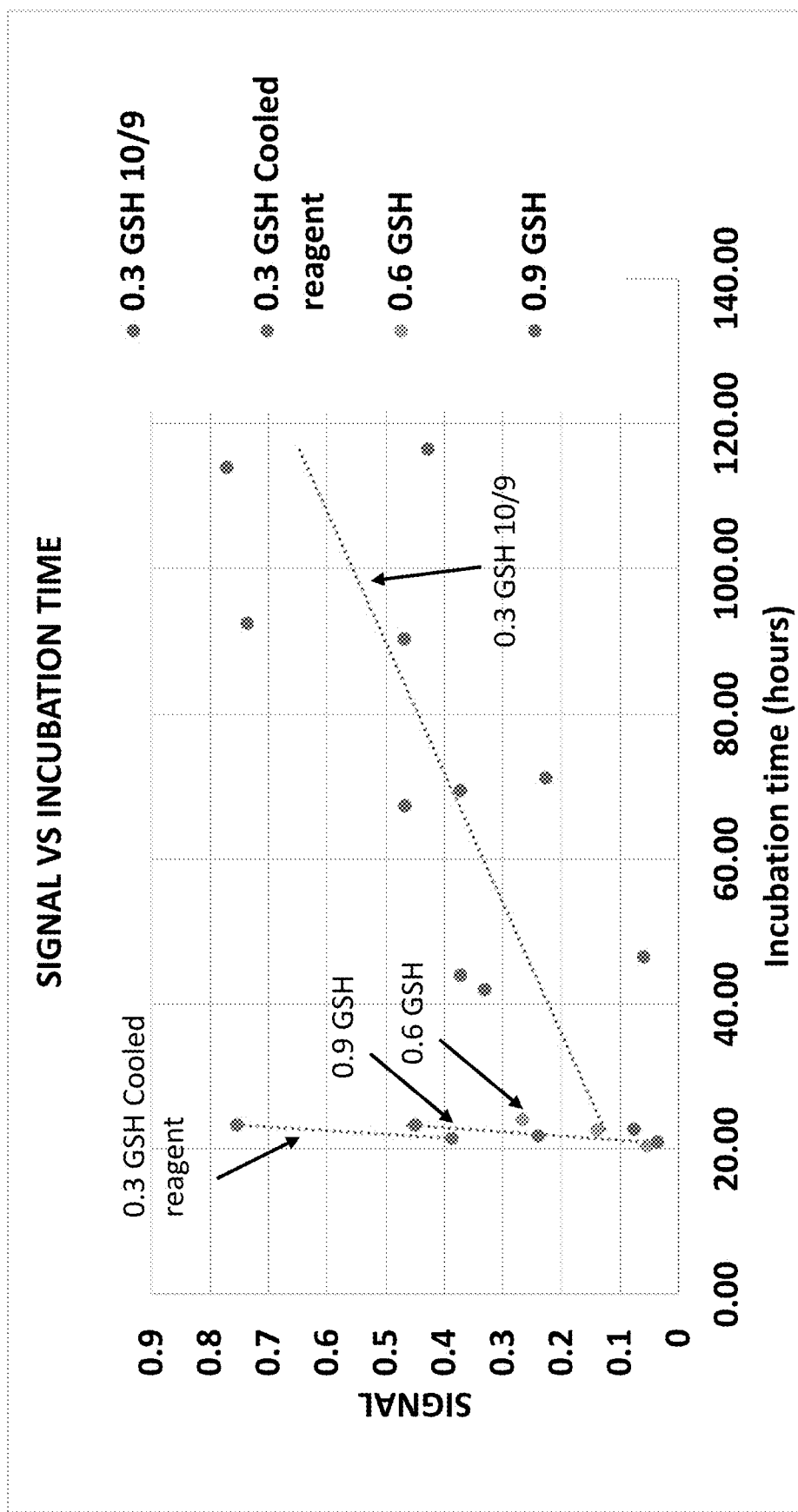
FIG. 17 depicts the relationship of signal magnitude and incubation time at a predetermined measurement time according to certain embodiments.

Samples for non-linear Resonant Raman spectroscopy were prepared as described in U.S. Patent Publication No. 2016/0324933. Briefly, lycopene that is non-covalently associated with albumin in the samples was extracted from tomatoes. Tomato paste is mixed with hexane, and the portion of the paste that dissolves in hexane is decanted off, and dried to powder. The composition is then refluxed over ethyl acetate, and dissolved in acetone. The acetone solution is mixed with an aqueous solution of albumin, and the acetone is gradually removed with a rotovapor. The process is monitored to ensure that all acetone is removed, thereby ensuring that the organic extract from tomato is transferred to albumin. Additional specifications include (1) ensure that there is no supersaturated gases in the reagent by incubating the buffer solution at a temperature of about 60° C. for over 24 hours (a temperature over 50° C. for over 24 hours is also suitable). Since the gas solubility decreases at elevated temperatures, prolonged incubation at elevated temperatures ensures that the dissolved gases will crash out of the system via a process of nucleated bubble formation. The buffer is cooled to 37° C., and is used to finalize the reagent. At 37° C., the buffer is undersaturated with respect to dissolved gases. This procedure ensures that there are no excess gases in the final reagent. (2) Active glutathione GSH is added to the reagent (as a reducing agent) and incubated for 18 hours or more and up to 5 days prior to use. Tests of the samples exhibit an increase in signal magnitude over time for incubation as well as added active glutathione. FIG. 16 depicts that the magnitude of the signal (defined as normalized rate of decrease of the Raman trace) from samples that contain 10 CFUs of added *S. aureus* in a 4.5 mL test sample. The signal increases with increasing glutathione level. For these tests, the testing was performed within 2 hours of GSH addition. FIG. 17 depicts the signal (difference in the rate of change of the average control sample and samples with 10 CFU/mL plasma/*S aureus*) at 1700 seconds measurement time. The "incubation time" on the X axis refers to the time when the GSH was added (concentration in the legend) to the reagent vial, and prior to the addition of infected plasma for testing.

Preparation of a Zwitterionic-Coated Glass Vial

A glass vial is coated with a special zwitterion layer. To 30.03 gm (0.246 mol) of 1,3-propanesultone was added 200 mL of acetone with a magnetic stirrer bar under nitrogen gas. After vigorous stirring for 3 min, and 50.0 gm (0.241 mmol) of 3-(N,N-dimethylaminopropyl)trimethoxysilane through a syringe. The resulting mixture was stirred vigorously overnight under $N_2$ gas. After adding another 100 mL of acetone, the mixtures were shaken well, and organic solvents were removed by rotavapor and the white product was further dried over a high vacuum pump very quickly (the desired product is highly hydroscopic). The white powder product was quickly transferred into another plastic bottle and weighed to give 78.5 gm (98.9%) of the zwitterions silane reagent.

250 clear glass vials (Pacific Vial Catalogue #VC151965, dia=18.75 mm, 3 DRAM) and the corresponding caps were rinsed once with deionized water, and autoclaved for 30 min. After cooling to room temperature, the glass vials are dried in an 80° C. oven and the autoclaved glass vials are transferred to a 6 quart aluminum pressure cooker. To this is added 5 L of autoclaved deionized water, 5 g of the zwitterions silane reagent (as described above). The pressure cooker is capped and shaken by hand to ensure that each vial is soaked with the silane solution. The cap is opened, and a visual inspection is made to ensure that each vial is covered with the solution. The pressure cooker is capped and shaken for 45 min. Next, another 5 g of the zwitterions silane reagent is added, and the handshaking/inspection/45 min shaking step is repeated. The procedure is repeated another 2 times, so that the total amount of the zwitterions silane reagent was 20 gm. The pressure cooker is then placed in an 80° C. oven for 2 hours (and up to 4 hours). The pressure cooker is then cooled to room temperature, opened and the aqueous solution decanted off. The glass vials are washed twice with autoclaved deionized water and once with ethanol/autoclaved deionized water (3:1 v/v) and dried in an 80° C. oven. After cooling to room temperature, the glass vials were transferred into a plastic bag and sealed for storage.

Laser Power

Without being bound to any particular theory or mechanism of action, the laser power and exposure time can affect Resonant Raman spectroscopy according to the subject methods via one of several mechanisms:

At very large laser exposure times, the height of the Raman peaks in control samples can start to decrease while the sum of pixels remains largely invariant. The laser's energy shifts the contributions that comprise the overall Raman peaks, and this shift results in a decrease in the observed peak height.

At very low laser exposure times, the read noise on the CCD can overwhelm small effects are which one is attempting to monitor. Since the Raman effect is non-linear, large changes in laser power (e.g., fluctuations in laser power) can result in changes in the observed Raman amplitude being dominated by changes in the laser power (and thus making it impossible to discern the effect of any bacteria presence).

Figure 18:
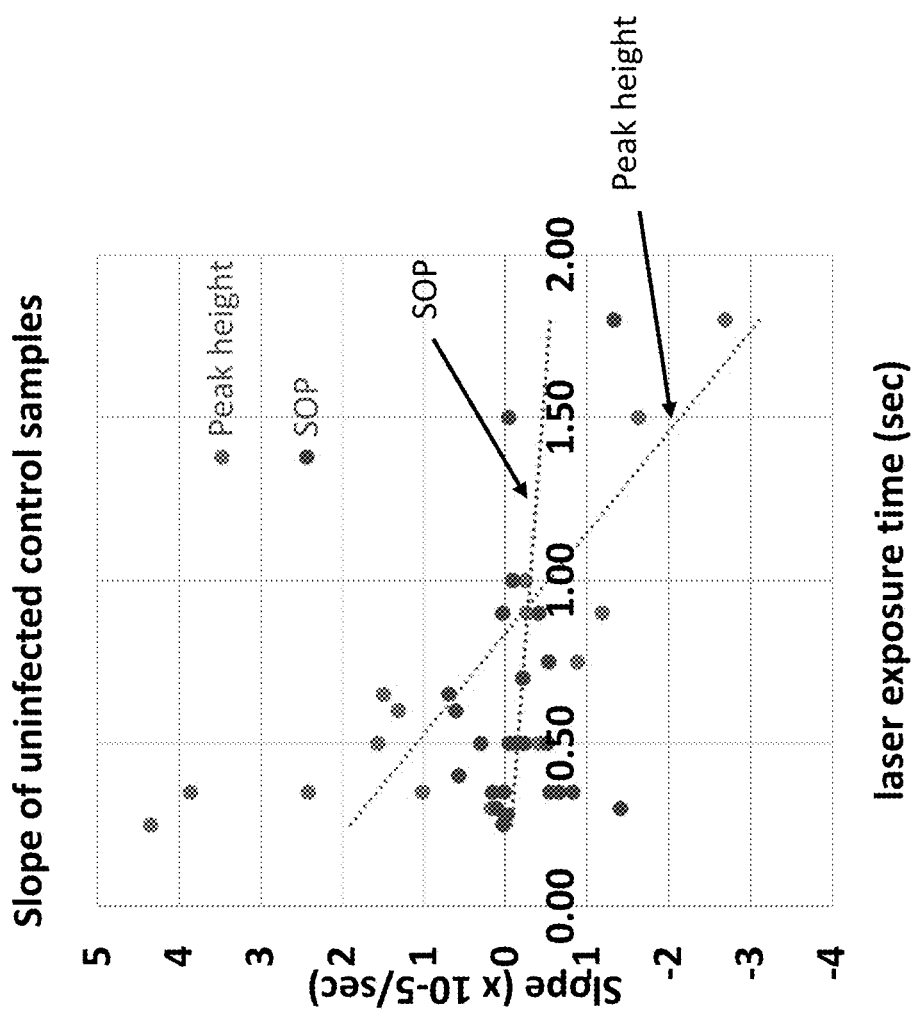
FIG. 18 depicts the relationship between the rate of change of the Raman peak height and the laser exposure time according to certain embodiments.

In some embodiments, suitable laser exposure conditions for practicing the subject methods include one that results in a maximum CCD count of about 10,000 to 40,000. In one example, the maximum saturation for the CCD is 65536 counts (corresponding to 16 bits), so this mode of operation results in a CCD that is well below saturation, but that also operates well above the region where read noise is an issue. In certain instances, the mode of operation results in a total laser exposure of about 1 second (broken up into 4 CCD exposures of 0.25 seconds each; with each 0.25 second exposure resulting in a max CCD count of about 30,000). At longer laser exposures, the observed peak heights decrease over time, and at shorter laser exposures, they increase over time. One way to mitigate this effect is by working with the area under the curve (which remains relatively invariant, as depicted in FIG. 18), but working with a 1 second laser exposure helps reduce this problem further. In particular, FIG. 18 depicts the rate of change of the Raman peak height and the "area under the curve" of the Raman peak height computed as the sum of all the pixels (SOP in the legend) that describe the Raman peak. As the laser exposure time increases above 1 second for each cycle of exposure, the Raman peak heights decrease significantly. By contrast, the area under the curve remains relatively invariant.

Detection and Signal Measurement System

The measurement system includes a spectrometer (equipped with a cryogenically cooled CCD detector, capable of low dark current operation) and a laser light source (532 nm incident wavelength and 100 mW power) that is capable of performing resonant Raman spectroscopy, a sample chamber that includes a rotary table that can switch between up to 8 samples, a NIST SRM 2242 standard that is used to calibrate the instrument, and a computer with appropriate software for controls and analysis.

One illustrative method includes the following steps: (1) irradiating the sample with the monochromatic light source (e.g., at 532 nm), (2) measuring the scattered light intensity profile between 535 and 600 nm (and converting wavelength to wavenumbers), (3) calibrating the CCD output with a calibration constant developed from the NIST standard SRM 2242, (4) separating the Raman contribution from the fluorescent background using an appropriate software algorithm, (5) repeating steps 1-4, and characterizing the rate of change of the Raman peaks as a function of time until the desired signal to noise ratio is attained (6) performing any necessary corrections for any systemic biases in the rate of change and (7) using the corrected rate of change to diagnose the sample based on preset threshold values.

Detection and Signal Measurement System: Alignment of the Collimating Lens

Figure 19:
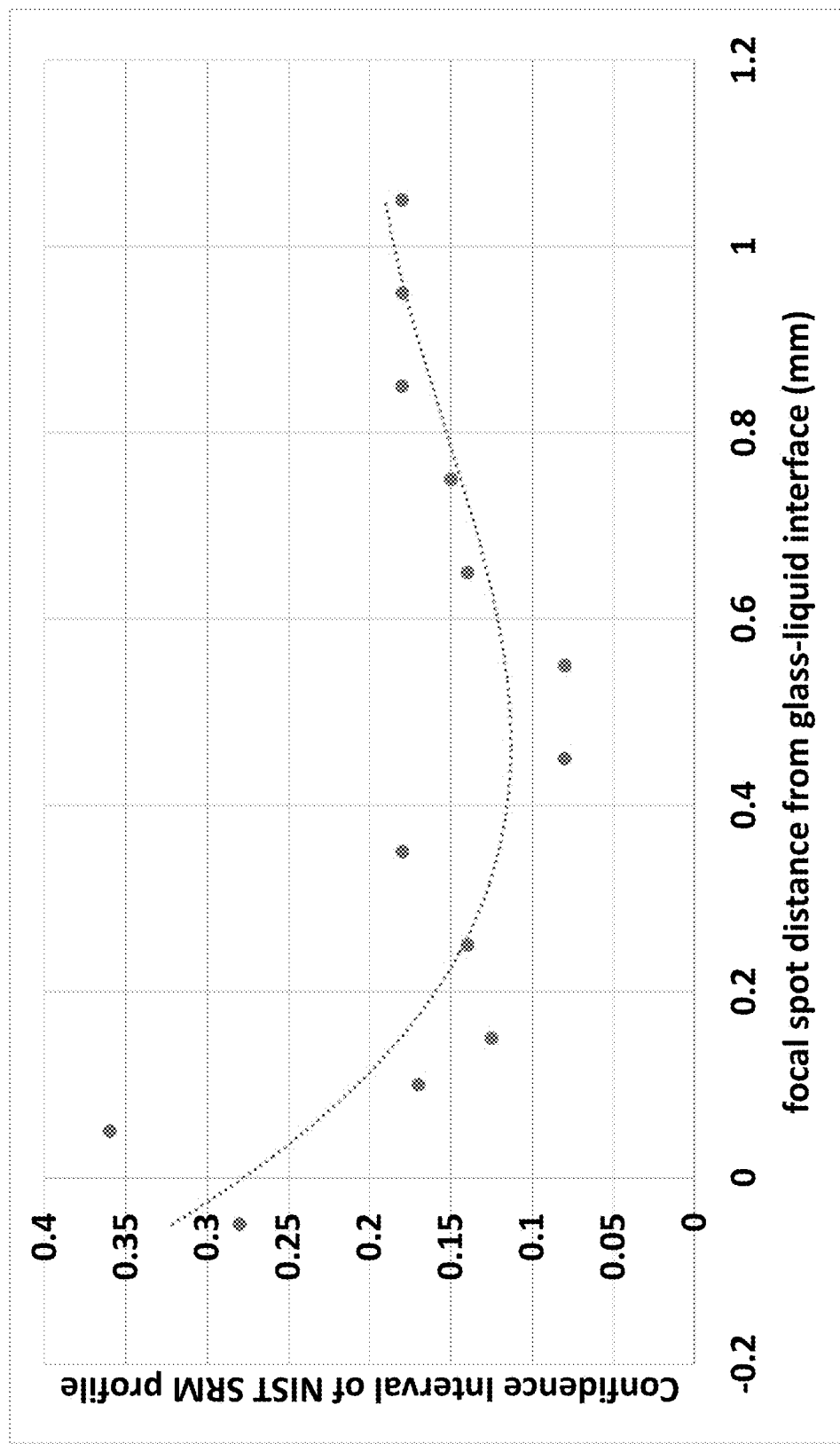
FIG. 19 depicts the relationship between the confidence interval of the NIST profile and distance from sample-container interface and focal spot of light irradiation according to certain embodiments.

In some embodiments, the subject systems include a collimating lens that focuses light from the monochromatic light source onto the sample and collects light scatter from the sample vial. If this lens is placed too close to the glass vial, then some of the scattered light can be lost outside of the collection area of the lens. Further, the magnitude of this loss can change with small changes in the laser beam position (or with mode hopping). Thus, when the lens position is sub-ideal, large changes in the measured Raman intensity may be present due to this effect. By systematically varying the collimating lens position, a suitable position is determined to be where the focal spot is about 0.4 mm deep into liquid layer within the glass vial, as shown in FIG. 19. FIG. 19 depicts the variation of the confidence interval of the NIST profile as a function of distance between the edge of the glass-liquid layer and the focal spot of the collimating lens.

Figure 20:
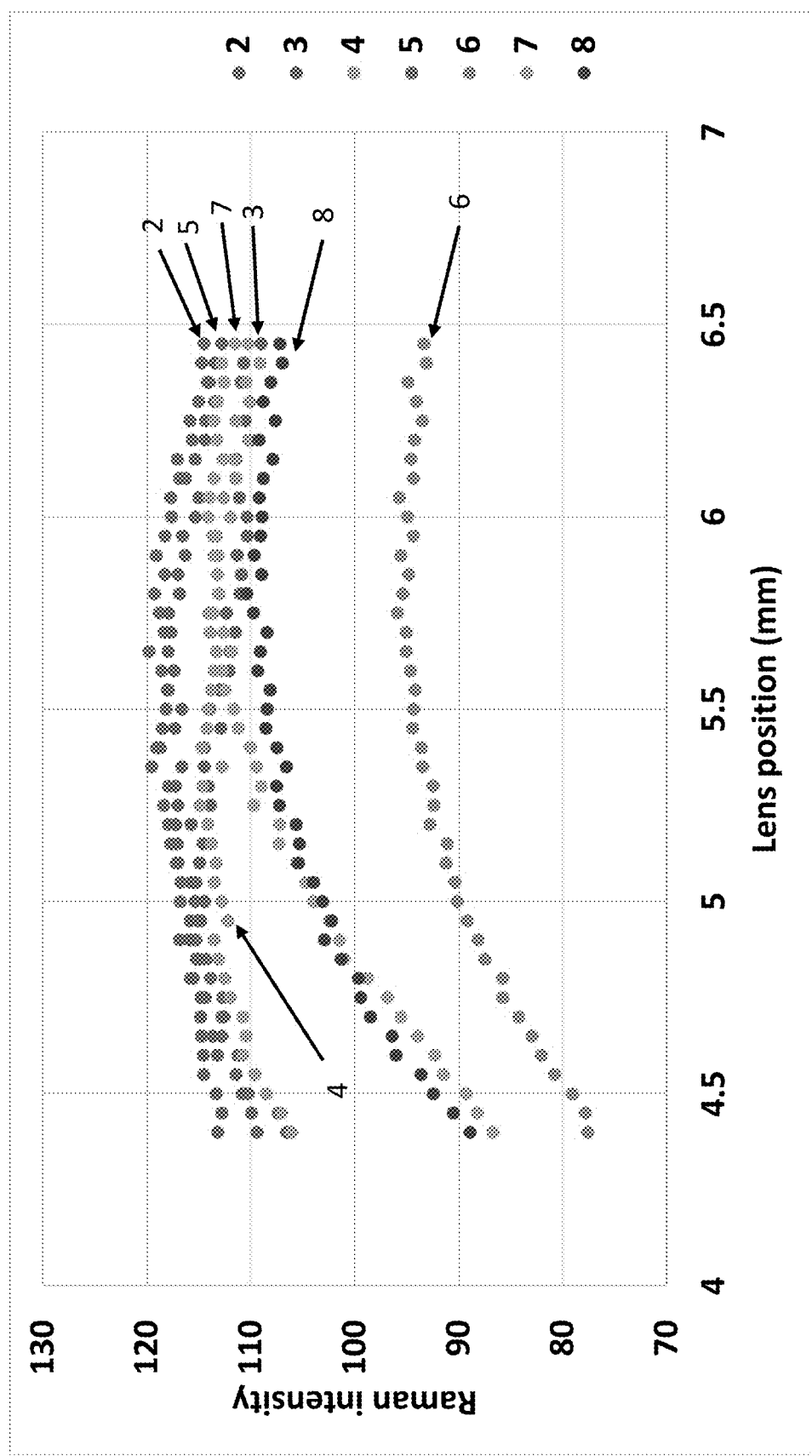
FIG. 20 depicts the relationship between Raman intensity profile and collimating lens position from the sample container according to certain embodiments.
Figure 21:
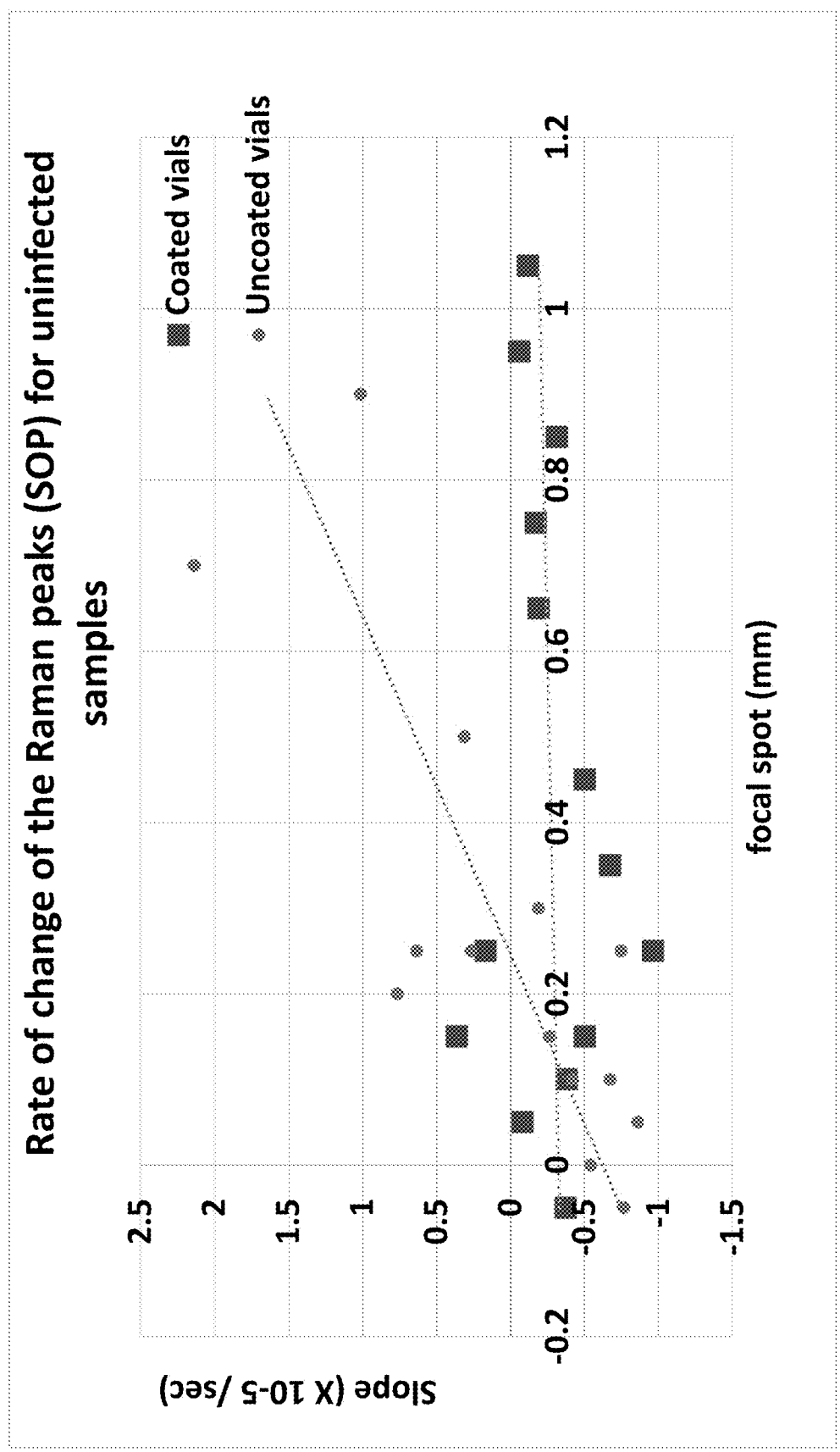
FIG. 21 depicts the relationship between the slope of uninfected control samples and the focal spot position of the monochromatic light source from the edge of the sample-container interface according to certain embodiments.

To characterize the collimating lens position, the position of the lens is varied and scattered light is measured. Starting from the glass walls, as the focal spot is moved into the liquid layer, the Raman intensity increases at first (as the focal spot covers more of the liquid), and then decreases (as the scattered light is attenuated by the absorption within the liquid). FIG. 20 depicts the variation of the Raman intensity profile as a function of collimating lens position for sample chambers 2-8 (sample chamber 1 is reserved for the NIST standard). The intensity is maximized at position 5.65 mm, which corresponds to the edge of the glass-liquid interface. The nature of the interface depends on the surface layer on the glass vial. FIG. 21 illustrates the use of the Zwitterionic layer (as described above) to make the measurement more robust against small changes in the focal spot position. FIG. 21 depicts the slope of the uninfected control samples, as a function of the focal spot position from the edge of the glass liquid layer. For uncoated samples, the slope changes significantly with position of the focal spot. For the glass vials that are coated with the Zwitterion layer, the slope appears to be independent of focal spot position, indicating that the interfacial layer extends deeper into the liquid.

Figure 22A:
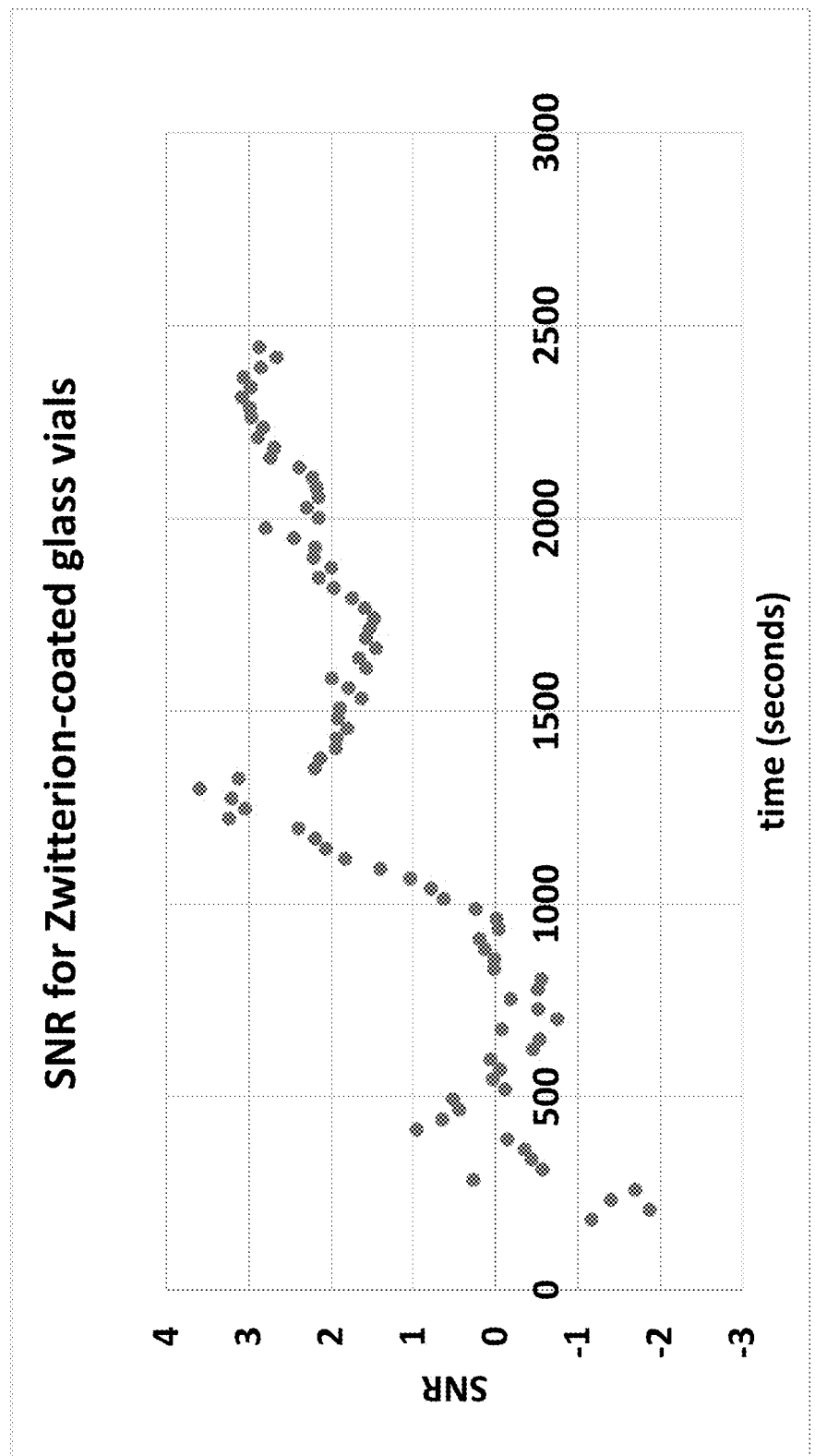
FIG. 22A depicts the signal-to-noise ratio of Raman spectra obtained for samples in Zwitterion coated glass vials according to certain embodiments.
Figure 22B:
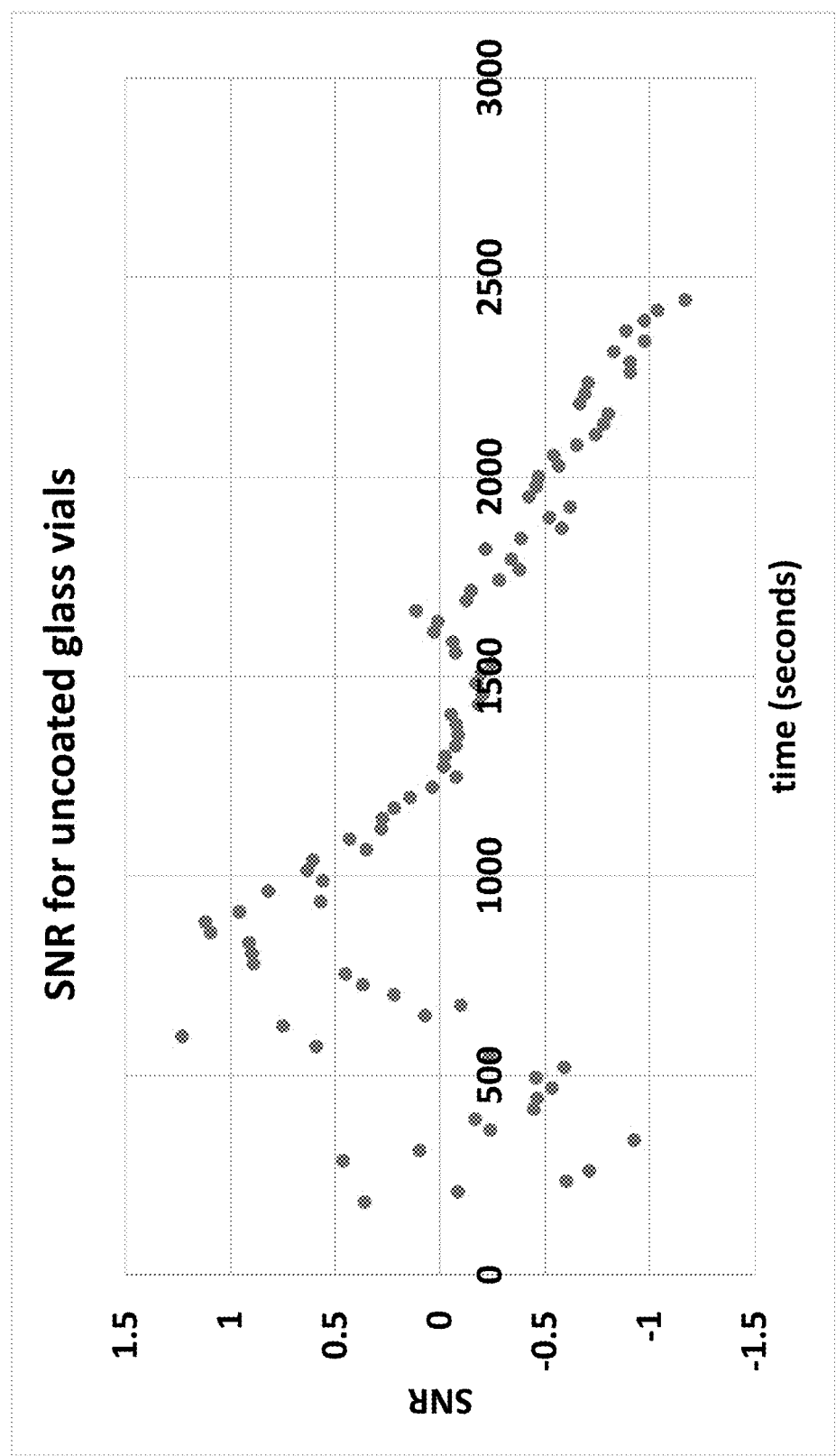
FIG. 22B depicts the signal-to-noise ratio of Raman spectra obtained for samples in uncoated glass vials according to certain embodiments.

(1) For uncoated glass vials, a significant signal is present at short times. But this signal rapidly decreases to zero, and can even reverse itself for longer times, as illustrated in FIGS. 22A and 22B. (2) For Zwitterion coated samples, the signal to noise ratio continues to build up over time. Thus, for the uncoated glass vials, reasonable signals can be attained, but can depend on the position of the focal spot and the time of signal recordation. For coated glass vials, the measurement is found to be significantly more robust. FIG. 22A depicts the signal-to-noise ratio of Zwitterion-coated and FIG. 22B depicts the signal-to-noise ratio of uncoated glass vials, both measured with the focal spot 0.4 mm from the glass surface. For the Zwitterion-coated vials, the SNR builds up steadily over time. For the uncoated vials, there is a significant signal at about 900 seconds, but this signal rapidly decreases to zero and even reverses itself for longer times.

Detection and Signal Measurement System: Flow at the Sample-Container Interface

Figure 23:
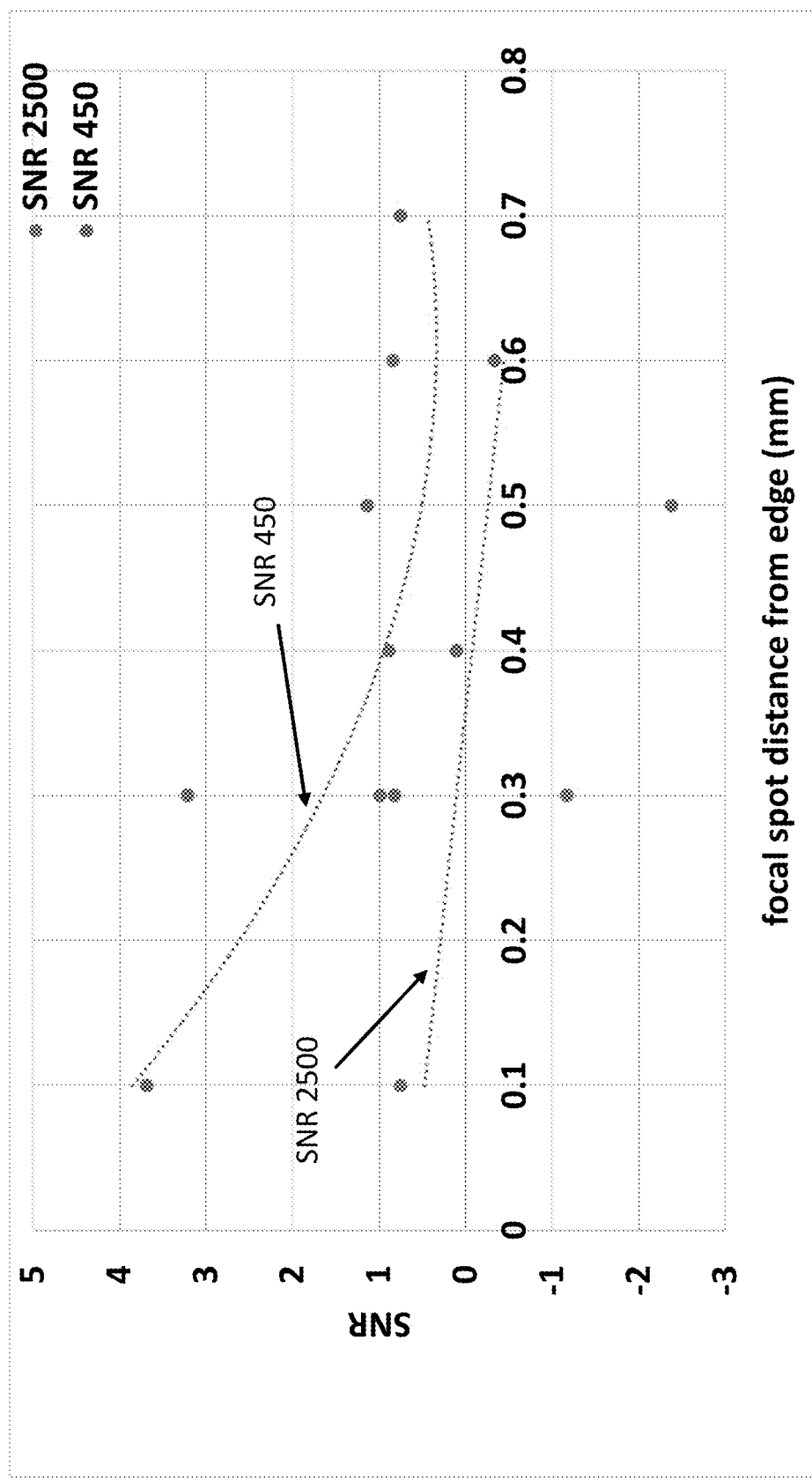
FIG. 23 depicts the relationship between signal-to-noise ratio and focal spot distance from sample-container interface according to certain embodiments.

If the volume of sample irradiated by the monochromatic light source is changed for every spectra acquired for that sample vial, then there would be no laser induced non-linear Raman Resonant signals that can be measured. To ensure that the same volume of sample is measured the following steps are taken: (a) maintaining the glass vial and the sample therein at or nearly at complete rest so that the optical system probes the same volume at every measurement; (b) ensuring that the optical system is probing a volume that is close to the glass surface. There is an interfacial layer at the glass-liquid interface, where the relative velocity of the liquid layer is close to zero. If this volume is probed, then this sampled volume will remain nearly invariant over multiple measurements. However, the results become very sensitive to both the nature of the interface layer, and the exact positioning of the collimating lens. If the focal spot of the collimating lens is not deep enough, then error is possible due to laser mode hopping. If the focal spot is too deep, then the sampled volume may change due to motion, and this will reduce the signal magnitude (or perhaps even flip it altogether). Based on these considerations, a suitable location of the collimating lens in certain embodiments is about 0.2 mm from the edge of the glass-liquid layer. FIG. 23 depicts the variation of the signal to noise ratio, estimated as the difference between the measured rate of change of the Raman peaks in 4 control samples and 3 with plasma that has 10 CFU/mL of $S$ $aureus$, and then divided by the rms standard deviation. As the collimating lens is moved deeper into the liquid layer, the Signal becomes smaller and effectively disappears. Further, the signal is also short lived~it can be measured at 900 seconds, but is very small at 2500 seconds. This behavior is typical of uncoated glass vials. The nature of the interfacial layer can be manipulated by applying a coating on the glass surface. As discussed above, the application of a Zwitterionic layer on the glass surface extends the interfacial layer deeper into the bulk sample volume.

Example Instrument Sequence of Operation

The control software instructs the spectrometer to "open" the mechanical shutter (i.e., to expose the test sample to laser light). After a delay of 0.05 seconds (to allow the shutter motion), the CCD is instructed to initiate data collection for 1.6 seconds. The CCD data is then shifted into the read electronics, and acquired by the laptop computer.

The instrument instructs the sample stage to rotate, such that the NIST calibration standard (in Chamber 1) is exposed to the light path for 1.6 seconds. It then instructs the rotary stage to move to the next chamber, and exposes the sample in that chamber. This process is repeated until the instrument has acquired one spectrum for all 7 chambers (if loaded) and the NIST calibration standard. This set of 8 measurements is called a cycle, and typically takes 26 seconds.

The instrument performs testing over 33 minutes (over 75 testing cycles, with each cycle taking 26 seconds). The first 5 cycles are "dark cycles", wherein the mechanical shutter is not opened. These 5 dark cycles give the instrument (laser/CCD etc) an opportunity to stabilize. After these 5 cycles, the mechanical shutter opens when instructed to do so during a cycle.

For each spectrum acquired, the software initiates a set of mathematical algorithms to analyze the data. (1) First, it subtracts the "dark current" from the CCD output, and converts the X axis on the resultant spectra from pixel number to frequency using a predefined linear conversion factor. (2) Next, it multiplies the raw CCD output with the calibration factor, thereby providing a spectrum that is nominally independent of instrument to instrument variations. (3) Third, it implements an algorithm based on the Lieber method to estimate the background fluorescence. (4) It then detects the peak in the spectral profiles at 1156, 1516 and 4000 cm-1 (the major peaks associated with the example biomarker; the last one is ignored for plasma samples), (5) Finally, the height and area under the curve for these peaks are stored in a table, and used in subsequent analysis steps.

The software starts computing the slope of the line defined by these data points. This is done by fitting the data (peak height and area under the curve versus time, separately and independently for both the 1516 and 1156 cm-1 peaks and also for the 4000 cm-1 peak) using a linear least square fitting algorithm that comes standard with National Instrument LabView packages. This algorithm also computes the 95% confidence interval (95% CI) around the slope and y intercept values. From this slope, the slope of the fluorescent background at 3000 $cm^{-1}$ is subtracted~this normalization step removes any systemic biases to the data introduced by distortions to the interfacial layer caused by large particle clumps.

The algorithm compares the slopes (along with the 95% CI around the slope) to a decision threshold that has been set via previous testing. The threshold is set to slope $>-0.5\times 10^{-5}$/sec for diagnosing uninfected samples (samples with observed slopes greater than this value are diagnosed as being uninfected) and slope $<-1.5\times 10^{-5}$/sec for diagnosing infected samples (samples with observed slopes less than this value are diagnosed as being infected) at a time period of 600 seconds~observed that for infected samples, the signal decays inversely with time. Samples that have a slope between these two values are diagnosed as "dichotomous". For diagnostic purposes, the average slope is computed from the 1156, 1516 and 4000 (if available) $cm^{-1}$ Raman peaks.

Figure 24:
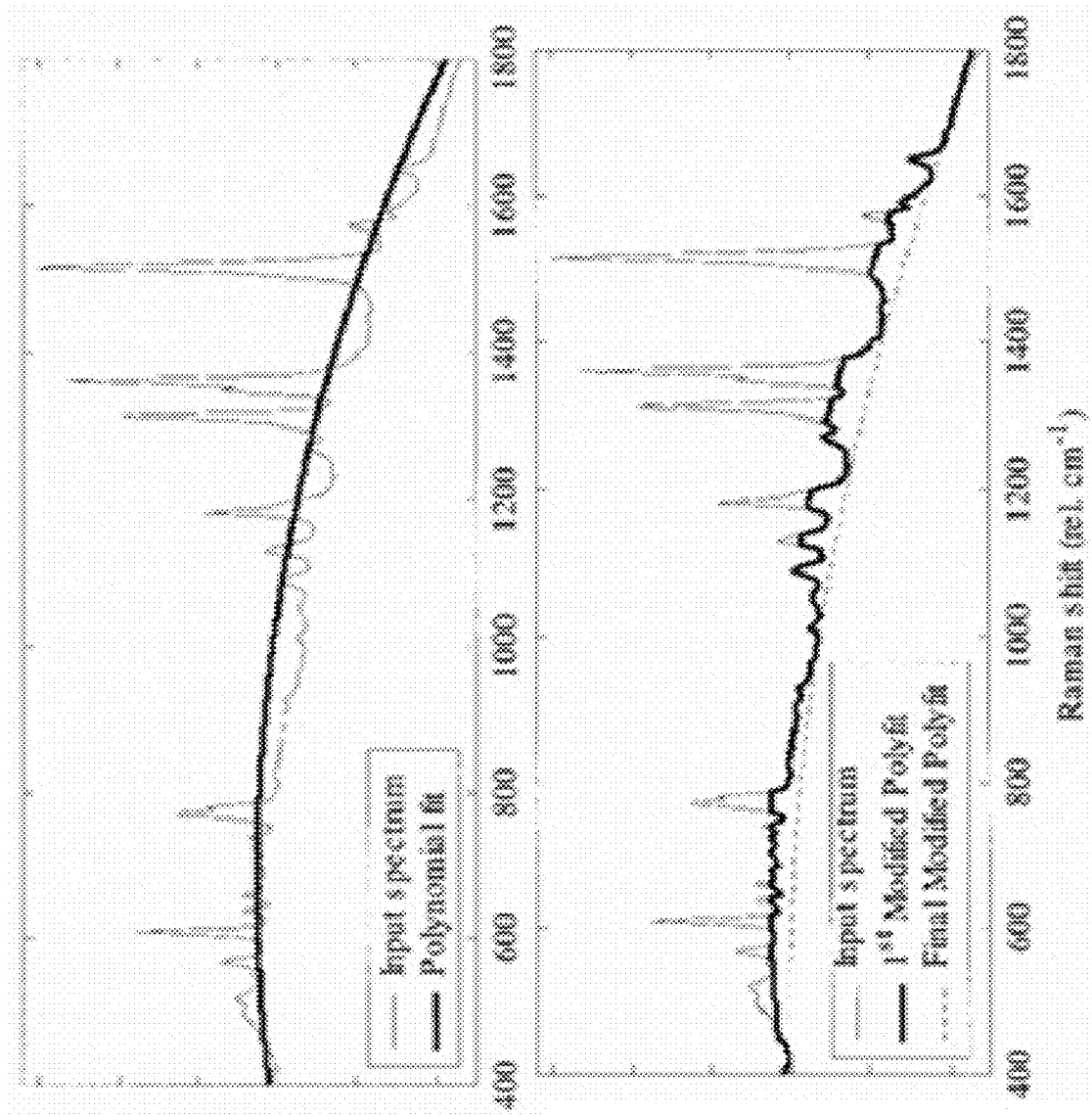
FIG. 24 depicts the Lieber method for fitting a $5^{th}$ order polynomial to a spectra having contributions from Raman peaks and background fluorescence according to certain embodiments.

Example Software Algorithm for Separating Raman and Fluorescence Signal Contributions Algorithms for maximizing test performance are implemented. The Lieber method is used to subtract background fluorescence. This method is illustrated in FIG. 24 which depicts the Lieber method for fitting a 5th order polynomial to a spectra that comprises contributions from Raman peaks and background fluorescence. The raw measured spectrum is fitted to a 5th order polynomial. The data points in the Input spectrum that are higher than the fitted polynomial are replaced by the fitted polynomial, and the modified spectrum is fitted to a new polynomial. In certain embodiments of the subject methods, the Lieber method is optimized by: (a) the Lieber method is implemented on the first spectrum. For background fluorescence, a $5^{th}$ order polynomial (in some instances, a $4^{th}$ order polynomial is used) between the wavenumbers 1050 and 1650 $cm^{-1}$; (b) for subsequent spectra, the background fluorescence fit (i.e., the $5^{th}$ order polynomial, above) is used with its amplitude varied. The approach of constraining the fit ensures that the results do not include amplified mathematical artifacts.

Laser Power Fluctuations and Instrument Errors

In embodiments, the rate of change of the Raman peaks as a function of time is measured. These measurements can be affected by changes in the laser power, and in various instabilities in the alignment of the instrument. Uniform drifts in the laser power can be corrected via the NIST standard, but higher order instabilities cannot be corrected with the NIST standard. Characterization of the instabilities (which include, potentially, laser mode hopping, and drifts in the position of any of the alignment lenses during the test) is however helpful to flag measurements that are suspect.

Figure 25A:
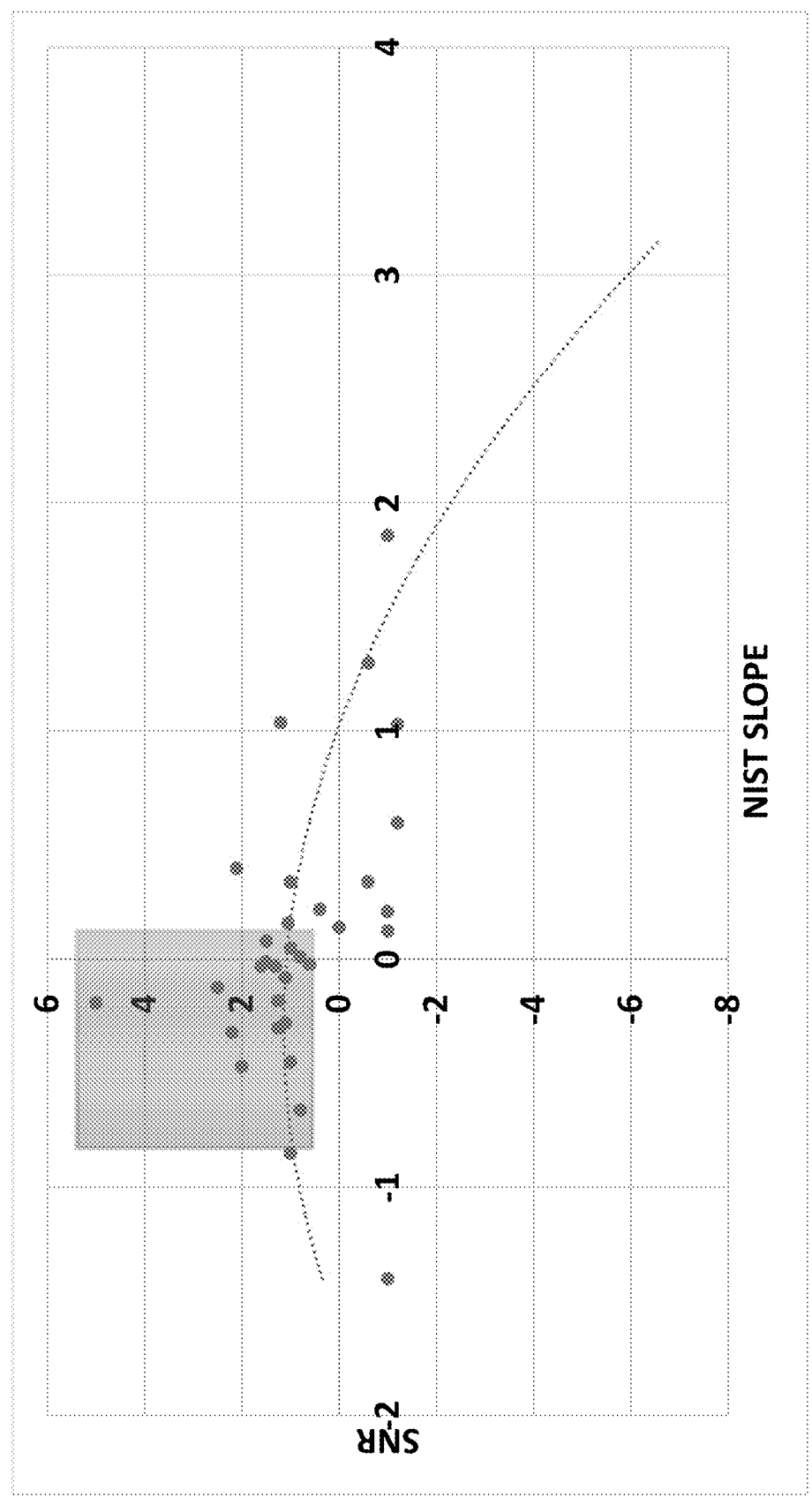
FIG. 25A depicts the relationship of signal-to-noise ratio with the slope and according to certain embodiments.
Figure 25B:
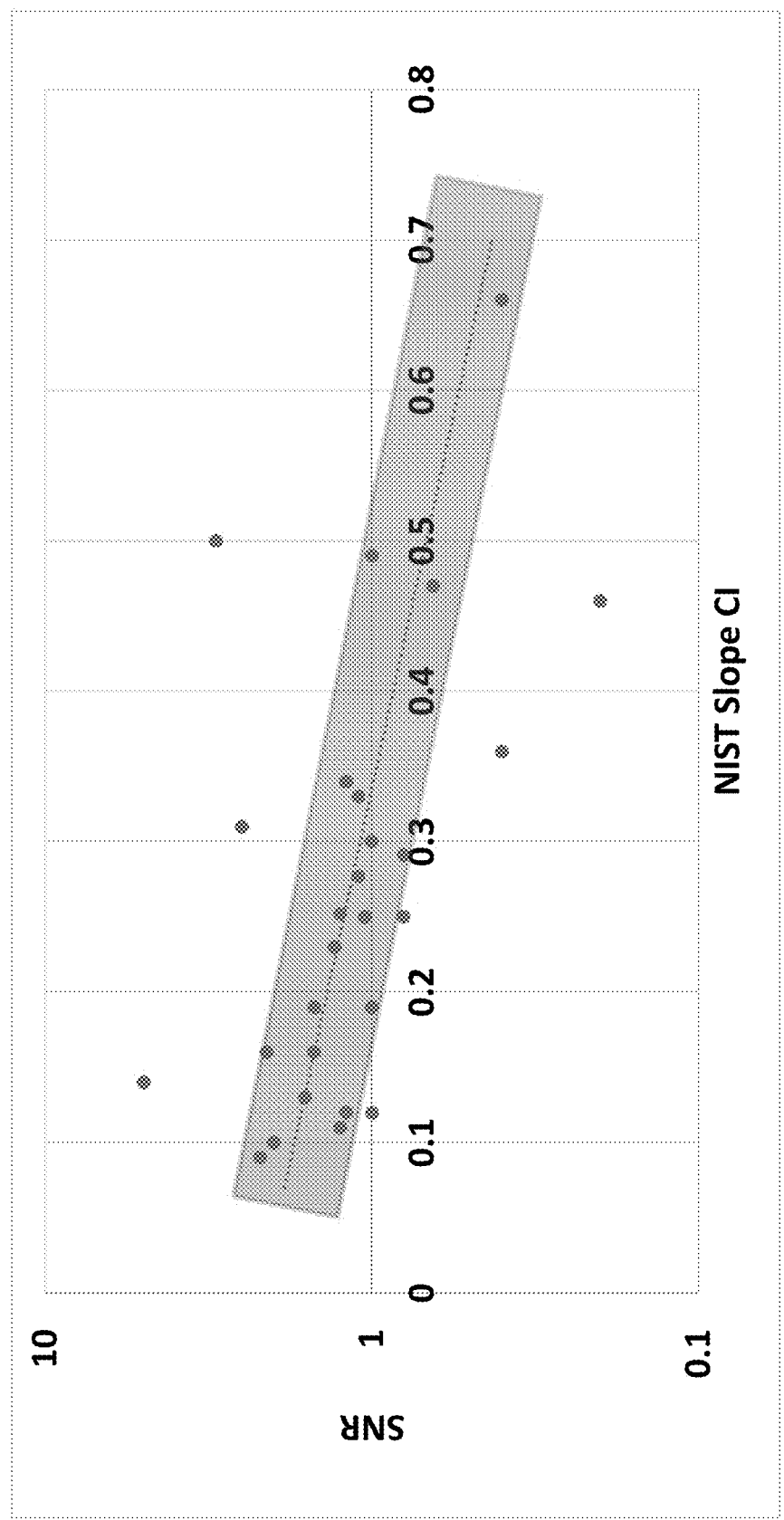
FIG. 25B depicts the relationship of signal-to-noise ratio with the confidence interval of slope according to certain embodiments.

To do this, the output from the NIST standard is characterized and the slope and confidence interval of that slope are measured at the end of an experiment. When working with artificially spiked samples, the Signal to Noise Ratio was found to vary with both the slope, and CI of the slope, as shown in FIG. 25. Specifically, FIG. 25 depicts variation of the Signal to noise ratio at the end of the measurement, with the collimating lens at the ideal position, and with coated glass vials being used in all measurements. Each SNR value represents one measurement set with 4 uninfected control samples, and 3 with plasma infected to 10 CFU/mL of added *S. aureus*. The measurements are repeated, and the SNR is plotted as a function of the confidence interval of the estimated slope of the NIST standard (top) and the slope itself (bottom).

Thus, measurements when the NIST profile is "clean" (i.e., where the SNR is expected to be >1), the CI of the NIST slope is less than 0.25, and the slope itself is between $-1$ and $0.1\times 10$-5/sec are then considered for further analysis.

Example 7: Characterizing the Presence of a Microorganism in a Sample

Figure 26A:
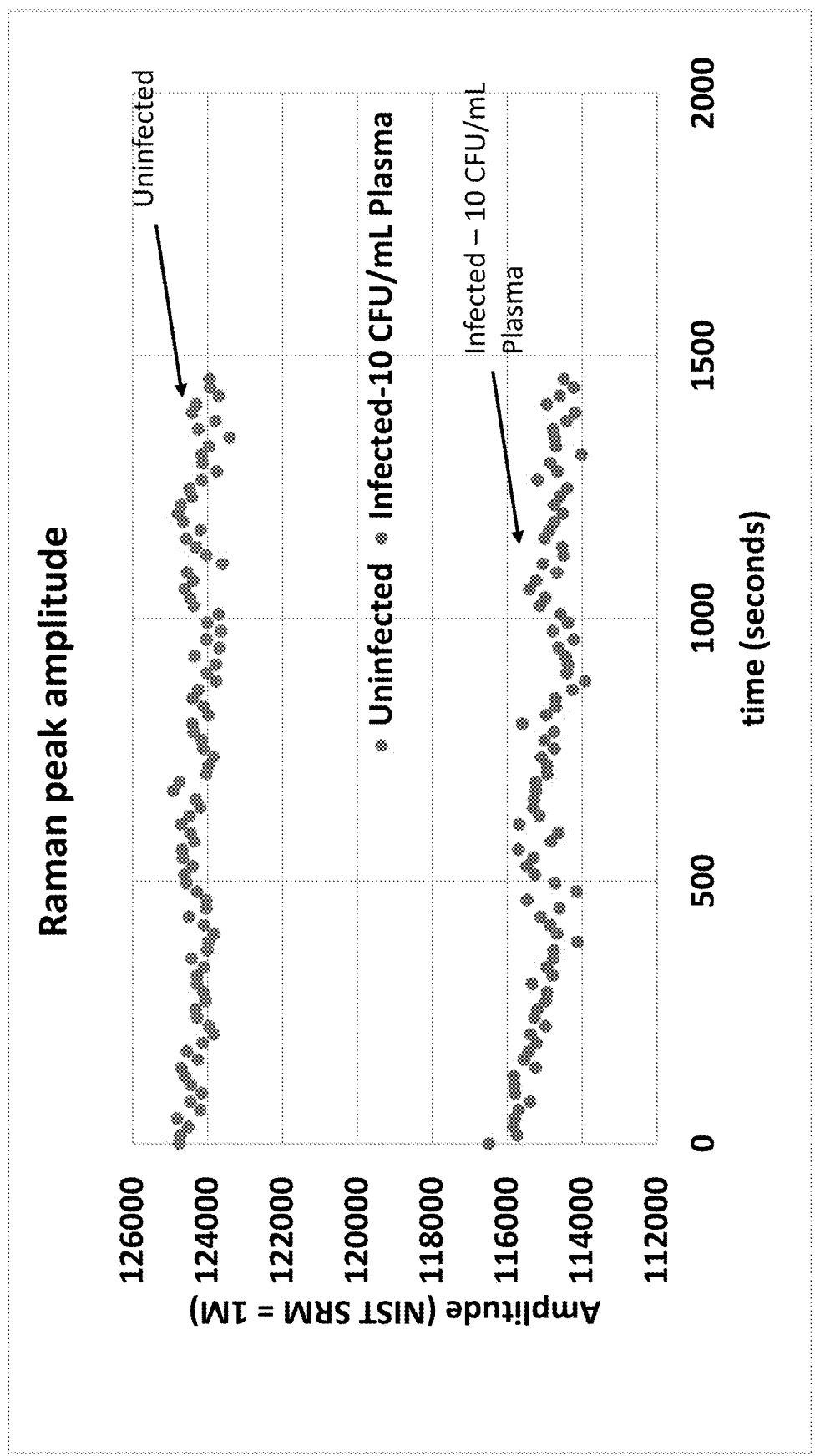
FIG. 26A depicts amplitude of Raman peaks, aggregated for the 4 uninfected control samples and the 3 infected samples according to certain embodiments.
Figure 26B:
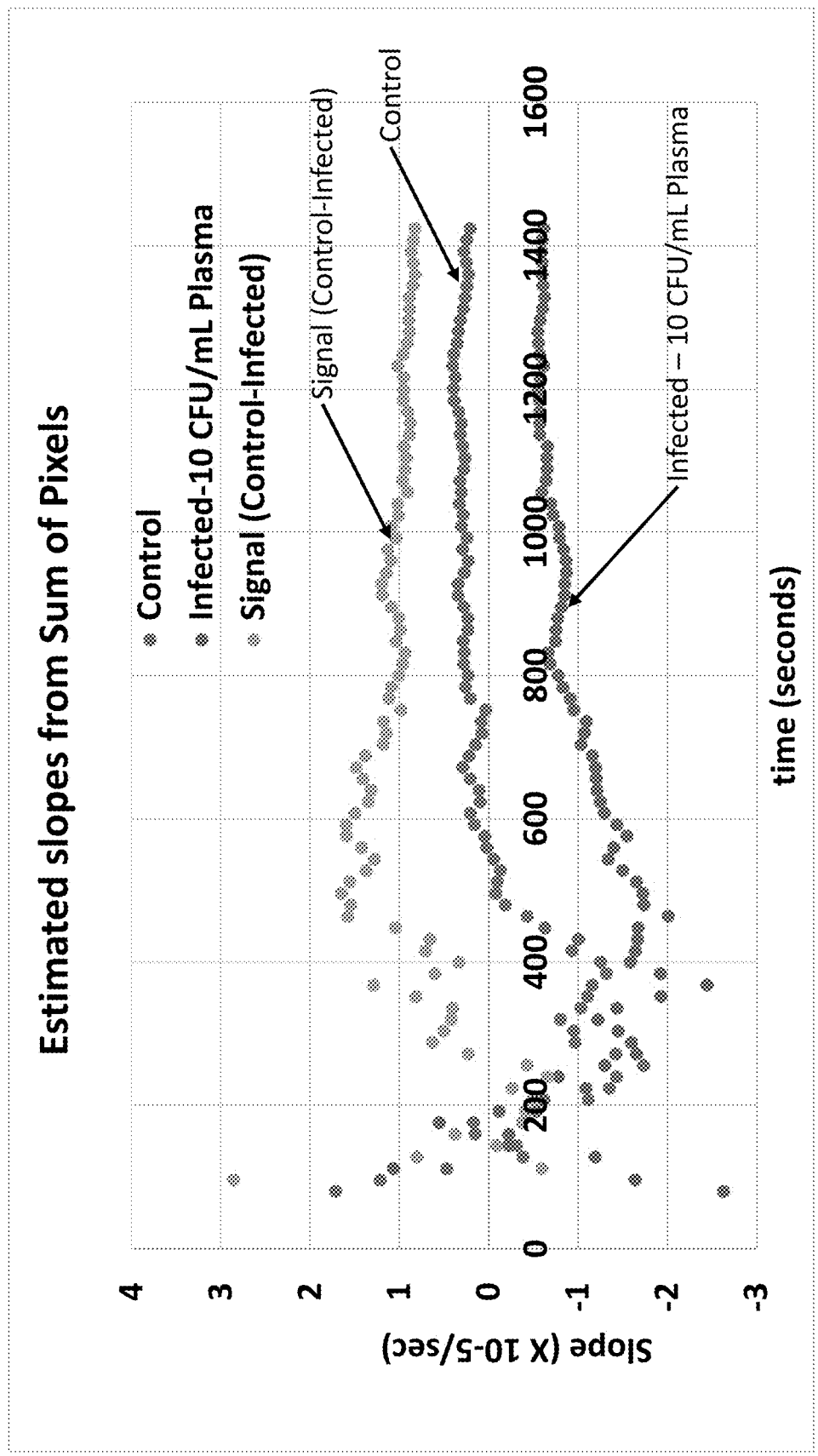
FIG. 26B depicts the estimated rate of change for uninfected samples and infected samples from the area under the curve.
Figure 26C:
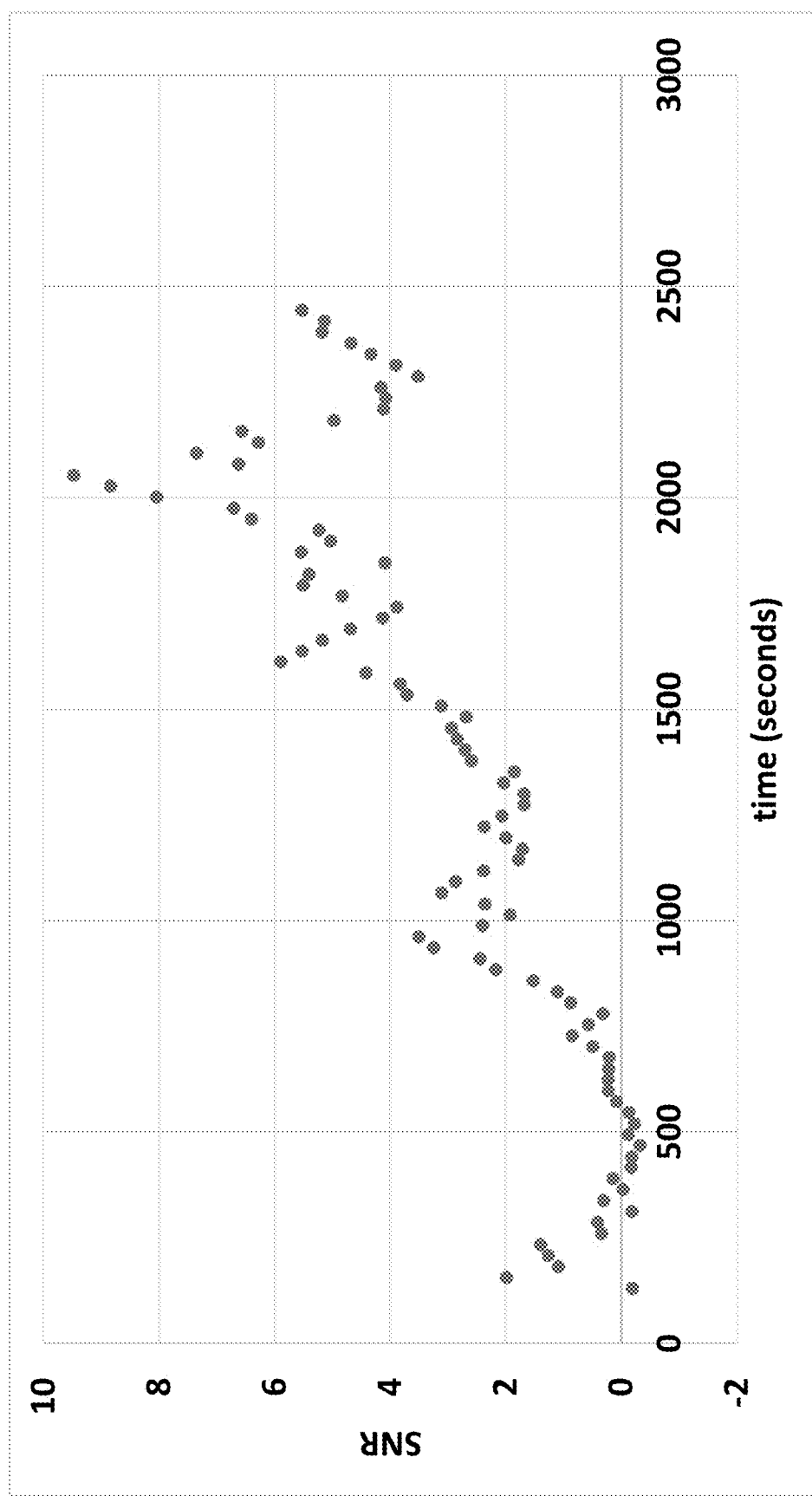
FIG. 26C depicts the estimated signal-to-noise ratio of uninfected and infected samples.

Determining the presence or absence of a pathogenic microorganism is depicted in FIG. 26. The example depicts the use of a test with artificially spiked samples that are created as follows: (a) first, a stock solution of *S. aureus* in buffer is prepared with a concentration of 1000 CFU/mL. 0.05 mL of this stock solution (or, an expected 50 CFUs) is added to 5 mL of plasma purchased from a blood bank and incubated for 2 hours. (b) 0.6 mL of this infected plasma is added to the standard reagent formulation that has a volume of 3.9 mL. Three "infected" samples are created from this plasma. (c) Four uninfected control samples are created by adding 0.6 mL of uninfected plasma (that has also been subject to 2 hour incubation) to the reagent formulation. All 7 test vials are tested simultaneously, with the results illustrated in FIGS. 26A-26C. Use of these known samples enables the use of simple statistical measures (such as signal to noise) to characterize the measurement.

While the test is running, the heights of the Raman peaks are continuously monitored, and their rate of change, for individual test vials. FIGS. 26A-26C illustrates these measurements as aggregates for control and infected samples. For the infected sample, Raman peaks decrease slowly over time. FIG. 26A depicts the amplitude of the Raman peaks, aggregated for the 4 uninfected control samples and the 3 infected samples. The rate of change of the area under the curve is shown in FIG. 26B. The signal is defined as the difference between the rate of change of the uninfected control, and the infected sample. The uninfected control samples demonstrate a rate of change that is consistent with the rate of change observed on the NIST standard~which is estimated to be $(0.59\pm 0.16)\times 10^{-5}$/sec at the end of the measurement. FIG. 26C depicts the signal-to-noise ratio, estimated as the signal divided by the rms standard deviation of the rate of change of uninfected and infected samples.

Figure 27:
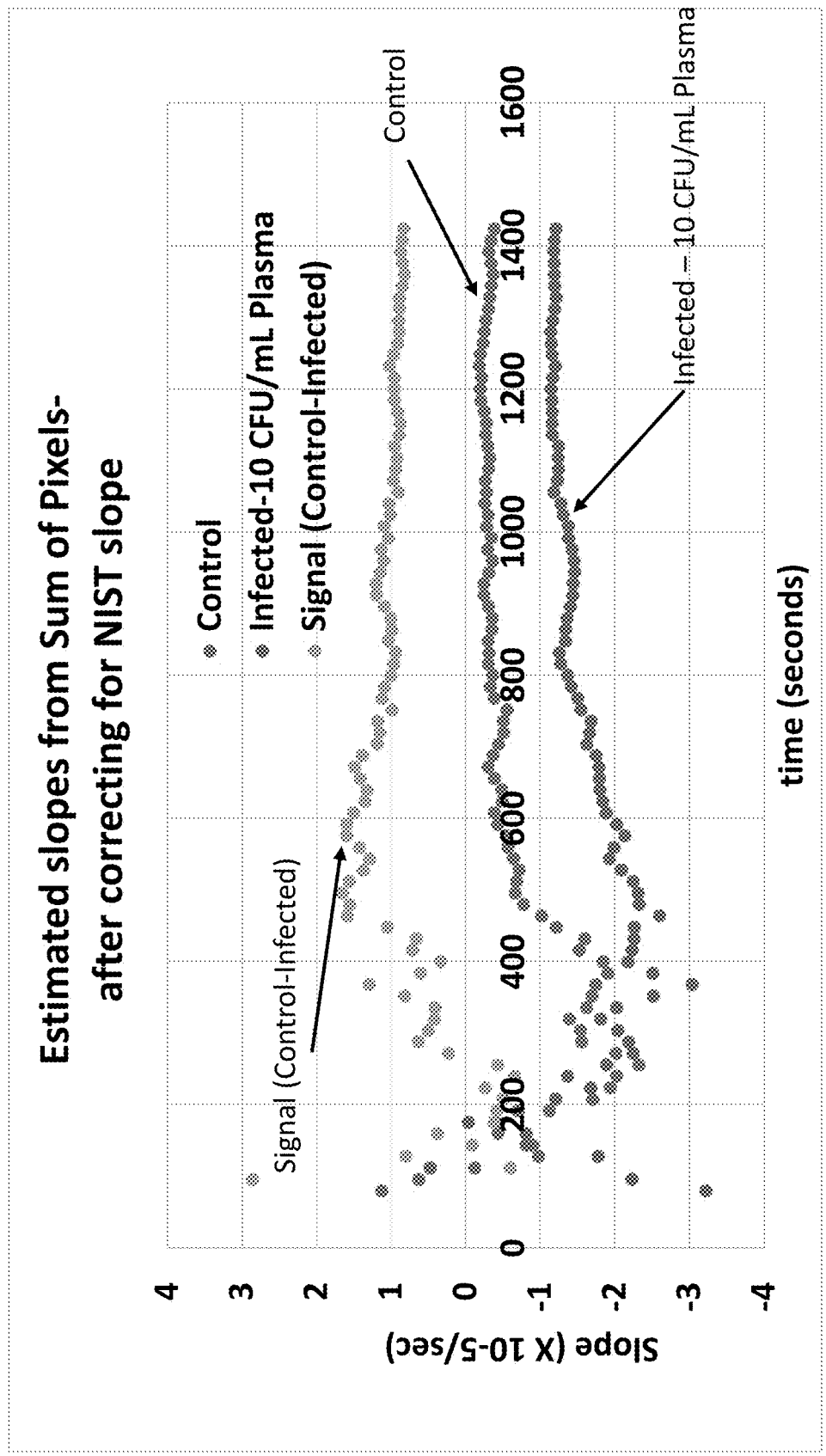
FIG. 27 depicts the estimated slopes, aggregated for control and infected samples and corrected for variation observed in an NIST standard according to certain embodiments.

For final diagnosis, this value is subtracted from the estimated slopes, which reduces the aggregate control slope (and also values for individual vials) slightly below the zero line, as illustrated in FIG. 27. Specifically, FIG. 27 depicts the estimated slopes aggregated for control and infected values and corrected for the variation observed in the NIST standard. After correcting for the drift in the NIST profiles, and collecting data for a long enough time period such that the SNR>>1, the samples can be analyzed to determine if a pathogenic microorganism is present. Bacterial cells are added to the plasma and the infected plasma is added to the standard reagent. Similar results are observed when bacterial cells are added to the plasma, incubated for 2 hours, and centrifuged at high speed (12 krpm, 5 mins) so as to remove the bacterial cells (this removal is verified by culture on broth media) from the plasma, and this infected/centrifuged plasma is added to the reagent vial.

Example 8: Infected Samples without Pathogens

In clinical scenarios, the effect of sampling volume needs to be considered. Most patients with a bloodstream infection have a blood pathogen concentration of about 1-10 CFU/mL. Further, the volume of blood sampled during the blood draw is generally limited to about 10 mL or so (and often less). Thus, for several infected patients, it is expected that 0 CFUs will be present in the blood draw simply due to Poisson sampling statistics. The methods described herein would still be able to identify those samples as "infected" because the subject methods can detect free radicals generated by the bacteria, and not just the bacteria itself.

To demonstrate this, a 2nd experiment is discussed below where the protocol is as follows: (a) first, a stock solution of *S. aureus* in buffer is prepared with a concentration of 1000 CFU/m L. 0.05 mL of this stock solution (or, an expected 50

Figure 28A:
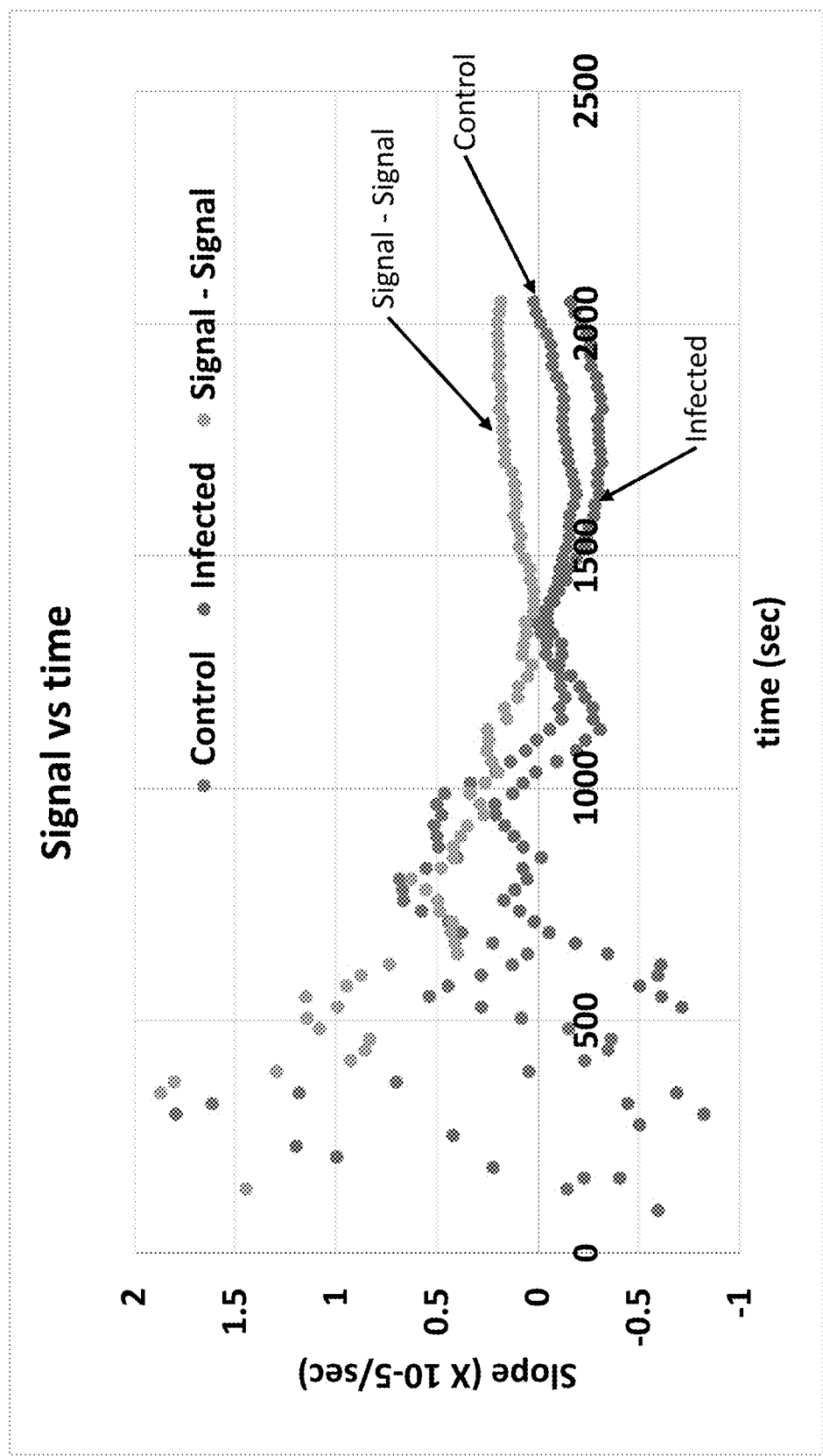
FIG. 28A depicts the estimated rate of change for the uninfected and infected samples, estimated from the area under the curve according to certain embodiments.
Figure 28B:
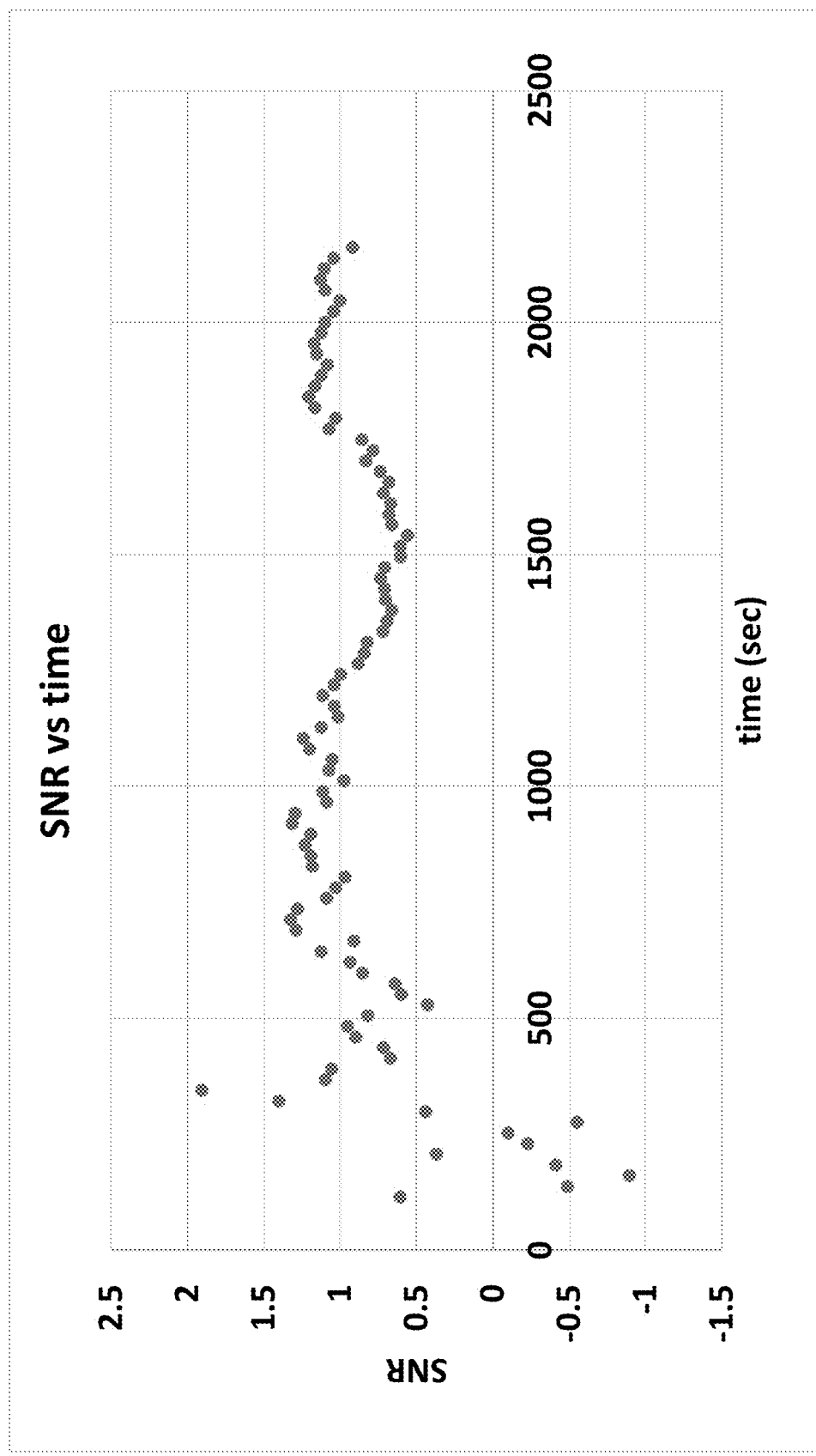
FIG. 28B signal-to-noise ratio, estimated as the signal divided by the rms standard deviation of the rate of change of uninfected and infected samples according to certain embodiments.
Figure 28C:
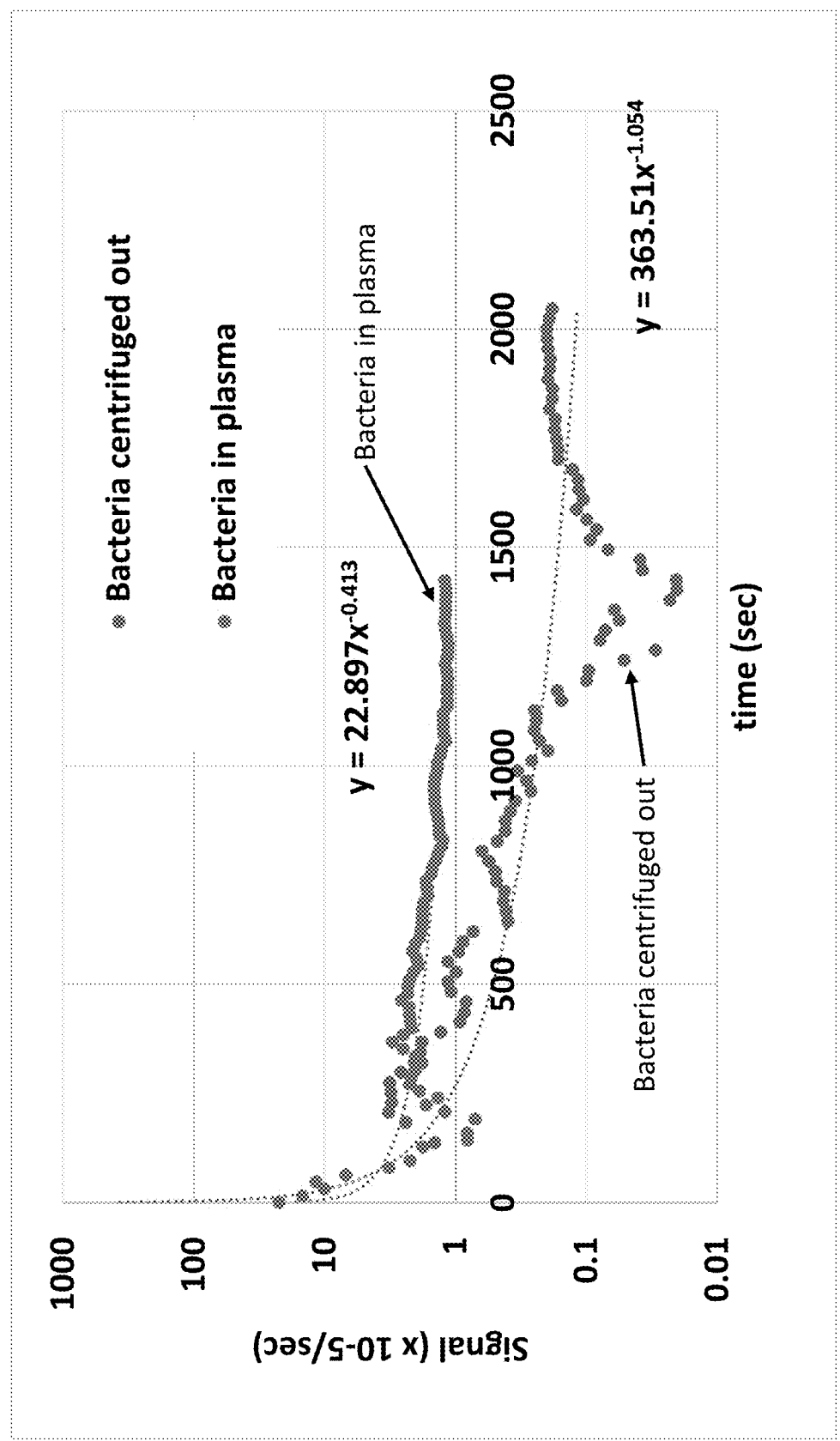
FIG. 28C depicts signal, as a function of time for this sample set in which the bacteria has been centrifuged and removed according to certain embodiments.

CFUs) is added to 5 mL of plasma purchased from a blood bank and incubated for 2 hours. (b) This plasma is centrifuged at 12000 rpm for 5 minutes so as to remove the bacteria from the plasma. The plate count method is used to characterize the pathogen concentration in the plasma before and after the centrifugation. (c) 0.6 mL of this infected plasma is added to the standard reagent formulation that has a volume of 3.9 mL. 3 "infected" samples are created from this plasma. (d) 4 uninfected control samples are created by adding 0.6 mL of uninfected plasma (that has also been subjected to 2 hour incubation) to the reagent formulation. All 7 test vials are tested simultaneously, with the results illustrated in FIG. 28A-28C. FIG. 28A depicts the estimated rate of change for the uninfected and infected samples, estimated from the area under the curve. The signal is defined as the difference between the rate of change of the uninfected control, and the infected sample. FIG. 28B depicts signal-to-noise ratio, estimated as the signal divided by the rms standard deviation of the rate of change of uninfected and infected samples. FIG. 28C depicts signal, as a function of time for this sample set in which the bacteria has been centrifuged and removed. Also shown for comparison is a sample set that does not have the centrifugation step to remove the bacteria. As is clear from the traces, the signal is weaker when the bacteria has been centrifuged out, and also decreases inversely with time. By contrast, when the bacteria is present in the test sample, then the signal decays with the square root of time.

Example 9: Characterizing Clinical Samples

For clinical samples (i.e., those that include plasma from human patients), a number of additional factors are further considered, e.g., the plasma can contain clumps of various proteins and lipids that can distort the flow at the interface and/or cause other changes that applies a systematic bias to the data. To normalize these biases, the slope of the fluorescence output is considered (e.g., at 3000 $cm^{-1}$). An algorithm used for normalization is as follows:
  (a) First, compute the slope of the Raman peaks using the methods described above.
  (b) Next, compute the slope of the fluorescent output at 3000 $cm^{-1}$. If this slope is less than a certain predefined threshold, then reject the measurement as being too noisy. In this case, this threshold is set to be $-4.5 \times 10^{-5}$/sec.
  (c) If the slope of the fluorescent output is less than the threshold, then subtract this value from the slope of the Raman peaks. This is the "signal".
  (d) Account for samples that may have a very low amplitude to begin with–this can be for any number of reasons, including the presence of a large number of red blood cells in the plasma, the aggregation of a large number of albumin molecules etc. The algorithm flags these samples as infected, so as to prevent the possibility of false negatives that can harm the patient.
  (e) Samples are diagnosed as infected if either the final slope (after subtracting the fluorescence slope) is less than $-1 \times 10^{-5}$/sec, or the amplitude of the Raman peaks is less than 0.22 (where the NIST profile=1). Samples are diagnosed as uninfected if both the final slope (measured at 1000 seconds) is greater than $-0.8 \times 10^{-5}$/sec and the amplitude of the Raman peak is greater than 0.22. The slope threshold is significantly greater than the threshold suggested by the scaling behavior without bacteria present (ca. $-0.25 \times 10^{-5}$/sec) but slightly less than the scaling behavior with bacteria present ($-1 \times 10^{-5}$/sec).

Figure 29A:
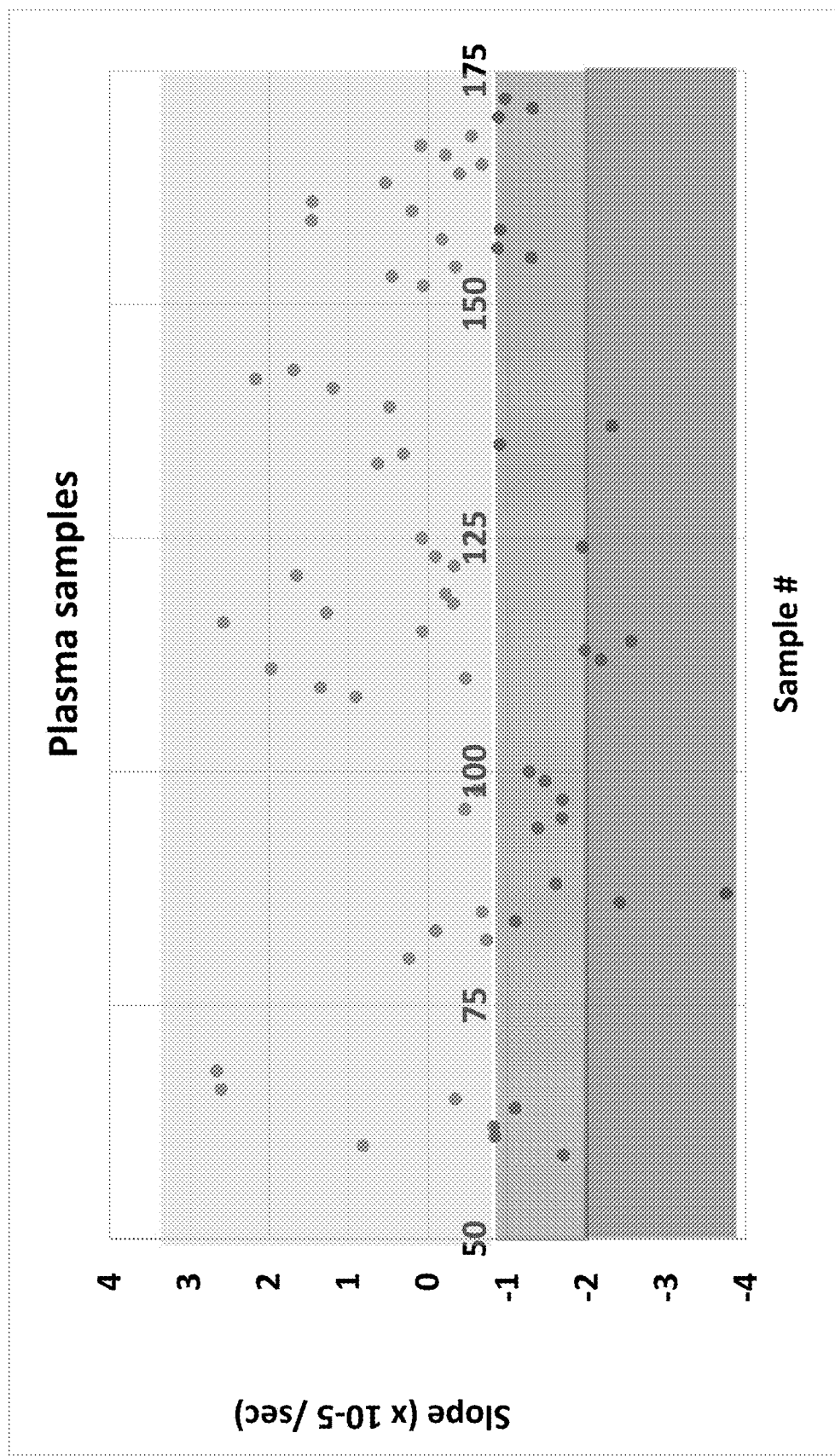
FIG. 29A depicts the rate of change of Raman peaks in clinical samples according to certain embodiments.
Figure 29B:
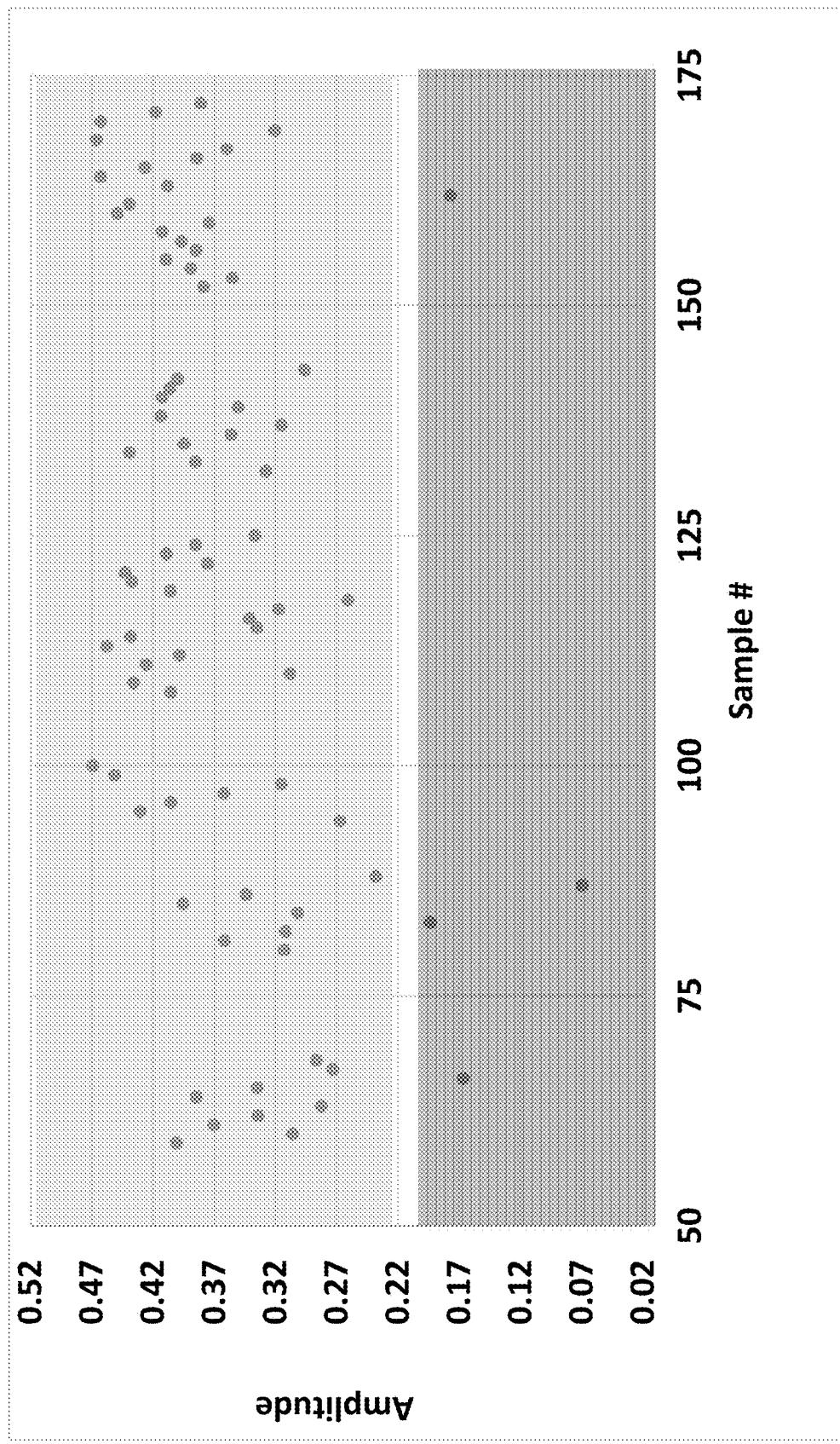
FIG. 29B depicts amplitude of the Raman peaks for a set of tests completed on clinical samples with added plasma from different patients according to certain embodiments.

One illustrative example is depicted in FIGS. 29A and 29B. The results from the subject rapid test methods are compared with the results from blood culture. The tests are done on discarded plasma samples obtained from the remnants of the CBC (complete blood count) test done on patients who are suspected of having a bloodstream infection (and for whom a blood culture test was also ordered). After the CBC test is done, the CBC test vacutainer is retrieved and 0.6 mL from the plasma layer is aliquoted (some of these plasma samples had a significant amount of red coloration due to remnant red blood cells). The 0.6 mL of the plasma layer is added to the reagent that had glutathione (GSH) of 0.3 mL and which had been incubated at 37° C. for 18 hours. The test vials were placed in the test instrument and tested immediately. FIG. 29A depicts the rate of change of the Raman peaks and FIG. 29B depicts the amplitude of the Raman peaks for a set of tests done with added plasma from different patients. With the above-described algorithm, the samples are diagnosed as infected if either the Amplitude (FIG. 29B), or the Slope (FIG. 29A) are in the "infected" band. The overall detection metrics are as follows:
  (a) 40 samples that were diagnosed as "negative" by the subject methods described herein, and that were also blood culture negative. "40 true negatives"
  (b) 0 samples that were diagnosed as blood culture positive that were diagnosed as negative by the subject methods described herein. "0 False negatives"
  (c) 6 samples that were blood culture positive and that were also diagnosed as positive by the subject methods described herein. "6 true positives"
  (d) 7 samples that were blood culture negative and that were diagnosed as positive by the subject methods described herein. "7 false positives"
  (e) 13 samples that were blood culture negative, but for which the subject methods described herein were unable to make any diagnosis (either because the slopes were in the intermediate range, or because the fluorescence slope was changing outside of the set threshold). 4 samples were blood culture positive, but for which no diagnosis was determined by the subject methods.

Figure 30:
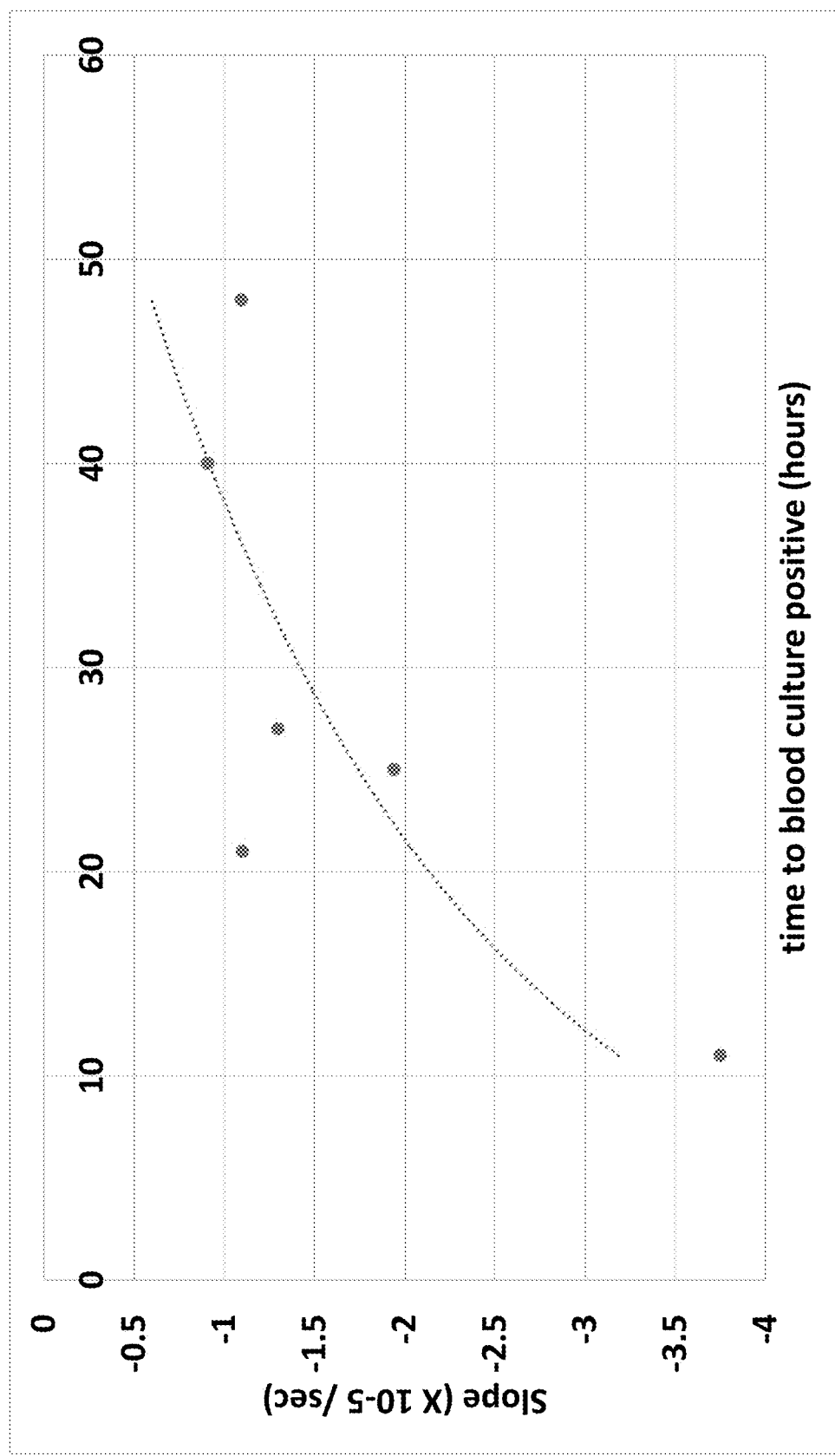
FIG. 30 depicts the relationship between the rate of change of Raman peaks and time to positivity in a blood culture test according to certain embodiments.

With these settings, for infected samples, the rate of change of the Raman peaks correlates with the time to positivity in the blood culture test, as depicted in FIG. 30.

Figure 31A:
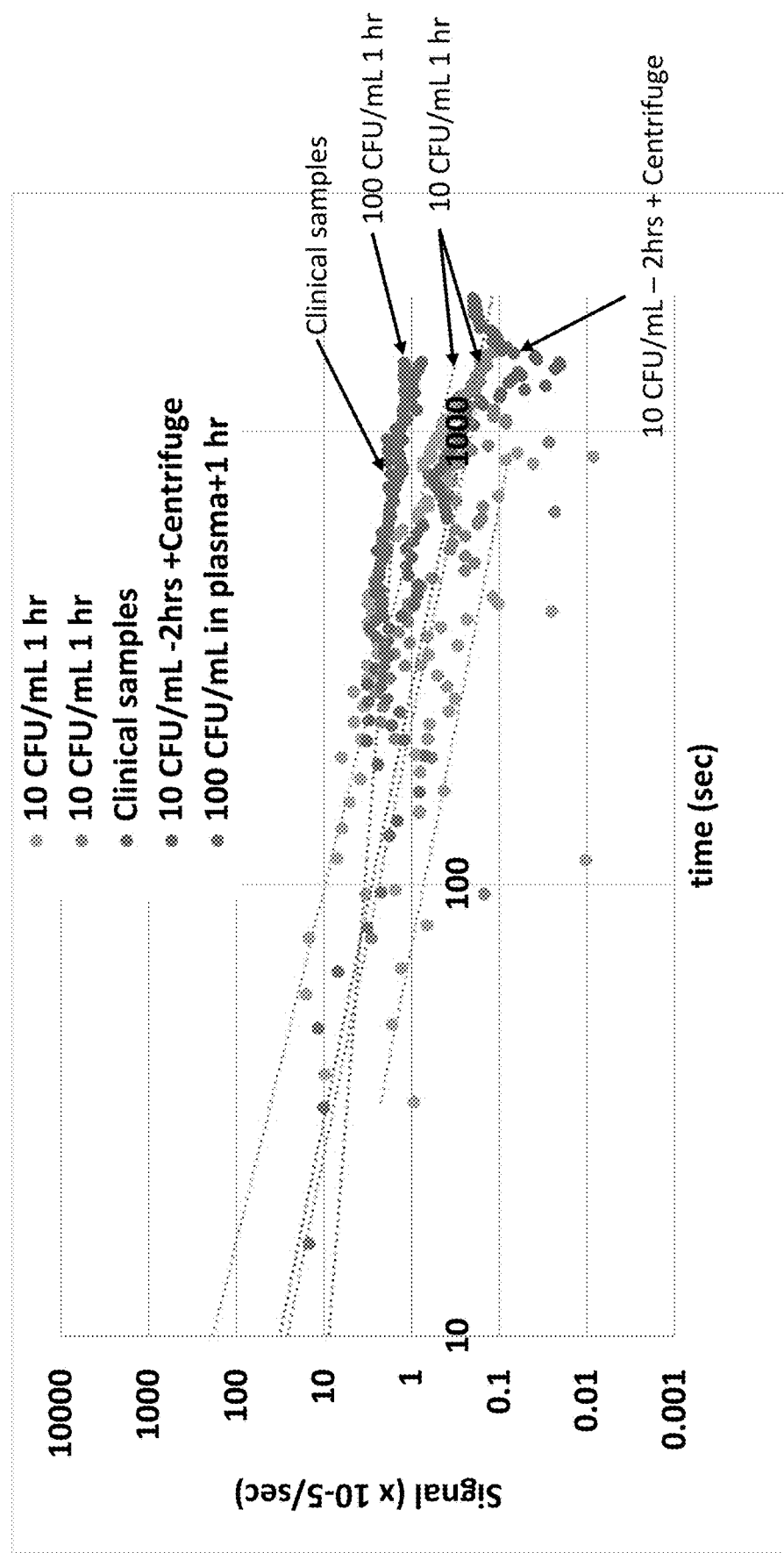
FIG. 31A depicts the change in signal magnitude of samples having different bacterial concentration in clinical samples according to certain embodiments.
Figure 31B:
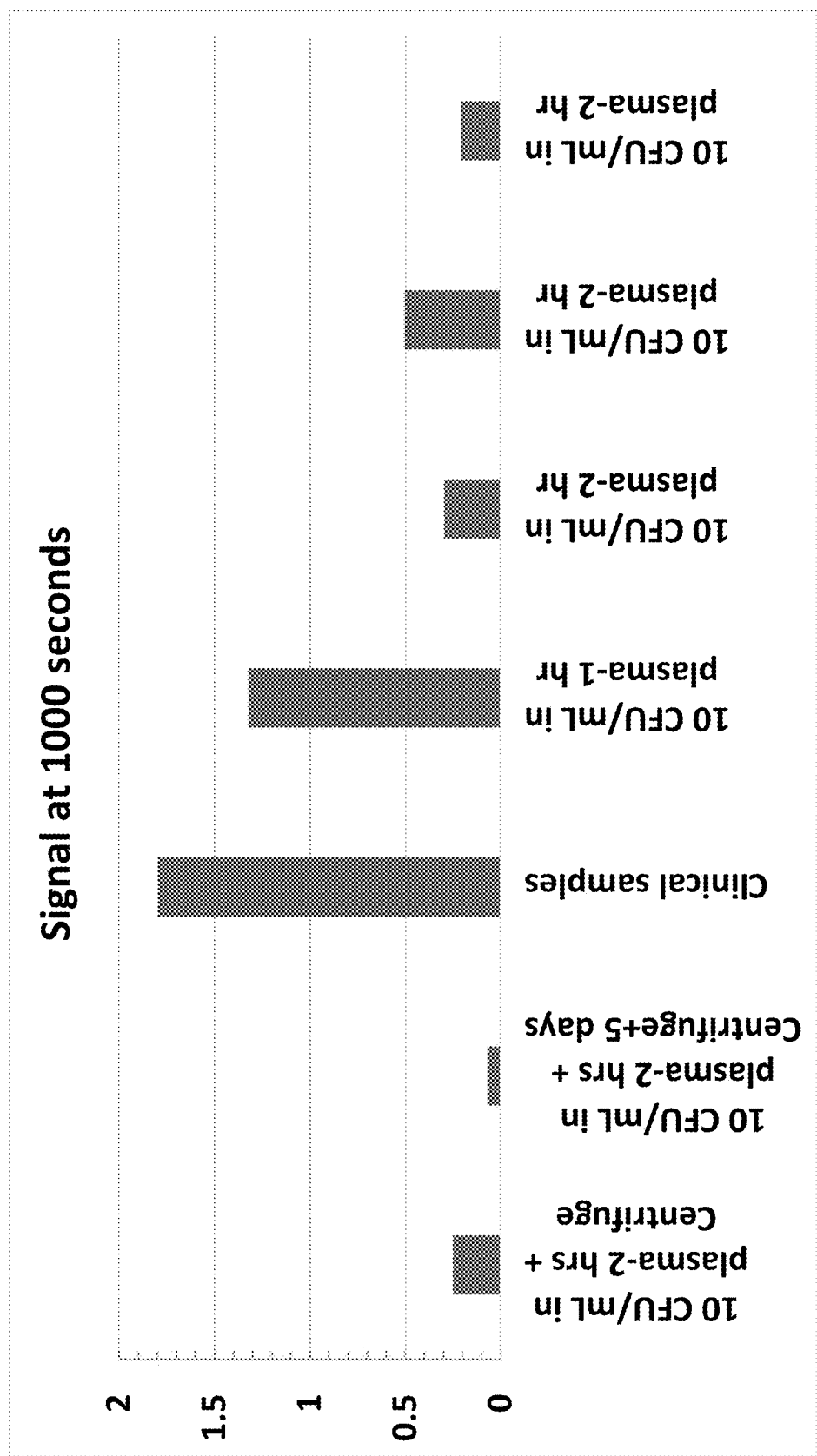
FIG. 31B depicts the signal strength at 1000 seconds for clinical samples having different bacterial concentration according to certain embodiments.

A comparison of the signal magnitude over time for different sample types is presented in FIGS. 31A and 31B. Specifically, FIG. 31A depicts the signal magnitude (rate of change of Raman peaks in uninfected control samples minus the rate of change of Raman peaks in infected samples) for multiple test runs summarizing the variation of the signal with time for different sample types. In all cases, the signal magnitude decays inversely with time. Multiple runs are demonstrated with 10 CFU/mL S. aureus present in the test sample. FIG. 31B depicts the signal strength at 1000 seconds for different sample types. When the bacteria are centrifuged out, then the signal appears to be smaller. The signal appears be significantly higher in the clinical samples.

Further, the signal strength in the clinical samples appears to be significantly greater than that in samples with 10 CFU/mL of S. aureus present in the test sample, even with 2 hours of incubation. Since the clinical samples are expected to have 1-10 CFU/mL pathogen concentration, and since only 0.6 mL of plasma is sampled, it is believed that many of the clinical samples do not have any active bacteria present in them. Given the large signal magnitude in these clinical samples, it is clear that the methods described herein are responding to the free radicals generated by bacteria.

Example 10: Measuring the Minimal Inhibitory Concentration of Antimicrobial Agents To measure the minimum inhibitory concentration, or to otherwise characterize the antimicrobial susceptibility of any unknown pathogen to a candidate antimicrobial:
(a) Incubate the unknown pathogen for about 3 hours in a rich media. This time period should suffice to increase the concentration of the causative pathogen by about >100×. Thus, the 1 CFU (or more) in the original sample will become >100 CFUs.
(b) Aliquot the pathogen into about 7 equal parts, and each part will be expected to have at least 14 CFUs, which is sufficiently greater than the poisson sampling error of square root of the number of expected CFUs (14, in this case).
(c) To each part, add a variable concentration of the candidate antimicrobial, starting at very low concentrations of 0.125 µg/mL, and increasing in steps of 2 to 0.25, 0.5, 1, 2, 4 & 8 µg/mL (this range is designed to span the desired MIC in 7 steps of 2). Incubate this mixture for another 20 minutes, which allows for sufficient time for the 10 CFUs to interact with the candidate antimicrobial.
(d) Add the 7 mixtures to the test vials, and test. The number of free radicals present in the mixed sample is a function of the concentration of the antimicrobial, and so the final slope can be plotted against antimicrobial concentration to develop estimates for the MIC. This is illustrated in FIGS. 32A and 32B.

Figure 32A:
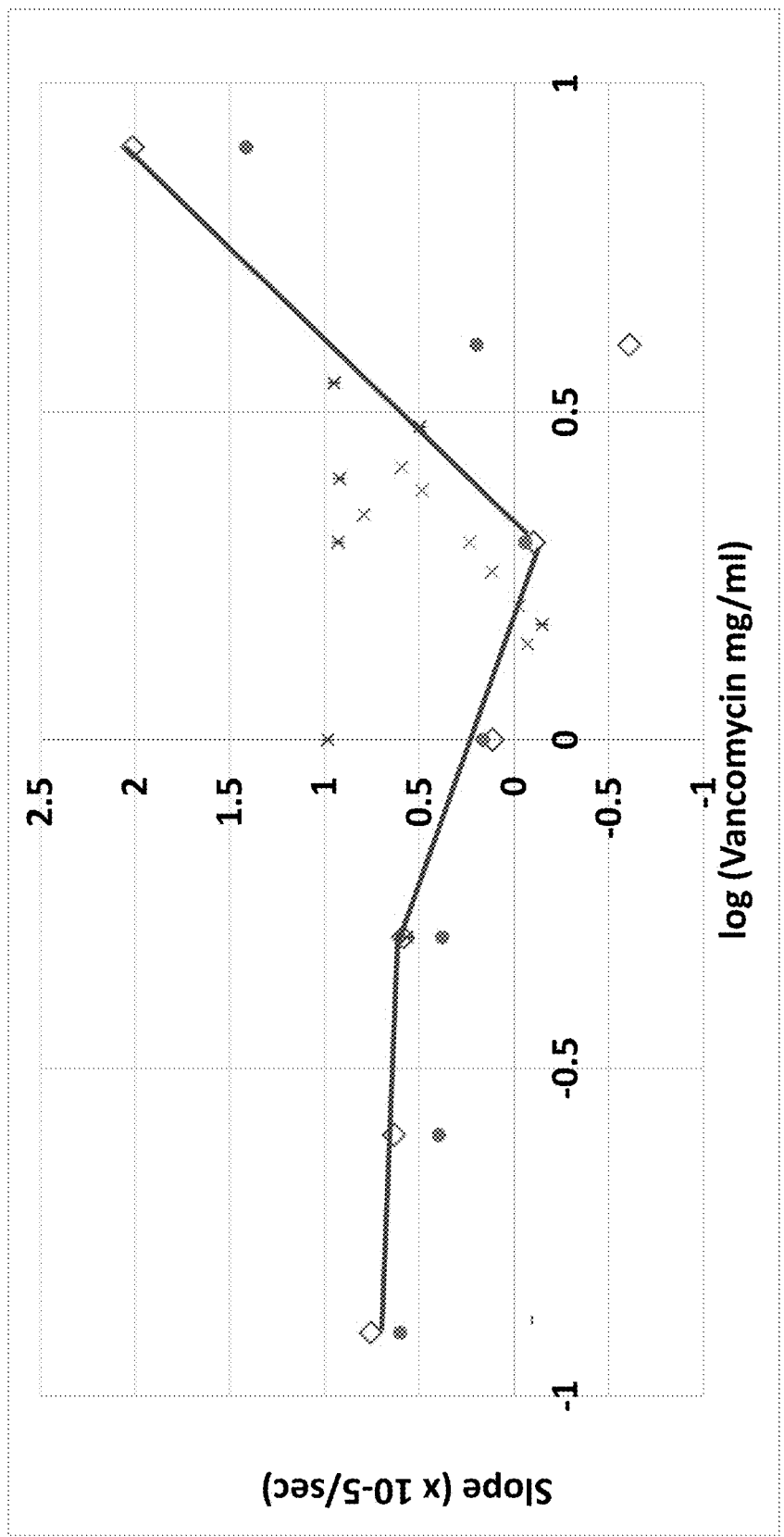
FIG. 32A depicts the measured slope of Raman intensity as a functional of antimicrobial (vancomycin) concentration according to certain embodiments.
Figure 32B:
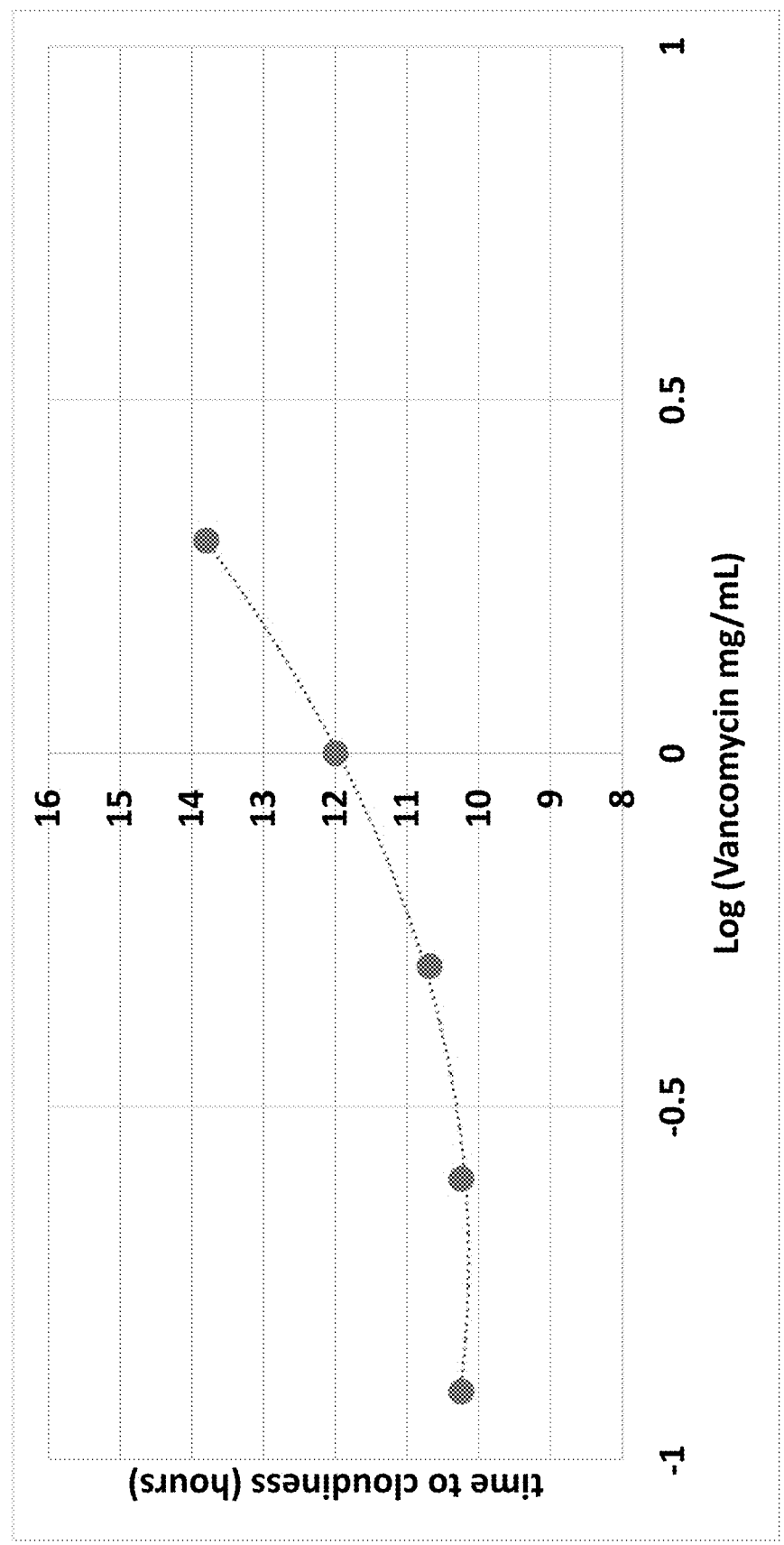
FIG. 32B depicts the time taken for the tested samples to become cloudy.

FIG. 32A depicts the measured slope as a function of antimicrobial agent (vancomycin) concentration. FIG. 32B depicts the time taken for the tested samples to become cloudy. Above 2 µg/m L, the samples remain clear for very long incubation periods (>96 hours). Thus, the Minimum Bactericidal Concentration MBC is about 2 µg/mL. Above 0.25 mg/mL, the time to cloudiness increases slightly. Thus, the MIC is about 0.25 mg/mL. As illustrated in FIGS. 32A and 32B, the MIC corresponds to the concentration at which the signal decreases slightly. Further, the MBC (Minimum Bactericidal Concentration) corresponds to the concentration at which the signal increases again.

Example 11: Methods for Determining the Phenotype of an Unknown Microorganism The phenotype of an unknown microorganism in a sample can be determined by employing an added crosslinking agent. Below, a peptidase is identified in the sample by adding a crosslinking agent that includes a cleavable peptide bond next to a glutamic acid group. The synthesis of a glutamic acid derivative with disulfide crosslinkers is shown in Scheme 1.

Scheme 1

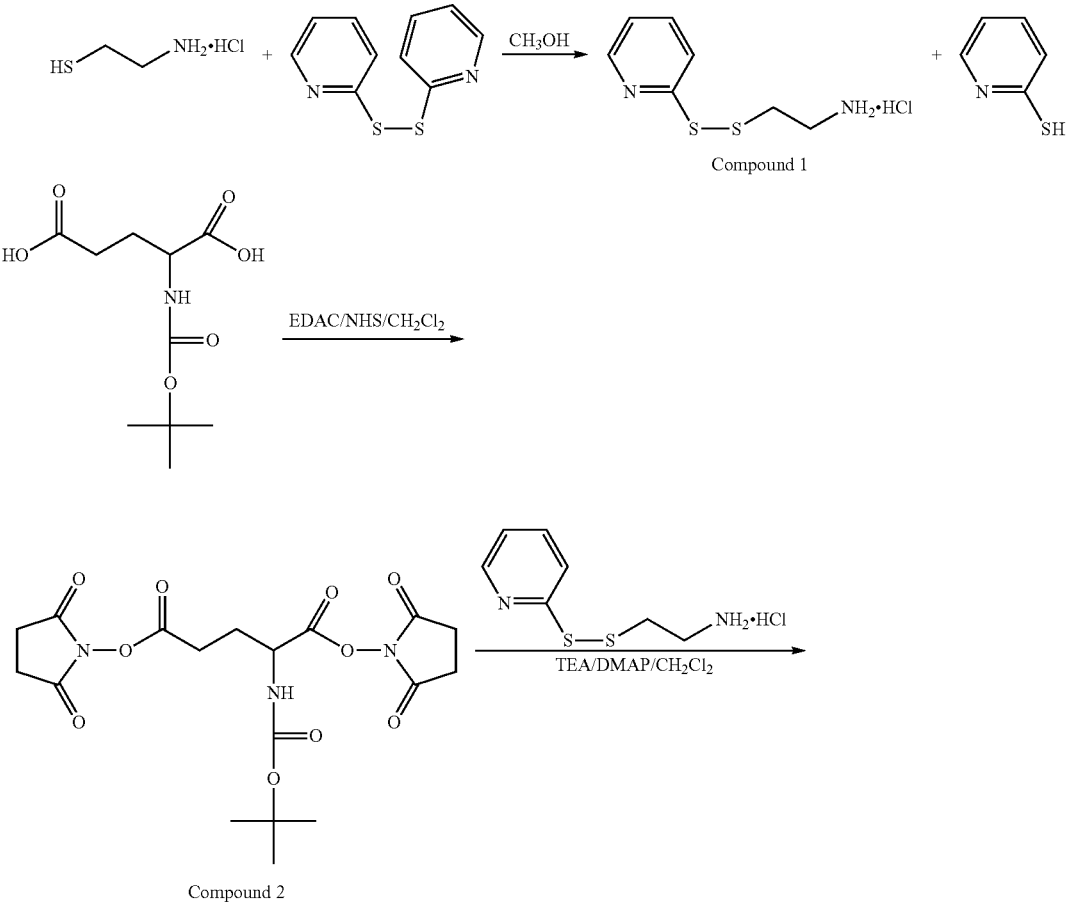

Compound 2

-continued

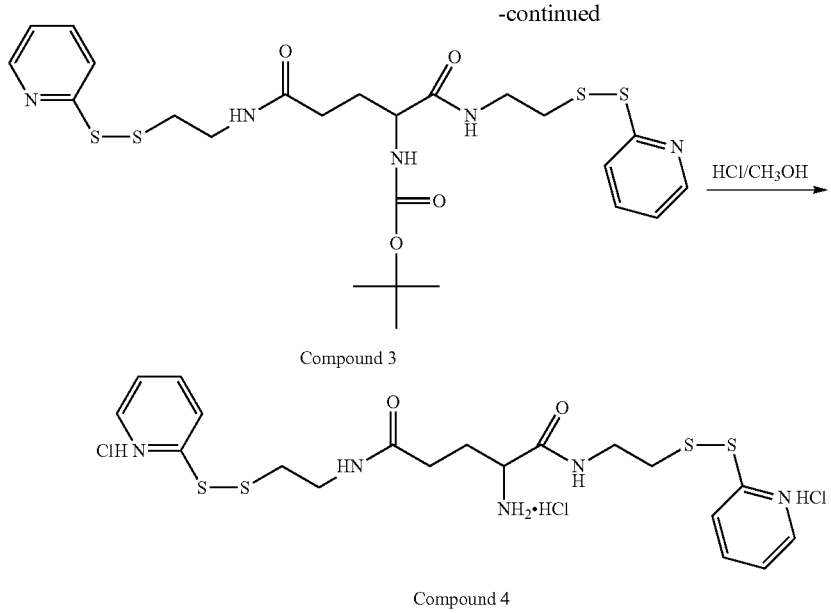

Compound 3

Compound 4

Compound 1: Into a 250 mL round bottom flask containing a magnetic stirring bar, were added 3.0 gm (26.4 mmole) of cysteamine hydrochloride (Sigma-Aldrich, cat. #: M6600) and 60 mL of methanol. The mixture was stirred at a magnetic stirrer to form a solution. Into this solution was added 6.2 gm (28.2 mmole) of 2,2'-dithioldipyridine (Sigma-Aldrich, cat. #: 43791) portion by portion. The resulting yellow solution was stirred overnight and concentrated to dry powder using a Rotavapor. The yellow product was further dried over a high vacuum pump for 4 to 5 h to give 9.03 gm of a yellow powder product (with about 98.2% yield). This product mixtures contained unreacted starting material, 2,2'-dithioldipyridine, the desired product, compound 1 and the side product, 2-thiolpyridine. Without further purifications, the product mixture was used for the next step reaction. Compound 2: Into a 250 mL round bottom flask containing a magnetic stirring bar, were added 0.5 gm (2.0 mmole) of BOC-L-glutamic acid (Sigma-Aldrich, cat. #: 16345), 0.86 gm (4.5 mmole) of EDAC [N-(3-dimethylaminopropyl)-N'-ethylcarbodiimde hydrochloride, Sigma-Aldrich, cat. #: E7760), 0.52 gm (4.5 mmole) of NHS (N-hydroxysuccinimide, Sigma-Aldrich, cat. #: 56480) and 40 mL of dichloromethane. The mixture was stirred at a magnetic stirrer for 2 h and the clear solution was formed. Into this solution was added 4 mL of TEA (trimethylamine, EMD, cat. #: 1200-5) and 100 mg of DMAP [4-(dimethylamino)pyridine, Aldrich, cat. #: 10,770-0), and then 1.4 gm of Compound 1 mixtures. The reaction mixtures were stirred overnight and washed three times with 30 mL of 5% $NaHCO_3$ aqueous solution, the bottom solution was dried over sodium sulfate. After the solvents were removed via a Rotavapor and the product residue was dissolved on 5 mL of $CH_2Cl_2$ for column purifications. 30 gm of silica gel was loaded with $CH_2Cl_2$ and the crude product solution was loaded onto the column, and the column was eluted with $CH_2Cl_2$, 1% $CH_3OH/CH_2Cl_2$ and 2% $CH_3OH/CH_2Cl_2$, 3% $CH_3OH/CH_2Cl_2$. The fractions were identified by the normal phase TLC plates, developing with 5% $CH_3OH/CH_2Cl_2$ (Rf=0.28). The desired fractions were pooled and concentrated to give 0.28 gm (0.48 mmole) of the semisolid Compound 3, 22.2% in yield. $^1$H NMR spectra in $CDCl_3$ matches to the proposed structure of Compound 3. Compound 4: Into a 100 mL round bottom flask containing a magnetic stirring bar, was added 0.28 gm (0.48 mmole) of Compound 3, 15 mL of methanol and 3 mL of concentrated hydrochloric acid solution. The resulting mixture was stirred for 15 min, and concentrated to small volume by a Rotavapor (mostly water). The product residue was further dried over a high vacuum to dryness. After adding about 3 mL of ethanol, the product mixture was further over a high vacuum to give 0.29 (0.479 mmole) gm of the powder product, Compound 4, 99.8% in yield. Without further purifications, the product can be dissolved in water and the pH was adjusted to 5.3 using 0.1 mM NaOH solution, which is used for crosslinking the proteins, such as albumin, through the disulfide exchanges by the cysteine residue of proteins with the activated disulfide.

Figure 33A:
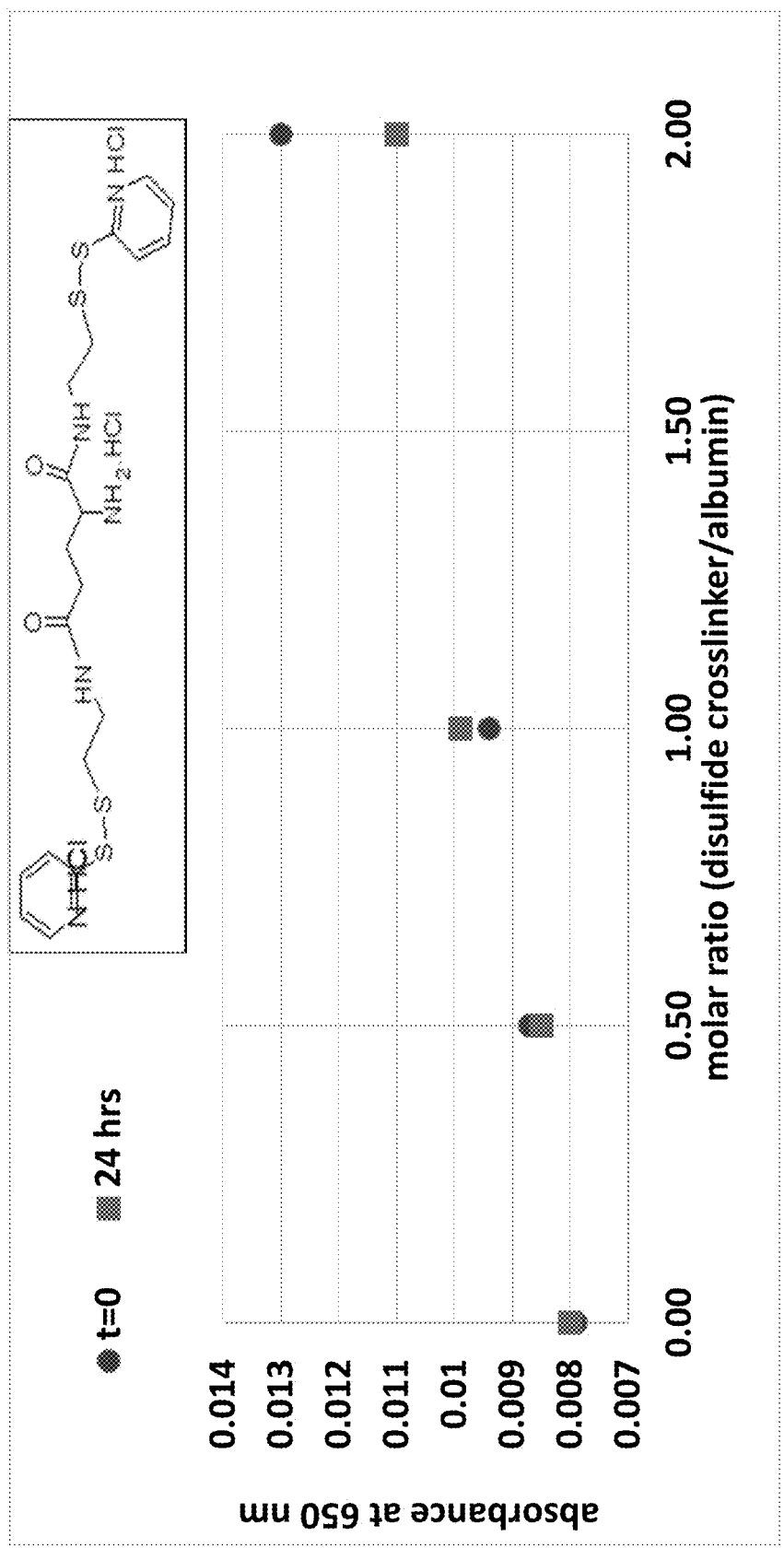
FIG. 33A depicts the effect of absorbance at 650 nm for a peptide crosslinker compound that contains two disulfide bonds according to certain embodiments.
Figure 33B:
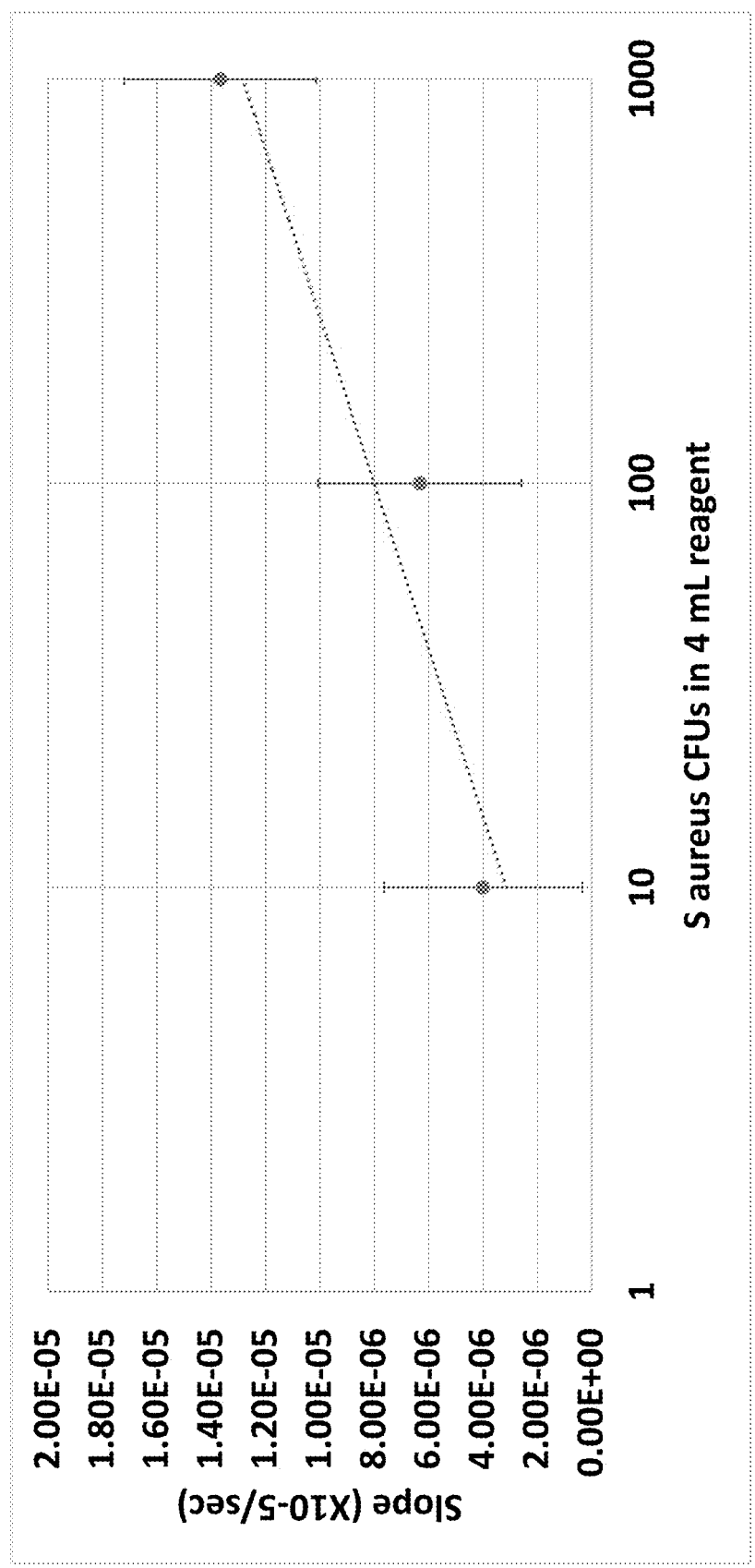
FIG. 33B depicts the increase in Raman signal over time as a function of concentration of microorganism.
Figure 34:
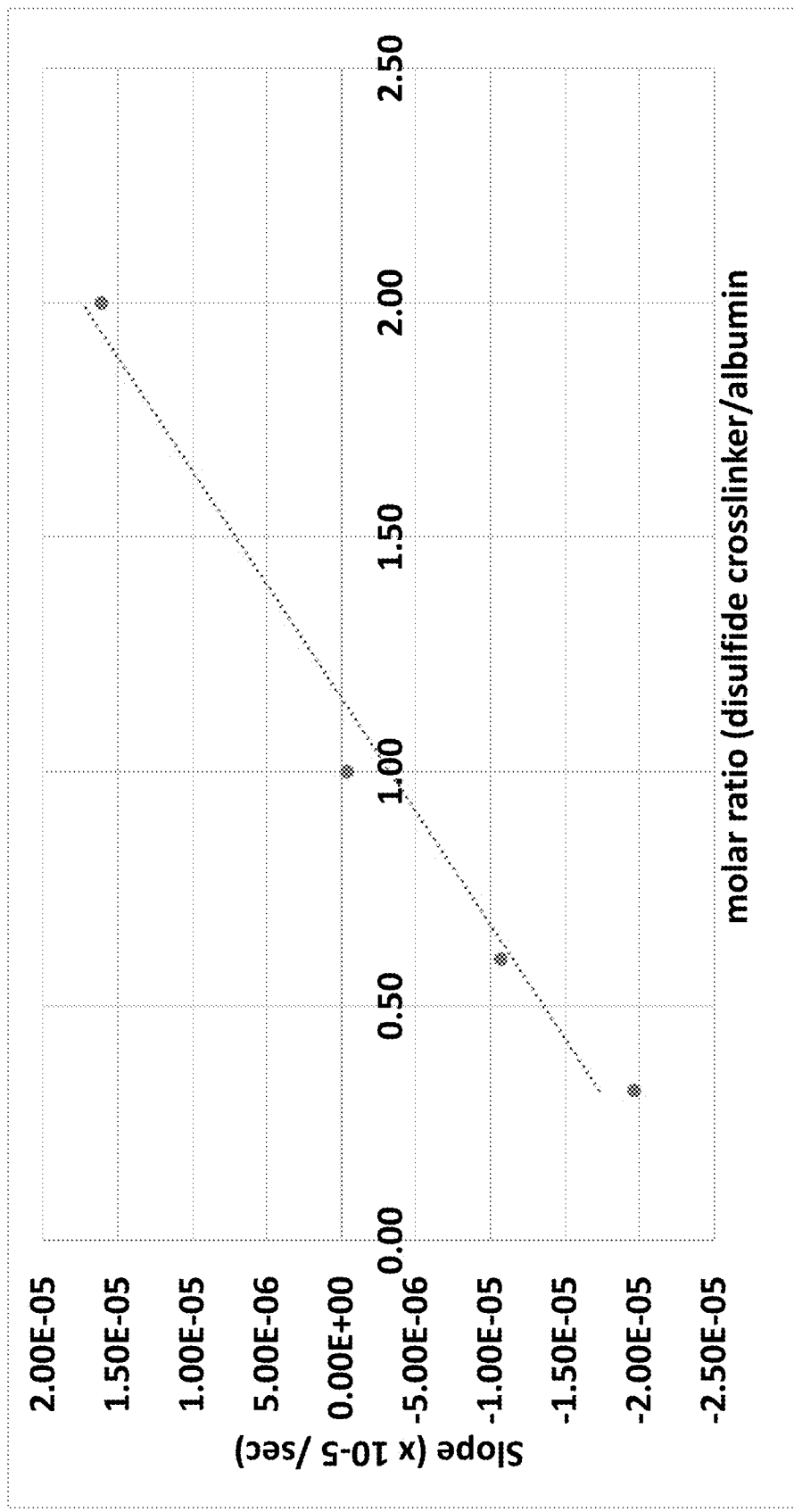
FIG. 34 depicts the increase in Raman signal as a function of molar ratio of added disulfide crosslinker according to certain embodiments.

The crosslinker increases the background UV-Vis absorption as depicted in FIG. 33A, however the UV-Vis absorption decreases over time for high crosslinker content (the albumin network is being reshuffled by the GSH). FIG. 33A depicts the effect of absorbance at 650 nm for a peptide crosslinker that contains two disulfide bonds that exchange with the reduced disulfide bonds on the albumin, thereby creating a network of albumin molecules. The background absorbance from albumin (from Rayleigh scattering) increases with crosslinker content (correspondingly, our reagent test vials that contain the crosslinker demonstrate a signal similar to what is observed with pathogenic microorganisms). Certain bacteria produce a peptidase that can cleave the glutamic acid peptide bond (e.g., S. aureus), resulting in an increase in the Raman signal over time (FIG. 33B). This rate of this increase scales with pathogen concentration. This corresponds to the Raman test results as well, as depicted in FIG. 34. At low crosslinker content, the Raman peaks decrease over time, consistent with the formation of an albumin network. At high crosslinker content, the Raman peaks increase. In certain embodiments, the crosslinked albumin network is reduced back to monomeric albumin by a bacterial metabolite (the peptidase in the current case). For example, for testing a peptidase, crosslinker:albumin ratio was set at 1:2.

Upon mixing with albumin, the disulfide bonds on the crosslinker exchanges with the cysteine groups on the albumin, and creates albumin dimers. In turn, this increases the background absorbance due to Rayleigh scattering (FIG. 33A). For reagent systems with very large amounts of crosslinkers, it appears that the crosslinked albumin reshuffles the disulfide bonds over time, and slowly reduces the Rayleigh scattering. Thus, in these experiments, the crosslinker:album in ratio was set to 1:2. For this system, Raman peaks decrease in amplitude over time, resembling the albumin crosslinking brought about by free radicals. If a reagent system that contains the peptide disulfide crosslinker is exposed to peptidase producing bacteria, then the cleavage of the crosslinker will result in a disruption of the interface layer, and an increase in the Raman peak amplitude. This suggests an inoculum dependence with a limit of detection better than 10 CFUs in 4 mL reagent. (FIG. 33B).

Example 12: Detection and Characterization Via Fluorescence

Figure 35A:
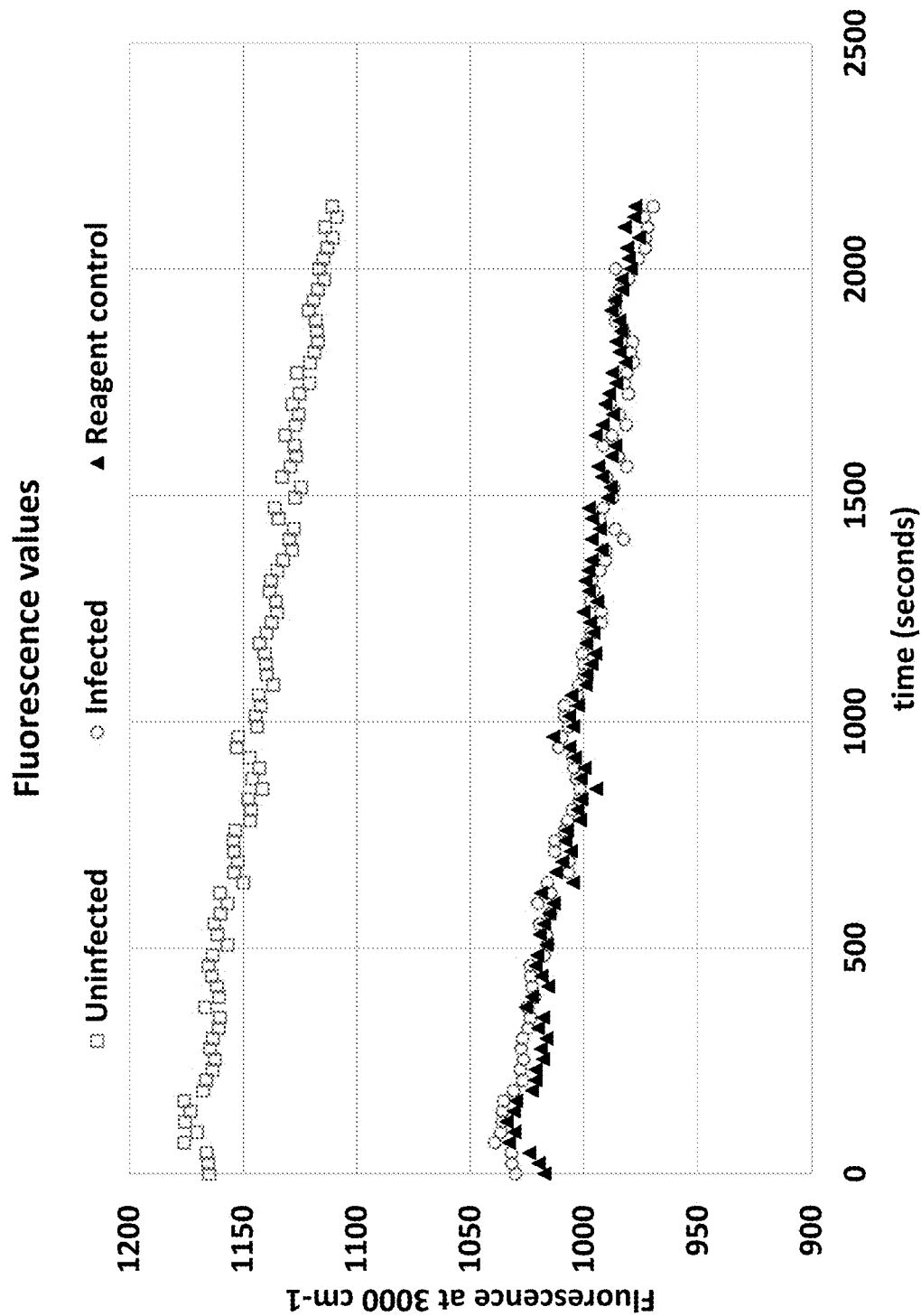
FIG. 35A depicts fluorescence measurements aggregated for the 3 uninfected control samples according to certain embodiments.
Figure 35B:
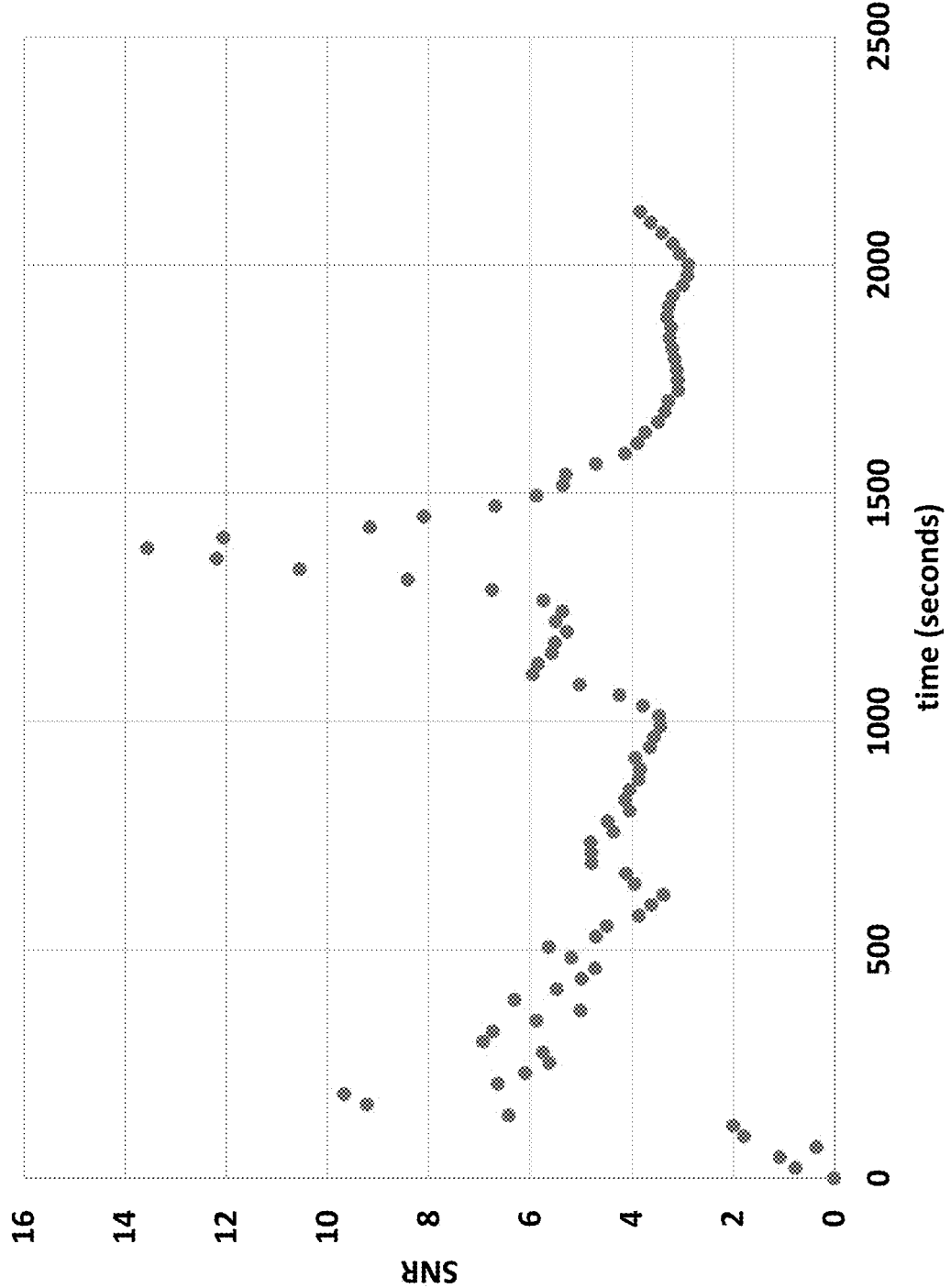
FIG. 35B depicts the signal-to-noise ratio for fluorescence detection, estimated as the signal divided by the rms standard deviation of the rate of change of uninfected and infected samples according to certain embodiments.

Determining the presence or absence of a pathogenic microorganism is depicted in FIGS. 35A and 35B. The example depicts the use of a test with artificially spiked samples that are created as follows: (a) first, a stock solution of *S. aureus* in buffer is prepared with a concentration of 1000 CFU/m L. 0.05 mL of this stock solution (or, an expected 50 CFUs) is added to 5 mL of plasma purchased from a blood bank and incubated for 2 hours. (b) This plasma is then centrifuged to remove the bacteria from the plasma. 0.6 mL of this infected plasma is added to the standard reagent formulation that has a volume of 3.9 mL. Three "infected" samples are created from this plasma. (c) Three uninfected control samples are created by adding 0.6 mL of uninfected plasma (that has also been subject to 2 hour incubation and then centrifuged) to the reagent formulation. (d) One reagent control sample vial is created by taking the reagent vial without any additions. All 7 test vials are tested simultaneously, with the results illustrated in FIGS. 35A-B. Use of these known samples enables the use of simple statistical measures (such as signal to noise) to characterize the measurement.

While the test is running, the fluorescence values at a suitable frequency is continuously monitored, and their rate of change, for individual test vials is calculated. FIG. 35A illustrates these measurements as aggregates for control and infected samples, and also that for the single reagent control sample. FIG. 35A depicts the fluorescence values, aggregated for the 3 uninfected control samples, the 3 infected samples and the reagent sample. The fluorescence values in the uninfected control samples decrease due to the process of fluorescence quenching. The rate of decrease in the infected samples is somewhat greater than this. The signal is defined as the difference between the rate of change of the fluorescence in uninfected control sample and that in the infected sample. The uninfected control samples demonstrate a rate of change that is consistent with the rate of change observed on reagent control sample--which is estimated to be $(-2.2\pm0.1)\times10^{-5}$/sec at the end of the measurement in this example. FIG. 35B depicts the signal-to-noise ratio, estimated as the signal divided by the rms standard deviation of the rate of change of uninfected and infected samples.

For final diagnosis, the rate of change of the fluorescence in the reagent vial is subtracted from the rate of change of fluorescence in the test vials. After correcting for the drift in the reagent control standard, and collecting data for a long enough time period such that the SNR$\gg$1, the samples can be analyzed to determine if a pathogenic microorganism is present.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for determining the presence of a microorganism in a sample, the method comprising:
   (a) combining in a sample holder a liquid sample and a reagent that contains albumin having an incorporated ligand which is a carotenoid;
   (b) irradiating the sample with a monochromatic light source that is absorbed by the carotenoid, wherein the irradiation is achieved with a focusing lens that is focused at a position located at the interface between the surface of the sample holder that is in contact with the sample, with either an invariant light intensity or one that varies over time and that is focused at an interface between the sample and a surface of the sample holder; and
   (c) collecting scattered light from the irradiated sample and measuring a Raman signal and a fluorescence signal from the scattered light at a plurality of different times;
   (d) calculating a rate of change in intensity of the Raman signal and fluorescence signal for the sample over time;
   (e) correcting the calculated rates of change in the intensities of the Raman signal and the fluorescence signal to obtain a net signal; and
   (f) determining the presence of a microorganism in the sample based on a comparison of the net signal versus one or more preset thresholds, wherein the carotenoid absorbs the monochromatic light from the light source and has a resonant Raman output that varies in the presence of dissolved gases and free radicals in the sample.

2. The method according to claim 1, wherein the one or more present thresholds are set by performing steps (a)-(e) of claim 1 on one or more control samples that contains an inoculum in an amount at a lower limit of concentration in a clinically infected sample.

3. The method according to claim 1, wherein the carotenoid is lycopene.

4. The method according to claim 1, wherein the monochromatic light source is a laser.

5. The method according to claim 1, wherein correcting the rate of change in the intensities of the Raman signal and the fluorescence signal comprises characterizing a spectral output from a standard sample.

6. The method according to claim 1, wherein correcting the rate of change in the intensities of the Raman signal comprises characterizing a fluorescence output from the reagent.

7. The method according to claim 1, further comprising pretreating the albumin of the reagent with a reducing agent prior to mixing with the sample.

8. The method according to claim 7, wherein the reducing agent is glutathione or bilirubin.

9. The method according to claim 7, further comprising contacting the pretreated albumin with a disulfide crosslinking agent.

10. The method according to claim 9, where the disulfide crosslinking agent comprises a core that is cleaved by enzymes or a metabolite produced by the microorganism in the sample.

11. The method according to claim 9, wherein the crosslinking agent comprises a compound of Formula (I):

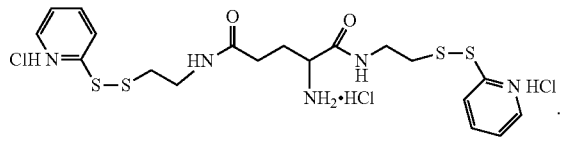

(Formula I)

12. The method according to claim 1, wherein the sample holder is a glass vial.

13. The method according to claim 12, wherein the surface of the glass vial that is in contact with the sample comprises a coating that modifies the absorption of albumin on the glass surface.

14. The method according to claim 13, wherein the coating is a zwitterionic coating.

15. The method according to claim 1, where the reagent further comprises an antimicrobial composition.

16. The method according to claim 15, further comprising plotting the net signal against antimicrobial concentration,
wherein a minima in the plot is used to estimate minimum bactericidal concentration of the antimicrobial composition; and/or
wherein a breakpoint in the plot is used to estimate minimum inhibitory concentration of the antimicrobial composition.

17. The method according to claim 1, wherein calculating the net signal comprises:
determining a rate of change in the intensity of fluorescence scattering from a standard reference sample; and
calculating the net signal as the rate of change in the intensity of the Raman signal minus the rate of change in the intensity of fluorescence scattering from the standard sample.

18. The method according to claim 1, wherein calculating the net signal comprises:
determining a rate of change in total output from a standard reference sample; and
calculating the net signal as the rate of change in the intensity of the Raman signal minus the rate of change in the intensity of Resonant Raman scattering from the standard sample.

19. The method according to claim 17, further comprising comparing the calculated net signal with preset thresholds and determining that the sample includes actively metabolizing microorganisms based on the comparison.

20. The method according to claim 1, wherein the sample is a clinical sample from a subject and the method further comprises diagnosing the clinical sample from the subject as being infected with the microorganism based on the comparison of the net signal versus the one or more preset thresholds.

21. The method according to claim 20, wherein the method comprises diagnosing the subject as being infected with the microorganism.

* * * * *